United States Patent
Shen et al.

(10) Patent No.: US 10,039,809 B2
(45) Date of Patent: Aug. 7, 2018

(54) MODIFIED THERAPEUTIC AGENTS, STAPLED PEPTIDE LIPID CONJUGATES, AND COMPOSITIONS THEREOF

(71) Applicants: THE CALIFORNIA INSTITUTE FOR BIOMEDICAL RESEARCH, La Jolla, CA (US); THE SCRIPPS RESEARCH INSTITUTE, La Jolla, CA (US)

(72) Inventors: Weijun Shen, San Diego, CA (US); Pengyu Yang, San Diego, CA (US); Huafei Zou, San Diego, CA (US); Peter G. Schultz, La Jolla, CA (US)

(73) Assignees: THE CALIFORNIA INSTITUTE FOR BIOMEDICAL RESEARCH, La Jolla, CA (US); THE SCRIPPS RESEARCH INSTITUTE, La Jolla, CA (US)

(*) Notice: Subject to any disclaimer, the term of this patent is extended or adjusted under 35 U.S.C. 154(b) by 6 days.

(21) Appl. No.: 15/104,807

(22) PCT Filed: Dec. 17, 2014

(86) PCT No.: PCT/US2014/070977
§ 371 (c)(1),
(2) Date: Jun. 15, 2016

(87) PCT Pub. No.: WO2015/095406
PCT Pub. Date: Jun. 25, 2015

(65) Prior Publication Data
US 2016/0317623 A1    Nov. 3, 2016

Related U.S. Application Data

(60) Provisional application No. 61/917,816, filed on Dec. 18, 2013.

(51) Int. Cl.
| A61K 31/23 | (2006.01) |
| A61K 31/20 | (2006.01) |
| A61K 47/48 | (2006.01) |
| A61K 47/30 | (2006.01) |
| A61K 38/22 | (2006.01) |
| A61K 9/00 | (2006.01) |
| A61K 38/26 | (2006.01) |
| A61K 45/06 | (2006.01) |
| A61K 47/60 | (2017.01) |
| A61K 47/54 | (2017.01) |
| A61K 9/70 | (2006.01) |

(52) U.S. Cl.
CPC .......... *A61K 38/22* (2013.01); *A61K 9/0019* (2013.01); *A61K 9/0021* (2013.01); *A61K 38/2278* (2013.01); *A61K 38/26* (2013.01); *A61K 45/06* (2013.01); *A61K 47/54* (2017.08); *A61K 47/542* (2017.08); *A61K 47/543* (2017.08); *A61K 47/554* (2017.08); *A61K 47/60* (2017.08); *A61K 9/703* (2013.01)

(58) Field of Classification Search
None
See application file for complete search history.

(56) References Cited

U.S. PATENT DOCUMENTS

| 5,750,497 A | 5/1998 | Havelund et al. |
| 5,759,807 A | 6/1998 | Breece et al. |
| 5,811,395 A | 9/1998 | Schwabe et al. |
| 5,866,538 A | 2/1999 | Norup et al. |
| 6,011,007 A | 1/2000 | Havelund et al. |
| 6,051,551 A | 4/2000 | Hughes et al. |
| 6,268,343 B1 | 7/2001 | Knudsen et al. |
| 6,444,641 B1 | 9/2002 | Flora |
| 6,869,930 B1 | 3/2005 | Havelund et al. |
| 6,890,518 B2 | 5/2005 | Patton et al. |
| 7,960,506 B2 | 6/2011 | Nash |
| 7,981,998 B2 | 7/2011 | Nash |
| 7,981,999 B2 | 7/2011 | Nash |
| 8,071,541 B2 | 12/2011 | Arora et al. |
| 8,129,343 B2 | 3/2012 | Lau et al. |
| 8,217,145 B2 | 7/2012 | Wang et al. |
| 8,399,405 B2 | 3/2013 | Nash et al. |
| 8,420,598 B2 | 4/2013 | Lee et al. |
| 8,524,653 B2 | 9/2013 | Nash et al. |
| 8,637,686 B2 | 1/2014 | Nash |
| 8,735,539 B2 | 5/2014 | Kraynov et al. |

(Continued)

FOREIGN PATENT DOCUMENTS

| CA | 2924109 A1 | 3/2015 |
| WO | WO-2006066258 A2 | 6/2006 |

(Continued)

OTHER PUBLICATIONS

International Application No. PCT/US16/37834 International Search Report dated Oct. 26, 2016.

(Continued)

*Primary Examiner* — Julie Ha
*Assistant Examiner* — Kristina M Hellman
(74) *Attorney, Agent, or Firm* — Wilson Sonsini Goodrich & Rosati

(57) ABSTRACT

Methods and compositions are provided for extending the half-life of a therapeutic agent. A modified therapeutic agent (mTA) comprises a therapeutic agent, a staple, and a half-life extending molecule. The mTAs disclosed herein may be used to treat a disease or a condition in a subject in need thereof.

13 Claims, 26 Drawing Sheets

(56) References Cited

U.S. PATENT DOCUMENTS

| | | |
|---|---|---|
| 8,808,694 B2 | 8/2014 | Nash et al. |
| 2003/0158376 A1 | 8/2003 | Schwabe et al. |
| 2005/0176108 A1 | 8/2005 | Kim et al. |
| 2005/0192217 A1 | 9/2005 | Muhlradt et al. |
| 2008/0262200 A1 | 10/2008 | Nash |
| 2008/0305519 A1 | 12/2008 | Lin et al. |
| 2009/0047711 A1 | 2/2009 | Nash |
| 2009/0088553 A1 | 4/2009 | Nash |
| 2009/0186817 A1 | 7/2009 | Ghosh et al. |
| 2009/0239784 A1 | 9/2009 | Jonassen et al. |
| 2009/0275519 A1 | 11/2009 | Nash et al. |
| 2009/0326192 A1 | 12/2009 | Nash et al. |
| 2010/0029554 A1 | 2/2010 | Ghosh et al. |
| 2010/0093086 A1 | 4/2010 | Lin et al. |
| 2010/0184133 A1 | 7/2010 | Norgaard et al. |
| 2010/0184628 A1 | 7/2010 | Nash |
| 2010/0210515 A1 | 8/2010 | Nash et al. |
| 2010/0216688 A1 | 8/2010 | Nash et al. |
| 2010/0239554 A1 | 9/2010 | Schellenberger et al. |
| 2010/0292172 A1 | 11/2010 | Ghosh et al. |
| 2010/0298201 A1 | 11/2010 | Nash et al. |
| 2011/0046056 A1* | 2/2011 | Bianchi .................. C07K 14/775 514/7.4 |
| 2011/0144303 A1 | 6/2011 | Nash et al. |
| 2011/0166321 A1 | 7/2011 | Garibay et al. |
| 2011/0223149 A1 | 9/2011 | Nash et al. |
| 2011/0243942 A1 | 10/2011 | Wang |
| 2011/0263815 A1 | 10/2011 | Nash |
| 2012/0040889 A1 | 2/2012 | Nash et al. |
| 2012/0046229 A1 | 2/2012 | Kraynov et al. |
| 2012/0149648 A1 | 6/2012 | Nash et al. |
| 2012/0172311 A1 | 7/2012 | Nash et al. |
| 2012/0178700 A1 | 7/2012 | Nash et al. |
| 2012/0190818 A1 | 7/2012 | Nash |
| 2012/0264674 A1 | 10/2012 | Nash et al. |
| 2013/0023646 A1 | 1/2013 | Nash et al. |
| 2013/0040884 A1 | 2/2013 | Lau et al. |
| 2013/0123169 A1 | 5/2013 | Kawahata et al. |
| 2013/0210745 A1 | 8/2013 | Guerlavais et al. |
| 2014/0057857 A1 | 2/2014 | Lin et al. |
| 2014/0128581 A1 | 5/2014 | Darlak et al. |
| 2014/0135255 A1 | 5/2014 | Nash et al. |
| 2014/0135473 A1 | 5/2014 | Nash |
| 2014/0148390 A1 | 5/2014 | Haupts et al. |
| 2016/0287713 A1 | 10/2016 | Shen |

FOREIGN PATENT DOCUMENTS

| | | |
|---|---|---|
| WO | WO-2006097537 A2 | 9/2006 |
| WO | WO-2007109135 A2 | 9/2007 |
| WO | WO-2008057298 A2 | 5/2008 |
| WO | WO-2010096052 A1 | 8/2010 |
| WO | WO-2010096142 A1 | 8/2010 |
| WO | WO-2011039096 A1 | 4/2011 |
| WO | WO-2012003995 A1 | 1/2012 |
| WO | WO-2012011752 A2 | 1/2012 |
| WO | WO-2012024452 A2 | 2/2012 |
| WO | WO-2012088116 A2 | 6/2012 |
| WO | WO-2012088379 A2 | 6/2012 |
| WO | WO-2012149563 A1 | 11/2012 |
| WO | WO-2013004607 A1 | 1/2013 |
| WO | WO-2013007563 A1 | 1/2013 |
| WO | WO-2013130683 A2 | 9/2013 |
| WO | WO-2015038938 A1 | 3/2015 |
| WO | WO-2016149501 A2 | 9/2016 |

OTHER PUBLICATIONS

Walensky, Loren D. et al. Hydrocarbon-Stapled Peptides: Principles, Practice, and Progress, Journal of Medicinal Chemistry 57:6275-6288 (2014).

U.S. Appl. No. 14/917,689 Restriction Requirement dated Feb. 6, 2017.

Bird, Gregory H. et al. Hydrocarbon double-stapling remedies the proteolytic instability of a lengthy peptide therapeutic. Proceedings of the National Academy of Sciences, 2010, vol. 107, No. 32, pp. 14093-14098.

Bloom, Stephen R. et al. Investigation of Structure-Activity Relationships of Oxyntomodulin (Oxm) Using Oxm Analogs. Endocrinology 150(4):1712-1721 (Apr. 2009).

Chang, Y. et al. Stapled α-helical peptide drug development: A potent dual inhibitor of MDM2 and MDMX for p53-dependent cancer therapy, Proceedings of the National Academy of Sciences, e-pub. Aug. 14, 2013, vol. 110, No. 36, pp. E3445-E3454.

Dimarchi, Richard D. et al. Functional association of the N-terminal residues with the central region in glucagon-related peptides. J. Pept. Sci. 17:659-666 (2011).

Dimarchi, Richard et al. A new glucagon and GLP-1 co-agonist eliminates obesity in rodents. Nature Chemical Biology, 5(10):749-757 (Oct. 2009).

Hossain, Mohammed A. et al. Chimeric relaxin peptides highlight the role of the A-chain in the function of H2 relaxin. Peptides 35:102-106 (2012).

International Application No. PCT/US2014/055457 International Search Report and Written Opinion dated Dec. 23, 2014.

International Application No. PCT/US2014/070977 International Search Report and Written Opinion dated Mar. 27, 2015.

International Application No. PCT/US2016/022880 International Search Report and Written Opinion dated Oct. 7, 2016.

Elling, Christian et al. Oxyntomodulin Differentially Affects Glucagon-Like Peptide-1 Receptor β-Arrestin Recruitment and Signaling through Gas.

Lin, Q. et al. rational Design of Proteolytically Stable, Cell-Permeable peptide-Based Selective Mcl-1 Inhibitors. J. Am. Chem. Soc. 134:14734-14737 (2012).

Metra, M. et al. Effect of Serelaxin on Cardiac, Renal, and Hepatic Biomarkers in the Relaxin in Acute Heart Failure (RELAX-AHF) Development Program. Journal of the American College of Cardiology 61(2): 196-206 (Jan. 15, 2013).

Santoprete, A. et al. DPP-IV-resistant, long-acting oxyntomodulin derivatives. Journal Peptide Science, 17:270-280 (2011).

Schultz, P.G. et al. General Approach to the Synthesis of Short a-Helical Peptides. J. Am. Chem. Soc. 113:9391-9392 (1991).

Soloff, M. et al. Cloning, characterization, and expression of the rat relaxin gene. Gene 323: 149-155 (2003).

Teerlink, et al. Serelaxin, recombinant human relaxin-2, for treatment of acute heart failure (RELAX-AHF): a randomised, placebo-controlled trial. Lancet 381:29-39 (2013).

Underwood, Christina R. et al. Crystal Structure of Glucagon-like Peptide-1 in Complex with the Extracellular Domain of the Glucagon-like Peptide-1 Receptor. The Journal of Biological Chemistry 285(1): 723-730 (Jan. 1, 2010).

Verdine, Gregory L. et al. Stapled Peptides for Intracellular Drug Targets. Methods in Enzymology, vol. 503, Chapter 1, pp. 1-31 (2012).

Wade, John D. et al. The Chemical Synthesis of Relaxin and Related peptides: A Historical Perspective. Ann. N.Y. Acad. Sci. 1160: 11-15 (2009).

Wu, Ye-Lin, et al. Addition of a cysteine to glucagon-like peptide-1 (GLP-1) conjugates GLP-1 to albumin in serum and prolongs GLP-1 action in vivo, Regulatory Peptides, 2010, vol. 164, No. 2, pp. 83-89.

Aicart-Ramos C. et al. Protein palmitoylation and subcellar trafficking. Biochim Biophys Acta 1808:2981-2994 (2011).

Backer, et al. Chapter 16: Cysteine-Containing Fusion Tag for Site-Specific Conjugation of Therapeutic and Imaging Agents to Targeting Proteins, Peptide-Based Drug Design Methods and Protocols, Springer Protocols, pp. 275-294 (2008).

Bader, et al., Bioorganic synthesis of lipid-modified proteins for the study of signal transduction. Nature, 403:223-226 (Jan. 13, 2000).

Baosheng, Liu, Peptide PEGylation: The Next Generation Linking peptides to polythylene glycol, or PEGylation, has helped improve pharmaceutical therapeutics in several ways. A wave of new techniques is now ushering in further advances. Pharmaceutical Technology, 2011(3): 1-3 (May 1, 2011).

(56) References Cited

OTHER PUBLICATIONS

Cheng, W. and Lee-Yong Lim, Design, synthesis, characterization and in-vivo activity of a novel salmon calcitonin conjugate containing a novel PEG-lipid moiety. Journal of Pharmacy and Pharmacology, 62(3):296-304 (Mar. 2010).

Cheng, W. et al. Lipeo-sCT: A novel reversible lipidized salmon calcitonin derivative, its biophysical properties and hypocalcemic activity. European Journal of Pharmaceutical Sciences 37(2):151-159 (May 12, 2009).

Co-pending U.S. Appl. No. 15/557,986, filed Sep. 13, 2017.

Guldenhaupt, et al. Secondary structure of lipidated Ras bound to lipid bilayer. FEBS Journal 275:5910-5918 (2008).

Havelund, S. The mechanism of protraction of insulin detemir, a long-acting, acylated analog of human insulin. Pharmaceutical Research, 21(9):1498-1504 (Aug. 2004).

Janout et al., Bioconjugate-Based Molecular Umbrellas. Bioconjugate Chemistry, 20(2):183-192 (E-Pub Nov. 20, 2008).

Lorenz, Martin et al. Recent progress and future options in the development of GLP-1 receptor agonists for the treatment of diabesity. Bioorganic & Medicinal Chemistry Letters 23 (14): 4011-4018 (May 16, 2013).

Muller, et al. Chapter 2: Peptide carier conjugation, Synthetic Peptides as Antigens, Laboratory Techniques in Biochemstry and Molecular Biology. 28:79-131 (1999).

Pan, et al. Design of a Long Acting Peptide Functioning as Both a Glucagon-like Peptide-1 Receptor Agonist and a Glucagon Receptor Angtagonist. The Journal of Biological Chemistry 281(18):12506-12515 (May 5, 2008).

Shah, Trishul, Bioconjugates: The Adaptable Challenge. BioPharm International the Science & Business of Biopharmaceuticals, 26(1):1-4 (Jan. 1, 2013).

Trussel, et al. New strategy for the extension of the serum half-life of antibody fragments. Bioconjug Chem. Dec. 2009;20(12):2286-92. doi: 10.1021/bc9002772.

U.S. Appl. No. 14/917,689 Final Office Action dated Dec. 22, 2017.

U.S. Appl. No. 14/917,689 Non-Final Office Action dated May 30, 2017.

U.S. Appl. No. 15/104,807 Non-final Office Action dated Nov. 27, 2017.

Day, J.W. et al. Optimization of co-agonism at GLP-1 and glucagon receptors to safely maximize weight reduction in DIO-rodents. Biopolymers, 98(5):443-450 (2012).

* cited by examiner

FIG. 4A
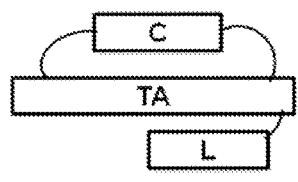
FIG. 4B
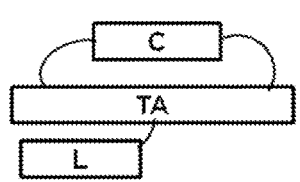
FIG. 4C
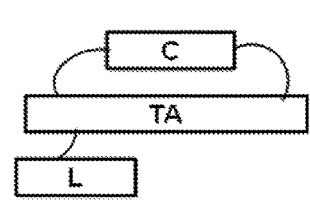
FIG. 4D
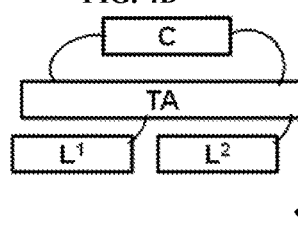
FIG. 4E
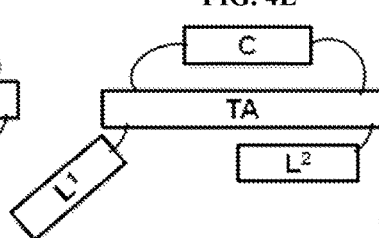
FIG. 4F
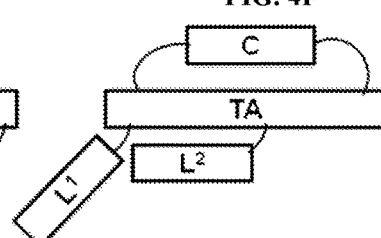
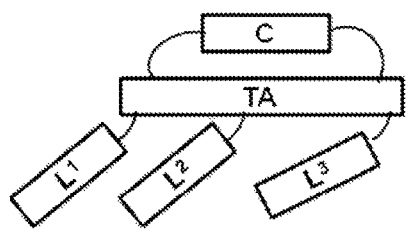
FIG. 4G
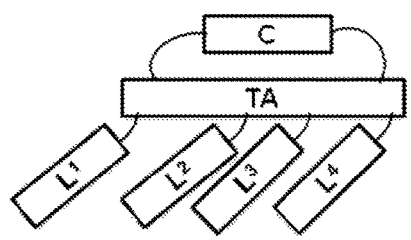
FIG. 4H FIG. 6A
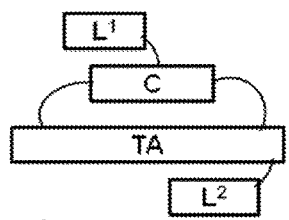
FIG. 6B
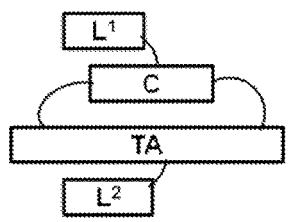
FIG. 6C
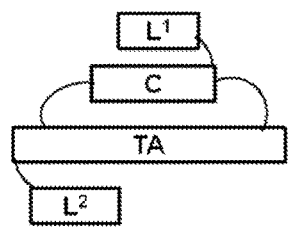
FIG. 6D
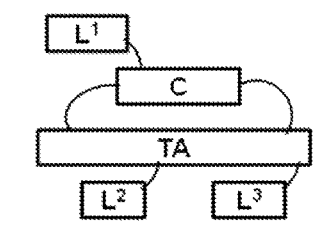
FIG. 6E
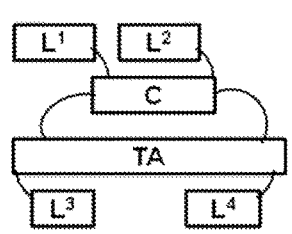
FIG. 6F
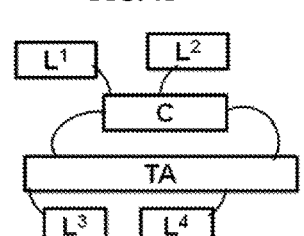
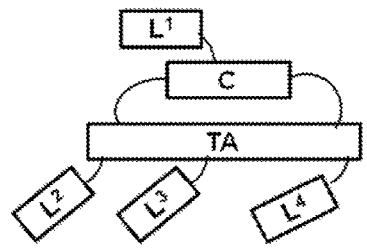
FIG. 6G
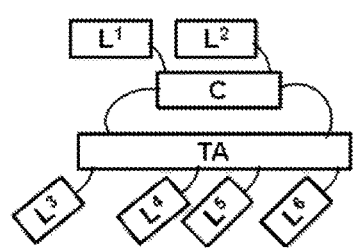
FIG. 6H

* p<0.05 vs vehicle
# p<0.05 vs mTA4 and Semaglutide

MODIFIED THERAPEUTIC AGENTS, STAPLED PEPTIDE LIPID CONJUGATES, AND COMPOSITIONS THEREOF

CROSS-REFERENCE TO RELATED APPLICATIONS

This application is a U.S. National Stage entry of International Application No. PCT/US2014/070977, filed Dec. 17, 2017; which claims the benefit of priority from U.S. Provisional Application No. 61/917,816 filed Dec. 18, 2013, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Dec. 6, 2016, is named 41135-717.831-SL_ST25.txt and is 26,748 bytes in size.

BACKGROUND OF THE INVENTION

The development of therapeutic agents (e.g., biological drugs) is often hampered by short half-lives. The biological half-life or elimination half-life of a substance is the time it takes for a substance (for example a metabolite, drug, signaling molecule, radioactive nuclide, or other substance) to lose half of its pharmacologic, physiologic, or radiologic activity. As a result of the short half-life, patients are often administered higher dosages more frequently, which may lead to reduced compliance, higher costs and greater risks of side effects.

Extended-release products are designed to prolong the absorption of drugs with short half-lives, thereby allowing longer dosing intervals while minimizing fluctuations in serum drug levels. Current strategies used for extending half-lives are those that increase hydrodynamic volume (PEGylation) or those that use FcRn-mediated recycling (albumin fusions). Attachment of polypeptides or lipophilic constituents to drugs has also been used to extend the half-life of a biological agent (U.S. Pat. No. 6,268,343; U.S. Pat. No. 5,750,497; U.S. Pat. No. 8,129,343).

The present disclosure provides modified therapeutic agents (mTAs) for improving the biological, chemical, physiologic, pharmacologic, pharmacokinetic, and/or pharmacodynamic properties of a therapeutic agent.

SUMMARY OF THE INVENTION

Disclosed herein are modified therapeutic agents (mTAs) comprising a therapeutic agent, a first staple, and a first half-life extending molecule, wherein the therapeutic agent is a modified or unmodified therapeutic peptide that is covalently attached to the first staple via two amino acid residues on the modified or unmodified therapeutic peptide and the half-life of the mTA is longer than the half-life of the unmodified therapeutic peptide alone. The first half-life extending molecule may be covalently attached to the first staple. The first half-life extending molecule may comprise a lipid, a polyglycol region, or a combination thereof. The first half-life extending molecule may comprise a lipid. The first half-life extending molecule may comprise a lipid and a polyglycol region. The first half-life extending molecule may comprise a polyglycol region. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region may comprise one or more polyethylene glycol units, polypropylene glycol units, or polybutylene glycol units, or a combination thereof. The polyglycol region may be selected from

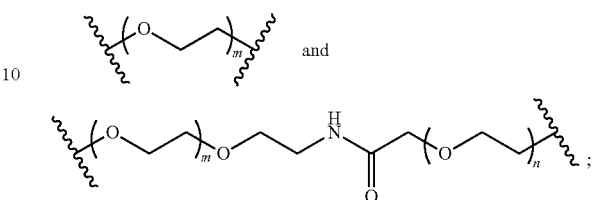

wherein m and n are independently 1, 2, 3, 4, 5, 6, 7, 8, 9, 10, 11, 12, 13, 14, 15, 16, 17, 18, 19, or 20. The modified therapeutic peptide may comprise one or more amino acid additions, deletions, or substitutions, or a combination thereof. The unmodified therapeutic peptide may be selected from GLP-1, glucagon, oxyntomodulin, exendin-4, GLP-2, GIP, GLP1R and GCGR dual agonist, GLP1R and GIPR dual agonist, and GLP1R, GCGR and GIPR tri-agonist. The modified therapeutic peptide may be a derivative of a peptide selected from GLP-1, glucagon, oxyntomodulin, exendin-4, GLP-2, GIP, GLP1R and GCGR dual agonist, GLP1R and GIPR dual agonist, and GLP1R, GCGR and GIPR tri-agonist; the derivative being a peptide comprising one or more amino acid additions, deletions, or substitutions, or a combination thereof. The modified or unmodified therapeutic peptide may comprise an amino acid sequence comprising at least a portion of a polypeptide sequence selected from a group consisting of selected from a group consisting of SEQ ID NO: 1-53. The modified or unmodified therapeutic peptide may comprise an amino acid sequence comprising 10 or more amino acids based on or derived from a polypeptide sequence selected from a group consisting of selected from a group consisting of SEQ ID NO: 1-53. The modified or unmodified therapeutic peptide may comprise an amino acid sequence that is at least about 50% homologous to an amino acid sequence selected from the group comprising SEQ ID NO: 1-53. The modified or unmodified therapeutic peptide may comprise an amino acid sequence that is at least 80% homologous to an amino acid sequence selected from the group comprising SEQ ID NO: 1-53. The modified or unmodified therapeutic peptide may comprise an amino acid sequence comprising at least a portion of a polypeptide sequence selected from a group consisting of selected from a group consisting of SEQ ID NO: 8-12. The modified or unmodified therapeutic peptide may comprise an amino acid sequence comprising 10 or more amino acids based on or derived from a polypeptide sequence selected from a group consisting of selected from a group consisting of SEQ ID NO: 8-12. The modified or unmodified therapeutic peptide may comprise an amino acid sequence that is at least about 50% homologous to an amino acid sequence selected from the group comprising SEQ ID NO: 8-12. The modified or unmodified therapeutic peptide may comprise an amino acid sequence that is at least 80% homologous to an amino acid sequence selected from the group comprising SEQ ID NO: 8-12. The modified or unmodified therapeutic peptide may comprise an amino acid sequence comprising at least a portion of a polypeptide sequence selected from a group consisting of selected from a group consisting of SEQ ID NO: 15-19. The modified or unmodified therapeutic peptide may comprise an amino acid sequence comprising 10 or more amino acids based on or derived from a polypeptide sequence selected from a group consisting of selected from a group consisting of SEQ ID NO: 15-19. The modified or unmodified therapeutic peptide may comprise an amino acid sequence that is at least about 50% homologous to an amino acid sequence selected from the group comprising SEQ ID NO: 15-19. The modified or unmodified therapeutic peptide may comprise an amino acid sequence that is at least 80% homologous to an amino acid sequence selected from the group comprising SEQ ID NO: 15-19. The modified or unmodified therapeutic peptide may comprise an amino acid sequence comprising at least a portion of a polypeptide sequence selected from a group consisting of selected from a group consisting of SEQ ID NO: 20-29. The modified or unmodified therapeutic peptide may comprise an amino acid sequence comprising 10 or more amino acids based on or derived from a polypeptide sequence selected from a group consisting of selected from a group consisting of SEQ ID NO: 20-29. The modified or unmodified therapeutic peptide may comprise an amino acid sequence that is at least about 50% homologous to an amino acid sequence selected from the group comprising SEQ ID NO: 20-29. The modified or unmodified therapeutic peptide may comprise an amino acid sequence that is at least 80% homologous to an amino acid sequence selected from the group comprising SEQ ID NO: 20-29. The modified or unmodified therapeutic peptide may comprise an amino acid sequence comprising at least a portion of a polypeptide sequence selected from a group consisting of selected from a group consisting of SEQ ID NO: 30-53. The modified or unmodified therapeutic peptide may comprise an amino acid sequence comprising 10 or more amino acids based on or derived from a polypeptide sequence selected from a group consisting of selected from a group consisting of SEQ ID NO: 30-53. The modified or unmodified therapeutic peptide may comprise an amino acid sequence that is at least about 50% homologous to an amino acid sequence selected from the group comprising SEQ ID NO: 30-53. The modified or unmodified therapeutic peptide may comprise an amino acid sequence that is at least 80% homologous to an amino acid sequence selected from the group comprising SEQ ID NO: 30-53. Each of the two amino acid residues may be cysteine. At least one of the two amino acid residues may be an amino acid addition or substitution on the modified therapeutic peptide. The two or more residues may be at least about 4 amino acid residues apart. The two or more residues may be at least about 7 amino acid residues apart. The two or more residues may be at least about 11 amino acid residues apart. The mTA may further comprise a second staple. The mTA may further comprise a second half-life extending molecule. The mTA may further comprise a second staple and a second half-life extending molecule, wherein the second half-life molecule is covalently attached to the second staple.

Further disclosed herein are modified therapeutic agents (mTAs) comprising a therapeutic agent, a first staple, and a first half-life extending molecule, wherein the therapeutic agent is a modified or unmodified therapeutic peptide that is covalently attached to the first staple via two amino acid residues on the modified or unmodified therapeutic peptide and the half-life of the mTA is longer than the half-life of the unmodified therapeutic peptide alone. The first staple may comprise:

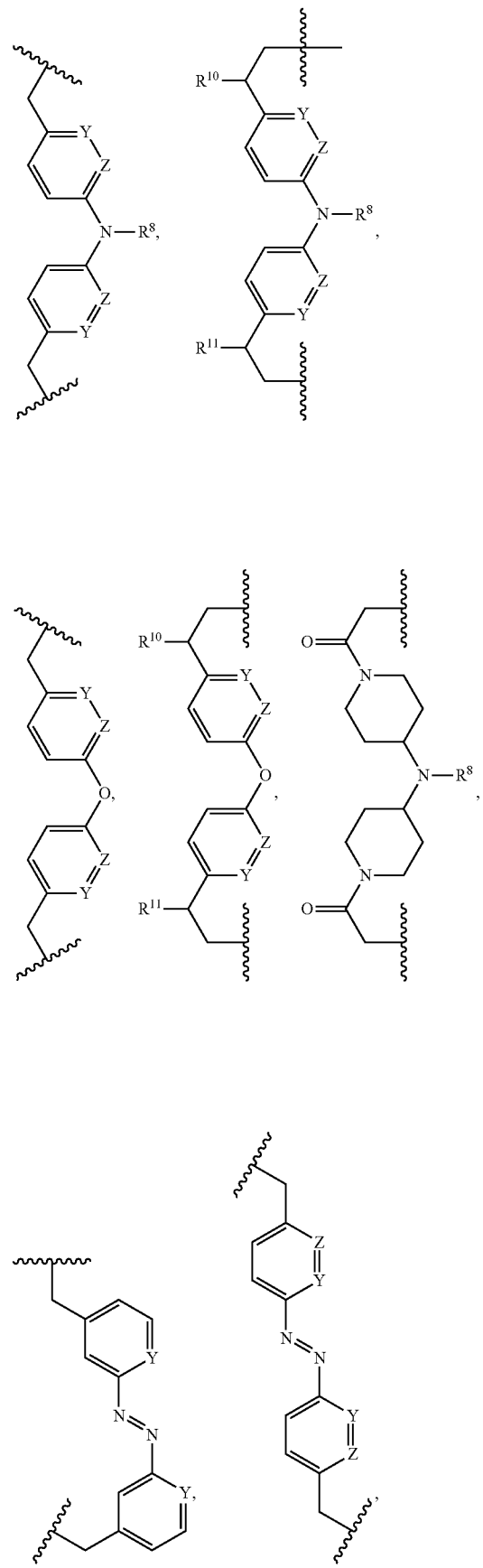

-continued
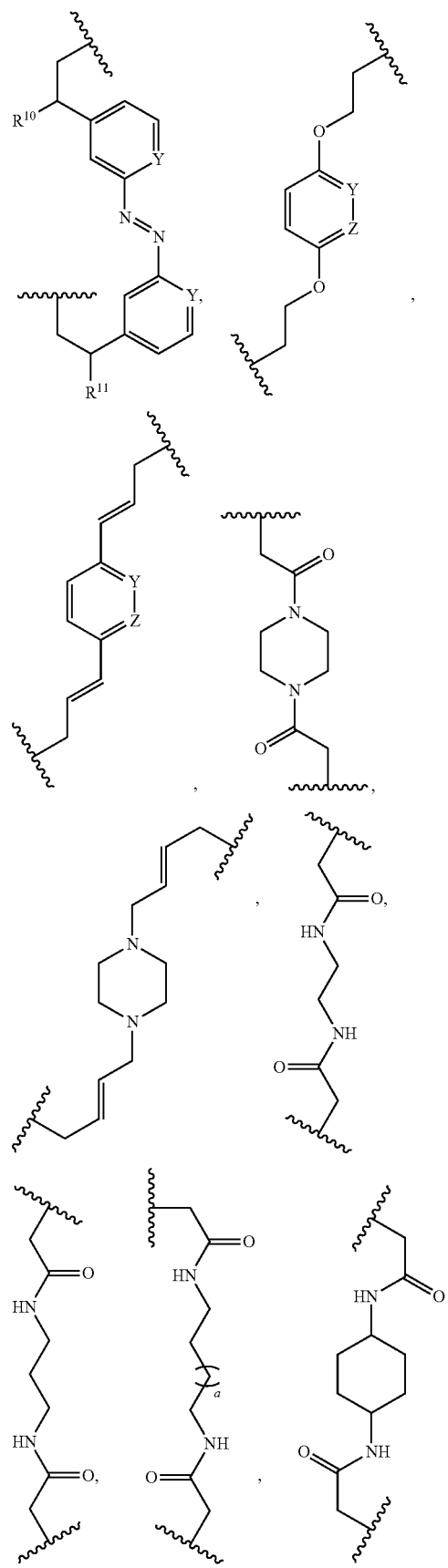
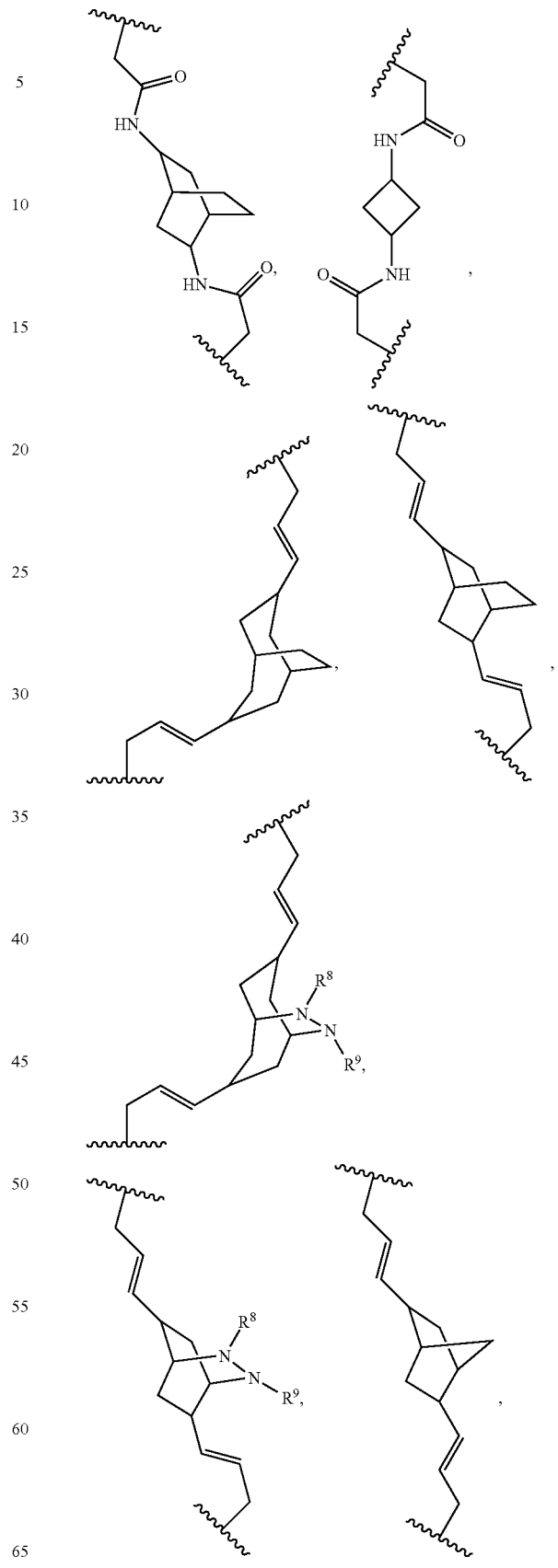

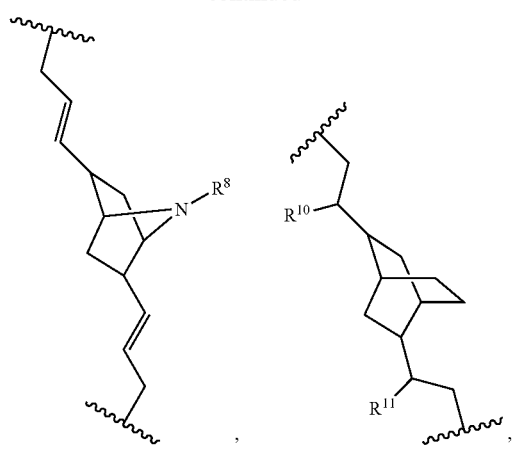
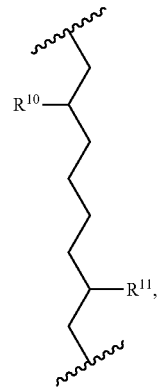
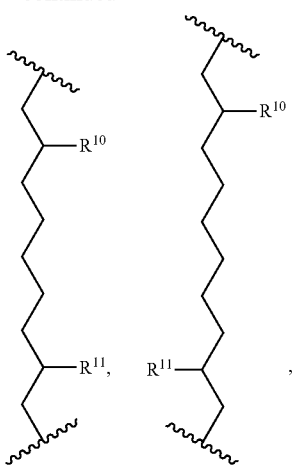
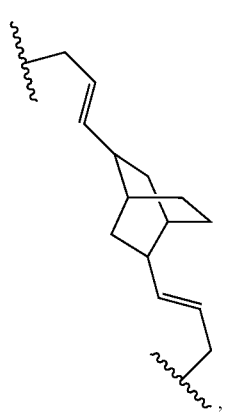
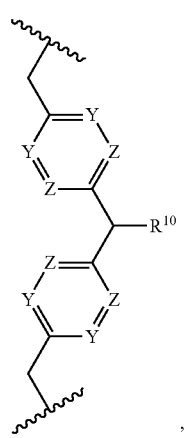
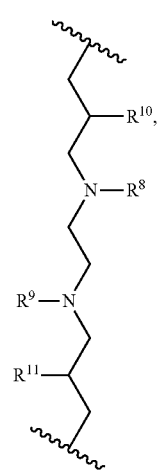
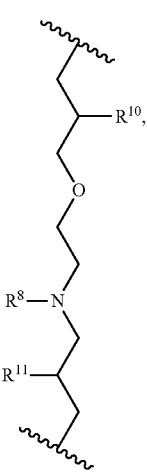
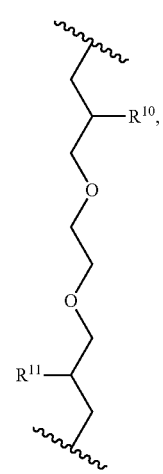
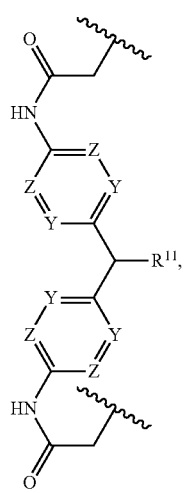
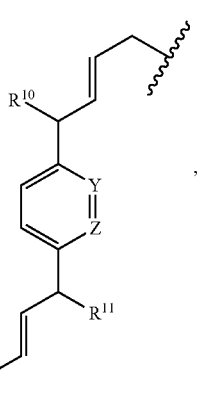
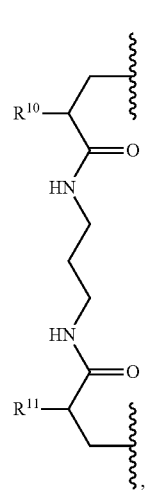
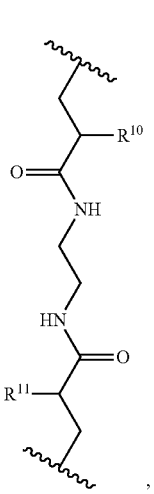
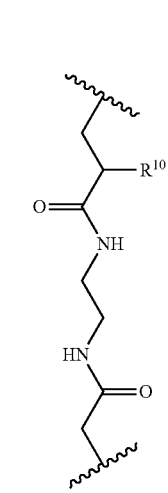

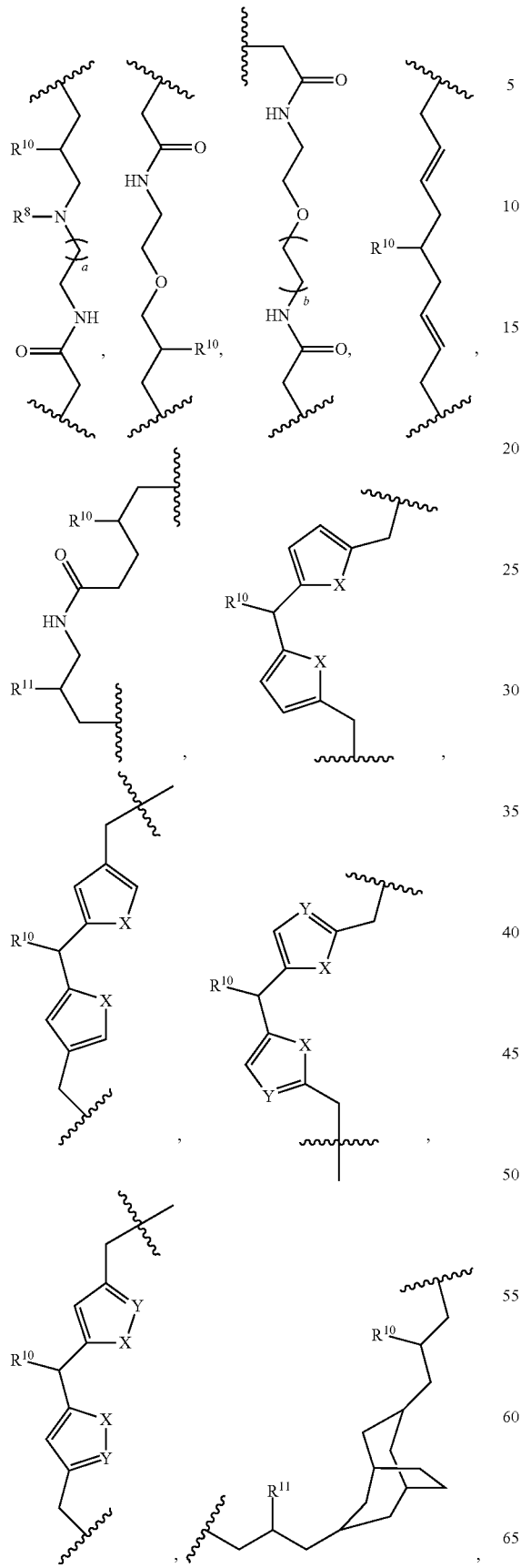
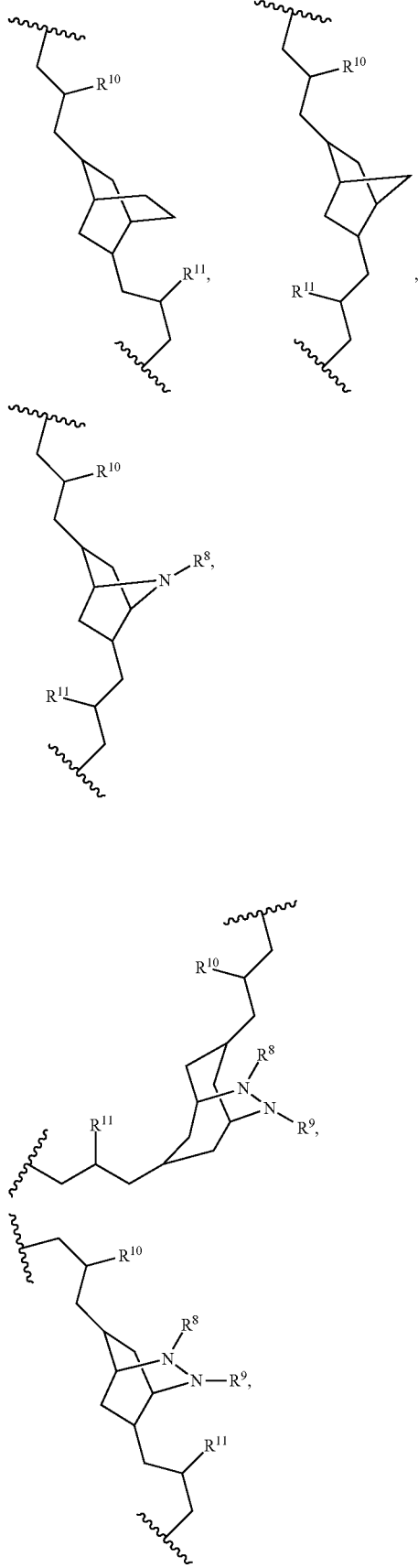

-continued

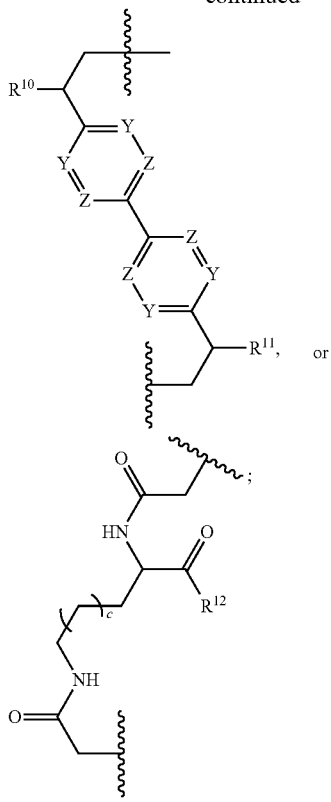

wherein each X is independently selected from O, NH, and S; each Y is independently selected from N and CH; each Z is independently selected from N and CH; each $R^8$ and $R^9$ is independently H or —C(O)(alkyl) or comprises a linker to the first half-life extending molecule; each $R^{10}$ and $R^{11}$ is independently oxo or comprises a linker to the first half-life extending molecule; $R^{12}$ is independently hydroxy, alkoxy, or comprises a linker to the first half-life extending molecule; a is 1, 2, 3, 4, 5, 6, 7, 8, 9, 10, 11, 12, 13, 14, 15, 16, or 17; b is 1, 2, 3, 4, 5, or 6; and c is 1 or 2. The first half-life extending molecule may comprise a lipid, a polyglycol region, or a combination thereof. The first half-life extending molecule may comprise a lipid. The first half-life extending molecule may comprise a lipid and a polyglycol region. The first half-life extending molecule may comprise a polyglycol region. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region may comprise one or more polyethylene glycol units, polypropylene glycol units, or polybutylene glycol units, or a combination thereof. The polyglycol region may be selected from m and

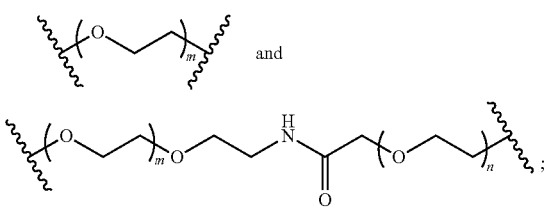

wherein m and n are independently 1, 2, 3, 4, 5, 6, 7, 8, 9, 10, 11, 12, 13, 14, 15, 16, 17, 18, 19, or 20. The modified therapeutic peptide may comprise one or more amino acid additions, deletions, or substitutions, or a combination thereof. The unmodified therapeutic peptide may be selected from GLP-1, glucagon, oxyntomodulin, exendin-4, GLP-2, GIP, GLP1R and GCGR dual agonist, GLP1R and GIPR dual agonist, and GLP1R, GCGR and GIPR tri-agonist. The modified therapeutic peptide may be a derivative of a peptide selected from GLP-1, glucagon, oxyntomodulin, exendin-4, GLP-2, GIP, GLP1R and GCGR dual agonist, GLP1R and GIPR dual agonist, and GLP1R, GCGR and GIPR tri-agonist; the derivative being a peptide comprising one or more amino acid additions, deletions, or substitutions, or a combination thereof. The modified or unmodified therapeutic peptide may comprise an amino acid sequence comprising at least a portion of a polypeptide sequence selected from a group consisting of selected from a group consisting of SEQ ID NO: 1-53. The modified or unmodified therapeutic peptide may comprise an amino acid sequence comprising at least a portion of a polypeptide sequence selected from a group consisting of selected from a group consisting of SEQ ID NO: 8-12. The modified or unmodified therapeutic peptide may comprise an amino acid sequence comprising at least a portion of a polypeptide sequence selected from a group consisting of selected from a group consisting of SEQ ID NO: 15-19. The modified or unmodified therapeutic peptide may comprise an amino acid sequence comprising at least a portion of a polypeptide sequence selected from a group consisting of selected from a group consisting of SEQ ID NO: 20-29. The modified or unmodified therapeutic peptide may comprise an amino acid sequence comprising at least a portion of a polypeptide sequence selected from a group consisting of selected from a group consisting of SEQ ID NO: 30-53. Each of the two amino acid residues may be independently selected from cysteine. At least one of the two amino acid residues may be an amino acid addition or substitution on the modified therapeutic peptide. The two or more residues may be at least about 4 amino acid residues apart. The two or more residues may be at least about 7 amino acid residues apart. The two or more residues may be at least about 11 amino acid residues apart. The mTA may further comprise a second staple. The mTA may further comprise a second half-life extending molecule. The mTA may further comprise a second staple and a second half-life extending molecule, wherein the second half-life molecule is covalently attached to the second staple. The half-life of the mTA may be 5-fold longer than the half-life of the unmodified therapeutic peptide alone.

Further disclosed herein are modified therapeutic agents (mTAs) comprising a therapeutic agent (TA), a first staple, and a first half-life extending molecule, wherein the TA is attached to the first staple. The TA may comprise a modified or unmodified therapeutic peptide. The modified therapeutic peptide may comprise one or more amino acid additions, deletions, or substitutions, or a combination thereof. The modified therapeutic peptide may be a derivative of a peptide selected from GLP-1, glucagon, oxyntomodulin, exendin-4, GLP-2, and GIP, GLP1R and GCGR dual agonist, GLP1R and GIPR dual agonist, and GLP1R, GCGR and GIPR tri-agonist; the derivative being a peptide comprising one or more amino acid additions, deletions, or substitutions, or a combination thereof. The unmodified therapeutic peptide may be selected from GLP-1, glucagon, oxyntomodulin, exendin-4, GLP-2, GIP, GLP1R and GCGR dual agonist, GLP1R and GIPR dual agonist, and GLP1R, GCGR and GIPR tri-agonist. The modified or unmodified therapeutic peptide may comprise an amino acid sequence comprising at least a portion of a polypeptide sequence selected from a group consisting of selected from a group consisting of SEQ ID NO: 1-53. The modified or unmodified therapeutic peptide may comprise an amino acid sequence comprising 10 or more amino acids based on or derived from a polypeptide sequence selected from a group consisting of selected from a group consisting of SEQ ID NO: 1-53. The modified or unmodified therapeutic peptide may comprise an amino acid sequence that is at least about 50% homologous to an amino acid sequence selected from the group comprising SEQ ID NO: 1-53. The modified or unmodified therapeutic peptide may comprise an amino acid sequence that is at least 80% homologous to an amino acid sequence selected from the group comprising SEQ ID NO: 1-53. The modified or unmodified therapeutic peptide may comprise an amino acid sequence comprising at least a portion of a polypeptide sequence selected from a group consisting of selected from a group consisting of SEQ ID NO: 8-12. The modified or unmodified therapeutic peptide may comprise an amino acid sequence comprising 10 or more amino acids based on or derived from a polypeptide sequence selected from a group consisting of selected from a group consisting of SEQ ID NO: 8-12. The modified or unmodified therapeutic peptide may comprise an amino acid sequence that is at least about 50% homologous to an amino acid sequence selected from the group comprising SEQ ID NO: 8-12. The modified or unmodified therapeutic peptide may comprise an amino acid sequence that is at least 80% homologous to an amino acid sequence selected from the group comprising SEQ ID NO: 8-12. The modified or unmodified therapeutic peptide may comprise an amino acid sequence comprising at least a portion of a polypeptide sequence selected from a group consisting of selected from a group consisting of SEQ ID NO: 15-19. The modified or unmodified therapeutic peptide may comprise an amino acid sequence comprising 10 or more amino acids based on or derived from a polypeptide sequence selected from a group consisting of selected from a group consisting of SEQ ID NO: 15-19. The modified or unmodified therapeutic peptide may comprise an amino acid sequence that is at least about 50% homologous to an amino acid sequence selected from the group comprising SEQ ID NO: 15-19. The modified or unmodified therapeutic peptide may comprise an amino acid sequence that is at least 80% homologous to an amino acid sequence selected from the group comprising SEQ ID NO: 15-19. The modified or unmodified therapeutic peptide may comprise an amino acid sequence comprising at least a portion of a polypeptide sequence selected from a group consisting of selected from a group consisting of SEQ ID NO: 20-29. The modified or unmodified therapeutic peptide may comprise an amino acid sequence comprising 10 or more amino acids based on or derived from a polypeptide sequence selected from a group consisting of selected from a group consisting of SEQ ID NO: 20-29. The modified or unmodified therapeutic peptide may comprise an amino acid sequence that is at least about 50% homologous to an amino acid sequence selected from the group comprising SEQ ID NO: 20-29. The modified or unmodified therapeutic peptide may comprise an amino acid sequence that is at least 80% homologous to an amino acid sequence selected from the group comprising SEQ ID NO: 20-29. The modified or unmodified therapeutic peptide may comprise an amino acid sequence comprising at least a portion of a polypeptide sequence selected from a group consisting of selected from a group consisting of SEQ ID NO: 30-53. The modified or unmodified therapeutic peptide may comprise an amino acid sequence comprising 10 or more amino acids based on or derived from a polypeptide sequence selected from a group consisting of selected from a group consisting of SEQ ID NO: 30-53. The modified or unmodified therapeutic peptide may comprise an amino acid sequence that is at least about 50% homologous to an amino acid sequence selected from the group comprising SEQ ID NO: 30-53. The modified or unmodified therapeutic peptide may comprise an amino acid sequence that is at least 80% homologous to an amino acid sequence selected from the group comprising SEQ ID NO: 30-53. The first half-life extending molecule may be attached to the first staple. The TA may be covalently attached to the first staple via two amino acid residues in the TA. Each of the two or more amino acid residues may be cysteine. The one or more of the two or more amino acid residues may be an amino acid addition or substitution. The two or more residues may be at least about 4 amino acid residues apart. The two or more residues may be at least about 7 amino acid residues apart. The two or more residues may be at least about 11 amino acid residues apart. The first half-life extending molecule may comprise a lipid, a polyglycol region, or a combination thereof. The first half-life extending molecule may be a lipid. The first half-life extending molecule may comprise a lipid and a polyglycol region. The first half-life extending molecule may comprise a polyglycol region. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region may comprise one or more polyethylene glycol units, polypropylene glycol units, or polybutylene glycol units, or a combination thereof. A half-life of the mTA may be longer than a half-life of the TA.

Disclosed herein are compositions comprising the mTAs disclosed herein.

Disclosed herein are methods for treating a disease or condition in a subject in need thereof, the method comprising administering to the subject a composition comprising a therapeutically effective amount of an mTA disclosed herein. The disease or condition may be diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be short bowel syndrome (SBS). The disease or condition may be inflammatory bowel disease (IBD), inflammatory bowel syndrome (IBS), or psoriasis. The disease or condition may be Crohn's disease or ulcerative colitis. The disease or condition may be Alzheimer's disease, Parkinson's disease or Huntington's disease. The method may further comprise administering to the subject one or more additional therapeutic agents. The one or more additional therapeutic agents may be selected from a group consisting of other diabetes drugs, DPP4 inhibitors, SGLT2 inhibitors, hypoglycemic drugs and biguanidine drugs, insulin secretogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, and a statin, or any combination thereof.

A modified therapeutic agent may be a peptide lipid conjugate. Disclosed herein are peptide lipid conjugates (PLCs) comprising (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The two or more residues in the peptide region may comprise cysteine. The one or more lipids may be attached to the one or more staples in the peptide region. Alternatively or additionally, the one or more lipids may be attached to the one or more peptide therapeutic agents in the peptide region.

Further disclosed herein are peptide lipid conjugates (PLCs) comprising (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more peptide conjugates. The two or more residues in the peptide region may comprise cysteine. The one or more lipids may be attached to the one or more staples in the peptide region. Alternatively or additionally, the one or more lipids may be attached to the one or more peptide therapeutic agents in the peptide region.

Further disclosed herein are peptide lipid conjugates (PLCs) comprising (a) one or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide (exendin-4), glucagon-like protein-1 (GLP-1), GLP-2, glucagon, a GLP-1R and GIPR dual agonist, a GLP-1R and GCGR dual agonist, a GLP1R, GCGR and GIPR tri-agonist, or a derivative thereof, wherein the one or more lipids are attached to the one or more peptide conjugates. The two or more residues in the peptide region may comprise cysteine. The one or more lipids may be attached to the one or more staples in the peptide region. Alternatively or additionally, the one or more lipids may be attached to the one or more peptide therapeutic agents in the peptide region.

Disclosed herein are peptide lipid conjugates (PLCs) comprising (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more staples. The two or more residues in the peptide region may comprise cysteine. At least one of the two or more residues may be cysteine. The two or more residues may be at least about 4 amino acid residues apart. The two or more residues may be at least about 7 amino acid residues apart. The two or more residues may be at least about 11 amino acid residues apart.

Further disclosed herein are peptide lipid conjugates (PLCs) comprising (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more staples. At least one of the two or more residues may be cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are peptide lipid conjugates (PLCs) comprising (a) one or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide (exendin-4), glucagon-like protein-1 (GLP-1), GLP-2, glucagon, a GLP-1R and GIPR dual agonist, a GLP-1R and GCGR dual agonist, a GLP1R, GCGR and GIPR tri-agonist, or a derivative thereof, wherein the one or more lipids are attached to the one or more staples. At least one of the two or more residues may be cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Disclosed herein are peptide lipid conjugates (PLCs) comprising (a) two or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The two or more residues in the peptide region may comprise cysteine.

Further disclosed herein are peptide lipid conjugates (PLCs) comprising (a) two or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The two or more residues in the peptide region may comprise cysteine.

Further disclosed herein are peptide lipid conjugates (PLCs) comprising (a) two or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide (exendin-4), glucagon-like protein-1 (GLP-1), GLP-2, glucagon, a GLP-1R and GIPR dual agonist, a GLP-1R and GCGR dual agonist, a GLP1R, GCGR and GIPR tri-agonist, or a derivative thereof, wherein at least one of the two or more lipids are attached to the one or more therapeutic agents and at least one of the two or more lipids are attached to the one or more staples. The two or more residues in the peptide region may comprise cysteine.

The PLCs disclosed herein may further comprise one or more polyethylene glycol subunits.

The PLCs disclosed herein may comprise one or more lipids. The one or more lipids may comprise one or more sterols, sterol derivatives, bile acids, vitamin E derivatives, fatty di-acids, fatty acids, fatty amides, or fatty alcohols. The one or more lipids may comprise one or more myristic acids, docosahexanoic acids, lithocholic acid esters, cholic acids and palmitic acids. The one or more lipids may comprise myristic acid. The one or more lipids may comprise docosahexanoic acid. The one or more lipids may comprise lithocholic acid ester. The one or more lipids may comprise cholic acid. The one or more lipids may comprise palmitic acid. The one or more lipids may be pegylated. Alternatively, the one or more lipids are not pegylated.

The one or more lipids may enhance one or more pharmacokinetic properties of the one or more TAs. The one or more lipids may enhance one or more pharmacokinetic properties of the one or more TAs by at least about 200% as measured by pharmacodynamics when compared to the one or more TAs not attached to the one or more lipids. The one or more pharmacokinetic properties may comprise a half-life.

The PLCs disclosed herein may comprise one or more peptide conjugates (PCs). The one or more peptide conjugates may comprise one or more peptide therapeutic agents (TAs). The one or more TAs may comprise at least a portion of one or more proteins, biomolecules, chemicals, toxins, or drugs, or any combination thereof. The one or more TAs may comprise at least a portion of one or more hormones, kinases, receptors, ligands, growth factors, regulatory proteins, metabolic proteins, cytokines, or antibodies, or any combination thereof. The growth factor may be a GCSF, GMCSF or FGF21. The GCSF may be a bovine GCSF. Alternatively, the GCSF may be a human GCSF. The GMCSF and/or the FGF21 may be from a human. The one or more TAs may be a derived from a cytokine. The cytokine may be a beta-interferon. TA may be a derived from a hormone. The hormone may be an exendin-4, GLP-1, somatostatin, or erythropoietin. The GLP-1 and/or erythropoietin may be from a human. The one or more TAs may be a derived from a toxin. The toxin may be a Mokal, VM-24, ziconotide, chlorotoxin, or protoxin2 (ProTxII). The one or more TAs may be IL8, ziconotide, somatostatin, chlorotoxin, SDF1(alpha), or IL21.

The one or more TAs may comprise glucagon or derivative thereof. The one or more TAs may comprise glucagon-like protein-1 (GLP-1) or derivative thereof. The one or more TAs may comprise exenatide or derivative thereof. The one or more TAs may comprise exendin-4 or derivative thereof. The one or more TAs may comprise oxyntomodulin or derivative thereof. The one or more TAs may comprise GLP-2 or derivative thereof. The one or more TAs may comprise a GLP-1R and GIPR dual agonist. The one or more TAs may comprise a GLP-1R and GCGR dual agonist. The one or more TAs may comprise a GLP1R, GCGR and GIPR tri-agonist.

The one or more TAs may comprise a polypeptide derivative. The polypeptide derivative may comprises at least a portion of a wild-type polypeptide comprising one or more amino acid mutations. The one or more amino acid mutations may comprise a deletion, substitution, addition or a combination thereof. The one or more amino acid mutations may comprise adding one or more amino acid residues to a wild-type polypeptide. The one or more amino acid mutations may comprise deletion of one or more amino acid residues of the wild-type polypeptide. The one or more amino acid mutations may comprise substitution of one or more amino acid residues of the wild-type polypeptide. The one or more amino acid mutations may comprise substituting one or more amino acid residues of the wild-type polypeptide with one or more cysteine residues. The one or more amino acid mutations may comprise substituting one or more amino acid residues of the wild-type polypeptide with one or more D-amino acid residues. The one or more amino acid residues of the wild-type polypeptide may comprise one or more alanines, methionines, arginines, serines, threonines, and tyrosines.

The one or more TAs may comprise at least a portion of a polypeptide sequence selected from a group comprising SEQ ID NO: 1-53. The one or more TAs may comprise 10 or more amino acids based on or derived from a polypeptide sequence selected from a group comprising SEQ ID NO: 1-53. The one or more TAs may comprise an amino acid sequence that is at least about 50% homologous to an amino acid sequence selected from the group comprising SEQ ID NO: 1-53. The one or more TAs may comprise an amino acid sequence that is at least 80% homologous to an amino acid sequence selected from the group comprising SEQ ID NO: 1-53. The one or more TAs may comprise at least a portion of a polypeptide sequence selected from a group comprising SEQ ID NO: 8-12. The one or more TAs may comprise 10 or more amino acids based on or derived from a polypeptide sequence selected from a group comprising SEQ ID NO: 8-12. The one or more TAs may comprise an amino acid sequence that is at least about 50% homologous to an amino acid sequence selected from the group comprising SEQ ID NO: 8-12. The one or more TAs may comprise an amino acid sequence that is at least 80% homologous to an amino acid sequence selected from the group comprising SEQ ID NO: 8-12. The one or more TAs may comprise at least a portion of a polypeptide sequence selected from a group comprising SEQ ID NO: 15-19. The one or more TAs may comprise 10 or more amino acids based on or derived from a polypeptide sequence selected from a group comprising SEQ ID NO: 15-19. The one or more TAs may comprise an amino acid sequence that is at least about 50% homologous to an amino acid sequence selected from the group comprising SEQ ID NO: 15-19. The one or more TAs may comprise an amino acid sequence that is at least 80% homologous to an amino acid sequence selected from the group comprising SEQ ID NO: 15-19. The one or more TAs may comprise at least a portion of a polypeptide sequence selected from a group comprising SEQ ID NO: 20-29. The one or more TAs may comprise 10 or more amino acids based on or derived from a polypeptide sequence selected from a group comprising SEQ ID NO: 20-29. The one or more TAs may comprise an amino acid sequence that is at least about 50% homologous to an amino acid sequence selected from the group comprising SEQ ID NO: 20-29. The one or more TAs may comprise an amino acid sequence that is at least 80% homologous to an amino acid sequence selected from the group comprising SEQ ID NO: 20-29. The one or more TAs may comprise at least a portion of a polypeptide sequence selected from a group comprising SEQ ID NO: 30-53. The one or more TAs may comprise 10 or more amino acids based on or derived from a polypeptide sequence selected from a group comprising SEQ ID NO: 30-53. The one or more TAs may comprise an amino acid sequence that is at least about 50% homologous to an amino acid sequence selected from the group comprising SEQ ID NO: 30-53. The one or more TAs may comprise an amino acid sequence that is at least 80% homologous to an amino acid sequence selected from the group comprising SEQ ID NO: 30-53.

Further disclosed herein are peptide lipid conjugates having the structure of Formula (II):

$$PC\text{-}A^1\text{-}P^1\text{-}L \qquad \text{Formula (II)}$$

wherein
PC is a peptide conjugate;
$A^1$ is a chemical group linking PC and $P^1$;
$P^1$ is a bond or -PEG-$A^2$-;
PEG is a chemical group comprising one or more polyethylene glycol subunits;
$A^2$ is a chemical group linking PEG and L; and
L is a lipid.

The PC of Formula (II) may comprise a peptide region comprising one or more peptide therapeutic agents (TAs) and one or more staples. The one or more staples may connect to two or more residues in the peptide region. The staple may connect two or more residues on the same TA. The staple may connect two or more residues on two or more TAs. Two or more staples may connect two or more residues on the same TA. Two or more staples may connect two or more residues on two or more TAs. The two or more residues may comprise cysteine.

Further disclosed herein are peptide lipid conjugates having the structure of Formula (III):

$$TA\!-\!\!\left[Q\!-\!\!\left(A^1\!-\!P^1\!-\!L\right)_a\right]_b \qquad \text{Formula (III)}$$

wherein:
TA is a therapeutic agent;
each Q is the same or different, and is a staple;
each $A^1$ is the same or different, and is a chemical group linking Q and $P^1$;
each $P^1$ is a bond or -PEG-$A^2$-;
each PEG is the same or different, and is a chemical group comprising one or more polyethylene glycol subunits;
each $A^2$ is the same or different, and is a chemical group linking PEG and L;
each L is the same or different, and is a lipid;
a is 1, 2, 3, 4, 5, 6, 7, 8, 9, or 10; and
b is 1, 2, 3, 4, 5, 6, 7, 8, 9, or 10.

The PLC of Formula (III) may comprise one or more staples. The one or more staples may connect to two or more residues in the peptide region. The staple may connect two or more residues on the same TA. The two or more residues may comprise cysteine.

Further disclosed herein are peptide lipid conjugates having the structure of Formula (IV):

$$(L\!-\!P^1\!-\!A^1\!)_c\!-\!TA\!-\!\!\left[Q\!-\!\!\left(A^1\!-\!P^1\!-\!L\right)_a\right]_b \qquad \text{Formula (IV)}$$

wherein:
TA is a therapeutic agent;
each Q is the same or different, and is a staple;
each $A^1$ is the same or different, and is a chemical group linking Q and $P^1$;
each $P^1$ is a bond or -PEG-$A^2$-;
each PEG is the same or different, and is a chemical group comprising one or more polyethylene glycol subunits;
each $A^2$ is the same or different, and is a chemical group linking PEG and L;
each L is the same or different, and is a lipid;
a is 1, 2, 3, 4, 5, 6, 7, 8, 9, or 10;
b is 1, 2, 3, 4, 5, 6, 7, 8, 9, or 10; and
c is 1, 2, 3, 4, 5, 6, 7, 8, 9, or 10.

The PLC of Formula (IV) may comprise one or more staples. The one or more staples may connect to two or more residues in the peptide region. The staple may connect two or more residues on the same TA. The two or more residues may comprise cysteine.

The $P^1$ of the PLC of Formula (II), Formula (III), or Formula (IV) may comprise PEG. PEG may be selected from

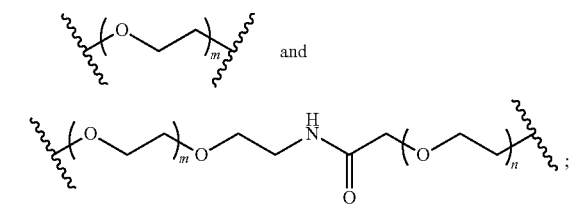

wherein m and n are independently 1, 2, 3, 4, 5, 6, 7, 8, 9, 10, 11, 12, 13, 14, 15, 16, 17, 18, 19, or 20.

The PLC of Formula (II), Formula (III), or Formula (IV) may comprise an $A^1$ selected from

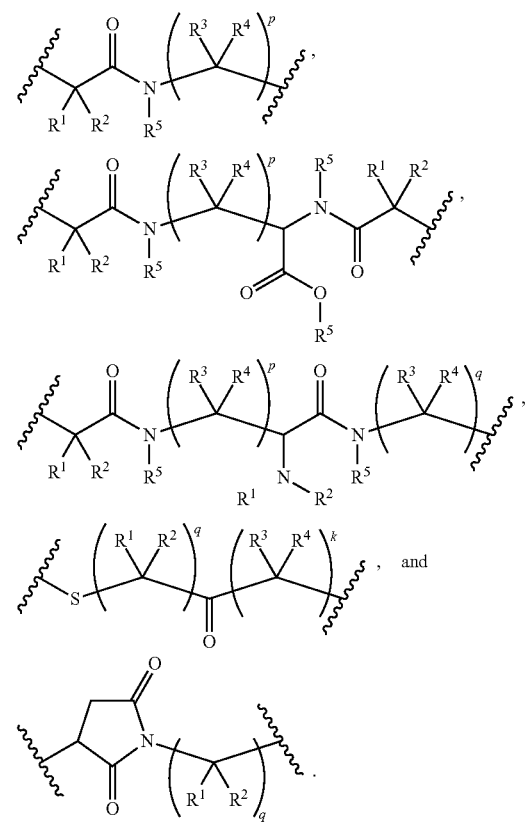

Each $R^1$, $R^2$, $R^3$, and $R^4$ may be independently selected from H, halo, CN, $-SR^5$, alkyl, cycloalkyl, haloalkyl, $-NR^5R^5$, and $-OR^5$. Each $R^5$ may be independently selected from H, alkyl, haloalkyl, arylalkyl, and heteroalkyl. K may be 1, 2, 3, 4, 5, 6, 7, 8, 9 or 10; p may be 2, 3, 4, 5, 6, 7, 8, 9, or 10; and q may be 2, 3, 4, 5, 6, 7, 8, 9, or 10.

The PLC of Formula (II), Formula (III), or Formula (IV) may comprise an $A^2$ selected from a bond,

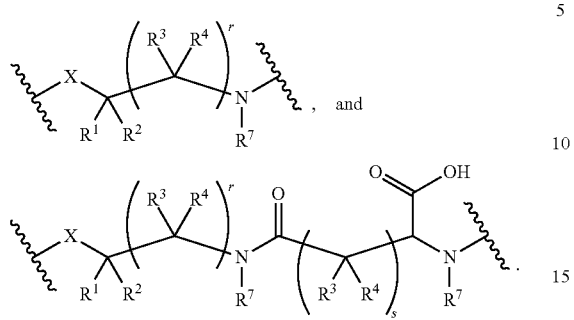

X may be a bond, $NR^5$, S, or O. $R^1$, $R^2$, $R^3$, and $R^4$ may be independently selected from H, halo, CN, —$SR^5$, alkyl, cycloalkyl, haloalkyl, —$NR^5R^5$, and —$OR^5$. $R^5$ may be H, alkyl, haloalkyl, arylalkyl, or heteroalkyl. $R^6$ may be H, alkyl, arylalkyl, —$(CR^1R^2)_tSR^5$, —$(CR^1R^2)_tNR^5R^5$, —$(CR^1R^2)_tOR^5$, or —$(CR^1R^2)_tCO_2R^5$. Each $R^7$ may be independently selected from H, alkyl, haloalkyl, arylalkyl, and heteroalkyl. R may be 1, 2, 3, 4, 5, 6, 7, 8, 9, or 10. S may be 1, 2, 3, 4, or 5. T may be 0, 1, 2, 3, 4, or 5.

The PLC of Formula (II), Formula (III), or Formula (IV) may comprise a $P^1$ comprising -PEG-$A^2$.

The PLCs disclosed herein may comprise one or more staples prepared from one or more precursor compounds comprising one or more:

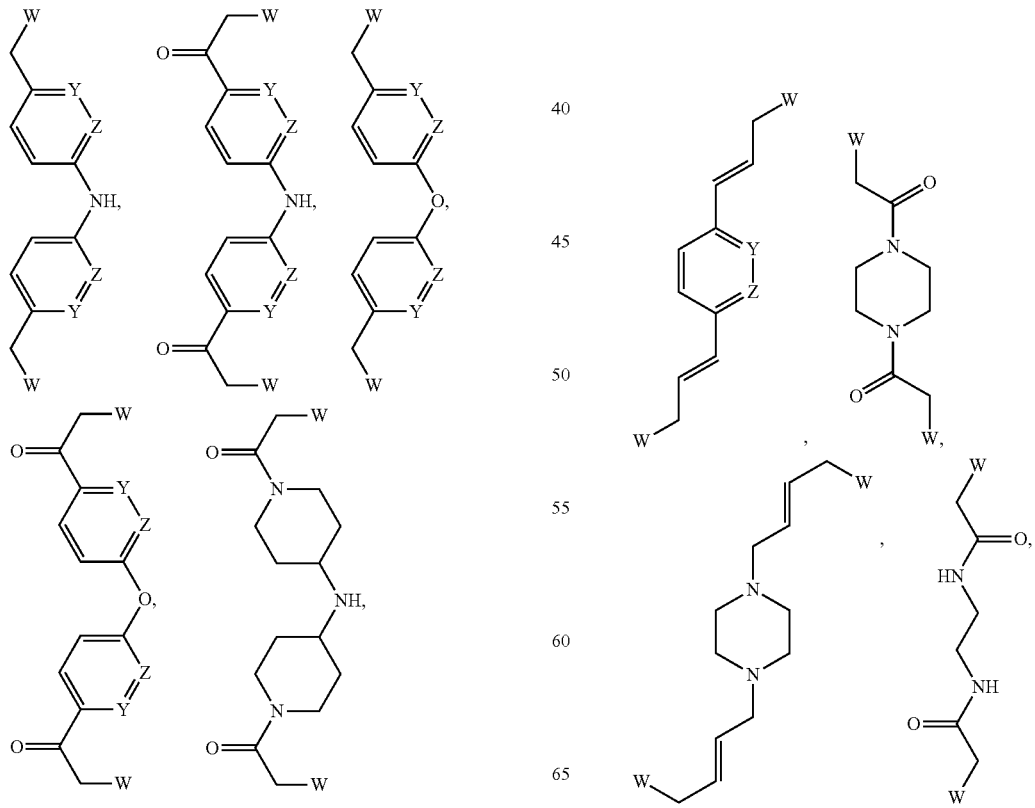

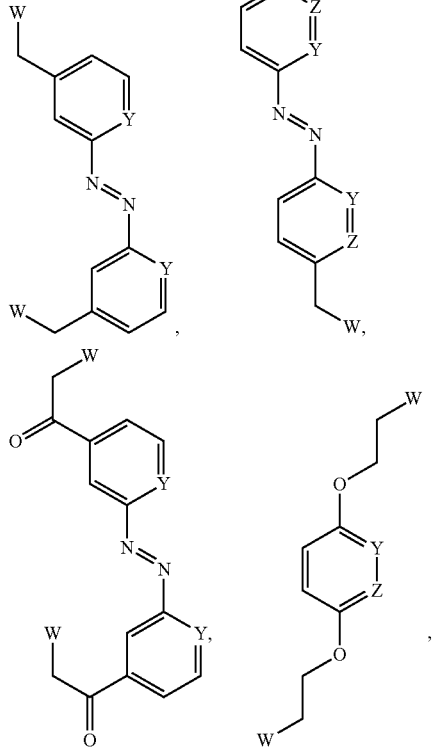

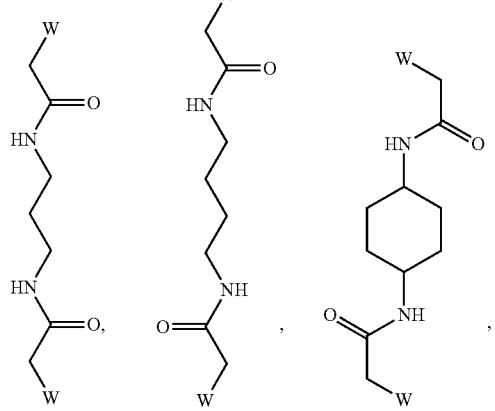
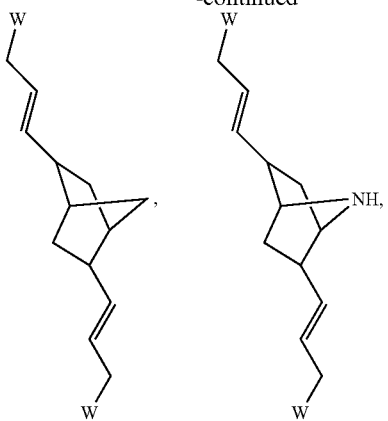
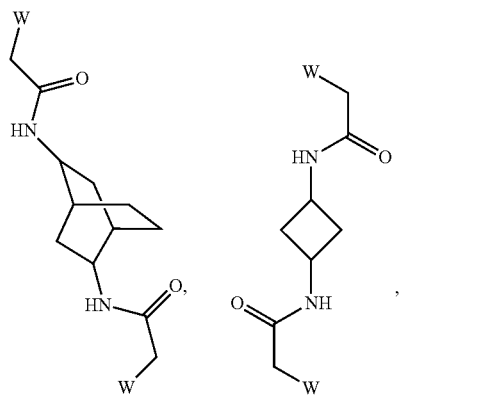
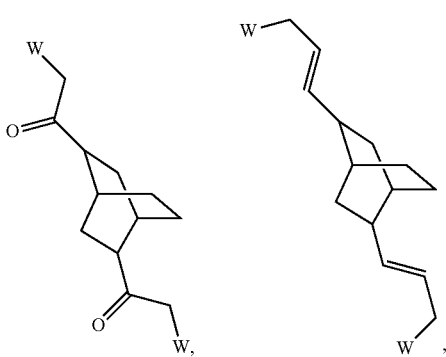
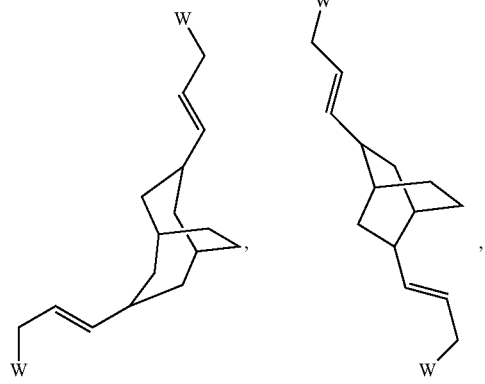
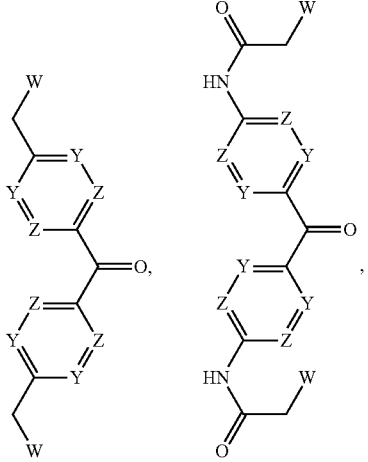
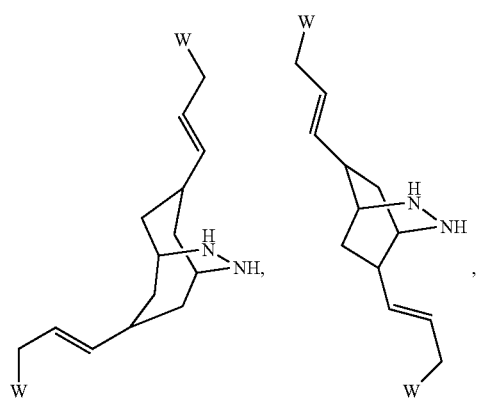
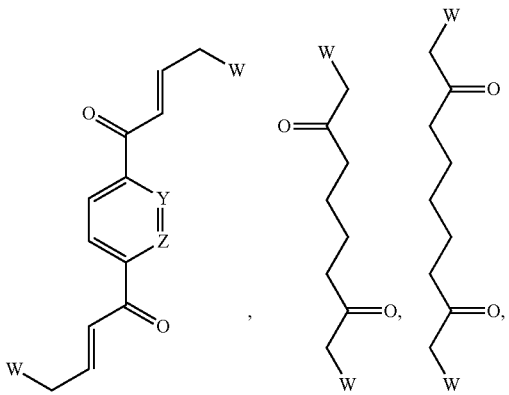

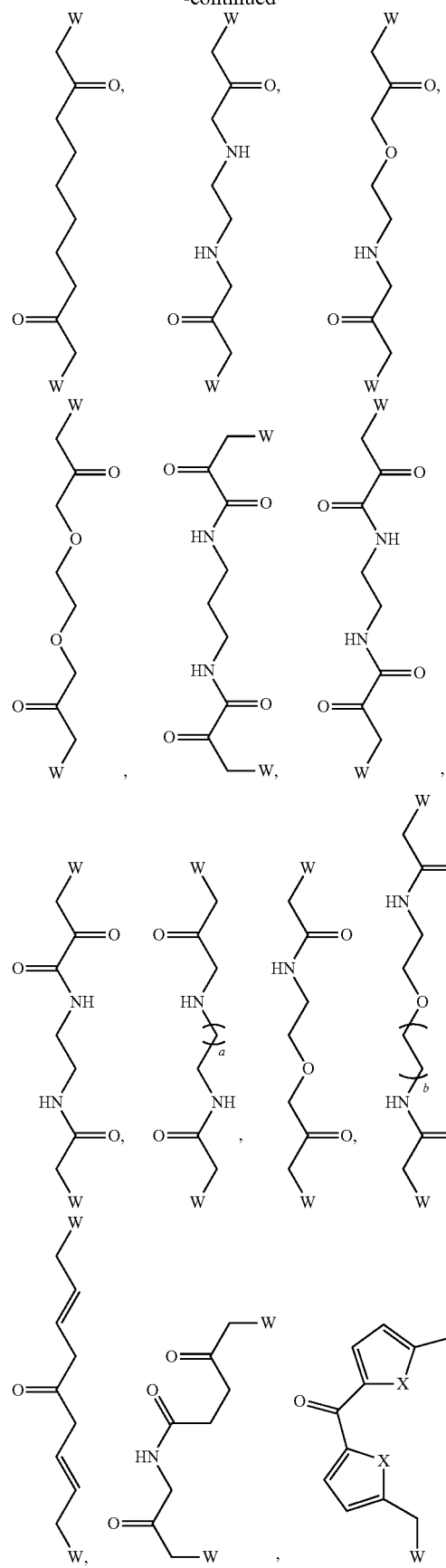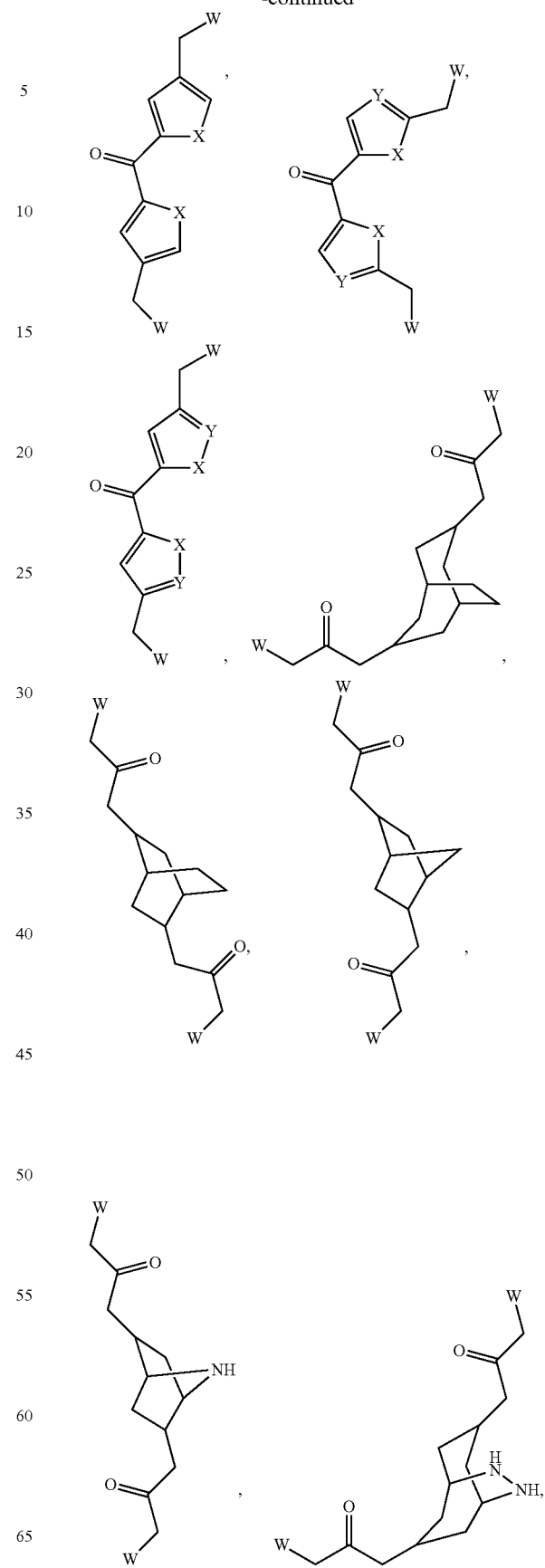

-continued

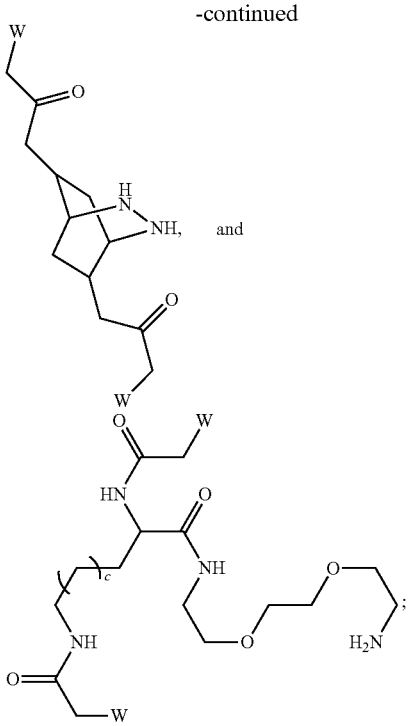

wherein
each W is independently selected from Cl, Br, I, and maleimide;
each X is independently selected from O, NH, and S;
each Y is independently selected from N and CH;
each Z is independently selected from N and CH;
a is 1, 2, 3, 4, 5, 6, 7, 8, 9, 10, 11, 12, 13, 14, 15, 16, or 17;
b is 1, 2, 3, 4, 5, or 6; and
c is 1 or 2.

The $A^1$ of the PLC of Formula (II) may be connected to PC via a chemical bond between $A^1$ and a functional group of a residue of PC. The $A^1$ of the PLC of Formula (II) may be connected to PC via a chemical bond between $A^1$ and the sulfur atom of a cysteine residue of PC. The $A^1$ of the PLC of Formula (II) may be connected to PC at the staple.

Each of the one or more lipids of the PLC of Formula (II) may be attached to the one or more staples to form a lipid staple precursor prior to forming the peptide conjugate. The lipid staple precursor may be

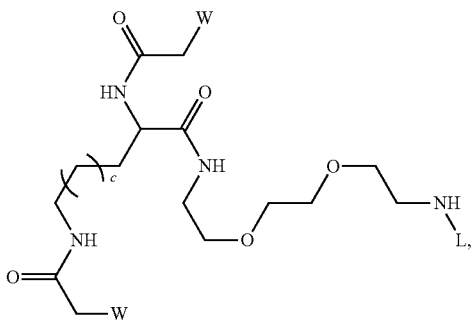

wherein each W is independently selected from Cl, Br, I, and maleimide; c is 1 or 2; and L is the lipid.

Further disclosed herein are methods of producing a peptide lipid conjugate (PLC) of Formula (II): PC-$A^1$-$P^1$-L, wherein PC is a peptide conjugate comprising (a) one or more peptide regions comprising one or more peptide therapeutic agents (TAs); and (b) one or more staples, wherein the staples connect two or more residues in the peptide region; $A^1$ is a chemical group linking PC and $P^1$; $P^1$ is a bond or -PEG-$A^2$-; PEG is a chemical group comprising one or more polyethylene glycol subunits; $A^2$ is a chemical group linking PEG and L; and L is a lipid. The two or more residues in the peptide region may comprise cysteine. The method may comprise reacting a cysteine residue of PC or a derivatizable functional group of the staple with $A^3$-$P^1$-L, wherein $A^3$ is a reactive precursor to form $A^1$. $A^3$ may be a haloacetamide, maleimide, benzyl halide, alkyl disulfide, or pyridyl disulfide. $A^3$ may be a haloacetamide. $A^3$ may be a bromoacetamide.

Further disclosed herein are methods of producing a peptide lipid conjugate (PLC) of Formula (III). The two or more residues in the peptide region of the PLC of Formula (III) may comprise cysteine. The method may comprise reacting a derivatizable functional group of the staple with $A^3$-$P^1$-L, wherein $A^3$ is a reactive precursor to form $A^1$. $A^3$ may be a haloacetamide, maleimide, benzyl halide, alkyl disulfide, or pyridyl disulfide. $A^3$ may be a haloacetamide. $A^3$ may be a bromoacetamide. $A^3$ may be an alkyl disulfide.

Further disclosed herein are methods of producing a peptide lipid conjugate (PLC) of Formula (IV). The two or more residues in the peptide region of the PLC of Formula (IV) may comprise cysteine. The method may comprise reacting a cysteine residue of PC or a derivatizable functional group of the staple with $A^3$-$P^1$-L, wherein $A^3$ is a reactive precursor to form $A^1$. The method may comprise reacting a cysteine residue of PC and a derivatizable functional group of the staple with $A^3$-$P^1$-L, wherein $A^3$ is a reactive precursor to form $A^1$. $A^3$ may be a haloacetamide, maleimide, benzyl halide, alkyl disulfide, or pyridyl disulfide. $A^3$ may be a haloacetamide. $A^3$ may be a bromoacetamide. $A^3$ may be an alkyl disulfide.

Disclosed herein are compositions comprising one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. The composition may further comprise one or more pharmaceutically acceptable salts, excipients or vehicles. The two or more residues in the peptide region may comprise cysteine.

Further disclosed herein are compositions comprising one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. The composition may further comprise one or more pharmaceutically acceptable salts, excipients or vehicles. The two or more residues in the peptide region may comprise cysteine.

Further disclosed herein are compositions comprising one or more PLCs, wherein the one or more peptide lipid conjugates (PLCs) comprise (a) one or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, glucagon, a GLP-1R and GIPR dual agonist, a GLP-1R and GCGR dual agonist, a GLP1R, GCGR and GIPR tri-agonist, or a derivative thereof, wherein the one or more lipids are attached to the one or more peptide conjugates. The one or more lipids may be attached to the one or more TAs. The one or more lipids may be attached to the one or more staples. The composition may further comprise one or more pharmaceutically acceptable salts, excipients or vehicles. The two or more residues in the peptide region may comprise cysteine.

Further disclosed herein are compositions comprising one or more peptide lipid conjugates (PLCs) of Formula (II): $PC-A^1-P^1-L$, wherein PC is a peptide conjugate comprising (a) one or more peptide regions comprising one or more peptide therapeutic agents (TAs); and (b) one or more staples, wherein the staples connect two or more residues in the peptide region; $A^1$ is a chemical group linking PC and $P^1$; $P^1$ is a bond or $-PEG-A^2-$; PEG is a chemical group comprising one or more polyethylene glycol subunits; $A^2$ is a chemical group linking PEG and L; and L is a lipid. The two or more residues in the peptide region may comprise cysteine.

Disclosed herein are compositions comprising one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more staples. The composition may further comprise one or more pharmaceutically acceptable salts, excipients or vehicles. At least one of the two or more residues may be cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. The one or more lipids may be attached to the one or more therapeutic agents. The one or more lipids may be attached to the one or more staples.

Further disclosed herein are compositions comprising one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more staples. The composition may further comprise one or more pharmaceutically acceptable salts, excipients or vehicles. At least one of the two or more residues may be cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. The one or more lipids may be attached to the one or more therapeutic agents. The one or more lipids may be attached to the one or more staples.

Further disclosed herein are compositions comprising one or more PLCs, wherein the one or more peptide lipid conjugates (PLCs) comprise (a) one or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide (exendin-4), glucagon-like protein-1 (GLP-1), GLP-2, glucagon, a GLP-1R and GIPR dual agonist, a GLP-1R and GCGR dual agonist, a GLP1R, GCGR and GIPR tri-agonist, or a derivative thereof, wherein the one or more lipids are attached to the one or more staples. The composition may further comprise one or more pharmaceutically acceptable salts, excipients or vehicles. At least one of the two or more residues may be cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. The one or more lipids may be attached to the one or more therapeutic agents. The one or more lipids may be attached to the one or more staples.

Further disclosed herein are compositions comprising one or more peptide lipid conjugates (PLCs) of Formula (III). The PLC of Formula (III) may comprise a peptide region comprising a plurality of amino acid residues. At least one of the plurality of amino acid residues may be cysteine. The PLC of Formula (III) may comprise one or more staples. The one or more staples may connect two or more residues in the peptide region. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. The PLC of Formula (III) may comprise one or more lipids. The PLC of Formula (III) may comprise a peptide region comprising one or more therapeutic agents. The one or more lipids may be attached to the one or more therapeutic agents. The one or more lipids may be attached to the one or more staples.

Further disclosed herein are compositions comprising one or more peptide lipid conjugates (PLCs) of Formula (IV). The PLC of Formula (IV) may comprise a peptide region comprising a plurality of amino acid residues. At least one of the plurality of amino acid residues may be cysteine. The PLC of Formula (IV) may comprise one or more staples. The one or more staples may connect two or more residues in the peptide region. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. The PLC of Formula (IV) may comprise one or more lipids. The PLC of Formula (IV) may comprise a peptide region comprising one or more therapeutic agents. The one or more lipids may be attached to the one or more therapeutic agents. The one or more lipids may be attached to the one or more staples.

Further disclosed herein are compositions comprising one or more PLCs, wherein the one or more peptide lipid conjugates (PLCs) comprise (a) two or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The composition may further comprise one or more pharmaceutically acceptable salts, excipients or vehicles. At least one of the two or more residues may be cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. At least one of the lipids may be attached to the one or more therapeutic agents. At least one of the lipids may be attached to the one or more staples.

Further disclosed herein are compositions comprising one or more PLCs, wherein the one or more peptide lipid conjugates (PLCs) comprise (a) two or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The composition may further comprise one or more pharmaceutically acceptable salts, excipients or vehicles. At least one of the two or more residues may be cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. At least one of the lipids may be attached to the one or more therapeutic agents. At least one of the lipids may be attached to the one or more staples.

Further disclosed herein are compositions comprising one or more PLCs, wherein the one or more peptide lipid conjugates (PLCs) comprise (a) two or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide (exendin-4), glucagon-like protein-1 (GLP-1), GLP-2, glucagon, a GLP-1R and GIPR dual agonist, a GLP-1R and GCGR dual agonist, a GLP1R, GCGR and GIPR tri-agonist, or a derivative thereof, wherein at least one of the two or more lipids are attached to the one or more therapeutic agents and at least one of the two or more lipids are attached to the one or more staples. The composition may further comprise one or more pharmaceutically acceptable salts, excipients or vehicles. At least one of the two or more residues may be cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. At least one of the lipids may be attached to the one or more therapeutic agents. At least one of the lipids may be attached to the one or more staples.

Disclosed herein are methods for treating a disease or condition in a subject in need thereof, the method comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are methods for treating a disease or condition in a subject in need thereof, the method comprising administering to the subject one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are methods for treating a disease or condition in a subject in need thereof, the method comprising administering to the subject one or more PLCs, wherein the one or more peptide lipid conjugates (PLCs) comprise (a) one or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide (exendin-4), glucagon-like protein-1 (GLP-1), GLP-2, glucagon, a GLP-1R and GIPR dual agonist, a GLP-1R and GCGR dual agonist, a GLP1R, GCGR and GIPR tri-agonis, or a derivative thereof, wherein the one or more lipids are attached to the one or more peptide conjugates. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are methods of treating a disease or condition in a subject in need thereof, the method comprising administering to the subject one or more peptide lipid conjugates (PLCs) of Formula (II): PC-A$^1$-P$^1$-L, wherein PC is a peptide conjugate comprising (a) one or more peptide regions comprising one or more peptide therapeutic agents (TAs); and (b) one or more staples, wherein the staples connect two or more residues in the peptide region; A$^1$ is a chemical group linking PC and P$^1$; P$^1$ is a bond or -PEG-A$^2$-; PEG is a chemical group comprising one or more polyethylene glycol subunits; A$^2$ is a chemical group linking PEG and L; and L is a lipid. L may be attached to the one or more TAs. L may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Disclosed herein are methods for treating a disease or condition in a subject in need thereof, the method comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more staples. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are methods for treating a disease or condition in a subject in need thereof, the method comprising administering to the subject one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more staples. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are methods for treating a disease or condition in a subject in need thereof, the method comprising administering to the subject one or more PLCs, wherein the one or more peptide lipid conjugates (PLCs) comprise (a) one or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, glucagon, a GLP-1R and GIPR dual agonist, a GLP-1R and GCGR dual agonist, a GLP1R, GCGR and GIPR tri-agonist, or a derivative thereof, wherein the one or more lipids are attached to the one or more staples. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are methods of treating a disease or condition in a subject in need thereof, the method comprising administering to the subject one or more peptide lipid conjugates (PLCs) of Formula (III). The PLC of Formula (III) may comprise one or more lipids. The PLC of Formula (III) may comprise one or more therapeutic agents (TAs). The PLC of Formula (III) may comprise one or more staples. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are methods of treating a disease or condition in a subject in need thereof, the method comprising administering to the subject one or more peptide lipid conjugates (PLCs) of Formula (IV). The PLC of Formula (IV) may comprise one or more lipids. The PLC of Formula (IV) may comprise one or more peptide regions. The one or more peptide regions may comprise one or more therapeutic agents (TAs). The PLC of Formula (IV) may comprise one or more staples. The one or more lipids may be attached to the one or more TAs. The one or more lipids may be attached to the one or more staples. The one or more staples may connect two or more residues in the peptide region. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Disclosed herein are methods for treating a disease or condition in a subject in need thereof, the method comprising administering to the subject one or more PLCs, wherein the one or more peptide lipid conjugates (PLCs) comprise (a) two or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are methods for treating a disease or condition in a subject in need thereof, the method comprising administering to the subject one or more PLCs, wherein the one or more peptide lipid conjugates (PLCs) comprise (a) two or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

Further disclosed herein are methods for treating a disease or condition in a subject in need thereof, the method comprising administering to the subject one or more PLCs, wherein the one or more peptide lipid conjugates (PLCs) comprise (a) two or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, glucagon, a GLP-1R and GIPR dual agonist, a GLP-1R and GCGR dual agonist, a GLP1R, GCGR and GIPR tri-agonist, or a derivative thereof, wherein at least one of the two or more lipids are attached to the one or more therapeutic agents and at least one of the two or more lipids are attached to the one or more staples. The one or more lipids may be attached to the one or more TAs. The one or more lipids may be attached to the one or more staples. At least one of the residues in the peptide region may be a cysteine. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart.

The PLCs disclosed herein may be used to treat a disease or condition. The disease or condition may be diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be short bowel syndrome (SBS), inflammatory bowel disease (IBD), psoriasis, ulcerative colitis, or Crohn's disease. The disease or condition may be Alzheimer's disease, Parkinson's disease or Huntington's disease. The PLCs disclosed herein may be administered with one or more additional therapeutic agents. The one or more additional therapeutic agents may comprise one or more anti-inflammatory drugs, statins, diuretics, beta-blockers, angiotensin converting enzyme inhibitors, or angiotensin II receptor blockers. The one or more additional therapeutic agents may be aspirin. The one or more additional therapeutic agents may be selected from a group consisting of other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, and a statin, or any combination thereof.

BRIEF DESCRIPTION OF THE DRAWINGS

The novel features of the invention are set forth with particularity in the appended claims. The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 3G depicts an exemplary staple-lipid construct comprising a staple (C) and four half-life extending molecules comprising a lipid ($L^1$, $L^2$, $L^3$, and $L^4$).

FIG. 4A depicts an exemplary peptide lipid conjugate comprising one therapeutic agent (TA), one staple (C), and one half-life extending molecule comprising a lipid (L) linked to the therapeutic agent.

FIG. 4B depicts an exemplary peptide lipid conjugate comprising one therapeutic agent (TA), one staple (C), and one half-life extending molecule comprising a lipid (L) linked to the therapeutic agent.

FIG. 4C depicts an exemplary peptide lipid conjugate comprising one therapeutic agent (TA), one staple (C), and one half-life extending molecule comprising a lipid (L) linked to the therapeutic agent.

FIG. 4D depicts an exemplary peptide lipid conjugate comprising one therapeutic agent (TA), one staple (C), and two half-life extending molecules comprising a lipid ($L^1$ and $L^2$) linked to the therapeutic agent.

FIG. 4E depicts an exemplary peptide lipid conjugate comprising one therapeutic agent (TA), one staple (C), and two half-life extending molecules comprising a lipid ($L^1$ and $L^2$) linked to the therapeutic agent.

FIG. 4F depicts an exemplary peptide lipid conjugate comprising one therapeutic agent (TA), one staple (C), and two half-life extending molecules comprising a lipid ($L^1$ and $L^2$) linked to the therapeutic agent.

FIG. 4G depicts an exemplary peptide lipid conjugate comprising one therapeutic agent (TA), one staple (C), and three half-life extending molecules comprising a lipid ($L^1$, $L^2$, and $L^3$) linked to the therapeutic agent.

FIG. 4H depicts an exemplary peptide lipid conjugate comprising one therapeutic agent (TA), one staple (C), and four half-life extending molecules comprising a lipid ($L^1$, $L^2$, $L^3$, and $L^4$) linked to the therapeutic agent.

FIG. 6A depicts an exemplary peptide lipid conjugate comprising one therapeutic agent (TA), one staple (C), one half-life extending molecule comprising a lipid ($L^1$) linked to the staple, and one half-life extending molecule comprising a lipid ($L^2$) linked to the therapeutic agent.

FIG. 6B depicts an exemplary peptide lipid conjugate comprising one therapeutic agent (TA), one staple (C), one half-life extending molecule comprising a lipid ($L^1$) linked to the staple, and one half-life extending molecule comprising a lipid ($L^2$) linked to the therapeutic agent.

FIG. 6C depicts an exemplary peptide lipid conjugate comprising one therapeutic agent (TA), one staple (C), one half-life extending molecule comprising a lipid ($L^1$) linked to the staple, and one half-life extending molecule comprising a lipid ($L^2$) linked to the therapeutic agent.

FIG. 6D depicts an exemplary peptide lipid conjugate comprising one therapeutic agent (TA), one staple (C), one half-life extending molecule comprising a lipid ($L^1$) linked to the staple, and two half-life extending molecules comprising a lipid ($L^2$ and $L^3$) linked to the therapeutic agent.

FIG. 6E depicts an exemplary peptide lipid conjugate comprising one therapeutic agent (TA), one staple (C), two half-life extending molecules comprising a lipid ($L^1$ and $L^2$) linked to the staple, and two half-life extending molecules comprising a lipid ($L^3$ and $L^4$) linked to the therapeutic agent.

FIG. 6F depicts an exemplary peptide lipid conjugate comprising one therapeutic agent (TA), one staple (C), two half-life extending molecules comprising a lipid ($L^1$ and $L^2$) linked to the staple, and two half-life extending molecules comprising a lipid ($L^3$ and $L^4$) linked to the therapeutic agent.

FIG. 6G depicts an exemplary peptide lipid conjugate comprising one therapeutic agent (TA), one staple (C), one half-life extending molecule comprising a lipid ($L^1$) linked to the staple, and three half-life extending molecules comprising a lipid ($L^2$, $L^3$, and $L^4$) linked to the therapeutic agent.

FIG. 6H depicts an exemplary peptide lipid conjugate comprising one therapeutic agent (TA), one staple (C), two half-life extending molecules comprising a lipid ($L^1$ and $L^2$) linked to the staple, and four half-life extending molecules comprising a lipid ($L^3$, $L^4$, $L^5$, and $L^6$) linked to the therapeutic agent.

DETAILED DESCRIPTION OF THE INVENTION

Figure 1A:
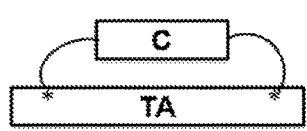
FIG. 1A depicts an exemplary peptide conjugate comprising one therapeutic agent (TA) and one staple (C).

Disclosed herein, in some embodiments, are compounds comprising: a therapeutic peptide, a staple and a non-peptide molecule, wherein the staple is conjugated to one or more amino acids of the therapeutic peptide. A first region of a staple may be conjugated to a first amino acid of the therapeutic peptide and a second region of a staple may be conjugated to a second amino acid of a therapeutic peptide. The non-peptide molecule may not be conjugated to the therapeutic peptide. The non-peptide molecule may be conjugated to the staple. The non-peptide molecule may be conjugated to the staple such that the non-peptide molecule is distal to an active site or binding site of the therapeutic peptide. The staple may stabilize the therapeutic peptide while providing a conjugation site for the non-peptide molecule, such that the non-peptide molecule does not hinder and/or interfere with the therapeutic peptide binding to a target. A property of the therapeutic peptide in the composition may be different than a respective property of the therapeutic peptide alone. A property of the therapeutic peptide in the composition may be different than a respective property of the therapeutic peptide that is conjugated to the non-peptide molecule. The property may be selected from an absorption rate constant, an absorption efficiency, an elimination rate constant, a half-life, a binding affinity, a binding efficiency, a disassociation constant, a target selectivity and a potency and in vivo efficacy. A therapeutic effect of the compound may be greater than a therapeutic effect of the therapeutic peptide alone. A therapeutic effect of the compound may be greater than a therapeutic effect of a respective therapeutic peptide that is conjugated to the non-peptide molecule. A therapeutic effect of the compound may be longer-lasting than a therapeutic effect of the therapeutic peptide alone. A therapeutic effect of the composition may be longer-lasting than a therapeutic effect of a respective therapeutic peptide that is conjugated to the non-peptide molecule. The staple may stabilize the therapeutic peptide. The non-peptide molecule may extend a half-life of the therapeutic peptide. The non-peptide molecule may comprise a lipid moiety. The non-peptide molecule may comprise a polyethylene glycol unit.

Disclosed herein are modified therapeutic agents (mTAs). Generally, the mTA may comprise a therapeutic agent (TA), a staple, and a half-life extending molecule (HEM). The TA may be a modified or unmodified therapeutic peptide. The TA may be a modified therapeutic peptide. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. The TA may be an unmodified therapeutic peptide. The unmodified therapeutic peptide may be selected from GLP-1, glucagon, oxyntomodulin, exendin-4, GLP-2, and GIP. The staple may be covalently attached to the TA. The HEM may be attached to the staple. The HEM may be attached to the TA. The staple may be attached to the TA via two amino acid residues on the modified or unmodified therapeutic peptide. One or both of the two amino acid residues may be an amino acid addition or substitution on the modified therapeutic peptide. One or both of the two amino acid residues may be cysteine. The two or more amino acid residues may be at least about 4 amino acid residues apart. The two or more amino acid residues may be at least about 7 amino acid residues apart. The two or more amino acid residues may be at least about 11 amino acid residues apart. The HEM may comprise a lipid, a polyglycol region, or a combination of both. The HEM may comprise a lipid. The HEM may comprise a lipid and a polyglycol region. The HEM may comprise a polyglycol region. The HEM may comprise a peptide or protein. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region may comprise one or more polyethylene glycol units, polypropylene glycol units, or polybutylene glycol units, or a combination thereof. The mTA may have more than one staple. The mTA may have more than one HEM. The mTA may have a longer half-life than the half-life of the unmodified therapeutic peptide alone. The mTA may have a higher potency than the potency of the unmodified therapeutic peptide alone. The mTA may have a higher target selectivity than the target selectivity of the unmodified therapeutic peptide alone. The mTA may have a higher binding affinity than the binding affinity of the unmodified therapeutic peptide alone.

Disclosed herein are peptide lipid conjugates (PLCs) which comprise one or more therapeutic agents (TAs), one or more half-life extending molecules (HEMs), and one or more staples that are directly attached to the one or more TAs. The one or more HEMs may comprise one or more lipids. The one or more HEMS may further comprise one or more polyethylene glycol subunits, wherein the one or more lipids are attached to the one or more polyethylene glycol subunits. Alternatively, the one or more HEMS may comprise one or more polyethylene glycol subunits. The one or more HEMS may comprise one or more peptides or proteins. The one or more HEMs may comprise one or more molecules selected from lipids, polyethylene glycol subunits, peptides, or proteins, or any combination thereof. The one or more HEMs may be attached directly to the TA. The one or more HEMs may be attached directly to the staple. The HEMS may be attached directly to the TA and to the staple. The HEM may be a lipid. The PLCs may comprise two or more therapeutic agents. The PLCs may comprise two or more staples. The PLCs may comprise two or more HEMs. The PLCs may comprise a plurality of HEMs attached to the one or more therapeutic agents. The PLCs may comprise a plurality of HEMs attached to the one or more staples.

Generally, the PLCs comprise one or more lipids attached to one or more peptide conjugates (PCs). The PLCs may comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The two or more residues in the peptide region may comprise cysteine. The one or more lipids may be attached to the one or more staples in the peptide region. Alternatively or additionally, the one or more lipids may be attached to the one or more peptide therapeutic agents in the peptide region.

The peptide lipid conjugates (PLCs) may comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. At least one of the residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

The PLCs may comprise comprising (a) one or more lipids; and (b) one or more peptide conjugates (PC), wherein the peptide conjugate comprises a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, glucagon, a GLP-1R and GIPR dual agonist, a GLP-1R and GCGR dual agonist, or a derivative thereof, wherein the one or more lipids are attached to the one or more peptide conjugates. The one or more lipids may be attached to the one or more TAs. The one or more lipids may be attached to the one or more staples. At least one of the residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

Disclosed herein are compositions comprising one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The composition may further comprise one or more pharmaceutically acceptable salts, excipients or vehicles. The one or more lipids may be attached to the one or more TAs. The one or more lipids may be attached to the one or more staples. At least one of the residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

Further disclosed herein are compositions comprising one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more peptide conjugates. The composition may further comprise one or more pharmaceutically acceptable salts, excipients or vehicles. The one or more lipids may be attached to the one or more TAs. The one or more lipids may be attached to the one or more staples. At least one of the residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

Further disclosed herein are compositions comprising one or more PLCs, wherein the one or more peptide lipid conjugates (PLCs) comprise (a) one or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, glucagon, a GLP-1R and GIPR dual agonist, a GLP-1R and GCGR dual agonist, or a derivative thereof, wherein the one or more lipids are attached to the one or more peptide conjugates. The composition may further comprise one or more pharmaceutically acceptable salts, excipients or vehicles. The one or more lipids may be attached to the one or more TAs. The one or more lipids may be attached to the one or more staples. At least one of the residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

Further disclosed herein are compositions comprising one or more peptide lipid conjugates (PLCs) of Formula (II): PC-$A^1$-$P^1$-L, wherein PC is a peptide conjugate comprising (a) one or more peptide regions comprising one or more peptide therapeutic agents (TAs); and (b) one or more staples, wherein the staples connect two or more residues in the peptide region; $A^1$ is a chemical group linking PC and $P^1$; $P^1$ is a bond or -PEG-$A^2$-; PEG is a chemical group comprising one or more polyethylene glycol subunits; $A^2$ is a chemical group linking PEG and L; and L is a lipid. The one or more lipids may be attached to the one or more TAs. The one or more lipids may be attached to the one or more staples. At least one of the residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

Further disclosed herein are compositions comprising one or more peptide lipid conjugates (PLCs) of Formula (III). The PLC of Formula (III) may comprise a peptide region comprising a plurality of amino acid residues. At least one of the plurality of amino acid residues may be cysteine. The PLC of Formula (III) may comprise one or more staples. The one or more staples may connect two or more residues in the peptide region. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. The PLC of Formula (III) may comprise one or more lipids. The PLC of Formula (III) may comprise a peptide region comprising one or more therapeutic agents. The one or more lipids may be attached to the one or more therapeutic agents. The one or more lipids may be attached to the one or more staples.

Further disclosed herein are compositions comprising one or more peptide lipid conjugates (PLCs) of Formula (IV). The PLC of Formula (IV) may comprise a peptide region comprising a plurality of amino acid residues. At least one of the plurality of amino acid residues may be cysteine. The PLC of Formula (IV) may comprise one or more staples. The one or more staples may connect two or more residues in the peptide region. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. The PLC of Formula (IV) may comprise one or more lipids. The PLC of Formula (IV) may comprise a peptide region comprising one or more therapeutic agents. The one or more lipids may be attached to the one or more therapeutic agents. The one or more lipids may be attached to the one or more staples.

Disclosed herein are methods for treating a disease or condition in a subject in need thereof, the method comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. At least one of the residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

Further disclosed herein are methods for treating a disease or condition in a subject in need thereof, the method comprising administering to the subject one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. At least one of the residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart. Further disclosed herein are methods for treating a disease or condition in a subject in need thereof, the method comprising administering to the subject one or more PLCs, wherein the one or more peptide lipid conjugates (PLCs) comprise (a) one or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, glucagon, a GLP-1R and GIPR dual agonist, a GLP-1R and GCGR dual agonist, or a derivative thereof, wherein the one or more lipids are attached to the one or more peptide conjugates. The one or more lipids may be attached to the one or more TAs. The one or more lipids may be attached to the one or more staples. At least one of the residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

Further disclosed herein are methods of treating a disease or condition in a subject in need thereof, the method comprising administering to the subject one or more peptide lipid conjugates (PLCs) of Formula (II): PC-$A^1$-$P^1$-L, wherein PC is a peptide conjugate comprising (a) one or more peptide regions comprising one or more peptide therapeutic agents (TAs); and (b) one or more staples, wherein the staples connect two or more residues in the peptide region; $A^1$ is a chemical group linking PC and $P^1$; $P^1$ is a bond or -PEG-$A^2$-; PEG is a chemical group comprising one or more polyethylene glycol subunits; $A^2$ is a chemical group linking PEG and L; and L is a lipid. L may be attached to the one or more TAs. L may be attached to the one or more staples. At least one of the two or more residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

Further disclosed herein are methods of treating a disease or condition in a subject in need thereof, the method comprising administering to the subject one or more peptide lipid conjugates (PLCs) of Formula (III). The PLC of Formula (III) may comprise a peptide region comprising a plurality of amino acid residues. At least one of the plurality of amino acid residues may be cysteine. The PLC of Formula (III) may comprise one or more staples. The one or more staples may connect two or more residues in the peptide region. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. The PLC of Formula (III) may comprise one or more lipids. The PLC of Formula (III) may comprise a peptide region comprising one or more therapeutic agents. The one or more lipids may be attached to the one or more therapeutic agents. The one or more lipids may be attached to the one or more staples.

Further disclosed herein are methods of treating a disease or condition in a subject in need thereof, the method comprising administering to the subject one or more peptide lipid conjugates (PLCs) of Formula (IV). The PLC of Formula (IV) may comprise a peptide region comprising a plurality of amino acid residues. At least one of the plurality of amino acid residues may be cysteine. The PLC of Formula (IV) may comprise one or more staples. The one or more staples may connect two or more residues in the peptide region. The two or more residues in the peptide region may comprise cysteine. The two or more residues may be at least about 4 amino acid residues apart. The two or more residues may be at least about 7 amino acid residues apart. The two or more residues may be at least about 11 amino acid residues apart. The PLC of Formula (IV) may comprise one or more lipids. The PLC of Formula (IV) may comprise a peptide region comprising one or more therapeutic agents. The one or more lipids may be attached to the one or more therapeutic agents. The one or more lipids may be attached to the one or more staples.

Before the present methods, kits and compositions are described in greater detail, it is to be understood that this invention is not limited to particular method, kit or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and compositions are provided for producing PLCs that extend the half-life of a therapeutic agent. These methods and compositions find therapeutic use in a number of diseases, for example, diabetes or obesity may be more effectively treated with a half-life extension molecule conjugated to a therapeutic peptide than by the therapeutic peptide alone. These and other objects, advantages, and features of the invention will become apparent to those persons skilled in the art upon reading the details of the compositions and methods as more fully described below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Modified Therapeutic Agent (mTA)

Disclosed herein are modified therapeutic agents (mTAs) comprising a therapeutic agent (TA), a staple, and a half-life extending molecule (HEM). The TA may be a modified or unmodified therapeutic peptide. The TA may be covalently attached to the staple. The TA may be covalently attached to the staple via two amino acid residues on the modified or unmodified therapeutic peptide. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The half-life of the mTA may be longer than the half-life of the modified or unmodified therapeutic peptide alone. The HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The HEM may comprise a protein or a peptide. The HEM may be covalently attached to the staple. The HEM may be covalently attached to the TA. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. Non-limiting examples of mTAs include peptide lipid conjugates (PLCs).

Disclosed herein are modified therapeutic agents (mTAs) comprising a therapeutic agent (TA), a first staple, and a first HEM. The TA may be a modified or unmodified therapeutic peptide. The TA may be covalently attached to the first staple. The TA may be covalently attached to the first staple via two amino acid residues on the modified or unmodified therapeutic peptide. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The half-life of the mTA may be longer than the half-life of the modified or unmodified therapeutic peptide alone. The first HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may comprise a protein or a peptide. The first HEM may be covalently attached to the first staple. The first HEM may be covalently attached to the TA. The mTA may further comprise a second staple. The mTA may further comprise a second HEM. The mTA may further comprise a second staple and a second HEM. The first staple and second staple may be the same or different. The first HEM and second HEM may be the same or different. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two amino acid residues on the modified or unmodified therapeutic peptide. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The half-life of the mTA may be longer than the half-life of the modified or unmodified therapeutic peptide alone. The first HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may comprise a protein or a peptide. The first HEM may be covalently attached to the first staple. The first HEM may be covalently attached to the TA. The mTA may further comprise a second staple. The mTA may further comprise a second HEM. The mTA may further comprise a second staple and a second HEM. The first staple and second staple may be the same or different. The first HEM and second HEM may be the same or different. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two amino acid residues on the modified or unmodified therapeutic peptide and the half-life of the mTA is longer than the half-life of the unmodified therapeutic peptide alone. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The first HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may comprise a protein or a peptide. The first HEM may be covalently attached to the first staple. The first HEM may be covalently attached to the TA. The mTA may further comprise a second staple. The mTA may further comprise a second HEM. The mTA may further comprise a second staple and a second HEM. The first staple and second staple may be the same or different. The first HEM and second HEM may be the same or different. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two amino acid residues on the modified or unmodified therapeutic peptide and the first HEM is covalently attached to the first staple. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The half-life of the mTA may be longer than the half-life of the modified or unmodified therapeutic peptide alone. The first HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may comprise a protein or a peptide. The mTA may further comprise a second staple. The mTA may further comprise a second HEM. The mTA may further comprise a second staple and a second HEM. The first staple and second staple may be the same or different. The first HEM and second HEM may be the same or different. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two amino acid residues on the modified or unmodified therapeutic peptide and the first HEM is covalently attached to the TA. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The half-life of the mTA may be longer than the half-life of the modified or unmodified therapeutic peptide alone. The first HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may comprise a protein or a peptide. The mTA may further comprise a second staple. The mTA may further comprise a second HEM. The mTA may further comprise a second staple and a second HEM. The first staple and second staple may be the same or different. The first HEM and second HEM may be the same or different. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two amino acid residues on the modified or unmodified therapeutic peptide; the first HEM is covalently attached to the first staple; and the half-life of the mTA is longer than the half-life of the unmodified therapeutic peptide alone. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The first HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may comprise a protein or a peptide. The mTA may further comprise a second staple. The mTA may further comprise a second HEM. The mTA may further comprise a second staple and a second HEM. The first staple and second staple may be the same or different. The first HEM and second HEM may be the same or different. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two cysteine residues on the modified or unmodified therapeutic peptide and the first HEM is covalently attached to the first staple. The two cysteines may be at least about 4 amino acid residues apart. The two cysteines may be at least about 7 amino acid residues apart. The two cysteines may be at least about 11 amino acid residues apart. The half-life of the mTA may be longer than the half-life of the modified or unmodified therapeutic peptide alone. The first HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may comprise a protein or a peptide. The mTA may further comprise a second staple. The mTA may further comprise a second HEM. The mTA may further comprise a second staple and a second HEM. The first staple and second staple may be the same or different. The first HEM and second HEM may be the same or different. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two amino acid residues on the modified or unmodified therapeutic peptide; the unmodified therapeutic peptide is selected from GLP-1, glucagon, oxyntomodulin, exendin-4, GLP-2, and GIP; the modified therapeutic peptide is a derivative of a peptide selected from GLP-1, glucagon, oxyntomodulin, exendin-4, GLP-2, and GIP, the derivative being a peptide comprising one or more amino acid additions, deletions, or substitutions, or a combination thereof; and the first HEM is covalently attached to the first staple. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The half-life of the mTA may be longer than the half-life of the modified or unmodified therapeutic peptide alone. The first HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may comprise a protein or a peptide. The mTA may further comprise a second staple. The mTA may further comprise a second HEM. The mTA may further comprise a second staple and a second HEM. The first staple and second staple may be the same or different. The first HEM and second HEM may be the same or different. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two amino acid residues on the modified or unmodified therapeutic peptide; the first HEM is covalently attached to the first staple; and the first HEM comprises a lipid, a polyglycol region, or a combination thereof. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The half-life of the mTA may be longer than the half-life of the modified or unmodified therapeutic peptide alone. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may further comprise a protein or a peptide. The mTA may further comprise a second staple. The mTA may further comprise a second HEM. The mTA may further comprise a second staple and a second HEM. The first staple and second staple may be the same or different. The first HEM and second HEM may be the same or different. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two amino acid residues on the modified or unmodified therapeutic peptide; the unmodified therapeutic peptide is selected from GLP-1, glucagon, oxyntomodulin, exendin-4, GLP-2, and GIP; the modified therapeutic peptide is a derivative of a peptide selected from GLP-1, glucagon, oxyntomodulin, exendin-4, GLP-2, and GIP, the derivative being a peptide comprising one or more amino acid additions, deletions, or substitutions, or a combination thereof; the first HEM is covalently attached to the first staple; and the first HEM comprises a lipid, a polyglycol region, or a combination thereof. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The half-life of the mTA may be longer than the half-life of the modified or unmodified therapeutic peptide alone. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The first HEM may further comprise a protein or a peptide. The mTA may further comprise a second staple. The mTA may further comprise a second HEM. The mTA may further comprise a second staple and a second HEM. The first staple and second staple may be the same or different. The first HEM and second HEM may be the same or different. The mTA may be a PLC.

Further disclosed herein are modified therapeutic agents (mTAs) comprising a therapeutic agent (TA), a first staple, and a first HEM, wherein the therapeutic agent is a modified or unmodified therapeutic peptide that is covalently attached to the first staple via two amino acid residues on the modified or unmodified therapeutic peptide; the unmodified therapeutic peptide is selected from GLP-1, glucagon, oxyntomodulin, exendin-4, GLP-2, and GIP; the modified therapeutic peptide is a derivative of a peptide selected from GLP-1, glucagon, oxyntomodulin, exendin-4, GLP-2, and GIP, the derivative being a peptide comprising one or more amino acid additions, deletions, or substitutions, or a combination thereof; the first HEM is covalently attached to the first staple; and the first HEM comprises a lipid, a polyglycol region, a peptide or protein, or a combination thereof. The two amino acid residues may be at least about 4 amino acid residues apart. The two amino acid residues may be at least about 7 amino acid residues apart. The two amino acid residues may be at least about 11 amino acid residues apart. The two amino acids may be cysteine. The half-life of the mTA may be longer than the half-life of the modified or unmodified therapeutic peptide alone. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The mTA may further comprise a second staple. The mTA may further comprise a second HEM. The mTA may further comprise a second staple and a second HEM. The first staple and second staple may be the same or different. The first HEM and second HEM may be the same or different. The mTA may be a PLC.

Further disclosed herein are modified therapeutic agents (mTAs) consisting essentially of a therapeutic agent (TA), a staple, and a half-life extending molecule (HEM). The TA may be a modified or unmodified therapeutic peptide. The TA may be covalently attached to the staple. The TA may be covalently attached to the staple via two amino acid residues on the modified or unmodified therapeutic peptide. One or both of the two amino acid residues may be cysteine. The two amino acid residues may be at least about 4 amino acid residues apart. The two amino acid residues may be at least about 7 amino acid residues apart. The two amino acid residues may be at least about 11 amino acid residues apart. The half-life of the mTA may be longer than the half-life of the modified or unmodified therapeutic peptide alone. The HEM may comprise a lipid, a polyglycol region, or a combination thereof. The lipid may be selected from a group consisting of sterols, sterol derivatives, bile acids, vitamin E derivatives, fatty di-acids, fatty acids, fatty amides, fatty amines, and fatty alcohols, and derivatives thereof. The polyglycol region comprises one or more polyethylene glycol units, polypropylene glycol units, or polybutylene glycol units, or a combination thereof. The HEM may comprise a protein or a peptide. The HEM may be covalently attached to the staple. The HEM may be covalently attached to the TA. The unmodified therapeutic peptide may be selected from GLP-1, glucagon, oxyntomodulin, exendin-4, GLP-2, and GIP. The modified therapeutic peptide may be a derivative of a peptide selected from GLP-1, glucagon, oxyntomodulin, exendin-4, GLP-2, and GIP; the derivative being a peptide comprising one or more amino acid additions, deletions, or substitutions, or a combination thereof. Non-limiting examples of mTAs include peptide lipid conjugates (PLCs).

In some embodiments of the mTAs disclosed herein, the HEM is directly attached to the staple which is covalently attached to the modified or unmodified therapeutic peptide. In other embodiments of the mTAs disclosed herein, the HEM is directly attached to the modified or unmodified therapeutic peptide. In some embodiments, HEM attachment to the staple is preferred over HEM attachment to the modified or unmodified therapeutic peptide. In some embodiments, HEM attachment to the modified or unmodified therapeutic peptide is preferred to HEM attachment to the staple. In some embodiments, a first mTA, wherein the HEM is directly attached to the staple which is covalently attached to the modified or unmodified therapeutic peptide, has better activity than a second mTA, wherein the HEM is directly attached to the modified or unmodified therapeutic peptide. In other embodiments, a first mTA, wherein the HEM is directly attached to the modified or unmodified therapeutic peptide, has better activity than a second mTA, wherein the HEM is directly attached to the staple which is covalently attached to the modified or unmodified therapeutic peptide.

Half-Life Extending Molecules (HEMs)

Disclosed herein are modified therapeutic agents (mTAs) comprising a therapeutic agent (TA), a staple, and a half-life extending molecule (HEM), wherein the therapeutic agent is a modified or unmodified therapeutic peptide and the half-life of the mTA is longer than the half-life of the modified or unmodified therapeutic peptide alone. The HEM may be attached to the staple. The HEM may be attached to the TA. The HEM may be non-proteinaceous or proteinaceous. The HEM may comprise a lipid, a polyglycol region, a peptide or a protein, or a combination thereof.

The HEM may be non-proteinaceous. The HEM may comprise a lipid, a polyglycol region, or a combination thereof. The HEM may be a non-proteinaceous polymer. Non-limiting examples of non-proteinaceous polymer include hydroxyalkyl starch, such as hydroxyethyl starch (HES), polyglycol, branched polyethylene glycols, polysialic acid, polyvinyl alcohol, polycarboxylate, poly(vinylpyrrolidone), dextran, or another biocompatible polymer.

The lipid may be selected from a group consisting of sterols, sterol derivatives, bile acids, vitamin E derivatives, fatty di-acids, fatty acids, fatty amides, fatty amines, and fatty alcohols, and derivatives thereof. The lipid may be a sterol or sterol derivative. The lipid may be a bile acid or derivative thereof. The lipid may be a vitamin E derivative. The lipid may be a fatty di-acid, fatty acid, fatty amide, fatty amine, or fatty alcohol. The fatty di-acid, fatty acid, fatty amide, fatty amine, or fatty alcohol may have 5-40 carbon atoms. The fatty di-acid, fatty acid, fatty amide, fatty amine, or fatty alcohol may have 5-30 carbon atoms. The fatty di-acid, fatty acid, fatty amide, fatty amine, or fatty alcohol may have 5-20 carbon atoms. The fatty di-acid, fatty acid, fatty amide, fatty amine, or fatty alcohol may have 6-40 carbon atoms. The fatty di-acid, fatty acid, fatty amide, fatty amine, or fatty alcohol may have 6-30 carbon atoms. The fatty di-acid, fatty acid, fatty amide, fatty amine, or fatty alcohol may have 7-40 carbon atoms. The fatty di-acid, fatty acid, fatty amide, fatty amine, or fatty alcohol may have 8-40 carbon atoms. The fatty di-acid, fatty acid, fatty amide, fatty amine, or fatty alcohol may have 9-40 carbon atoms. The fatty di-acid, fatty acid, fatty amide, fatty amine, or fatty alcohol may have 10-40 carbon atoms.

The lipid may be selected from a group consisting of propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, myristic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid and hexatriacontanoic acid. The lipid may be selected from a group consisting of malonic acid, succinic acid, glutaric acid, adipic acid, pimelic acid, suberic acid, azelaic acid, sebacic acid, undecanedioic acid, dodecanedioic acid, tridecanedioic acid, tetradecanedioic acid, pentadecanedioic acid, hexadecanedioic acid, heptadecanedioic acid, octadecanedioic acid, and nonadecanedioic acid. The lipid may be selected from a group consisting of myristoleic acid, palmitoleic acid, sapienic acid, oleic acid, elaidic acid, vaccenic acid, linoleic acid, linoelaidic acid, α-linolenic acid, arachidonic acid, eicosapentanoic acid, erucic acid, docosahexaenoic acid. The lipid may be selected from a group consisting of cholesterol, 7-OH cholesterol, 7,25-dihydroxycholesterol, cholic acid, chenodeoxycholic acid, lithocholic acid, deoxycholic acid, glycocholic acid, glycodeoxycholic acid, glycolithocholic acid, and glycochenodeoxycholic acid.

The polyglycol region may comprise one or more polyethylene glycol units, polypropylene glycol units, or polybutylene glycol units, or a combination thereof. The polyglycol region may comprise one or more polyethylene glycol units. The polyglycol region may comprise one or more polypropylene glycol units. The polyglycol region may comprise one or more polybutylene glycol units.

The polyglycol region may comprise 10, 20, 30, 40, 50, 60, 70, 80, 90, 100, or more polyethylene glycol units, polypropylene glycol units, or polybutylene glycol units, or a combination thereof. The polyglycol region may comprise 10, 20, 30, 40, 50, 60, 70, 80, 90, 100, or more polyethylene glycol units. The polyglycol region may comprise 10, 20, 30, 40, 50, 60, 70, 80, 90, 100, or more polypropylene glycol units. The polyglycol region may comprise 10, 20, 30, 40, 50, 60, 70, 80, 90, 100, or more polybutylene glycol units.

The polyglycol region may comprise 100, 200, 300, 400, 500, 600, 700, 800, 900, 1000, or more polyethylene glycol units, polypropylene glycol units, or polybutylene glycol units, or a combination thereof. The polyglycol region may comprise 100, 200, 300, 400, 500, 600, 700, 800, 900, 1000, or more polyethylene glycol units. The polyglycol region may comprise 100, 200, 300, 400, 500, 600, 700, 800, 900, 1000, or more polypropylene glycol units. The polyglycol region may comprise 100, 200, 300, 400, 500, 600, 700, 800, 900, 1000, or more polybutylene glycol units.

The polyglycol region may comprise 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, 50000, or more polyethylene glycol units, polypropylene glycol units, or polybutylene glycol units, or a combination thereof. The polyglycol region may comprise 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, 50000, or more polyethylene glycol units. The polyglycol region may comprise 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, 50000, or more polypropylene glycol units. The polyglycol region may comprise 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, 50000, or more polybutylene glycol units.

The polyglycol region may comprise a molecular weight of 500-50,000 daltons. The polyglycol region may comprise a molecular weight of 500-40,000 daltons. The polyglycol region may comprise a molecular weight of 500-30,000 daltons. The polyglycol region may comprise a molecular weight of 500-20,000 daltons. The polyglycol region may comprise a molecular weight of 500, 600, 700, 800, 900, 1000, 2000, 3000, 4000, 5000, 6000, 7000, 8000, 9000, 10000, 15000, 20000, 25000, 30000, 35000, 40000, or 45000 daltons or more, including increments therein.

The HEM may comprise a peptide or protein. Non-limiting examples include serum albumin, transferrin, or the Fc domain of immunoglobulins, or variants thereof. Variants may occur naturally or be non-naturally occurring. Non-naturally occurring variants may be produced using mutagenesis techniques known in the art. Variants may comprise one or more conservative or non-conservative amino acid substitutions, deletions, or additions, or a combination thereof. The HEM may comprise an extended recombinant polypeptide (XTEN).

Peptide Lipid Conjugate (PLC)

Disclosed herein are peptide lipid conjugates (PLCs) comprising one or more lipids attached to one or more peptide conjugates, the peptide conjugate (PC) comprising (a) one or more peptide regions comprising therapeutic agents (TAs); and (b) one or more staples, the one or more staples connecting two or more residues in the peptide region. The lipid conjugate may further comprise one or more polyethylene glycol subunits. The one or more lipids may be pegylated. The one or more lipids may be conjugated to the one or more therapeutic agents. The one or more lipids may be conjugated to the one or more staples. At least one of the two or more residues in the peptide region may be cysteine. The two or more residues in the peptide region may comprise cysteine. The two or more residues may be at least about 4 amino acids apart. The two or more residues may be at least about 7 amino acids apart. The two or more residues may be at least about 11 amino acids apart.

Figure 2A:
FIG. 2A depicts an exemplary peptide lipid conjugate comprising one peptide conjugate (PC) and one half-life extending molecule comprising a lipid (L).
Figure 2B:
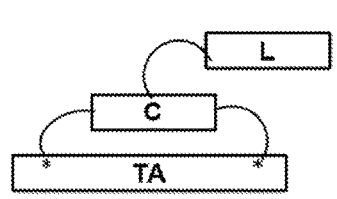
FIG. 2B depicts an exemplary peptide lipid conjugate comprising one therapeutic agent (TA), one staple (C), and one half-life extending molecule comprising a lipid (L).
Figure 2C:
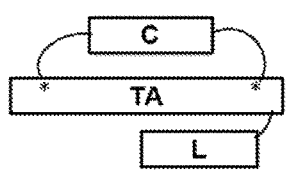
FIG. 2C depicts an exemplary peptide lipid conjugate comprising one therapeutic agent (TA), one staple (C), and one half-life extending molecule comprising a lipid (L).
Figure 2D:
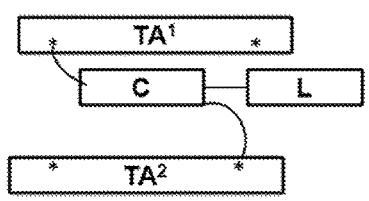
FIG. 2D depicts an exemplary peptide lipid conjugate comprising two therapeutic agents ($TA^1$ and $TA^2$), one staple (C), and one half-life extending molecule comprising a lipid (L).
Figure 2E:
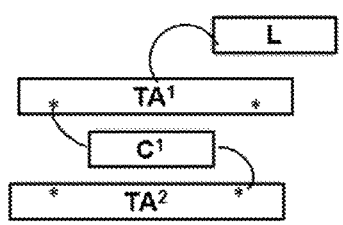
FIG. 2E depicts an exemplary peptide lipid conjugate comprising two therapeutic agents ($TA^1$ and $TA^2$), one staple ($C^1$), and one half-life extending molecule comprising a lipid (L).
Figure 2F:
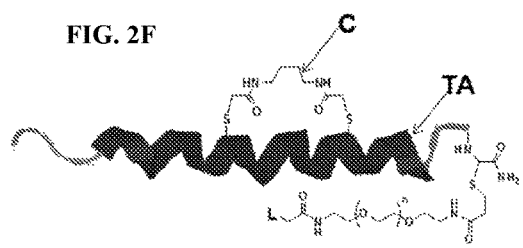
FIG. 2F depicts an exemplary peptide lipid conjugate comprising one therapeutic agent (TA), one staple (C), and one half-life extending molecule comprising a lipid linked to the therapeutic agent.
Figure 2G:
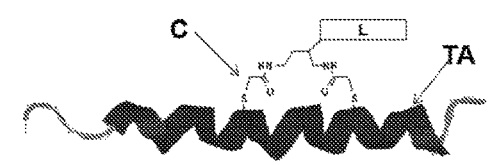
FIG. 2G depicts an exemplary peptide lipid conjugate comprising one therapeutic agent (TA), one staple (C), and one half-life extending molecule comprising a lipid (L) linked to the staple (C).

FIG. 2A-G depict schematics of exemplary peptide lipid conjugates. FIG. 2A depicts a peptide lipid conjugate comprising a peptide conjugate (PC) attached to a lipid (L). FIG. 2B depicts a peptide lipid conjugate comprising (a) a peptide conjugate comprising a staple (C) attached to two cysteine residues (*) on a peptide therapeutic agent (TA); and (b) a lipid (L), wherein the lipid is attached to the staple. FIG. 2C depicts a peptide lipid conjugate comprising (a) a peptide conjugate comprising a staple (C) attached to two cysteine residues (*) on a peptide therapeutic agent (TA); and (b) a lipid (L), wherein the lipid is attached to the TA. FIG. 2D depicts a peptide lipid conjugate comprising (a) a peptide conjugate comprising a staple (C) attached to two cysteine residues (*) on two peptide therapeutic agents (TA$^1$ and TA$^2$); and (b) a lipid (L), wherein the lipid is attached to the staple. FIG. 2E depicts a peptide lipid conjugate comprising (a) a peptide conjugate comprising a staple (C) attached to two cysteine residues (*) on two peptide therapeutic agents (TA$^1$ and TA$^2$); and (b) a lipid (L), wherein the lipid is attached to the peptide therapeutic agent (TA$^1$). FIG. 2F depicts a peptide lipid conjugate comprising (a) a peptide conjugate comprising a staple (C) attached to two cysteine residues on a peptide therapeutic agent (TA); and (b) a pegylated lipid (L), wherein the lipid is attached to the TA. FIG. 2G depicts a peptide lipid conjugate comprising (a) a peptide conjugate comprising a staple (C) attached to two cysteine residues on a peptide therapeutic agent (TA); and (b) a lipid (L), wherein the lipid is attached to the TA. The lipid may be attached to an amino acid residue within the therapeutic agent. The amino acid residue may be a cysteine residue. Alternatively, the amino acid residue is not a cysteine residue.

Additional exemplary peptide lipid conjugates are depicted in FIGS. 4A-H, 5A-H and 6A-H. FIG. 4A-C depict a peptide lipid conjugate comprising (a) a peptide conjugate comprising a staple (C) attached to a therapeutic agent (TA); and (b) a lipid (L). The TA may be a protein. The lipid may be attached to any portion of the TA. For example, as shown in FIG. 4A, the lipid may be attached to the C-terminus of a therapeutic agent comprising a protein. As shown in FIG. 4B, the lipid may be attached to an internal region of a therapeutic agent comprising a protein. As shown in FIG. 4C, the lipid may be attached to the N-terminus of a therapeutic agent comprising a protein. FIG. 4D-F depict a peptide lipid conjugate comprising (a) a peptide conjugate comprising a staple (C) attached to a therapeutic agent (TA); and (b) two lipids (L$^1$ and L$^2$). The two lipids may be attached to any portion of the TA. The two lipids may be attached to one or more ends of the TA. The two lipids may be attached to an internal region of the TA. The two lipids may be attached to an end of the TA and to an internal region of the T. As shown in FIG. 4D, the first lipid (L$^1$) is attached to an internal region of the TA and the second lipid (L$^2$) is attached to one end of the TA. As shown in FIG. 4E, the first lipid (L$^1$) and the second lipid (L$^2$) are attached to opposite ends of the TA. As shown in FIG. 4F, the first lipid (L$^1$) is attached to one end of the TA and the second lipid (L$^2$) is attached to an internal region of the TA. The PLCs disclosed herein may comprise (a) a peptide conjugate comprising a staple (C) and a therapeutic agent (TA); and (b) a plurality of lipids (L$^1$ ... L$^n$). FIG. 4G depicts a PLC comprising (a) a peptide conjugate comprising a staple (C) attached to a therapeutic agent (TA); and (b) three lipids (L$^1$, L$^2$ and L$^3$). As shown in FIG. 4G, all three lipids are attached to various regions within the TA. FIG. 4H depicts a PLC comprising (a) a peptide conjugate comprising a staple (C) attached to a therapeutic agent (TA); and (b) four lipids (L$^1$, L$^2$, L$^3$ and L$^4$). As shown in FIG. 4H, all four lipids are attached to various regions within the TA.

Figure 5A:
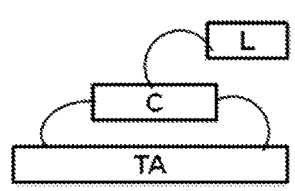
FIG. 5A depicts an exemplary peptide lipid conjugate comprising one therapeutic agent (TA), one staple (C), and one half-life extending molecule comprising a lipid (L) linked to the staple.
Figure 5B:
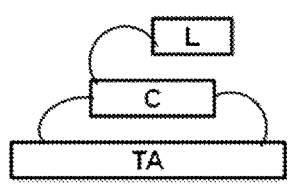
FIG. 5B depicts an exemplary peptide lipid conjugate comprising one therapeutic agent (TA), one staple (C), and one half-life extending molecule comprising a lipid (L) linked to the staple.
Figure 5C:
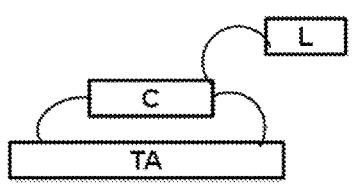
FIG. 5C depicts an exemplary peptide lipid conjugate comprising one therapeutic agent (TA), one staple (C), and one half-life extending molecule comprising a lipid (L) linked to the staple.
Figure 5D:
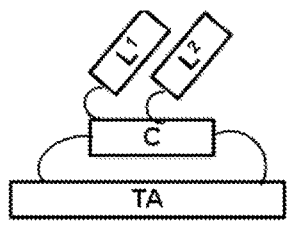
FIG. 5D depicts an exemplary peptide lipid conjugate comprising one therapeutic agent (TA), one staple (C), and two half-life extending molecules comprising a lipid ($L^1$ and $L^2$) linked to the staple.
Figure 5E:
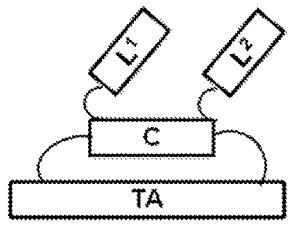
FIG. 5E depicts an exemplary peptide lipid conjugate comprising one therapeutic agent (TA), one staple (C), and two half-life extending molecules comprising a lipid ($L^1$ and $L^2$) linked to the staple.
Figure 5F:
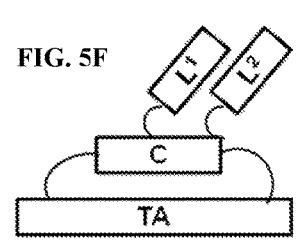
FIG. 5F depicts an exemplary peptide lipid conjugate comprising one therapeutic agent (TA), one staple (C), and two half-life extending molecules comprising a lipid ($L^1$ and $L^2$) linked to the staple.
Figure 5G:
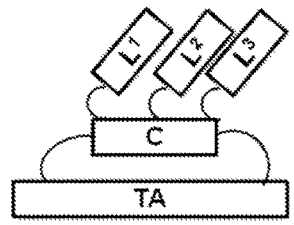
FIG. 5G depicts an exemplary peptide lipid conjugate comprising one therapeutic agent (TA), one staple (C), and three half-life extending molecules comprising a lipid ($L^1$, $L^2$, and $L^3$) linked to the staple.
Figure 5H:
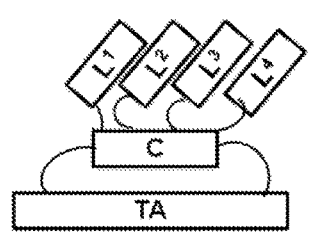
FIG. 5H depicts an exemplary peptide lipid conjugate comprising one therapeutic agent (TA), one staple (C), and four half-life extending molecules comprising a lipid ($L^1$, $L^2$, $L^3$, and $L^4$) linked to the staple.

FIG. 5A-C depict a peptide lipid conjugate comprising (a) a peptide conjugate comprising a staple (C) attached to a therapeutic agent (TA); and (b) a lipid (L). The lipid may be attached to any portion of the staple (C). For example, as shown in FIGS. 5A and 5C, the lipid may be attached to one end of the staple (C). As shown in FIG. 5B, the lipid may be attached to an internal region of the staple. FIG. 5D-F depict a peptide lipid conjugate comprising (a) a peptide conjugate comprising a staple (C) attached to a therapeutic agent (TA); and (b) two lipids (L$^1$ and L$^2$). The two lipids may be attached to any portion of the staple. The two lipids may be attached to one or more ends of the staple. The two lipids may be attached to an internal region of the staple. The two lipids may be attached to an end of the staple and to an internal region of the staple. As shown in FIG. 5D, the first lipid (L$^1$) is attached to one end of the TA and the second lipid (L$^2$) is attached to an internal region of the TA. As shown in FIG. 5E, the first lipid (L$^1$) and the second lipid (L$^2$) are attached to opposite ends of the staple. As shown in FIG. 5F, the first lipid (L$^1$) is attached to an internal region of the staple and the second lipid (L$^2$) is attached to one end of the staple. The PLCs disclosed herein may comprise (a) a peptide conjugate comprising a staple (C) and a therapeutic agent (TA); and (b) a plurality of lipids (L$^1$ ... L$^n$). FIG. 5G depicts a PLC comprising (a) a peptide conjugate comprising a staple (C) attached to a therapeutic agent (TA); and (b) three lipids (L$^1$, L$^2$ and L$^3$). As shown in FIG. 5G, all three lipids are attached to various regions within the staple. FIG. 5H depicts a PLC comprising (a) a peptide conjugate comprising a staple (C) attached to a therapeutic agent (TA); and (b) four lipids (L$^1$, L$^2$, L$^3$ and L$^4$). As shown in FIG. 5H, all four lipids are attached to various regions within the staple.

FIG. 6A-C depict a peptide lipid conjugate comprising (a) a peptide conjugate comprising a staple (C) attached to a therapeutic agent (TA); and (b) two lipids (L$^1$ and L$^2$). The two lipids may be attached to any portion of the TA, staple (C), or a combination thereof. At least one lipid may be attached to any portion of the TA. At least one lipid may be attached to any portion of the staple. The two lipids may be attached to any portion of the TA and the staple. For example, as shown in FIG. 6A, the first lipid (L$^1$) is attached to an internal region of the staple and the second lipid (L$^2$) is attached to one end of the therapeutic agent. As shown in FIG. 6B, the first lipid (L$^1$) is attached to an internal region of the staple and the second lipid (L$^2$) is attached to an internal region of the therapeutic agent. As shown in FIG. 6C, the first lipid (L$^1$) is attached to one end of the staple and the second lipid (L$^2$) is attached to one end of the therapeutic agent. FIG. 6D-H depict a peptide lipid conjugate comprising (a) a peptide conjugate comprising a staple (C) attached to a therapeutic agent (TA); and (b) a plurality of lipids (L$^1$ ... L$^n$). The plurality of lipids may be attached to any portion of the TA. The plurality of lipids may be attached to one or more ends of the TA. The plurality of lipids may be attached to an internal region of the TA. The plurality of lipids may be attached to any portion of the staple. The plurality of lipids may be attached to one or more ends of the staple. The plurality of lipids may be attached to an internal region of the staple. The plurality of lipids may be attached to one or more ends of the TA, one or more internal regions of the TA, one or more ends of the staple (C), one or more internal regions of the staple (C), or a combination thereof. FIG. 6D depicts a peptide lipid conjugate comprising (a) a peptide conjugate comprising a therapeutic agent (TA) and a staple (C); and (b) three lipids ($L^1$, $L^2$ and $L^3$). As shown in FIG. 6D, the first lipid ($L^1$) is attached to one end of the staple (C), the second lipid ($L^2$) is attached to an internal region of the TA and the third lipid ($L^3$) is attached to one end of the TA. FIG. 6E-F depict a peptide lipid conjugate comprising (a) a peptide conjugate comprising a therapeutic agent (TA) and a staple (C); and (b) four lipids ($L^1$, $L^2$, $L^3$ and $L^4$). As shown in FIG. 6E, the first lipid ($L^1$) and the second lipid ($L^2$) are attached to opposite ends of the staple (C) and the third lipid ($L^3$) and fourth lipid ($L^4$) are attached to opposite ends of the TA. As shown in FIG. 6F, the first lipid ($L^1$) is attached to one end of the staple (C); the second lipid ($L^2$) is attached to an internal region of the staple (C); the third lipid ($L^3$) is attached to one end of the TA and the fourth lipid ($L^4$) is attached to an internal region of the TA. As shown in FIG. 6G, at least one lipid ($L^1$) is attached to the staple (C) and three lipids ($L^2$, $L^3$ and $L^4$) are attached to various regions within the TA. As shown in FIG. 6H, at least two lipids (($L^1$ and $L^2$) are attached to the staple and four lipids ($L^3$, $L^4$, $L^5$ and $L^6$) are attached to various regions within the TA.

The PLCs disclosed herein may have the structure:

$$PC-A^1-P^1-L \qquad \text{Formula (II)}$$

wherein:
PC is the peptide conjugate;
$A^1$ is a chemical group linking PC and $P^1$;
$P^1$ is a bond or -PEG-$A^2$-;
PEG is a chemical group comprising one or more polyethylene glycol subunits;
$A^2$ is a chemical group linking PEG and L; and
L is the lipid.

The PEG of Formula (II) may be selected from:

[chemical structure with $(O)_m$ and]

[chemical structure with $(O)_m O$, NH, $(O)_n$];

wherein
m and n are independently 1, 2, 3, 4, 5, 6, 7, 8, 9, 10, 11, 12, 13, 14, 15, 16, 17, 18, 19, or 20.

In some embodiments of a PLC of Formula (II) disclosed herein,
$A^1$ is selected from

[chemical structure with $R^1$, $R^2$, $R^5$, $(R^3 R^4)_p$]

[chemical structure],

[chemical structure],

[chemical structure with S, $(R^1 R^2)_q$, $(R^3 R^4)_k$, and]

[chemical structure with $(R^1 R^2)_q$];

each $R^1$, $R^2$, $R^3$, and $R^4$ are independently selected from H, halo, CN, —$SR^5$, alkyl, cycloalkyl, haloalkyl, —$NR^5R^5$, and —$OR^5$;
each $R^5$ is independently selected from H, alkyl, haloalkyl, arylalkyl, and heteroalkyl;
k is 1, 2, 3, 4, 5, 6, 7, 8, 9, or 10;
p is 2, 3, 4, 5, 6, 7, 8, 9, or 10; and
q is 2, 3, 4, 5, 6, 7, 8, 9, or 10.

In some embodiments described of a PLC of Formula (II) disclosed herein,
$A^2$ is selected from a bond,

[chemical structure with X, $(R^3 R^4)_r$, $R^1$, $R^2$, $R^7$, and]

[chemical structure with X, $(R^3 R^4)_s$, $R^1$, $R^2$, $R^7$];

X is a bond, $NR^5$, S, or O;
$R^1$, $R^2$, $R^3$, and $R^4$ are independently selected from H, halo, CN, —$SR^5$, alkyl, cycloalkyl, haloalkyl, —$NR^5R^5$, and —$OR^5$;
$R^5$ is H, alkyl, haloalkyl, arylalkyl, or heteroalkyl;
$R^6$ is H, alkyl, arylalkyl, —$(CR^1R^2)_tSR^5$, —$(CR^1R^2)_tNR^5R^5$, —$(CR^1R^2)_tOR^5$, or —$(CR^1R^2)_tCO_2R^5$;
each $R^7$ is independently selected from H, alkyl, haloalkyl, arylalkyl, and heteroalkyl;
r is 1, 2, 3, 4, 5, 6, 7, 8, 9, or 10;
s is 1, 2, 3, 4, or 5; and
t is 0, 1, 2, 3, 4, or 5.

In some embodiments described of a PLC of Formula (II) disclosed herein, $P^1$ is -PEG-$A^2$.

Disclosed herein are methods of producing a PLC of Formula (II), the method comprising reacting an amino acid residue of TA with $A^3$-$P^1$-L, wherein $A^3$ is a reactive precursor to form $A^1$. $A^3$ may be a haloacetamide, maleimide, benzyl halide, alkyl disulfide, or pyridyl disulfide. $A^3$ may be a haloacetamide. $A^3$ may be a bromoacetamide. $A^3$ may be an alkyl disulfide.

The peptide lipid conjugates (PLCs) may comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. The one or more lipids may be attached to one or more ends of the TA, to an internal region of the TA, to one or more ends of the staple, to an internal region of the staple, or a combination thereof. The one or more lipids may be attached to both the TA and the staple. At least one of the two or more residues may be cysteine. The two or more residues in the peptide region may comprise cysteine. In some instances, at least one of the two or more residues is not cysteine. The two or more residues may be at least about 4 amino acid residues apart. The two or more residues may be at least about 7 or more residues apart. The two or more residues may be at least about 11 or more residues apart.

The peptide lipid conjugates (PLCs) may comprise (a) one or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, glucagon, a GLP-1R and GIPR dual agonist, a GLP-1R and GCGR dual agonist, or a derivative thereof, wherein the one or more lipids are attached to the one or more peptide conjugates. The one or more lipids may be attached to the one or more TAs. The one or more lipids may be attached to the one or more staples. The one or more lipids may be attached to one or more ends of the TA, to an internal region of the TA, to one or more ends of the staple, to an internal region of the staple, or a combination thereof. The one or more lipids may be attached to both the TA and the staple. At least one of the two or more residues may be cysteine. The two or more residues in the peptide region may comprise cysteine. In some instances, at least one of the two or more residues is not cysteine. The two or more residues may be at least about 4 amino acid residues apart. The two or more residues may be at least about 7 or more residues apart. The two or more residues may be at least about 11 or more residues apart.

The peptide lipid conjugates (PLCs) may comprise (a) one or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof, wherein the one or more lipids are attached to the one or more peptide conjugates. The one or more lipids may be attached to the one or more TAs. The one or more lipids may be attached to the one or more staples. The one or more lipids may be attached to one or more ends of the TA, to an internal region of the TA, to one or more ends of the staple, to an internal region of the staple, or a combination thereof. The one or more lipids may be attached to both the TA and the staple. At least one of the two or more residues may be cysteine. The two or more residues in the peptide region may comprise cysteine. In some instances, at least one of the two or more residues is not cysteine. The two or more residues may be at least about 4 amino acid residues apart. The two or more residues may be at least about 7 or more residues apart. The two or more residues may be at least about 11 or more residues apart.

The PLCs disclosed herein may have the structure:

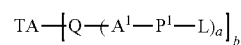

Formula (III)

wherein:

TA is the therapeutic agent;

each Q is the same or different, and is a staple;

each $A^1$ is the same or different, and is a chemical group linking Q and $P^1$;

each $P^1$ is a bond or -PEG-$A^2$-;

each PEG is the same or different, and is a chemical group comprising one or more polyethylene glycol subunits;

each $A^2$ is the same or different, and is a chemical group linking PEG and L;

each L is the same or different, and is a lipid;

a is 1, 2, 3, 4, 5, 6, 7, 8, 9, or 10; and b is 1, 2, 3, 4, 5, 6, 7, 8, 9, or 10.

The PEG of Formula (III) may be selected from:

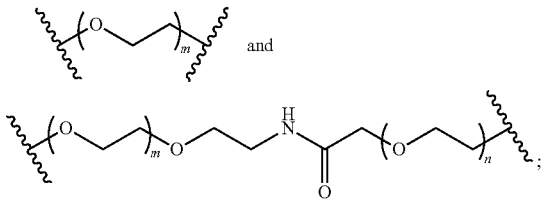

wherein m and n are independently 1, 2, 3, 4, 5, 6, 7, 8, 9, 10, 11, 12, 13, 14, 15, 16, 17, 18, 19, or 20.

In some embodiments of a PLC of Formula (III) disclosed herein, $A^1$ is selected from

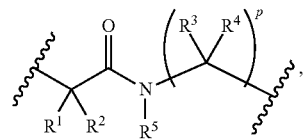

-continued

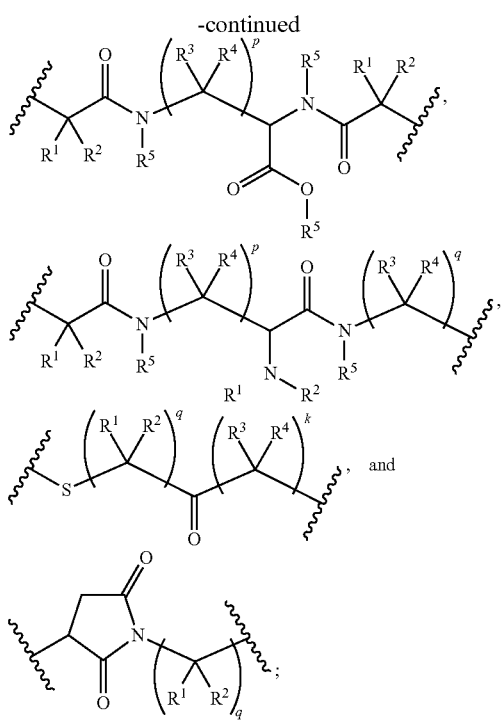

each $R^1$, $R^2$, $R^3$, and $R^4$ are independently selected from H, halo, CN, —$SR^5$, alkyl, cycloalkyl, haloalkyl, —$NR^5R^5$, and —$OR^5$;
each $R^5$ is independently selected from H, alkyl, haloalkyl, arylalkyl, and heteroalkyl;
k is 1, 2, 3, 4, 5, 6, 7, 8, 9, or 10;
p is 2, 3, 4, 5, 6, 7, 8, 9, or 10; and
q is 2, 3, 4, 5, 6, 7, 8, 9, or 10.

In some embodiments described of a PLC of Formula (III) disclosed herein,
$A^2$ is selected from a bond,

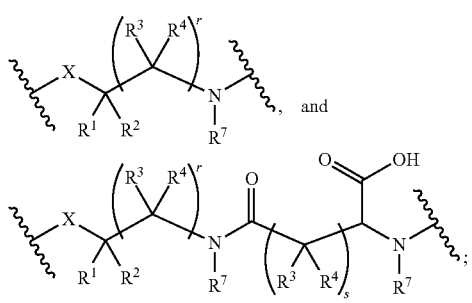

X is a bond, $NR^5$, S, or O;
$R^1$, $R^2$, $R^3$, and $R^4$ are independently selected from H, halo, CN, —$SR^5$, alkyl, cycloalkyl, haloalkyl, —$NR^5R^5$, and —$OR^5$;
$R^5$ is H, alkyl, haloalkyl, arylalkyl, or heteroalkyl;
$R^6$ is H, alkyl, arylalkyl, —$(CR^1R^2)_tSR^5$, —$(CR^1R^2)_tNR^5R^5$, —$(CR^1R^2)_tOR^5$, or —$(CR^1R^2)_tCO_2R^5$;
each $R^7$ is independently selected from H, alkyl, haloalkyl, arylalkyl, and heteroalkyl;
r is 1, 2, 3, 4, 5, 6, 7, 8, 9, or 10;
s is 1, 2, 3, 4, or 5; and
t is 0, 1, 2, 3, 4, or 5.

In some embodiments described of a PLC of Formula (III) disclosed herein, $P^1$ is -PEG-$A^2$.

Disclosed herein are methods of producing a PLC of Formula (III), the method comprising reacting one or more staples with $A^3$-$P^1$-L, wherein $A^3$ is a reactive precursor to form $A^1$. $A^3$ may be a haloacetamide, maleimide, benzyl halide, alkyl disulfide, or pyridyl disulfide. $A^3$ may be a haloacetamide. $A^3$ may a bromoacetamide. $A^3$ may be an alkyl disulfide.

The peptide lipid conjugates (PLCs) may comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more staples. The two or more residues in the peptide region may comprise cysteine.

The peptide lipid conjugates (PLCs) may comprise (a) one or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, glucagon, a GLP-1R and GIPR dual agonist, a GLP-1R and GCGR dual agonist, or a derivative thereof, wherein the one or more lipids are attached to the one or more staples. The two or more residues in the peptide region may comprise cysteine.

The peptide lipid conjugates (PLCs) may comprise (a) one or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof, wherein the one or more lipids are attached to the one or more staples. The two or more residues in the peptide region may comprise cysteine.

The PLCs disclosed herein may have the structure:

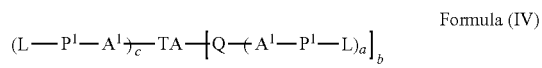

Formula (IV)

wherein:
TA is a therapeutic agent;
each Q is the same or different, and is a staple;
each $A^1$ is the same or different, and is a chemical group linking Q and $P^1$;
each $P^1$ is a bond or -PEG-$A^2$-;
each PEG is the same or different, and is a chemical group comprising one or more polyethylene glycol subunits;
each $A^2$ is the same or different, and is a chemical group linking PEG and L;
each L is the same or different, and is a lipid;
a is 1, 2, 3, 4, 5, 6, 7, 8, 9, or 10;
b is 1, 2, 3, 4, 5, 6, 7, 8, 9, or 10; and
c is 1, 2, 3, 4, 5, 6, 7, 8, 9, or 10.

The peptide lipid conjugates (PLCs) may comprise (a) two or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The one or more lipids may be attached to one or more ends of the TA, to an internal region of the TA, to one or more ends of the staple, to an internal region of the staple, or a combination thereof. At least one or more lipids may be attached to one or more ends of the TA, to an internal region of the TA, to one or more ends of the staple, to an internal region of the staple, or a combination thereof. At least one of the two or more lipids may be attached to both the TA and the staple. At least one of the two or more residues may be cysteine. The two or more residues in the peptide region may comprise cysteine. In some instances, at least one of the two or more residues is not cysteine. The two or more residues may be at least about 4 amino acid residues apart. The two or more residues may be at least about 7 or more residues apart. The two or more residues may be at least about 11 or more residues apart.

The peptide lipid conjugates (PLCs) may comprise (a) two or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, glucagon, a GLP-1R and GIPR dual agonist, a GLP-1R and GCGR dual agonist, or a derivative thereof, wherein at least one of the two or more lipids are attached to the one or more therapeutic agents and at least one of the two or more lipids are attached to the one or more staples. At least one or more lipids may be attached to one or more ends of the TA, to an internal region of the TA, to one or more ends of the staple, to an internal region of the staple, or a combination thereof. At least one of the two or more lipids may be attached to both the TA and the staple. At least one of the two or more residues may be cysteine. The two or more residues in the peptide region may comprise cysteine. In some instances, at least one of the two or more residues is not cysteine. The two or more residues may be at least about 4 amino acid residues apart. The two or more residues may be at least about 7 or more residues apart. The two or more residues may be at least about 11 or more residues apart.

The peptide lipid conjugates (PLCs) may comprise (a) two or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof, wherein at least one of the two or more lipids are attached to the one or more therapeutic agents and at least one of the two or more lipids are attached to the one or more staples. At least one or more lipids may be attached to one or more ends of the TA, to an internal region of the TA, to one or more ends of the staple, to an internal region of the staple, or a combination thereof. At least one of the two or more lipids may be attached to both the TA and the staple. At least one of the two or more residues may be cysteine. The two or more residues in the peptide region may comprise cysteine. In some instances, at least one of the two or more residues is not cysteine. The two or more residues may be at least about 4 amino acid residues apart. The two or more residues may be at least about 7 or more residues apart. The two or more residues may be at least about 11 or more residues apart.

Lipids

The mTAs or PLCs disclosed herein may comprise one or more lipids. The lipid may be attached to one or more peptide conjugates. The attachment of the one or more lipids to the one or more peptide conjugates may comprise a covalent attachment. The lipid may be attached to one or more TAs. The lipid may be attached to one or more staples. The lipid may be attached to the peptide conjugate, TA, or staple via one or more amino acid residues. The one or more amino acid residues may comprise a cysteine residue. Alternatively, the one or more amino acid residues do not comprise a cysteine residue. The lipid may be attached to the peptide conjugate or lipid via one or more functional groups. The one or more functional groups may comprise a ketone. The one or more functional groups may comprise a carbonyl. Attachment of the lipid to the peptide conjugate, TA, or staple may enhance one or more pharmacokinetic properties of the TAs.

The one or more lipids may be fatty acids. Fatty acids may be fatty di-acids, fatty amines, fatty amides or fatty alcohols. Fatty acids may be saturated or unsaturated Saturated fatty acids include, but are not limited to, lauric acid, myristic acid, palmitic acid, stearic acid, arachidic acid. Unsaturated fatty acids include, but are not limited to palmitoleic acid, oleic acid, linoleic acid, linolenic acid, erucic acid and arachidonic acid. Fatty acids may be short-chain fatty acids, medium chain fatty acids, long chain fatty acids or very long chain fatty acids. Fatty acids may be monounsaturated or polyunsaturated. Fatty acids may be omega fatty acids, essential fatty acids, partially hydrogenated fatty acids, cis-isomer fatty acids, or trans-isomer fatty acids. Fatty acids may be omega-3 fatty acids, omega-6 fatty acids or omega-9 fatty acids.

The fatty acid may comprise a chain of about 6, 7, 8, 9, 10, 11, 12, 13, 14, 15, 16, 17, 18, 19, 20, 21, 22, 23, 24, 25, 26 or more carbon atoms. The fatty acid may comprise a chain of 6-40 carbon atoms. The fatty acid may comprise a chain of 7-40 carbon atoms. The fatty acid may comprise a chain of 8-40 carbon atoms. The fatty acid may comprise a chain of 9-40 carbon atoms. The fatty acid may comprise a chain of 10-40 carbon atoms. The fatty acid may comprise a carbon chain further comprising 1, 2, 3, 4, 5, 6 or more double bonds. The fatty acid may be naturally occurring. The fatty acid may not be naturally occurring. The fatty acid may be synthesized.

The PLCs or mTAs disclosed herein may further comprise one or more fatty acids. The PLCs or mTAs disclosed herein may further comprise two or more fatty acids. The PLCs or mTAs disclosed herein may further comprise three or more fatty acids. The PLCs or mTAs disclosed herein may further comprise four or more fatty acids. The PLCs or mTAs disclosed herein may further comprise five or more fatty acids. The fatty acids may be different. The fatty acids may be the same.

The one or more lipids of the PLC or mTA may be selected from the group consisting of myristic acid, docosahexanoic acid, lithocholic acid ester, cholic acid and palmitic acid. The one or more lipids of the PLC or mTA may be myristic acid. The one or more lipids of the PLC or mTA may be docosahexanoic acid. The one or more lipids of the PLC or mTA may be lithocholic acid ester. The one or more lipids of the PLC or mTA may be cholic acid. The one or more lipids of the PLC or mTA may be palmitic acid.

The PLCs or mTAs may comprise one or more sterols or sterol derivatives. The sterols or sterol derivatives may be selected from a group comprising cholesterol, 7-OH cholesterol, 7,25-dihydroxycholesterol, cholic acid, chenodeoxycholic acid, lithocholic acid, deoxycholic acid, glycocholic acid, glycodeoxycholic acid, glycolithocholic acid, and glycochenodeoxycholic acid.

The PLCs or mTAs may comprise one or more bile acids. The bile acids may be selected from a group comprising cholic acid, chenodeoxycholic acid, lithocholic acid, deoxycholic acid, glycocholic acid, glycodeoxycholic acid, glycolithocholic acid, and glycochenodeoxycholic acid.

The PLC or mTA may comprise one or more Vitamin E derivatives. The Vitamin E derivatives may be selected from a group comprising α-tocopherol, β-tocopherol, γ-tocopherol, δ-tocopherol, α-tocotrienol, β-tocotrienol, γ-tocotrienol and δ-tocotrienol.

Pegylated Lipid

The PLCs disclosed herein may comprise one or more pegylated lipids. The mTAs disclosed herein may comprise one or more pegylated lipids.

The pegylated lipid may be attached to the therapeutic agent. The pegylated lipid may be attached to any portion of the therapeutic agent. For example, the pegylated lipid may be attached to one or more ends of the therapeutic agent. The pegylated lipid may be attached to one or more internal regions of the therapeutic agent.

The pegylated lipid may be attached to one or more peptide conjugates. The pegylated lipid may be attached to one or more TAs. The pegylated lipid may be attached to one or more staples. The pegylated lipid may be attached to the peptide conjugate, TA, or staple via one or more amino acid residues. The one or more amino acid residues may comprise a cysteine residue. Alternatively, the one or more amino acid residues do not comprise a cysteine residue. The pegylated lipid may be attached to the staple, peptide conjugate or pegylated lipid via one or more functional groups. The one or more functional groups may comprise a ketone. The one or more functional groups may comprise a carbonyl. Attachment of the pegylated lipid to the peptide conjugate, TA, or staple may enhance one or more pharmacokinetic properties of the TAs.

A pegylated lipid may comprise at least one polyethylene glycol subunit. The connection between the lipid and the one or more polyethylene glycol subunits may be a direct bond or a linker ($A^2$). Non-limiting examples of a linker between the lipid and the one or more polyethylene glycol subunits include:

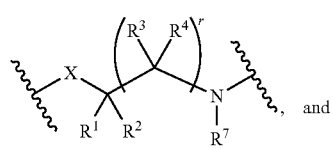
and

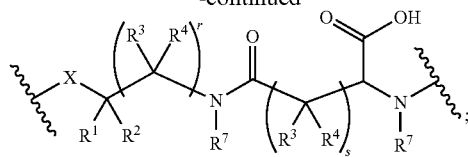

wherein

X is a bond, $NR^5$, S, or O;

$R^1$, $R^2$, $R^3$, and $R^4$ are independently selected from H, halo, CN, $-SR^5$, alkyl, cycloalkyl, haloalkyl, $-NR^5R^5$, and $-OR^5$;

$R^5$ is H, alkyl, haloalkyl, arylalkyl, or heteroalkyl;

$R^6$ is H, alkyl, arylalkyl, $-(CR^1R^2)_tSR^5$, $-(CR^1R^2)_t NR^5R^5$, $-(CR^1R^2)_tOR^5$, or $-(CR^1R^2)_tCO_2R^5$;

each $R^7$ is independently selected from H, alkyl, haloalkyl, arylalkyl, and heteroalkyl;

r is 1, 2, 3, 4, 5, 6, 7, 8, 9, or 10;

s is 1, 2, 3, 4, or 5; and t is 0, 1, 2, 3, 4, or 5.

A pegylated lipid may have the structure $P^1$-L, wherein $P^1$ is -PEG-$A^2$-; PEG is a chemical group comprising one or more polyethylene glycol subunits; $A^2$ is a chemical group linking PEG and L; and L is a lipid. PEG may be selected from:

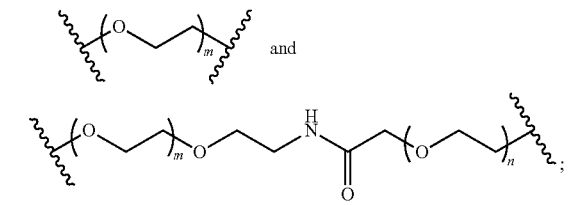

wherein m and n are independently 1, 2, 3, 4, 5, 6, 7, 8, 9, 10, 11, 12, 13, 14, 15, 16, 17, 18, 19, or 20.

A pegylated lipid may be connected to a therapeutic agent through a linker. A pegylated lipid may be connected to a staple through a linker.

Lipid Derivatives

The lipid derivatives may be directly attached to a TA or a staple. Such attachment of the lipid derivative to the TAs may enhance the pharmacokinetic properties of the TAs. The mTAs and PLCs disclosed herein may comprise one or more lipid derivatives.

The lipid derivatives may be attached to the therapeutic agent. The lipid derivatives may be attached to any portion of the therapeutic agent. For example, lipid derivatives may be attached to one or more ends of the therapeutic agent. The lipid derivatives may be attached to one or more internal regions of the therapeutic agent.

The lipid derivatives may be attached to a peptide conjugate. The lipid derivatives may be attached to a TA. The lipid derivatives may be attached to a staple. The lipid derivative may be attached to the peptide conjugate, TA, or staple via one or more amino acid residues. The lipid derivative may be attached to one or more ends and/or internal regions of the peptide conjugate. The lipid derivative may be attached to one or more ends and/or internal regions of the therapeutic agent. The lipid derivative may be attached to one or more ends and/or internal regions of the staple. The lipid derivative may be attached to one or more ends and/or internal regions of the peptide conjugate, TA, staple, or a combination thereof. The one or more amino acid residues may comprise a cysteine residue. Alternatively, the one or more amino acid residues do not comprise a cysteine residue. The lipid derivative may be attached to the peptide conjugate or lipid via one or more functional groups. The one or more functional groups may comprise a ketone. The one or more functional groups may comprise a carbonyl. Attachment of the lipid derivative to the peptide conjugate, TA or staple may enhance the pharmacokinetic properties of the TAs.

Lipid derivatives may be pegylated. A pegylated lipid may comprise at least one polyethylene glycol subunit. The lipid derivatives may be not pegylated. Lipids may be broadly defined as hydrophobic or amphiphilic small molecules. Lipids may be naturally occurring or synthetic. Lipids may be eicosanoids, prostaglandins, leukotrienes, thromboxanes, wax esters, coenzyme A derivatives, fatty acid carnitines, fatty acid amides, ethanolamines, bile acids, vitamin E, vitamin A, vitamin D, vitamin K, fat-soluble vitamin derivatives, monoglycerides, diglycerides, triglycerides, phospholipids, phosphatidylcholine, glycerolipids, glycerols, glycerophospholipids, sphingolipids, saccharolipids, polyketides, sterols, sterol derivatives, sterol lipids, steroid hormones, prenol lipids, carotenoids, fatty acids, and fatty alcohols.

In one aspect, disclosed herein are lipid derivatives having the structure of $A^3$-$P^1$-L, wherein:

$A^3$ is a haloacetamide, maleimide, benzyl halide, alkyl disulfide, or pyridyl disulfide;

$P^1$ is a bond or -PEG-$A^2$-;

PEG is a chemical group comprising one or more polyethylene glycol subunits;

$A^2$ is a chemical group linking PEG and L; and

L is a lipid selected from sterols, sterol derivatives, bile acids, vitamin E derivatives, fatty di-acids, fatty acids, fatty amides, and fatty alcohols.

In some embodiments described herein, PEG is selected from:

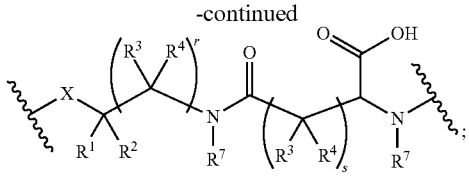

wherein m and n are independently 1, 2, 3, 4, 5, 6, 7, 8, 9, 10, 11, 12, 13, 14, 15, 16, 17, 18, 19, or 20.

In some embodiments described herein, $A^2$ is selected from a bond,

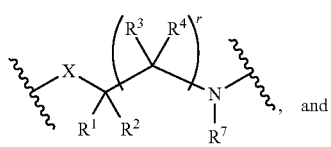

and

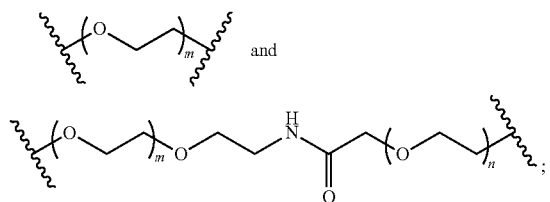

X is a bond, $NR^5$, S, or O;

$R^1$, $R^2$, $R^3$, and $R^4$ are independently selected from H, halo, CN, —$SR^5$, alkyl, cycloalkyl, haloalkyl, —$NR^5R^5$, and —$OR^5$;

$R^5$ is H, alkyl, haloalkyl, arylalkyl, or heteroalkyl;

$R^6$ is H, alkyl, arylalkyl, —$(CR^1R^2)_tSR^5$, —$(CR^1R^2)_tNR^5R^5$, —$(CR^1R^2)_tOR^5$, or —$(CR^1R^2)_tCO_2R^5$;

each $R^7$ is independently selected from H, alkyl, haloalkyl, arylalkyl, and heteroalkyl;

r is 1, 2, 3, 4, 5, 6, 7, 8, 9, or 10;

s is 1, 2, 3, 4, or 5; and t is 0, 1, 2, 3, 4, or 5.

Reaction of a lipid derivative with a staple precursor compound may produce a lipid staple precursor. The lipid staple precursor may subsequently be reacted with one or more therapeutic agents to form a PLC or mTA. Alternatively, reaction of a lipid derivative with a derivatizable functional group of the staple already attached to one or more therapeutic agents produces the PLC or mTA. Similarly, reaction of a lipid derivative with an amino acid on the TA produces an PLC or mTA.

Peptide Conjugate

The PLCs or mTAs disclosed herein may comprise one or more peptide conjugates. The peptide conjugates may comprise one or more staples connected two or more amino acid residues on one or more therapeutic agents. The peptide conjugates may further comprise one or more additional staples. The one or more additional staples may be attached to one or more amino acid residues on the one or more therapeutic agents. The one or more amino acid residues may comprise a cysteine residue on the one or more therapeutic agents. Alternatively, the one or more amino acid residues do not comprise a cysteine residue on the one or more therapeutic agents. The one or more additional staples may be attached to the one or more staples.

The peptide conjugates may comprise one or more staples connected one or more therapeutic agents, wherein at least two residues on the one or more therapeutic agents are connected to the one or more staples. The two residues may be on the same therapeutic agent. The two residues may be on different therapeutic agents. The two residues may be connected to the same staple. The two residues may be connected to different staples. Additional therapeutic agents may be attached to the one or more therapeutic agents or one or more staples. Attachment of the additional therapeutic agents to the one or more staples may occur via one or more amino acid residues. The one or more amino acid residues may comprise a cysteine residue. Alternatively, the one or more amino acid residues do not comprise a cysteine residue. Additional staples may be attached to the one or more therapeutic agents or one or more staples. Attachment of the additional staples to the one or more therapeutic agents may occur via one or more amino acid residues. The one or more amino acid residues may comprise a cysteine residue. Alternatively, the one or more amino acid residues do not comprise a cysteine residue.

Figure 1B:
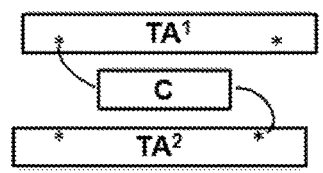
FIG. 1B depicts an exemplary peptide conjugate comprising two therapeutic agents ($TA^1$ and $TA^2$) and one staple (C).
Figure 1C:
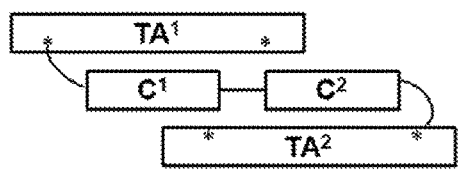
FIG. 1C depicts an exemplary peptide conjugate comprising two therapeutic agents ($TA^1$ and $TA^2$) and one staple containing two moieties ($C^1$ and $C^2$).
Figure 1D:
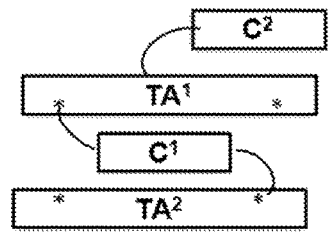
FIG. 1D depicts an exemplary peptide conjugate comprising two therapeutic agents ($TA^1$ and $TA^2$) and two staples ($C^1$ and $C^2$).
Figure 1E:
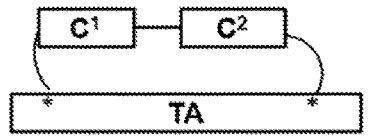
FIG. 1E depicts an exemplary peptide conjugate comprising one therapeutic agent (TA) and one staple containing two moieties ($C^1$ and $C^2$).
Figure 1F:
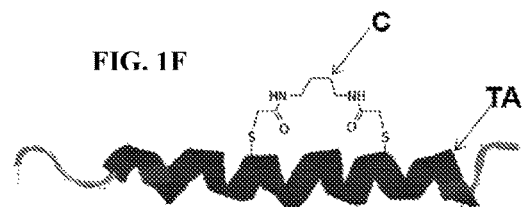
FIG. 1F depicts an exemplary peptide conjugate comprising one therapeutic agent (TA) and one staple (C).

FIG. 1A depicts a peptide conjugate comprising a staple (C) connected to two cysteine residues (*) in a single peptide therapeutic agent (TA). FIG. 1B depicts a peptide conjugate comprising a staple (C) connected to two cysteine residues (*) in two peptide therapeutic agents ($TA^1$ and $TA^2$). FIG. 1C depicts a peptide agent comprising two staples ($C^1$ and $C^2$) and two peptide therapeutic agents ($TA^1$ and $TA^2$), wherein $C^1$ connects to a cysteine residue (*) in $TA^1$ and $C^2$ connects to a cysteine residue (*) in $TA^2$ and $C^1$ and $C^2$ are connected to each other. FIG. 1D depicts a peptide agent comprising two staples ($C^1$ and $C^2$) and two peptide therapeutic agents ($TA^1$ and $TA^2$), wherein $C^1$ connects to a cysteine residue (*) in $TA^1$ and a cysteine residue (*) in $TA^2$ and $C^2$ is connected to $TA^1$. FIG. 1E depicts a peptide agent comprising two staples ($C^1$ and $C^2$) and a peptide therapeutic agent ($TA^1$), wherein C1 connects to a cysteine residue (*) in TA and $C^2$ connects to a cysteine residue (*) in TA and $C^1$ and $C^2$ are connected to each other. FIG. 1F depicts a peptide conjugate comprising a staple (C) connected to two cysteine residues in a single peptide therapeutic agent (TA). The one or more staples may be attached to an amino acid in the peptide therapeutic agent. The amino acid residue may be a cysteine residue. Alternatively, the amino acid residue is not a cysteine residue.

Staple

The PLCs or mTAs disclosed herein may comprise one or more staples. The PLCs or mTAs disclosed herein may comprise two or more staples. The PLCs or mTAs disclosed herein may comprise three or more staples. The PLCs or mTAs disclosed herein may comprise four or more staples. The PLCs or mTAs disclosed herein may comprise five or more staples. The PLCs or mTAs disclosed herein may comprise 6, 7, 8, 9, 10 or more staples.

The one or more staples may connect two or more amino acid residues in a peptide region of a peptide conjugate. At least one of the two or more amino acid residues may be a cysteine residue. The two or more amino acid residues may both be cysteine residues. The one or more staples may connect two or more cysteine residues on the same TA. The one or more staples may connect two or more cysteine residues on two or more TAs. Two or more staples may connect two or more cysteine residues on the same TA. Two or more staples may connect two or more cysteine residues on two or more TAs. In some instances, at least one of the two or more amino acid residues are not cysteine. In some instances, at least two of the two or more amino acid residues are not cysteine. At least one of the two or more amino acid residues may be a cysteine residue. The one or more staples may connect two or more amino acid residues on the same TA. The one or more staples may connect two or more amino acid residues on two or more TAs. Two or more staples may connect two or more amino acid residues on the same TA. Two or more staples may connect two or more amino acid residues on two or more TAs. The two or more TAs may be the same. The two or more TAs may be different.

At least one staple may connect at least two amino acid residues on a therapeutic agent. The two amino acid residues may be adjacent. The two amino acid residues may be non-adjacent. The two amino acid residues may be at least about 1, 2, 3, 4, 5, 6, 7, 8, 9, 10, 11, 12, 13, 14, 15, 16, 17, 18, 19, 20 or more amino acid residues apart. The two amino acid residues may be at least about 4 amino acid residues apart. The two amino acid residues may be at least about 7 amino acid residues apart. The two amino acid residues may be at least about 11 amino acid residues apart. The two amino acid residues may be at least about 15 amino acid residues apart. The two amino acid residues may be at least about 19 amino acid residues apart.

Figure 3A:
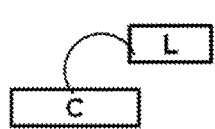
FIG. 3A depicts an exemplary staple-lipid construct comprising a staple (C) and one half-life extending molecule comprising a lipid (L).
Figure 3B:
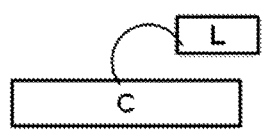
FIG. 3B depicts an exemplary staple-lipid construct comprising a staple (C) and one half-life extending molecule comprising a lipid (L).
Figure 3C:
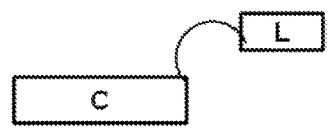
FIG. 3C depicts an exemplary staple-lipid construct comprising a staple (C) and one half-life extending molecule comprising a lipid (L).
Figure 3D:
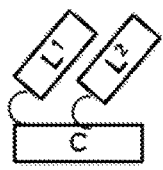
FIG. 3D depicts an exemplary staple-lipid construct comprising a staple (C) and two half-life extending molecules comprising a lipid ($L^1$ and $L^2$).
Figure 3E:
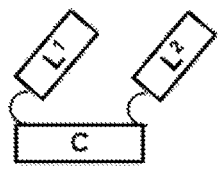
FIG. 3E depicts an exemplary staple-lipid construct comprising a staple (C) and two half-life extending molecules comprising a lipid ($L^1$ and $L^2$).
Figure 3F:
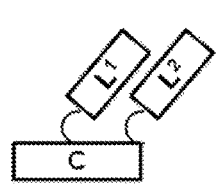
FIG. 3F depicts an exemplary staple-lipid construct comprising a staple (C) and two half-life extending molecules comprising a lipid ($L^1$ and $L^2$).
Figure 3G:
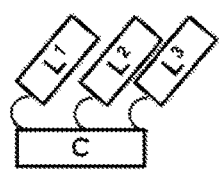
FIG. 3G depicts an exemplary staple-lipid construct comprising a staple (C) and three half-life extending molecules comprising a lipid ($L^1$, $L^2$, and $L^3$).
Figure 3H:
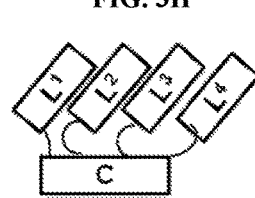

The staple may be conjugated to one or more lipids to produce a staple-lipid construct. Exemplary staple lipid constructs are shown in FIG. 3A-H. FIG. 3A-C depict a staple lipid construct comprising (a) a staple (C); and (b) a lipid (L). The lipid may be attached to any portion of the staple. As shown in FIG. 3A, the lipid (L) is attached to an internal region of the staple (C). As shown in FIGS. 3B and 3C, the lipid (L) is attached to one end of the staple (C). FIG. 3D-F depict a staple lipid construct comprising (a) a staple (C); and (b) two lipids ($L^1$ and $L^2$). As shown in FIG. 3D, the first lipid ($L^1$) is attached to one end of the staple (C) and the second lipid ($L^2$) is attached to an internal region of the staple (C). As shown in FIG. 3E, the first lipid ($L^1$) and the second lipid ($L^2$) are attached opposite ends of the staple (C). As shown in FIG. 3F, the first lipid ($L^1$) is attached to an internal region of the staple (C) and the second lipid ($L^2$) is attached to one end of the staple (C). The staple lipid construct may comprise (a) a staple (C); and (b) a plurality of lipids ($L^1$ ... $L^n$). FIG. 3G depicts a staple lipid construct comprising (a) a staple (C); and (b) three lipids ($L^1$, $L^2$ and $L^3$). As shown in FIG. 3G, the three lipids ($L^1$, $L^2$ and $L^3$) are attached to various regions within the staple (C). FIG. 3H depicts a staple lipid construct comprising (a) a staple (C); and (b) four lipids ($L^1$, $L^2$, $L^2$ and $L^3$). As shown in FIG. 3G, the four lipids ($L^1$, $L^2$, $L^2$ and $L^3$) are attached to various regions within the staple (C). The staple lipid constructs may further comprise one or more additional staples. The one or more additional staples may be attached to the staple, lipid, or a combination thereof. For example, the one or more additional staples may be attached to the staple and the lipid. Alternatively, the one or more additional staples are attached to the staple. The one or more additional staples may be attached to two or more staples. The one or more additional staples may be attached to the lipid. The one or more additional staples may be attached to the two or more lipids.

The staple may be prepared from a precursor compound comprising two or more chemical groups. The two or more chemical groups may react with a nucleophilic or electrophilic amino acid residue on the same TA. The two or more chemical groups may react with a nucleophilic amino acid residue on the same TA. The two or more chemical groups may react with an electrophilic amino acid residue on the same TA. The two or more chemical groups may react with a nucleophilic or electrophilic amino acid residue on two or more TAs. The two or more chemical groups may react with a nucleophilic amino acid residue on two or more TAs. The two or more chemical groups may react with an electrophilic amino acid residue on two or more TAs.

The staple may be prepared from a precursor compound with two chemical groups, each of which reacts with a nucleophilic or electrophilic amino acid residue on one or more TAs. The staple may be prepared from a precursor compound with two chemical groups, each of which reacts with a nucleophilic amino acid residue on the same TA. The staple may be prepared from a precursor compound with two chemical groups, each of which reacts with an electrophilic amino acid residue on the same TA.

The precursor compound may further comprise one or more additional chemical groups that react with one or more lipid derivatives to form the PLC or mTA. Additional chemical groups include, but are not limited to, alkenes, alkynes, amines, hydrazines, azides, carboxylic acids, esters, anilines, ketones, ketoamides, and hydroxy groups.

The precursor compound may be selected from:
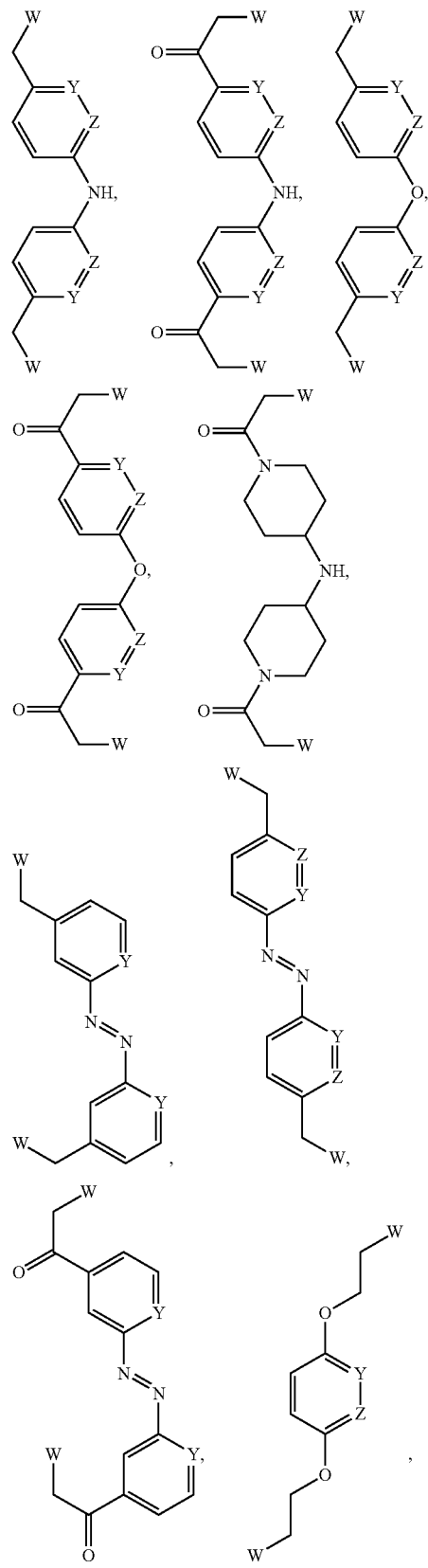
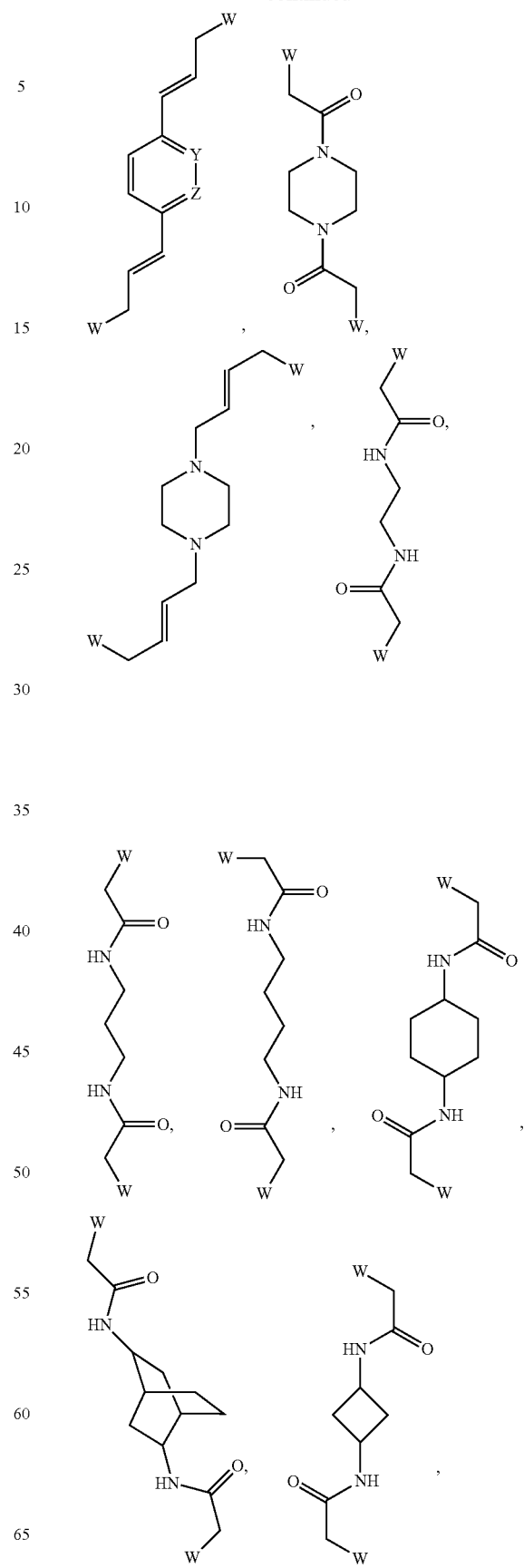

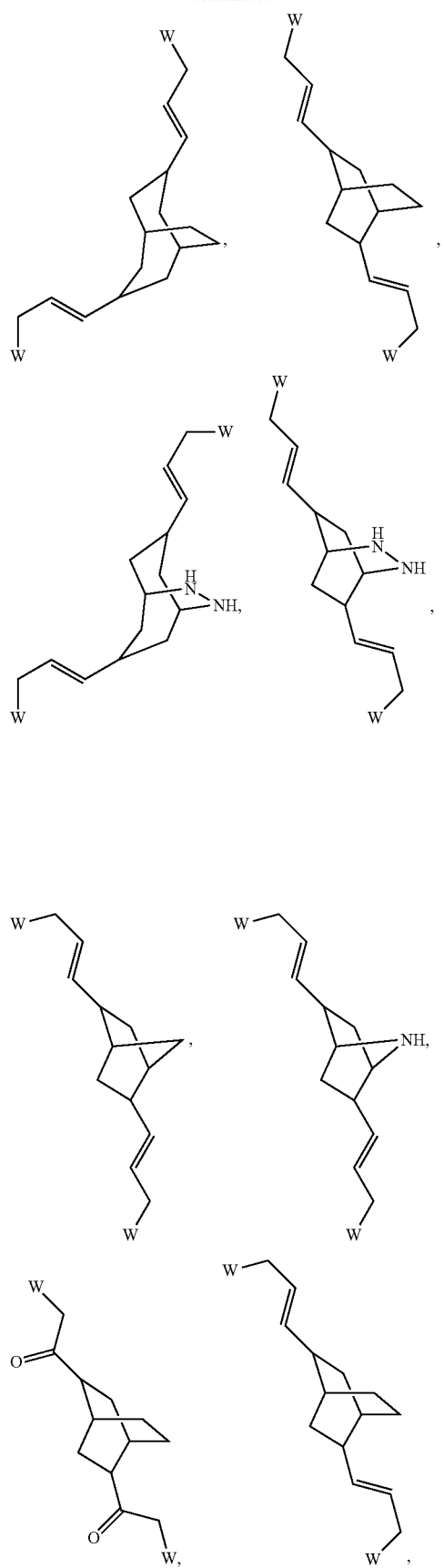
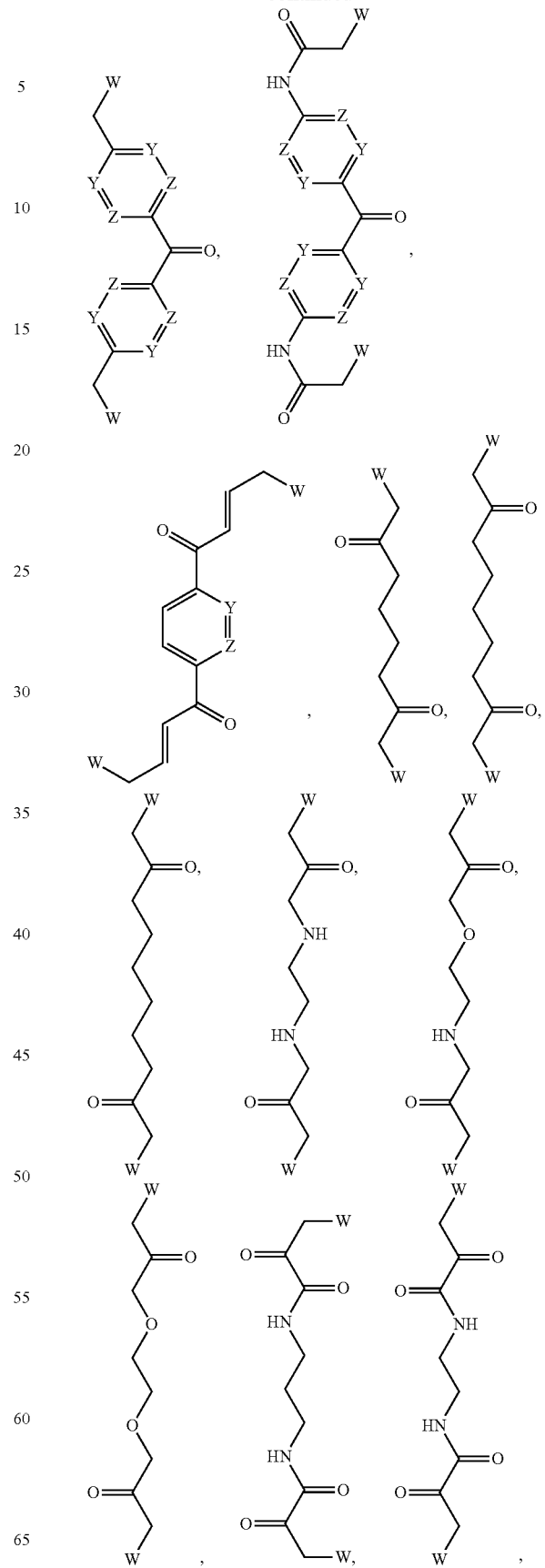

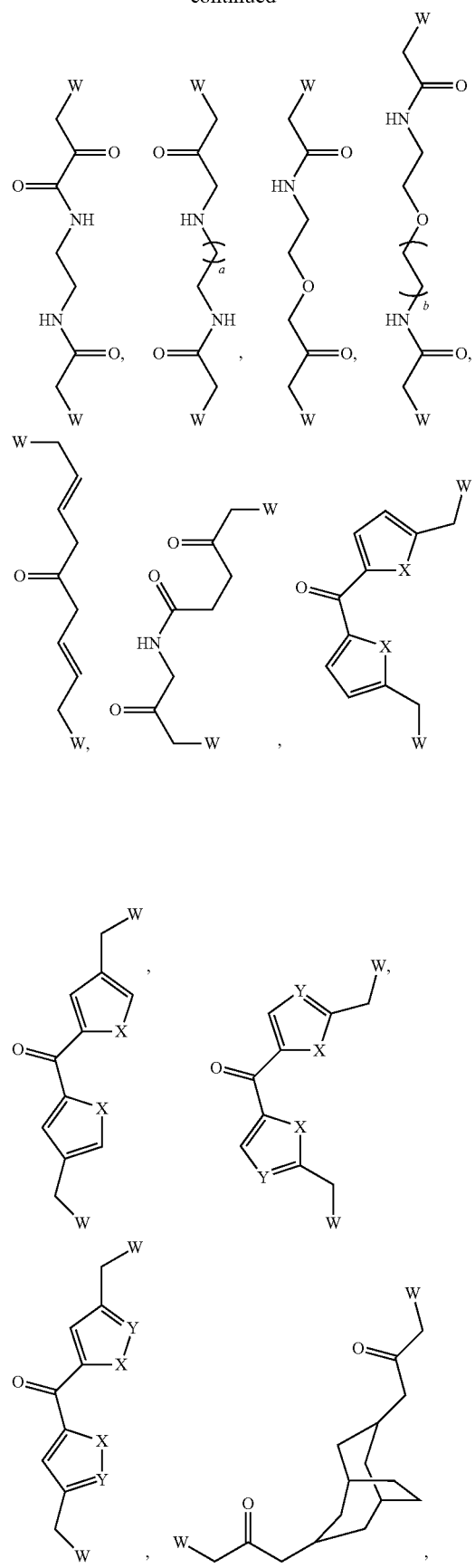
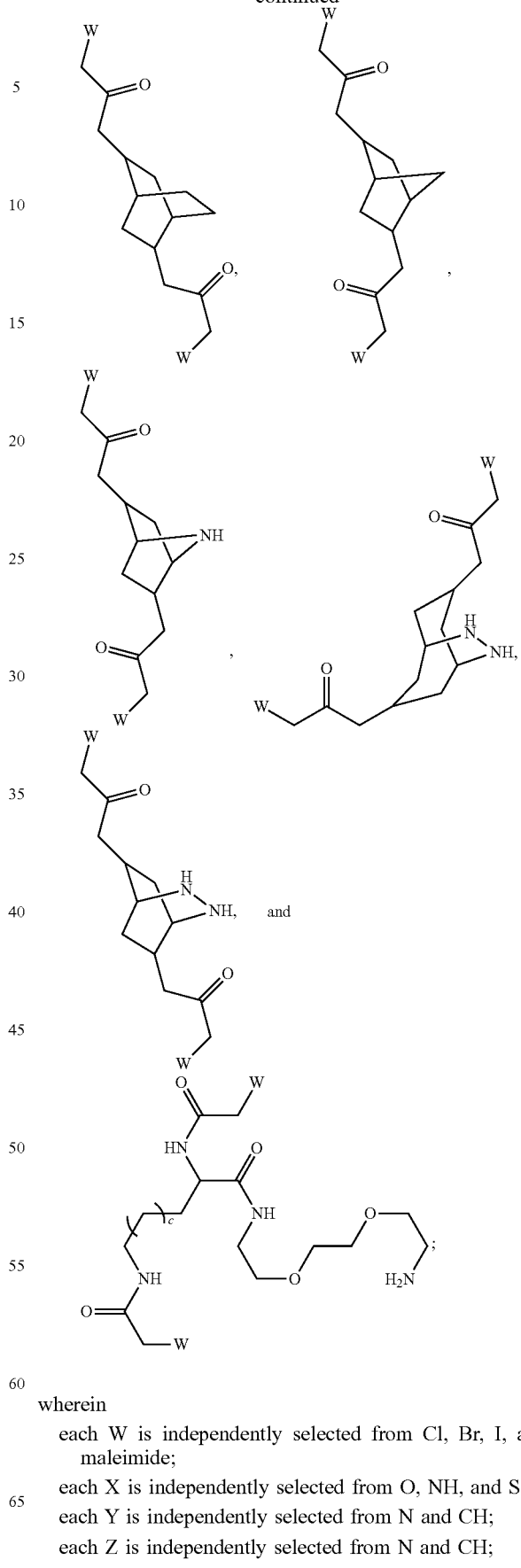
wherein
each W is independently selected from Cl, Br, I, and maleimide;
each X is independently selected from O, NH, and S;
each Y is independently selected from N and CH;
each Z is independently selected from N and CH;

a is 1, 2, 3, 4, 5, 6, 7, 8, 9, 10, 11, 12, 13, 14, 15, 16, or 17;
b is 1, 2, 3, 4, 5, or 6; and
c is 1 or 2.
The precursor compound may be selected from:
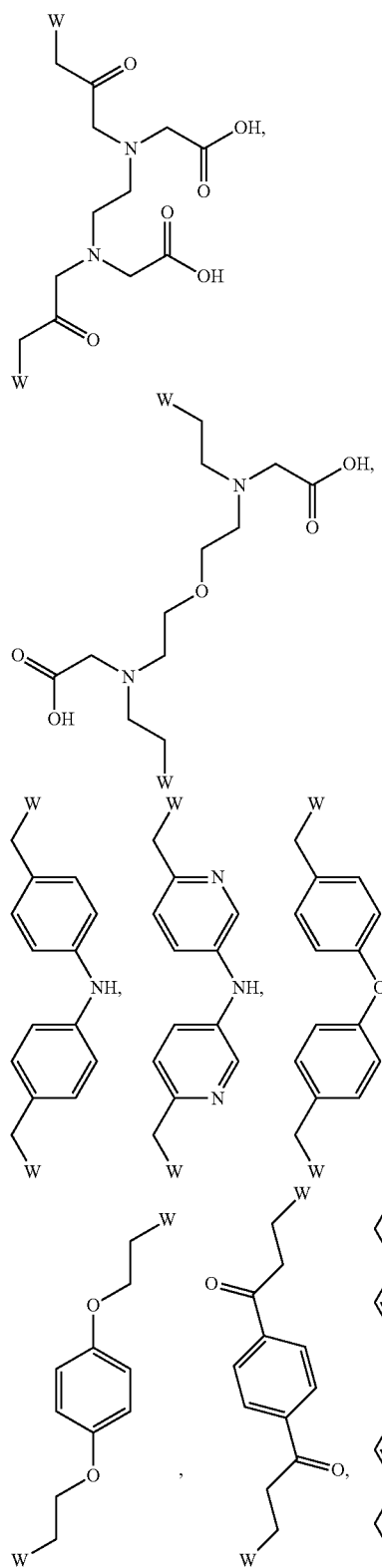
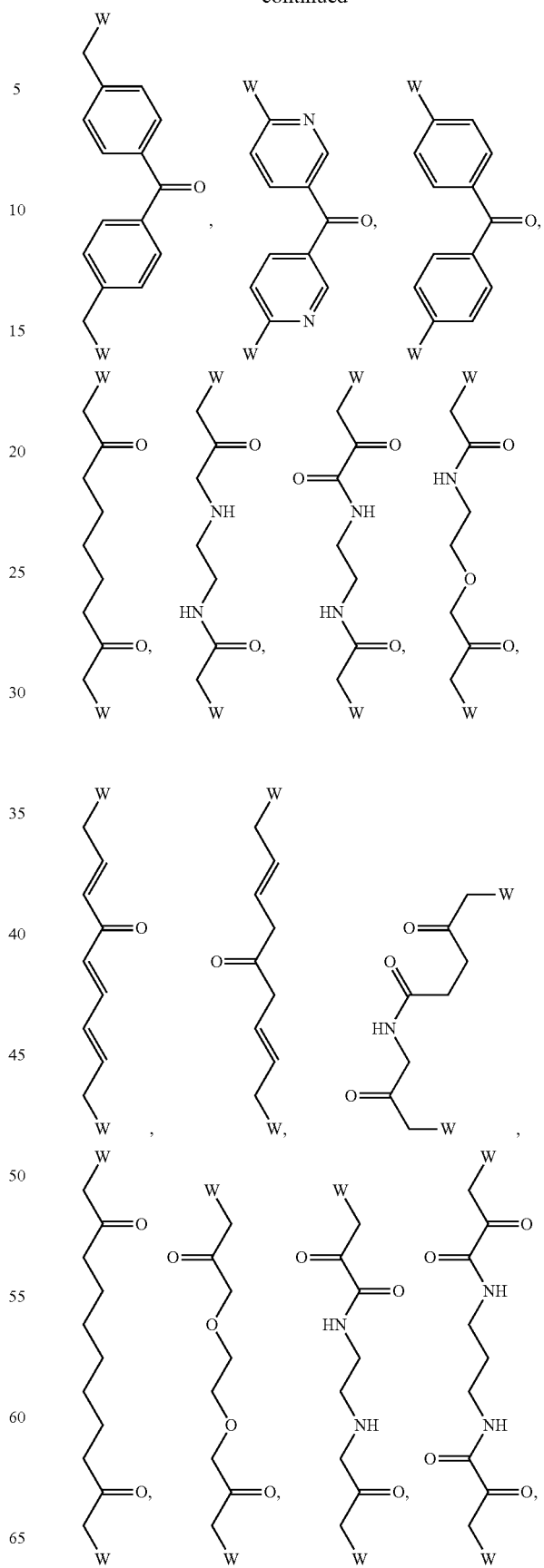

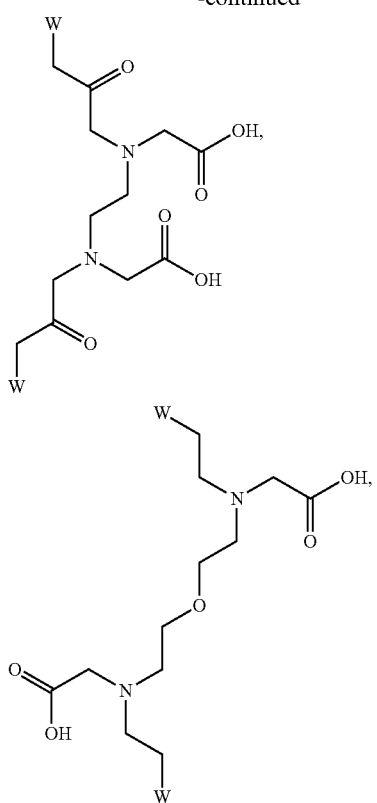
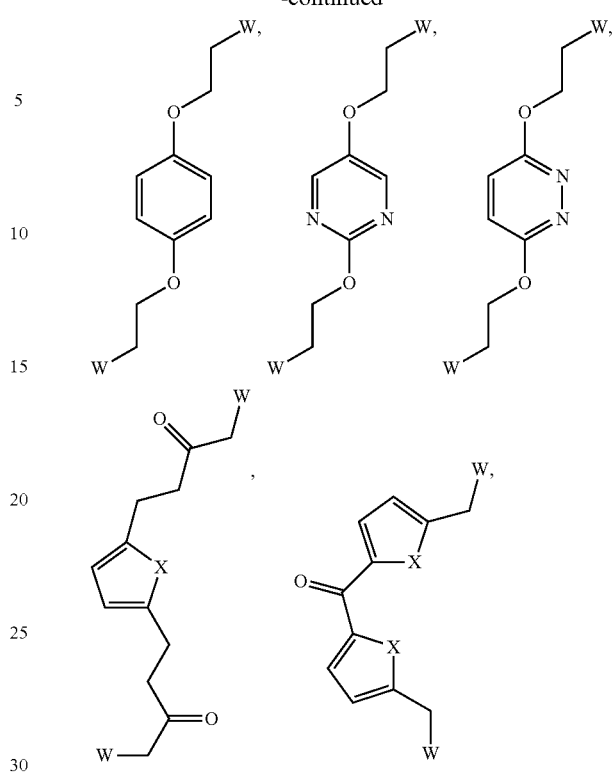
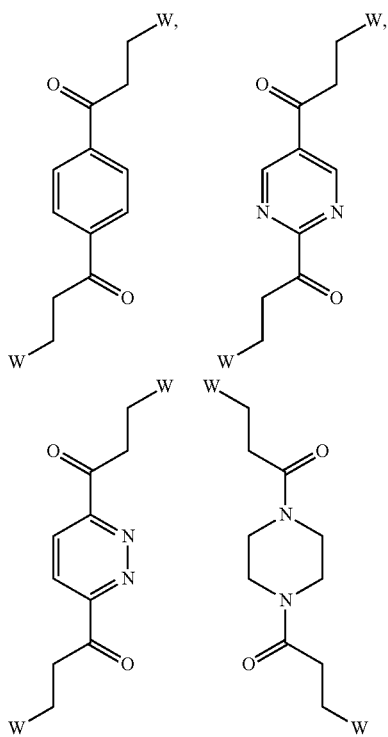

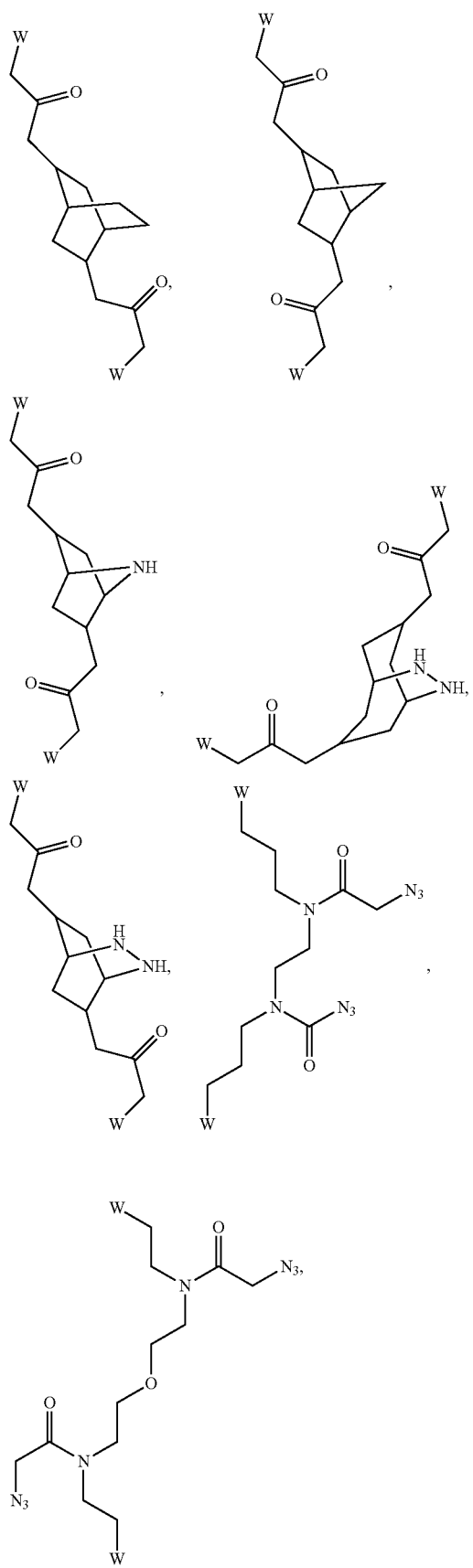
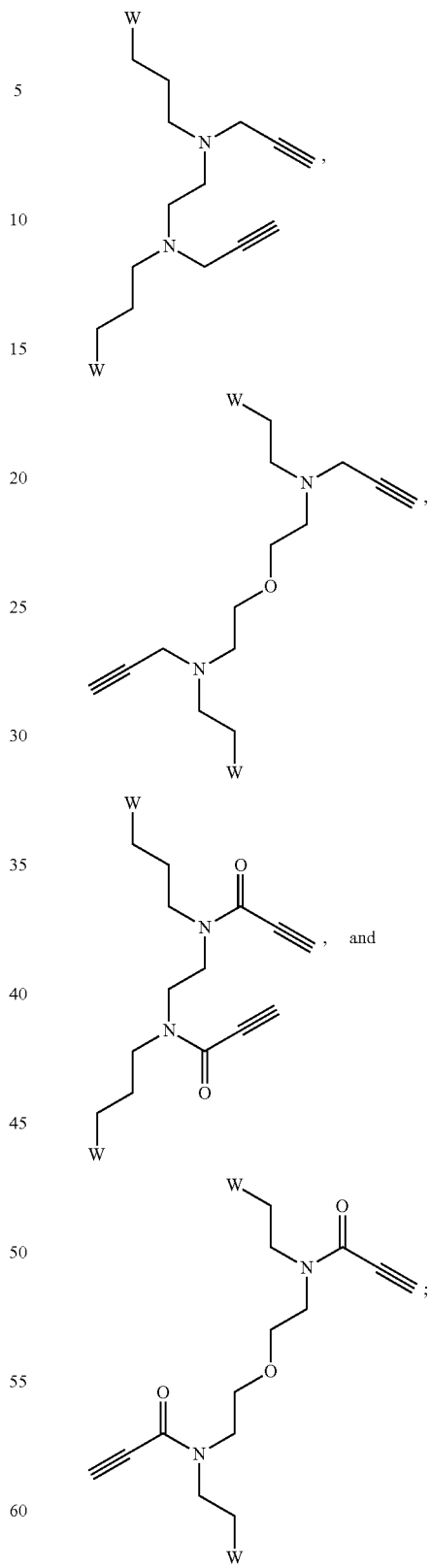
wherein
each W is independently selected from Cl, Br, I, and maleimide;

X is O, NH, or S; and
Y is N or CH.

The precursor may be selected from Table 2.

At least one or more lipids of the PLC of Formula (II), Formula (III), or Formula (IV) may be attached to the one or more staples to form a lipid staple precursor prior to forming the peptide conjugate. Each of the lipids of the PLC of Formula (II), Formula (III), or Formula (IV) may be attached to the one or more staples to form a lipid staple precursor prior to forming the peptide conjugate. The lipid staple precursor may be

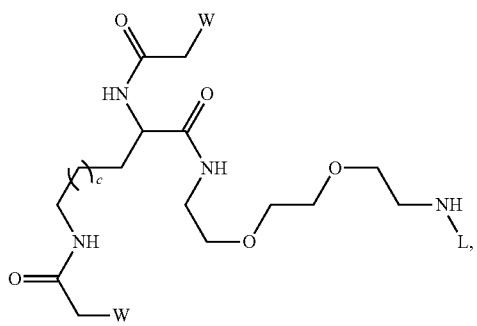

wherein each W is independently selected from Cl, Br, I, and maleimide; c is 1 or 2; and L is the lipid.

Therapeutic Agent (TA)

The mTAs disclosed herein may comprise one or more therapeutic agents. The mTAs may comprise one therapeutic agent. The mTAs may comprise two therapeutic agents. The mTAs may comprise 3, 4, 5, 6, 7 or more therapeutic agents. The therapeutic agents may be different. The therapeutic agents may be the same.

The PCs disclosed herein may comprise one or more therapeutic agents. The PCs may comprise two or more therapeutic agents. The PCs may comprise 3, 4, 5, 6, 7 or more therapeutic agents. The two or more therapeutic agents may be different. The two or more therapeutic agents may be the same. Exemplary TAs are depicted in Tables 3, 4, and 5. Exemplary TAs may comprise a peptide sequence disclosed in Tables 3, 4, and 5. Exemplary TAs may comprise a polynucleotide encoding a peptide disclosed in Tables 3, 4, and 5.

The TA may be selected from peptides listed Table 5, wherein X is cysteine. The TA may be selected from analogs of peptides listed in Table 5, wherein X is homocysteine.

In some embodiments, the TA may be a modified therapeutic peptide with a D-serine in place of L-serine. In some embodiments, the TA may be a modified therapeutic peptide with an aminoisobutyric acid (Aib) in place of L-serine.

The TA may be a hormone. Examples of hormones include, but are not limited to, peptide hormones, lipid and phospholipid-derived hormones, and monoamines. Peptide hormones generally consist of chains of amino acids. Examples of small peptide hormones include, but are not limited to thyrotropin-releasing hormone (TRH) and vasopressin. Peptides composed of scores or hundreds of amino acids are referred to as proteins. Examples of protein hormones include insulin and growth hormone. More complex protein hormones may bear carbohydrate side-chains and may be called glycoprotein hormones. Luteinizing hormone, follicle-stimulating hormone and thyroid-stimulating hormone are examples of glycoprotein hormones. Lipid and phospholipid-derived hormones are generally derived from lipids such as linoleic acid and arachidonic acid and phospholipids. Examples of protein hormones may comprise steroid hormones that may be derived from cholesterol and the eicosanoids. Examples of steroid hormones are testosterone and cortisol. Eicosanoids may comprise prostaglandins. Monoamines may be derived from aromatic amino acids like phenylalanine, tyrosine, and tryptophan by the action of aromatic amino acid decarboxylase enzymes. The TA may be leptin. The TA may be betatrophin. The TA may be a peptide agonist or peptide hormone. The peptide agonist or hormone may be exendin-4, exenatide, glucagon, glucagon-like protein-1 (GLP-1), or oxyntomodulin. The TA may be exendin-4. The TA may be exenatide. The TA may be glucagon. The TA may be glucagon-like protein-1 (GLP-1). The TA may be oxyntomodulin. The TA may be GLP-2. The TA may be a GLP-1R and GIPR dual agonist. The TA may be a GLP-1R and GCGR dual agonist. The TA may be a GLP1R, GCGR and GIPR tri-agonist. The TA may bind to a receptor. The receptor may be a GLP-1 receptor or glucagon receptor. The TA may be selected from GLP-1, glucagon, oxyntomodulin, exendin-4, GLP-2, GIP, GLP1R and GCGR dual agonist, GLP1R and GIPR dual agonist, and GLP1R, GCGR and GIPR tri-agonist. The TA may be selected from GLP-1, glucagon, oxyntomodulin, exendin-4, GLP-2, and GIP.

The TA may be a growth factor. Growth factors may include, but are not limited to, cytokines and hormones. Examples of growth factors include, but are not limited to, adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF) and other neurotrophins, platelet-derived growth factor (PDGF), thrombopoietin (TPO), transforming growth factor alpha (TGF-α), transforming growth factor beta(TGF-β), tumor necrosis factor-alpha(TNF-α) and vascular endothelial growth factor (VEGF). The TA may be fibroblast growth factor 21 (FGF21).

The TA may be a cell regulatory protein. The TA may be a cell regulatory protein of the transforming growth factor beta superfamily. The TA may be a member of the decapentaplegic-Vg related (DVR) related subfamily. The TA may be a member of the activin/inhibin subfamily. The TA may be a member of the TGF-beta subfamily. The TA may be a growth differentiation factor (GDF). The GDF may be GDF1, GDF2, GDF3, GDF5, GDF6, GFD8, GDF9, GDF10, GDF11, and GDF15. The TA may be growth differentiation factor 11 (GDF11).

The TA may be a protein. The protein may be a member of the angiopoietin-like family of secreted factors. The protein may be an angiopoietin-like protein (ANGPTL). Examples of ANGPTLs include, but are not limited to, ANGPTL1, ANGPTL2, ANGPTL3, ANGPTL4, ANGPTL5, ANGPTL6 and ANGPTL7. The TA may be ANGPTL3.

The TA may comprise an amino acid sequence selected from the group comprising SEQ ID NO: 1-6. The TA may comprise an amino acid sequence that is at least about 50% homologous to an amino acid sequence selected from the group comprising SEQ ID NO: 1-6. The TA may comprise an amino acid sequence that is at least about 55%, 60%, 65%, 70%, 75%, 80%, 85%, 90%, 92%, 95%, 97%, 99%, or 100% homologous to an amino acid sequence selected from the group comprising SEQ ID NO: 1-6. The TA may comprise an amino acid sequence that is at least about 70% homologous to an amino acid sequence selected from the group comprising SEQ ID NO: 1-6. The TA may comprise an amino acid sequence that is at least about 75% homologous to an amino acid sequence selected from the group comprising SEQ ID NO: 1-6. The TA may comprise an amino acid sequence that is at least about 80% homologous to an amino acid sequence selected from the group comprising SEQ ID NO: 1-6.

The TA may comprise 20 or more consecutive amino acids from an amino acid sequence selected from the group comprising SEQ ID NO: 1-6. The TA may comprise 30, 40, 50, 60, 70, 80, 90, 100, 110, 120, 130 or more consecutive amino acids from an amino acid sequence selected from the group comprising SEQ ID NO: 1-6.

The TA may comprise an amino acid sequence selected from the group comprising SEQ ID NO: 7-53. The TA may comprise an amino acid sequence that is at least about 50% homologous to an amino acid sequence selected from the group comprising SEQ ID NO: 7-53. The TA may comprise an amino acid sequence that is at least about 55%, 60%, 65%, 70%, 75%, 80%, 85%, 90%, 92%, 95%, 97%, 99%, or 100% homologous to an amino acid sequence selected from the group comprising SEQ ID NO: 7-53. The TA may comprise an amino acid sequence that is at least about 70% homologous to an amino acid sequence selected from the group comprising SEQ ID NO: 7-53. The TA may comprise an amino acid sequence that is at least about 75% homologous to an amino acid sequence selected from the group comprising SEQ ID NO: 7-53. The TA may comprise an amino acid sequence that is at least about 80% homologous to an amino acid sequence selected from the group comprising SEQ ID NO: 7-53.

The TA may comprise 10 or more consecutive amino acids from an amino acid sequence selected from the group comprising SEQ ID NO: 7-53. The TA may comprise 5, 6, 7, 8, 9, 10 or more consecutive amino acids from an amino acid sequence selected from the group comprising SEQ ID NO: 7-53.

The TA may comprise an amino acid sequence selected from the group comprising SEQ ID NO: 8-12. The TA may comprise an amino acid sequence that is at least about 50% homologous to an amino acid sequence selected from the group comprising SEQ ID NO: 8-12. The TA may comprise an amino acid sequence that is at least about 55%, 60%, 65%, 70%, 75%, 80%, 85%, 90%, 92%, 95%, 97%, 99%, or 100% homologous to an amino acid sequence selected from the group comprising SEQ ID NO: 8-12. The TA may comprise an amino acid sequence that is at least about 70% homologous to an amino acid sequence selected from the group comprising SEQ ID NO: 8-12. The TA may comprise an amino acid sequence that is at least about 75% homologous to an amino acid sequence selected from the group comprising SEQ ID NO: 8-12. The TA may comprise an amino acid sequence that is at least about 80% homologous to an amino acid sequence selected from the group comprising SEQ ID NO: 8-12.

The TA may comprise 10 or more consecutive amino acids from an amino acid sequence selected from the group comprising SEQ ID NO: 8-12. The TA may comprise 5, 6, 7, 8, 9, 10 or more consecutive amino acids from an amino acid sequence selected from the group comprising SEQ ID NO: 8-12.

The TA may comprise an amino acid sequence selected from the group comprising SEQ ID NO: 15-19. The TA may comprise an amino acid sequence that is at least about 50% homologous to an amino acid sequence selected from the group comprising SEQ ID NO: 15-19. The TA may comprise an amino acid sequence that is at least about 55%, 60%, 65%, 70%, 75%, 80%, 85%, 90%, 92%, 95%, 97%, 99%, or 100% homologous to an amino acid sequence selected from the group comprising SEQ ID NO: 15-19. The TA may comprise an amino acid sequence that is at least about 70% homologous to an amino acid sequence selected from the group comprising SEQ ID NO: 15-19. The TA may comprise an amino acid sequence that is at least about 75% homologous to an amino acid sequence selected from the group comprising SEQ ID NO: 15-19. The TA may comprise an amino acid sequence that is at least about 80% homologous to an amino acid sequence selected from the group comprising SEQ ID NO: 15-19.

The TA may comprise 10 or more consecutive amino acids from an amino acid sequence selected from the group comprising SEQ ID NO: 15-19. The TA may comprise 5, 6, 7, 8, 9, 10 or more consecutive amino acids from an amino acid sequence selected from the group comprising SEQ ID NO: 15-19.

The TA may comprise an amino acid sequence selected from the group comprising SEQ ID NO: 20-29. The TA may comprise an amino acid sequence that is at least about 50% homologous to an amino acid sequence selected from the group comprising SEQ ID NO: 20-29. The TA may comprise an amino acid sequence that is at least about 55%, 60%, 65%, 70%, 75%, 80%, 85%, 90%, 92%, 95%, 97%, 99%, or 100% homologous to an amino acid sequence selected from the group comprising SEQ ID NO: 20-29. The TA may comprise an amino acid sequence that is at least about 70% homologous to an amino acid sequence selected from the group comprising SEQ ID NO: 20-29. The TA may comprise an amino acid sequence that is at least about 75% homologous to an amino acid sequence selected from the group comprising SEQ ID NO: 20-29. The TA may comprise an amino acid sequence that is at least about 80% homologous to an amino acid sequence selected from the group comprising SEQ ID NO: 20-29.

The TA may comprise 10 or more consecutive amino acids from an amino acid sequence selected from the group comprising SEQ ID NO: 20-29. The TA may comprise 5, 6, 7, 8, 9, 10 or more consecutive amino acids from an amino acid sequence selected from the group comprising SEQ ID NO: 20-29.

The TA may comprise an amino acid sequence selected from the group comprising SEQ ID NO: 30-53. The TA may comprise an amino acid sequence that is at least about 50% homologous to an amino acid sequence selected from the group comprising SEQ ID NO: 30-53. The TA may comprise an amino acid sequence that is at least about 55%, 60%, 65%, 70%, 75%, 80%, 85%, 90%, 92%, 95%, 97%, 99%, or 100% homologous to an amino acid sequence selected from the group comprising SEQ ID NO: 30-53. The TA may comprise an amino acid sequence that is at least about 70% homologous to an amino acid sequence selected from the group comprising SEQ ID NO: 30-53. The TA may comprise an amino acid sequence that is at least about 75% homologous to an amino acid sequence selected from the group comprising SEQ ID NO: 30-53. The TA may comprise an amino acid sequence that is at least about 80% homologous to an amino acid sequence selected from the group comprising SEQ ID NO: 30-53.

The TA may comprise 10 or more consecutive amino acids from an amino acid sequence selected from the group comprising SEQ ID NO: 30-53. The TA may comprise 5, 6, 7, 8, 9, 10 or more consecutive amino acids from an amino acid sequence selected from the group comprising SEQ ID NO: 30-53.

The TA may comprise one or more cysteine residues. The one or more cysteine residues may be used for connecting the staple to the TA. The one or more cysteine residues may be used for connecting the lipid to the TA. The one or more cysteine residues may be used for connecting a first TA to a second TA. The one or more cysteine residues may be naturally occurring in the TA. Alternatively, the one or more cysteine residues are introduced into the TA. The one or more cysteine residues may be inserted into the TA. The one or more amino acid residues may replace one or more amino acid residues in the TA. Methods for amino acid substitution and/or insertion are known in the art.

The one or more TAs may comprise a polypeptide derivative. The polypeptide derivative may comprise at least a portion of a wild-type polypeptide comprising one or more amino acid mutations. The one or more amino acid mutations may comprise a deletion, substitution, addition or a combination thereof. The one or more amino acid mutations may comprise adding one or more amino acid residues to a wild-type polypeptide. The one or more amino acid mutations may comprise deletion of one or more amino acid residues of the wild-type polypeptide. The one or more amino acid mutations may comprise substitution of one or more amino acid residues of the wild-type polypeptide. The one or more amino acid mutations may comprise substituting one or more amino acid residues of the wild-type polypeptide with one or more cysteine residues. The one or more amino acid mutations may comprise substituting one or more amino acid residues of the wild-type polypeptide with one or more D-amino acid residues. The one or more amino acid residues of the wild-type polypeptide may comprise one or more alanines, methionines, arginines, serines, threonines, and tyrosines.

The one or more TAs may comprise a modified therapeutic peptide. Methods of modifying peptides are known in the art (see for example, Gentilucci L et al., 2010, *Curr Pharm Des*). Examples of peptide modifications include, but are not limited to, acetylation, phosphorylation, and methylation. The peptide modification may comprise a chemical modification. Peptide modifications may occur on the N-terminus of the peptide. Alternatively, or additionally, peptide modifications may occur on the C-terminus of the peptide. Peptide modifications may occur at one or more internal amino acids of the peptide. Peptide modifications may comprise replacing the carboxyl group at the C-terminus of the peptide. Peptide modifications may comprise modifying the carboxyl group at the C-terminus of the peptide. The carboxyl group at the C-terminus of the peptide may be modified to produce an amide group. The carboxyl group at the C-terminus of the peptide may be modified to produce an amine group.

The one or more staples of the PLC or mTA may be attached to two or more residues in the one or more TAs. The TA may comprise a fusion peptide. The two or more residues may be adjacent. The two or more residues may be non-adjacent. The two or more residues may be at least about 1 amino acid residue apart. The two or more residues may be at least about 2, 3, 4, 5 or more amino acid residues apart. The two or more residues may be at least about 4 amino acid residues apart. The two or more residues may be at least about 5 amino acid residues apart. The two or more residues may be at least about 6 amino acid residues apart. The two or more residues may be at least about 7 amino acid residues apart. The two or more residues may be at least about 8 amino acid residues apart. The two or more residues may be at least about 9 amino acid residues apart. The two or more residues may be at least about 10 amino acid residues apart. The two or more residues may be at least about 11 amino acid residues apart. The two or more residues may be at least about 12 amino acid residues apart. The two or more residues may be at least about 13 amino acid residues apart. The two or more residues may be at least about 14 amino acid residues apart. The two or more residues may be at least about 15 amino acid residues apart. The two or more residues may be at least about 4, 7, 11, or 14 amino acid residues apart. The two or more residues may be less than about 100 amino acid residues apart. The two or more residues may be less than about 90, 85, 80, 75, 70, 65, 60, 55 amino acid residues apart. The two or more residues may be less than about 50 amino acid residues apart. The two or more residues may be less than about 30 amino acid residues apart. The two or more residues may be less than about 20 amino acid residues apart.

The TAs may be from a mammal or non-mammal. The TAs may be from a human. Alternatively, the TAs may be from a goat, sheep, cow, rabbit, monkey, dog, cat or a combination thereof. The TAs may be from a reptile. The TAs may be from a snake or lizard. The TAs may be from an amphibian. The TAs may be from a frog or toad. The TAs may be from an avian. The TAs may be recombinant peptide.

Linker

The PLCs or mTAs disclosed herein may further comprise one or more linkers. The PLCs or mTAs disclosed herein may further comprise two or more linkers. The PLCs or mTAs disclosed herein may further comprise three or more linkers. The PLCs or mTAs disclosed herein may further comprise four or more linkers. The PLCs or mTAs disclosed herein may further comprise five or more linkers.

The one or more linkers may enable attachment of a lipid to a peptide conjugate. The one or more linkers may enable attachment of a lipid to a therapeutic agent. The one or more linkers may enable attachment of a lipid to a staple. The linker may enable attachment of a lipid to another lipid. The linker may enable attachment of a lipid to a chemical group comprising one or more polyethylene glycol subunits. The linker may enable attachment of a PEG to another PEG. The linker may enable attachment of a PEG to a therapeutic agent. The linker may enable attachment of a therapeutic agent to another therapeutic agent. The linker may be an amino acid. The linker may be an amino acid of the therapeutic agent. The linker may be a substituted amino acid of the therapeutic agent. The linker may be a cysteine. The linker may be an L-cysteine. The linker may be an ether or an amide. The linker may be a thioether. The linker may be a carbamate. The linker may be a Michael reaction adduct. The linker may link a PEG molecule to a lipid.

The linker may be formed by reaction of an amino acid on the peptide region with an electrophilic linker precursor. The linker may be formed by reaction of a cysteine on the peptide region with an electrophilic linker precursor. The electrophilic linker precursor may be a staple precursor compound, a lipid staple precursor, or a lipid derivative. The linker may be formed by reaction of a derivatizable functional group on the staple precursor compound with a lipid derivative to produce a lipid staple precursor. The linker may be formed by reaction of a derivatizable functional group on the staple already attached to the therapeutic agent with a lipid derivative.

The linker may be the product of a bioorthogonal reaction. The linker may be an oxime, a tetrazole, a Diels Alder adduct, a hetero Diels Alder adduct, an aromatic substitution reaction product, a nucleophilic substitution reaction product, an ester, an amide, a carbamate, or a Michael reaction product. The linker may be a metathesis reaction product, a metal-mediated cross-coupling reaction product, a radical polymerization product, an oxidative coupling product, an acyl-transfer reaction product, or a photo click reaction product.

Pharmacokinetics

Mechanisms by which the PLCs or mTAs positively influence pharmacokinetic or pharmacodynamic behavior include, but are not limited to, (i) preventing or mitigating in vivo proteolytic degradation or other activity-diminishing chemical modification of the therapeutic agent; (ii) improving half-life or other pharmacokinetic properties by reducing renal filtration, decreasing receptor-mediated clearance or increasing bioavailability; (iii) reducing toxicity; (iv) improving solubility; and/or (v) increasing biological activity and/or target selectivity of the therapeutic agent or unmodified therapeutic peptide.

The PLCs or mTAs may enhance one or more pharmacokinetic properties of a therapeutic agent (TA) when attached to the TA. The PLCs or mTAs disclosed herein may enhance the one or more pharmacokinetic properties of the TA by at least about 200% as measured by pharmacodynamics when compared to the TA or unmodified therapeutic peptide alone. The PLCs or mTAs disclosed herein may enhance the one or more pharmacokinetic properties of the TA by at least about 300%, 400%, 500%, 600%, 700%, 800%, 900%, 1000% as measured by pharmacodynamics when compared to the TA or unmodified therapeutic peptide alone.

The pharmacokinetic properties may comprise a half-life. The half-life of the PLC or mTA may be at least about two-fold longer compared to the half-life of the TA or unmodified therapeutic peptide alone. The half-life of the PLC or mTA disclosed herein may be at least about 3-fold, 4-fold, or 5-fold longer compared to the half-life of the TA or unmodified therapeutic peptide alone. The half-life of the PLC or mTA disclosed herein may be at least about 6-, 7-, 8-, 9-, 10-, 15-, 20-, 25-, 30-, 35-, 40-, 45-, or 50-fold longer compared to the half-life of the TA or unmodified therapeutic peptide alone.

In addition, the PLCs or mTAs may have positive effects on terms of increasing manufacturability, and/or reducing immunogenicity of the therapeutic agent, compared to an unconjugated form of the therapeutic agent or unmodified therapeutic peptide.

Therapeutic Use

Further disclosed herein are PLCs or mTAs for treating, alleviating, inhibiting and/or preventing one or more diseases and/or conditions. The disease and/or condition may be a chronic disease or condition. Alternatively, the disease and/or condition is an acute disease or condition. The disease or condition may be recurrent, refractory, accelerated, or in remission. The disease or condition may affect one or more cell types. The one or more diseases and/or conditions may be an autoimmune disease, inflammatory disease, or metabolic disease.

Disclosed herein are methods for treating a disease or condition in a subject in need thereof, the method comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. The two or more residues in the peptide region may comprise cysteine. The one or more TAs may comprise a GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (IBS), or psoriasis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Further disclosed herein are methods for treating a disease or condition in a subject in need thereof, the method comprising administering to the subject one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more lipids. The two or more residues in the peptide region may comprise cysteine. The one or more TAs may comprise GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (B S), or psoriasis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin. The additional therapeutic agent may be aspirin.

Further disclosed herein are methods of treating a disease or condition in a subject in need thereof, the method comprising administering to the subject one or more peptide lipid conjugates (PLCs) of Formula (II): PC-A$^1$-P$^1$-L, wherein PC is a peptide conjugate comprising (a) one or more peptide regions comprising one or more peptide therapeutic agents (TAs); and (b) one or more staples, wherein the staples connect two or more residues in the peptide region; A$^1$ is a chemical group linking PC and P$^1$; P$^1$ is a bond or -PEG-A$^2$-; PEG is a chemical group comprising one or more polyethylene glycol subunits; A$^2$ is a chemical group linking PEG and L; and L is a lipid. The two or more residues in the peptide region may comprise cysteine. The one or more TAs may comprise GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (IBS), or psoriasis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Disclosed herein are methods for treating a disease or condition in a subject in need thereof, the method comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise a GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof. The disease or condition may be a diabetes or obesity, or a medical condition associated with diabetes or obesity The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (IBS), or psoriasis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Further disclosed herein are methods for treating a disease or condition in a subject in need thereof, the method comprising administering to the subject one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise a GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (B S), or psoriasis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Further disclosed herein are methods of treating a disease or condition in a subject in need thereof, the method comprising administering to the subject one or more peptide lipid conjugates (PLCs) of Formula (III). At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise a GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (B S), or psoriasis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Further disclosed herein are methods of treating a disease or condition in a subject in need thereof, the method comprising administering to the subject one or more peptide lipid conjugates (PLCs) of Formula (IV). At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise a GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (B S), or psoriasis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Disclosed herein are methods for treating a disease or condition in a subject in need thereof, the method comprising administering to the subject one or more PLCs, wherein the one or more peptide lipid conjugates (PLCs) comprise (a) two or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise a GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (IBS), or psoriasis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Further disclosed herein are methods for treating a disease or condition in a subject in need thereof, the method comprising administering to the subject one or more PLCs, wherein the one or more peptide lipid conjugates (PLCs) comprise (a) two or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise a GLP-1, glucagon, oxyntomodulin, exendin-4, GLP-2, GIP, GLP1R and GCGR dual agonist, GLP1R and GIPR dual agonist, or GLP1R, GCGR and GIPR tri-agonist, or a derivative thereof. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (IBS), or psoriasis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Provided herein is a method of preventing or treating a metabolic disease or condition in a subject in need thereof comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise GLP-1, GLP-2, Exendin-4, exenatide, oxyntomodulin, glucagon, FGF21, a GLP-1R and GIPR dual agonist, a GLP-1R and GCGR dual agonist, or derivative thereof. The GLP-1 may be a human GLP-1. The FGF21 may be a human FGF21. The one or more lipids may comprise one or more sterols, sterol derivatives, bile acids, vitamin E derivatives, fatty di-acids, fatty acids, fatty amides, and fatty alcohols. The metabolic disease or condition may be diabetes. The metabolic disease or condition may be obesity. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a metabolic disease or condition in a subject in need thereof comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise GLP-1, GLP-2, Exendin-4, exenatide, oxyntomodulin, glucagon, FGF21, a GLP-1R and GIPR dual agonist, a GLP-1R and GCGR dual agonist, or derivative thereof. The GLP-1 may be a human GLP-1. The FGF21 may be a human FGF21. The one or more lipids may comprise one or more sterols, sterol derivatives, bile acids, vitamin E derivatives, fatty di-acids, fatty acids, fatty amides, and fatty alcohols. The metabolic disease or condition may be diabetes. The metabolic disease or condition may be obesity. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a metabolic disease or condition in a subject in need thereof comprising administering to the subject one or more PLCs, wherein the one or more peptide lipid conjugates (PLCs) comprise (a) two or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise GLP-1, GLP-2, Exendin-4, exenatide, oxyntomodulin, glucagon, FGF21, a GLP-1R and GIPR dual agonist, a GLP-1R and GCGR dual agonist, or derivative thereof. The GLP-1 may be a human GLP-1. The FGF21 may be a human FGF21. The one or more lipids may comprise one or more sterols, sterol derivatives, bile acids, vitamin E derivatives, fatty di-acids, fatty acids, fatty amides, and fatty alcohols. The metabolic disease or condition may be diabetes. The metabolic disease or condition may be obesity. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a metabolic disease or condition in a subject in need thereof comprising administering to the subject one or more peptide lipid conjugates (PLCs) of Formula (II), Formula (III), or Formula (IV). The one or more lipids may be attached to the one or more TAs. The one or more lipids may be attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more TAs may comprise GLP-1, GLP-2, Exendin-4, exenatide, oxyntomodulin, glucagon, FGF21, a GLP-1R and GIPR dual agonist, a GLP-1R and GCGR dual agonist, or derivative thereof. The GLP-1 may be a human GLP-1. The FGF21 may be a human FGF21. The one or more lipids may comprise one or more sterols, sterol derivatives, bile acids, vitamin E derivatives, fatty di-acids, fatty acids, fatty amides, and fatty alcohols. The metabolic disease or condition may be diabetes. The metabolic disease or condition may be obesity. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating NAFLD, NASH, or cardiovascular disease in a subject in need thereof comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates The one or more lipids may be attached to the one or more TAs. The one or more lipids may be attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more lipids may comprise one or more sterols, sterol derivatives, bile acids, vitamin E derivatives, fatty di-acids, fatty acids, fatty amides, and fatty alcohols. The one or more TAs may comprise GLP-1, GLP-2, Exendin-4, exenatide, oxyntomodulin, glucagon, a GLP-1R and GIPR dual agonist, a GLP-1R and GCGR dual agonist, or derivative thereof. The GLP-1 may be a human GLP-1.

Provided herein is a method of preventing or treating NAFLD, NASH, or cardiovascular disease in a subject in need thereof comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more staples. The one or more lipids may be attached to the one or more TAs. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more lipids may comprise one or more sterols, sterol derivatives, bile acids, vitamin E derivatives, fatty di-acids, fatty acids, fatty amides, and fatty alcohols. The one or more TAs may comprise GLP-1, GLP-2, Exendin-4, exenatide, oxyntomodulin, glucagon, a GLP-1R and GIPR dual agonist, a GLP-1R and GCGR dual agonist, or derivative thereof. The GLP-1 may be a human GLP-1.

Provided herein is a method of preventing or treating NAFLD, NASH, or cardiovascular disease in a subject in need thereof comprising administering to the subject one or more PLCs, wherein the one or more peptide lipid conjugates (PLCs) comprise (a) two or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The one or more lipids may be attached to the one or more TAs. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more lipids may comprise one or more sterols, sterol derivatives, bile acids, vitamin E derivatives, fatty di-acids, fatty acids, fatty amides, and fatty alcohols. The one or more TAs may comprise GLP-1, GLP-2, Exendin-4, exenatide, oxyntomodulin, glucagon, a GLP-1R and GIPR dual agonist, a GLP-1R and GCGR dual agonist, or derivative thereof. The GLP-1 may be a human GLP-1.

Provided herein is a method of preventing or treating NAFLD, NASH, or cardiovascular disease in a subject in need thereof comprising administering to the subject one or more peptide lipid conjugates (PLCs) of Formula (II), Formula (III), or Formula (IV). At least one of the two or more residues may comprise a cysteine. The two or more residues in the peptide region may comprise cysteine. In some instances, at least one of the two or more residues is not cysteine. In some instances, at least two of the two or more residues are not cysteine. The one or more lipids may comprise one or more sterols, sterol derivatives, bile acids, vitamin E derivatives, fatty di-acids, fatty acids, fatty amides, and fatty alcohols. The one or more lipids may comprise one or more sterols, sterol derivatives, bile acids, vitamin E derivatives, fatty di-acids, fatty acids, fatty amides, and fatty alcohols. The one or more TAs may comprise GLP-1, GLP-2, Exendin-4, exenatide, oxyntomodulin, glucagon, a GLP-1R and GIPR dual agonist, a GLP-1R and GCGR dual agonist, or derivative thereof. The GLP-1 may be a human GLP-1.

Provided herein is a method of preventing or treating a disease or condition which benefits from a GLP-1R and/or glucagon receptor (GCGR) agonist in a subject in need thereof comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more lipids may comprise one or more sterols, sterol derivatives, bile acids, vitamin E derivatives, fatty di-acids, fatty acids, fatty amides, and fatty alcohols. The one or more TAs may comprise GLP-1, GLP-2, Exendin-4, exenatide, oxyntomodulin, glucagon, a GLP-1R and GIPR dual agonist, a GLP-1R and GCGR dual agonist, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases.

Provided herein is a method of preventing or treating a disease or condition which benefits from a GLP-1R and/or glucagon receptor (GCGR) agonist in a subject in need thereof comprising administering to the subject one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more staples. The one or more lipids may be attached to the one or more TAs. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more lipids may comprise one or more sterols, sterol derivatives, bile acids, vitamin E derivatives, fatty di-acids, fatty acids, fatty amides, and fatty alcohols. The one or more TAs may comprise GLP-1, GLP-2, Exendin-4, exenatide, oxyntomodulin, glucagon, a GLP-1R and GIPR dual agonist, a GLP-1R and GCGR dual agonist, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases.

Provided herein is a method of preventing or treating a disease or condition which benefits from a GLP-1R and/or glucagon receptor (GCGR) agonist in a subject in need thereof comprising administering to the subject one or more PLCs, wherein the one or more peptide lipid conjugates (PLCs) comprise (a) two or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The one or more lipids may comprise one or more sterols, sterol derivatives, bile acids, vitamin E derivatives, fatty di-acids, fatty acids, fatty amides, and fatty alcohols. The one or more TAs may comprise GLP-1, GLP-2, Exendin-4, exenatide, oxyntomodulin, glucagon, a GLP-1R and GIPR dual agonist, a GLP-1R and GCGR dual agonist, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases.

Provided herein is a method of preventing or treating a disease or condition which benefits from a GLP-1R and/or glucagon receptor (GCGR) agonist in a subject in need thereof comprising administering to the subject one or more peptide lipid conjugates (PLCs) of Formula (II), Formula (III), or Formula (IV). At least one of the two or more residues may comprise a cysteine. The two or more residues in the peptide region may comprise cysteine. In some instances, at least one of the two or more residues is not cysteine. In some instances, at least two of the two or more residues are not cysteine. The one or more lipids may comprise one or more sterols, sterol derivatives, bile acids, vitamin E derivatives, fatty di-acids, fatty acids, fatty amides, and fatty alcohols. The one or more lipids may comprise one or more sterols, sterol derivatives, bile acids, vitamin E derivatives, fatty di-acids, fatty acids, fatty amides, and fatty alcohols. The one or more TAs may comprise GLP-1, GLP-2, Exendin-4, exenatide, oxyntomodulin, glucagon, a GLP-1R and GIPR dual agonist, a GLP-1R and GCGR dual agonist, or derivative thereof. The GLP-1 may be a human GLP-1. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases.

Disclosed herein are methods of treating a disease or condition in a subject in need thereof, the method comprising administering to the subject a composition disclosed herein comprising one or more mTAs.

Further disclosed herein are methods of treating a disease or condition in a subject in need thereof, the method comprising administering to the subject a composition comprising a mTA, wherein the mTA comprises a therapeutic agent (TA), a staple, and a half-life extending molecule (HEM). The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be short bowel syndrome (SBS). The disease or condition may be inflammatory bowel disease (IBD), inflammatory bowel syndrome (IBS), or psoriasis. The disease or condition may be Crohn's disease or ulcerative colitis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Further disclosed herein are methods for treating a disease or condition in a subject in need thereof, the method comprising administering to the subject one or more mTAs, wherein each of the one or more mTAs comprise a therapeutic agent (TA), a staple, and a half-life extending molecule (HEM). The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be short bowel syndrome (SBS). The disease or condition may be inflammatory bowel disease (IBD), inflammatory bowel syndrome (IBS), or psoriasis. The disease or condition may be Crohn's disease or ulcerative colitis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Further disclosed herein are methods of treating a disease or condition in a subject in need thereof, the method comprising administering to the subject one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be short bowel syndrome (SBS). The disease or condition may be inflammatory bowel disease (IBD), inflammatory bowel syndrome (IBS), or psoriasis. The disease or condition may be Crohn's disease or ulcerative colitis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Further disclosed herein are methods of treating a disease or condition in a subject in need thereof, the method comprising administering to the subject one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide and the first HEM is covalently attached to the first staple. The disease or condition may be a diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be short bowel syndrome (SBS). The disease or condition may be inflammatory bowel disease (IBD), inflammatory bowel syndrome (IBS), or psoriasis. The disease or condition may be Crohn's disease or ulcerative colitis. The disease or condition may be Alzheimer's disease, Parkinson's disease or Huntington's disease. The PLC may be administered with one or more additional therapeutic agents. The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

Provided herein is a method of preventing or treating a metabolic disease or condition in a subject in need thereof, the method comprising administering to the subject a composition disclosed herein comprising one or more mTAs.

Provided herein is a method of preventing or treating a metabolic disease or condition in a subject in need thereof comprising administering to the subject one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide and the first HEM is covalently attached to the first staple. The metabolic disease or condition may be diabetes. The metabolic disease or condition may be obesity. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating NAFLD, NASH, or cardiovascular disease in a subject in need thereof, the method comprising administering to the subject a composition disclosed herein comprising one or more mTAs.

Provided herein is a method of preventing or treating NAFLD, NASH, or cardiovascular disease in a subject in need thereof comprising administering to the subject one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide and the first HEM is covalently attached to the first staple.

Provided herein is a method of preventing or treating short bowel syndrome (SBS) in a subject in need thereof, the method comprising administering to the subject a composition disclosed herein comprising one or more mTAs.

Provided herein is a method of preventing or treating short bowel syndrome (SBS) in a subject in need thereof comprising administering to the subject one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide and the first HEM is covalently attached to the first staple.

Provided herein is a method of preventing or treating inflammatory bowel disease (IBD), inflammatory bowel syndrome (IBS), or psoriasis in a subject in need thereof, the method comprising administering to the subject a composition disclosed herein comprising one or more mTAs.

Provided herein is a method of preventing or treating inflammatory bowel disease (IBD), inflammatory bowel syndrome (IBS), or psoriasis in a subject in need thereof comprising administering to the subject one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide and the first HEM is covalently attached to the first staple.

Provided herein is a method of preventing or treating Crohn's disease or ulcerative colitis in a subject in need thereof, the method comprising administering to the subject a composition disclosed herein comprising one or more mTAs.

Provided herein is a method of preventing or treating Crohn's disease or ulcerative colitis in a subject in need thereof comprising administering to the subject one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide and the first HEM is covalently attached to the first staple.

Provided herein is a method of preventing or treating Alzheimer's disease, Parkinson's disease or Huntington's disease in a subject in need thereof, the method comprising administering to the subject a composition disclosed herein comprising one or more mTAs.

Provided herein is a method of preventing or treating Alzheimer's disease, Parkinson's disease or Huntington's disease in a subject in need thereof comprising administering to the subject one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide and the first HEM is covalently attached to the first staple.

Provided herein is a method of preventing or treating a disease or condition which benefits from a GLP-1R and/or glucagon receptor (GCGR) agonist in a subject in need thereof comprising administering to the subject one or more mTAs disclosed herein.

Provided herein is a method of preventing or treating a disease or condition which benefits from a GLP-1R and/or glucagon receptor (GCGR) agonist in a subject in need thereof comprising administering to the subject one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide and the first HEM is covalently attached to the first staple. The disease or condition may be a metabolic disease or disorder. The disease or condition may be diabetes. The disease or condition may be obesity. Additional diseases and/or conditions which benefit from a GLP-1R and/or GCGR agonist include, but are not limited to, dyslipidemia, cardiovascular and fatty liver diseases.

Compositions

Disclosed herein are pharmaceutical compositions comprising a PLC disclosed herein. The compositions may comprise 1, 2, 3, 4, 5, 6, 7, 8, 9, 10 or more PLCs. The PLCs may be different. Alternatively, the PLCs may be the same or similar. The compositions may comprise 1, 2, 3, 4, 5, 6, 7, 8, 9, 10 or more PLCs. The PLCs may be different. The PLCs may comprise different therapeutic agents, different lipids, or a combination thereof. The PLCs may be the same or similar.

Disclosed herein are pharmaceutical compositions comprising a mTA disclosed herein. The compositions may comprise 1, 2, 3, 4, 5, 6, 7, 8, 9, 10 or more mTAs. The mTAs may be different. Alternatively, the mTAs may be the same or similar. The compositions may comprise 1, 2, 3, 4, 5, 6, 7, 8, 9, 10 or more mTAs. The mTAs may be different. The mTAs may comprise different therapeutic agents, different HEMs, or a combination thereof. The mTAs may be the same or similar.

Further disclosed herein are compositions comprising one or more mTAs, wherein each of the one or more mTAs comprises a therapeutic agent (TA), a staple, and a half-life extending molecule (HEM). The TA may be a modified or unmodified therapeutic peptide. The TA may be covalently attached to the staple via two amino acid residues on the modified or unmodified therapeutic peptide. At least one of the two amino acid residues may comprise a cysteine. The composition may further comprise one or more pharmaceutically acceptable salts, excipients or vehicles.

Further disclosed herein are compositions comprising one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide. At least one of the two amino acid residues may comprise a cysteine. The first HEM may be covalently attached to the first staple. The first HEM may be covalently attached to the TA. The composition may further comprise one or more pharmaceutically acceptable salts, excipients or vehicles.

Further disclosed herein are compositions comprising one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide and the first HEM is covalently attached to the first staple. At least one of the two amino acid residues may comprise a cysteine. The composition may further comprise one or more pharmaceutically acceptable salts, excipients or vehicles.

Further disclosed herein are compositions comprising one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide; the unmodified therapeutic peptide is selected from GLP-1, glucagon, oxyntomodulin, exendin-4, GLP-2, and GIP; the modified therapeutic peptide is a derivative of a peptide selected from GLP-1, glucagon, oxyntomodulin, exendin-4, GLP-2, and GIP, the derivative being a peptide comprising one or more amino acid additions, deletions, or substitutions, or a combination thereof, and the first HEM is covalently attached to the first staple. At least one of the two amino acid residues may comprise a cysteine. The composition may further comprise one or more pharmaceutically acceptable salts, excipients or vehicles.

Further disclosed herein are compositions comprising one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide; the first HEM is covalently attached to the first staple; and the first HEM comprises a lipid, a polyglycol region, or a combination thereof. At least one of the two amino acid residues may comprise a cysteine. The composition may further comprise one or more pharmaceutically acceptable salts, excipients or vehicles.

Further disclosed herein are compositions comprising one or more mTAs, wherein each of the one or more mTAs comprises a therapeutic agent (TA), a first staple, and a first half-life extending molecule (HEM); wherein the therapeutic agent is a modified or unmodified therapeutic peptide that is covalently attached to the first staple via two amino acid residues on the modified or unmodified therapeutic peptide; the unmodified therapeutic peptide is selected from GLP-1, glucagon, oxyntomodulin, exendin-4, GLP-2, and GIP; the modified therapeutic peptide is a derivative of a peptide selected from GLP-1, glucagon, oxyntomodulin, exendin-4, GLP-2, and GIP, the derivative being a peptide comprising one or more amino acid additions, deletions, or substitutions, or a combination thereof; the first HEM is covalently attached to the first staple; and the first HEM comprises a lipid, a polyglycol region, or a combination thereof. At least one of the two amino acid residues may comprise a cysteine. The composition may further comprise one or more pharmaceutically acceptable salts, excipients or vehicles.

Disclosed herein are compositions comprising one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The composition may further comprise one or more pharmaceutically acceptable salts, excipients or vehicles.

Further disclosed herein are compositions comprising one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more peptide conjugates. The one or more lipids may be attached to the one or more TAs. The one or more lipids may be attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The composition may further comprise one or more pharmaceutically acceptable salts, excipients or vehicles.

Further disclosed herein are compositions comprising one or more PLCs, wherein the one or more peptide lipid conjugates (PLCs) comprise (a) one or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, a GLP-1R and GIPR dual agonist, a GLP-1R and GCGR dual agonist, or glucagon, wherein the one or more lipids are attached to the one or more peptide conjugates. The one or more lipids may be attached to the one or more TAs. The one or more lipids may be attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The composition may further comprise one or more pharmaceutically acceptable salts, excipients or vehicles.

Disclosed herein are compositions comprising one or more PLCs, wherein the one or more peptide lipid conjugates (PLCs) comprise (a) one or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein the one or more lipids are attached to the one or more staples. The one or more lipids may be attached to the one or more TAs. At least one of the two or more residues may comprise a cysteine. The two or more residues in the peptide region may comprise cysteine. In some instances, at least one of the two or more residues is not cysteine. In some instances, at least two of the two or more residues are not cysteine. The composition may further comprise one or more pharmaceutically acceptable salts, excipients or vehicles.

Further disclosed herein are compositions comprising one or more PLCs, wherein the one or more peptide lipid conjugates (PLCs) comprise (a) one or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein the one or more lipids are attached to the one or more staples. The one or more lipids may be attached to the one or more TAs. At least one of the two or more residues may comprise a cysteine. The two or more residues in the peptide region may comprise cysteine. In some instances, at least one of the two or more residues is not cysteine. In some instances, at least two of the two or more residues are not cysteine. The composition may further comprise one or more pharmaceutically acceptable salts, excipients or vehicles.

Further disclosed herein are compositions comprising one or more PLCs, wherein the one or more peptide lipid conjugates (PLCs) comprise (a) one or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, a GLP-1R and GIPR dual agonist, a GLP-1R and GCGR dual agonist, or glucagon, wherein the one or more lipids are attached to the one or more staples. The one or more lipids may be attached to the one or more TAs. The one or more lipids may be attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine. The composition may further comprise one or more pharmaceutically acceptable salts, excipients or vehicles.

Disclosed herein are compositions comprising one or more PLCs, wherein the one or more peptide lipid conjugates (PLCs) comprise (a) two or more lipids; and (b) one or more peptide conjugates (PC), the peptide conjugate (PC) comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The one or more lipids may be attached to the one or more TAs. At least one of the two or more residues may comprise a cysteine. The two or more residues in the peptide region may comprise cysteine. In some instances, at least one of the two or more residues is not cysteine. In some instances, at least two of the two or more residues are not cysteine. The composition may further comprise one or more pharmaceutically acceptable salts, excipients or vehicles.

Further disclosed herein are compositions comprising one or more PLCs, wherein the one or more peptide lipid conjugates (PLCs) comprise (a) two or more lipids, the lipids selected from a group consisting of sterols, sterol derivatives, bile acids, vitamin E derivatives, fatty di-acids, fatty acids, fatty amides, and fatty alcohols; and (b) one or more peptide conjugates (PC), the peptide conjugate comprising a peptide region comprising one or more peptide therapeutic agents (TA) and a staple region comprising one or more staples, the one or more staples connect two or more residues in the peptide region, wherein at least one of the two or more lipids are attached to the one or more therapeutic agents and at least one of the two or more lipids are attached to the one or more staples. The one or more lipids may be attached to the one or more TAs. At least one of the two or more residues may comprise a cysteine. The two or more residues in the peptide region may comprise cysteine. In some instances, at least one of the two or more residues is not cysteine. In some instances, at least two of the two or more residues are not cysteine. The composition may further comprise one or more pharmaceutically acceptable salts, excipients or vehicles.

Further disclosed herein are compositions comprising one or more PLCs, wherein the one or more peptide lipid conjugates (PLCs) comprise (a) two or more lipids; and (b) one or more peptide conjugates (PC), wherein the peptide conjugate comprising a peptide region comprising one or more peptide therapeutic agents (TA) and a staple region comprising one or more staples, the one or more staples connect two or more residues in the peptide region, the one or more peptide therapeutic agents comprising one or more oxyntomodulin, exenatide, exendin-4, glucagon-like protein-1 (GLP-1), GLP-2, a GLP-1R and GIPR dual agonist, a GLP-1R and GCGR dual agonist, or glucagon, wherein at least one of the two or more lipids are attached to the one or more therapeutic agents and at least one of the two or more lipids are attached to the one or more staples. The one or more lipids may be attached to the one or more TAs. At least one of the two or more residues may comprise a cysteine. The two or more residues in the peptide region may comprise cysteine. In some instances, at least one of the two or more residues is not cysteine. In some instances, at least two of the two or more residues are not cysteine. The composition may further comprise one or more pharmaceutically acceptable salts, excipients or vehicles.

Further disclosed herein are compositions comprising one or more peptide lipid conjugates (PLCs) of Formula (II), Formula (III), or Formula (IV). The one or more lipids may be attached to the one or more TAs. The one or more lipids may be attached to the one or more staples. At least one of the two or more residues may comprise a cysteine. The two or more residues in the peptide region may comprise cysteine. In some instances, at least one of the two or more residues is not cysteine. In some instances, at least two of the two or more residues are not cysteine.

The compositions disclosed herein may further comprise one or more pharmaceutically acceptable salts, excipients or vehicles. Pharmaceutically acceptable salts, excipients, or vehicles may include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically may be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions can include the formulation of mTAs, PLCs, polypeptides, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies comprising an ultralong CDR3). See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141).

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxyethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which a PLC, mTA, nucleic acid, or vector disclosed herein has been absorbed or encapsulated. Where an implantation device is used, the device may be implanted into any suitable tissue or organ, and delivery of an antibody comprising an ultralong CDR3 antibody fragment, nucleic acid, or vector disclosed herein can be directly through the device via bolus, or via continuous administration, or via catheter using continuous infusion.

A pharmaceutical composition comprising a PLC, mTA, nucleic acid, or vector disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 µm to 5 µm; however, larger particles may be used, for example, if each particle is fairly porous.

Certain formulations containing antibodies comprising a PLC, mTA, nucleic acid, or vector disclosed herein may be administered orally. Formulations administered in this fashion may be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also can be employed.

Another preparation may involve an effective quantity of an antibody comprising a PLC, mTA, nucleic acid, or vector disclosed herein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

Vectors, Host Cells and Recombinant Methods

A TA, as disclosed herein, may be expressed by recombinant methods. Generally, a nucleic acid encoding a TA may be isolated and inserted into a replicable vector for further cloning (amplification of the DNA) or for expression. DNA encoding the TA may be prepared by PCR amplification and sequenced using conventional procedures (e.g., by using oligonucleotide probes that are capable of binding specifically to nucleotides encoding a TA). In an exemplary embodiment, nucleic acid encoding a TA is PCR amplified, restriction enzyme digested and gel purified. The digested DNA may be inserted into a replicable vector. The replicable vector containing the digested DNA insertion may be transformed or transduced into a host cell for further cloning (amplification of the DNA) or for expression. Host cells may be prokaryotic or eukaryotic cells.

Polynucleotide sequences encoding polypeptide components of the mTAs or PLCs disclosed herein may be obtained by PCR amplification with overlapping oligonucleotide primers. Polynucleotide sequences may be isolated and sequenced from TA producing cells. Alternatively, polynucleotides may be synthesized using nucleotide synthesizer or PCR techniques. Once obtained, sequences encoding the polypeptides are inserted into a recombinant vector capable of replicating and expressing heterologous polynucleotides in prokaryotic and/or eukaryotic hosts.

In addition, phage vectors containing replicon and control sequences that are compatible with the host microorganism may be used as transforming vectors in connection with these hosts. For example, bacteriophage such as λGEM™-11 may be utilized in making a recombinant vector which can be used to transform susceptible host cells such as *E. coli* LE392.

TAs may be expressed in intracellularly (e.g., cytoplasm) or extracellularly (e.g., secretion). For extracellular expression, the vector may comprise a secretion signal which enables translocation of the TA to the outside of the cell.

Suitable host cells for cloning or expression of TA-encoding vectors include prokaryotic or eukaryotic cells. The host cell may be a eukaryotic. Examples of eukaryotic cells include, but are not limited to, Human Embryonic Kidney (HEK) cell, Chinese Hamster Ovary (CHO) cell, fungi, yeasts, invertebrate cells (e.g., plant cells and insect cells), lymphoid cell (e.g., YO, NSO, Sp20 cell). Other examples of suitable mammalian host cell lines are monkey kidney CV1 line transformed by SV40 (COS-7); baby hamster kidney cells (BHK); mouse Sertoli cells; monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (HepG2); mouse mammary tumor (MMT 060562); TR1 cells; MRC 5 cells; and FS4 cells. The host cell may be a prokaryotic cell (e.g., *E. coli*).

Host cells may be transformed with vectors containing nucleotides encoding a TA. Transformed host cells may be cultured in media. The media may be supplemented with one or more agents for inducing promoters, selecting transformants, or amplifying or expressing the genes encoding the desired sequences. Methods for transforming host cells are known in the art and may include electroporation, calcium chloride, or polyethylene glycol/DMSO.

Alternatively, host cells may be transfected or transduced with vectors containing nucleotides encoding a TA. Transfected or transduced host cells may be cultured in media. The media may be supplemented with one or more agents for inducing promoters, selecting transfected or transduced cells, or expressing genes encoding the desired sequences.

The expressed TAs may be secreted into and recovered from the periplasm of the host cells or transported into the culture media. Protein recovery from the periplasm may involve disrupting the host cell. Disruption of the host cell may comprise osmotic shock, sonication or lysis. Centrifugation or filtration may be used to remove cell debris or whole cells. The TAs may be further purified, for example, by affinity resin chromatography.

Alternatively, TAs that are secreted into the culture media may be isolated therein. Cells may be removed from the culture and the culture supernatant being filtered and concentrated for further purification of the proteins produced.

The expressed polypeptides can be further isolated and identified using commonly known methods such as polyacrylamide gel electrophoresis (PAGE) and Western blot assay.

TA production may be conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (a preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the TAs disclosed herein, various fermentation conditions can be modified. For example, to improve the proper assembly and folding of the secreted TA polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) may be used to co-transform the host prokaryotic cells. The chaperone proteins have been demonstrated to facilitate the proper folding and solubility of heterologous proteins produced in bacterial host cells.

To minimize proteolysis of expressed heterologous proteins (especially those that are proteolytically sensitive), certain host strains deficient for proteolytic enzymes can be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some $E.$ $coli$ protease-deficient strains are available.

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, hydroxylapatite chromatography, gel electrophoresis, dialysis, and affinity chromatography and gel filtration using, for example, Sephadex G-75.

TAs may be concentrated using a commercially available protein concentration filter, for example, an Amicon or Millipore Pellicon® ultrafiltration unit.

Protease inhibitors or protease inhibitor cocktails may be included in any of the foregoing steps to inhibit proteolysis of the TA.

In some cases, a TA or fragment thereof may not be biologically active upon isolation. Various methods for "refolding" or converting a polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cystein/cystamine, glutathione (GSH)/dithiobis GSH, cupric chloride, dithiothreitol(DTT)/dithiane DTT, and 2-mercaptoethanol(bME)/di-thio-b(ME). In many instances, a cosolvent may be used to increase the efficiency of the refolding, and common reagents used for this purpose include glycerol, polyethylene glycol of various molecular weights, arginine and the like.

Kits/Articles of Manufacture

As an additional aspect, the present disclosure includes kits which comprise one or more compounds or compositions packaged in a manner which facilitates their use to practice methods of the present disclosure. In one embodiment, such a kit includes a compound or composition described herein (e.g. a PLC or mTA alone or in combination with a second agent), packaged in a container with a label affixed to the container or a package insert that describes use of the compound or composition in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The article of manufacture may comprise (a) a first container with a composition contained therein, wherein the composition comprises a PLC or mTA as disclosed herein; and (b) a second container with a composition contained therein, wherein the composition comprises a further therapeutic agent. The article of manufacture in this embodiment disclosed herein may further comprise a package insert indicating that the first and second compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. Preferably, the compound or composition is packaged in a unit dosage form. The kit may further include a device suitable for administering the composition according to a specific route of administration or for practicing a screening assay. Preferably, the kit contains a label that describes use of the PLC or mTA composition.

In certain embodiments, the composition comprising the antibody is formulated in accordance with routine procedures as a pharmaceutical composition adapted for intravenous administration to mammals, such as humans, bovines, felines, canines, and murines. Typically, compositions for intravenous administration are solutions in sterile isotonic aqueous buffer. Where necessary, the composition may also include a solubilising agent and a local anaesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the composition described herein which will be effective in the treatment, inhibition and prevention of a disease or disorder associated with aberrant expression and/or activity of a Therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

Definitions

The terms below, as used herein, have the following meanings, unless indicated otherwise:

"Amino" refers to the —NH$_2$ radical.

"Hydroxy" or "hydroxyl" refers to the —OH radical.

"Nitro" refers to the —NO$_2$ radical.

"Oxo" refers to the =O substituent.

"Oxime" refers to the =N—OH substituent.

"Alkyl" refers to a straight or branched hydrocarbon chain radical, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, vinyl, allyl, propynyl, and the like. Alkyl comprising unsaturations include alkenyl and alkynyl groups. Unless stated otherwise specifically in the specification, an alkyl group may be optionally substituted as described below.

"Alkylene" or "alkylene chain" refers to a straight or branched divalent hydrocarbon chain, as described for alkyl above. Unless stated otherwise specifically in the specification, an alkylene group may be optionally substituted as described below.

"Alkoxy" refers to a radical of the formula —OR$_a$ where R$_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, ace- phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted. Illustrative examples of cycloalkyl groups include, but are not limited to, the following moieties:

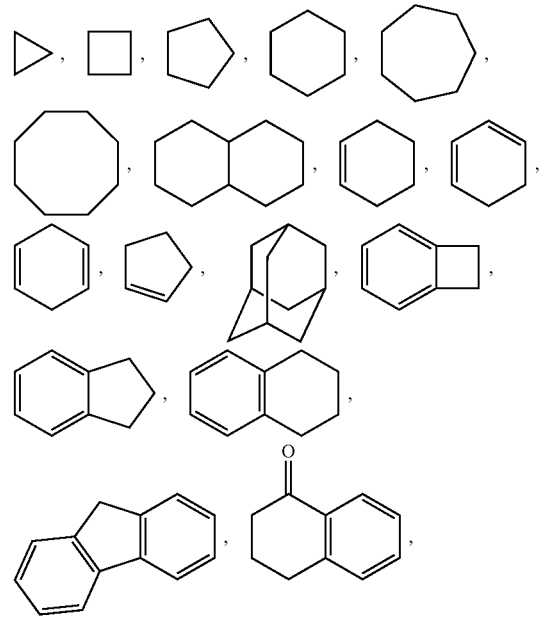

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —$OR_a$ where $R_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4,15-crown-5,18-crown-6,21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

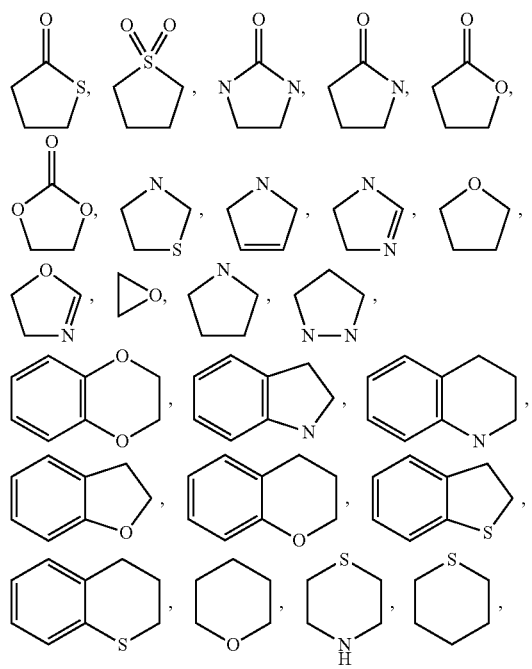

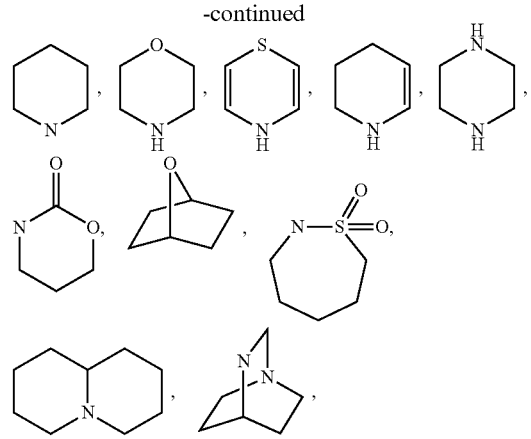

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, azepinyl, phenazinyl, benzimidazolyl, benzindolyl, benzofuranyl, benzofuranonyl, benzoxazolyl, benzothiazolyl, benzothiadiazolyl, benzothiophenyl, benzoxadiazolyl, benzodioxolyl, benzo[b][1,4]dioxepinyl, 1,4-benzodioxanyl, benzonaphthofuranyl, benzotriazolyl, benzodioxolyl, benzodioxinyl, benzopyranyl, benzopyranonyl, benzothienyl (benzothiophenyl), benzo[4,6]imidazo[1,2-a]pyridinyl, carbazolyl, cinnolinyl, dibenzofuranyl, dibenzothiophenyl, furanonyl, imidazolyl, indolyl, isoxazolyl, isoquinolinyl, indolizinyl, indazolyl, isoindolyl, indolinyl, isoindolinyl, indolizinyl, isothiazolyl, isoindolyloxadiazolyl, indazolyl, naphthyridinyl, oxadiazolyl, 2-oxoazepinyl, oxiranyl, 1-oxidopyridinyl, 1-oxidopyrimidinyl, 1-oxidopyrazinyl, 1-oxidopyridazinyl, 1-phenyl-1H-pyrrolyl, phenothiazinyl, phenoxazinyl, pyridinyl, pyridazinyl, pyrimidinyl, pyrazinyl, pyrrolyl, pyrazinyl, pyrazolyl, purinyl, phthalazinyl, pteridinyl, quinolinyl, quinazolinyl, quinoxalinyl, quinuclidinyl, triazolyl, tetrazolyl, thiazolyl, triazinyl, thiadiazolyl, tetrahydroquinolinyl, thiazolyl, and thiophenyl and the like, and their oxides, such as for example pyridyl-N-oxide. Illustrative examples of heteroaryl groups include the following moieties:

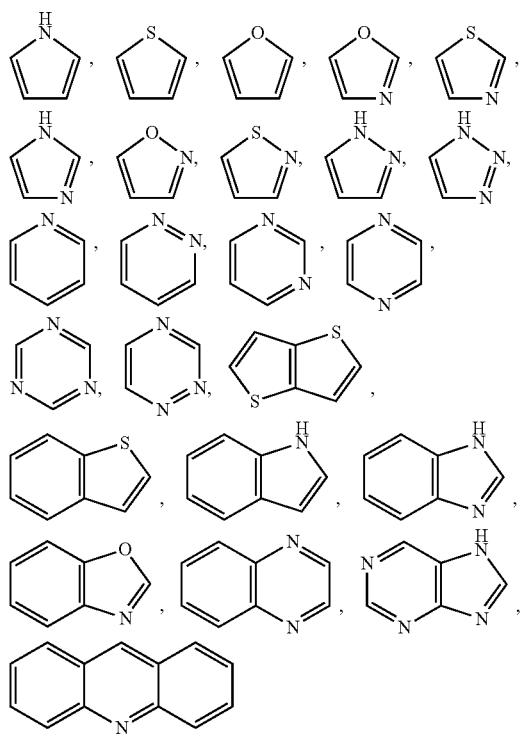

and the like.

All the above groups may be either substituted or unsubstituted. The term "substituted" as used herein means any of the above groups (e.g., alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —CO$_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NH$_2$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

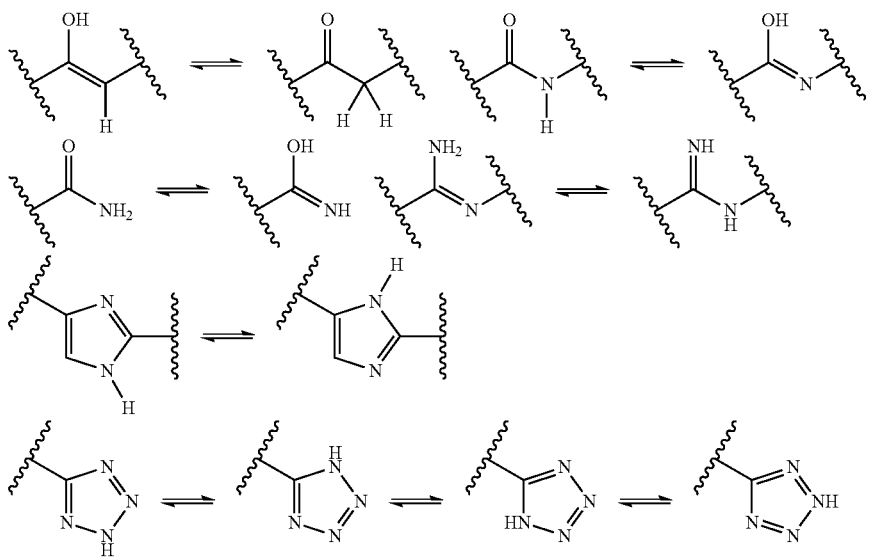

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. Metabolites of a compound may be formed by oxidative processes and correspond to the corresponding hydroxy-containing compound. A compound may be metabolized to one or more pharmacologically active metabolites.

As used herein, a derivative of a peptide refers to, but is not limited to, a modified peptide that allows for staple and/or HEM attachment (such as one or more amino acid residue replacements or L- vs D-amino acid replacements), a fragment, an analog with one or more additional amino acids, a complex and/or an aggregate of the peptide. A derivative of a peptide may be a homolog that has at least 50% homology with respect to the peptide. A derivative of a peptide may be a homolog that has at least 60% homology with respect to the peptide. A derivative of a peptide may be a homolog that has at least 70% homology with respect to the peptide. A derivative of a peptide may be a homolog that has at least 80% homology with respect to the peptide. A derivative of a peptide may be a homolog that has at least 90% homology with respect to the peptide.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that may be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

Terms such as "treating" or "treatment" or "to treat" or "alleviating" or "to alleviate" may refer to: 1) therapeutic measures that cure, slow down, lessen symptoms of, and/or halt progression of a diagnosed pathologic condition or disorder; and/or 2) prophylactic or preventative measures that prevent and/or slow the development of a targeted pathologic condition or disorder. "Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. Thus those in need of treatment may include those already with the disorder; those prone to have the disorder; and those in whom the disorder is to be prevented.

"Amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

As used herein, the term "therapeutic agent" or "peptide therapeutic agent" or "therapeutic peptide" refers to a protein or peptide that modulates the activity of another protein, peptide, cell or tissue. Modulating the activity can comprise increasing, decreasing, stimulating, or preventing the activity or expression of the protein, peptide, cell or tissue. Therapeutic agents may modulate the activity of proteins or peptides involved in the etiology of a disease or disorder. Exemplary TAs may include, but are not limited to, at least a portion of a hormone, kinase, receptor, ligand, growth factor, regulatory protein, metabolic protein, cytokine, chemokine, interferon, phosphatase, antibody or any combination thereof.

"Disorder" or "disease" refers to a condition that would benefit from treatment with a substance/molecule (e.g., a mTA or PLC as disclosed herein) or method disclosed herein. This includes chronic and acute disorders or diseases including those pathological conditions which predispose the mammal to the disorder in question.

"Mammal" for purposes of treatment refers to any animal classified as a mammal, including humans, rodents (e.g., mice and rats), and monkeys; domestic and farm animals; and zoo, sports, laboratory, or pet animals, such as dogs, cats, cattle, horses, sheep, pigs, goats, rabbits, etc. In some embodiments, the mammal is selected from a human, rodent, or monkey.

EXAMPLES

Example 1. Synthesis of Exemplary Lipid Derivatives (Scheme A)

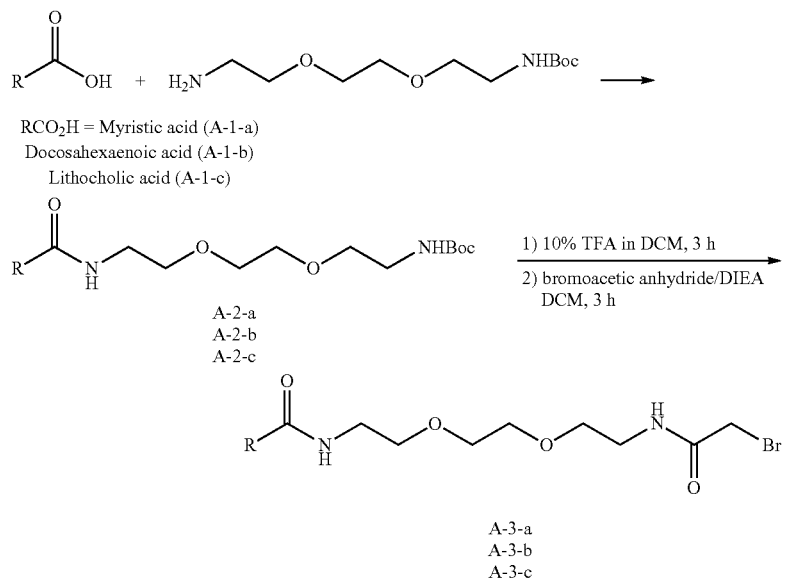

tert-Butyl (2-(2-(2-tetradecanamidoethoxy)ethoxy)ethyl) carbamate (A-2-a).

N-t-Boc-amido-dPEG3-amine (0.5 g, 2.0 mmol) was added to a solution of myristic acid (0.46 g, 2.0 mmol) in 10 ml of dry DMF, followed by HATU (0.8 g, 2.1 mmol) and DIEA (0.45 mL, 2.4 mmol). The mixture was stirred at RT for 6 h and the solvent was evaporated in vacuo. The crude material was dissolved in EtOAc, washed with cold 1% HCl, saturated NaHCO$_3$ and brine, dried over Na$_2$SO$_4$, filtered and concentrated. The crude material was purified by flash column chromatography on silica gel with a gradient 25-50% EtOAc in hexanes to afford 0.83 g of desired compound as a white solid (Yield 90%). m/z (ESI+) 459.6 (M+H).

tert-Butyl (2-(2-(2-((4Z,7Z,10Z,13Z,16Z,19Z)-docosa-4,7,10,13,16,19-hexaenamido)ethoxy)ethoxy)ethyl)carbamate (A-2-b).

The title compound was prepared using analogous conditions as the procedure for A-2-a, using N-t-Boc-amido-dPEG3-amine (0.25 g, 1.0 mmol), docosahexaenoic acid (0.33 g, 1.0 mmol), HATU (0.41 g, 1.1 mmol) and DIEA (0.22 mL, 1.2 mmol in dry DMF (5 mL). Yield 68%, brown oil. $^1$H NMR (500 MHz; CDCl$_3$): δ 0.97 (t, J=6.0 Hz, 3H), 1.44 (s, 9H), 2.07 (t, J=5.0 Hz, 2H), 2.25 (J=5.0 Hz, 2H), 2.41 (dd, J=5.0, 6.5 Hz, 2H), 2.79-2.87 (m, 10H), 3.32 (t, J=5.5 Hz, 2H), 3.45 (dd, J=5.0, 6.0 Hz, 2H), 3.55 (t, J=5.0 Hz, 4H), 3.59-3.62 (m, 4H), 4.97 (s, 1H), 5.30-5.42 (m, 12H), 6.03 (s, 1H).

tert-Butyl (2-(2-(2-((R)-4-((3R,5R,8R,9S,10S,13R,14S,17R)-3-hydroxy-10,13-dimethylhexadecahydro-1H-cyclopenta[a]phenanthren-17-yl)pentanamido)ethoxy)ethoxy)ethyl)carbamate (A-2-c).

N-t-Boc-amido-dPEG3-amine (0.14 g, 0.55 mmol) was added to a solution of NHS-activated lithocholic acid ester (0.24 g, 0.5 mmol) in 5 ml of dry DMF, followed by DIEA (0.18 mL, 1.0 mmol). The mixture was stirred at RT for 16 h, and the solvent was evaporated in vacuo. The crude material is dissolved in DCM, washed with cold 1% HCl, saturated NaHCO$_3$ and brine, dried over Na$_2$SO$_4$, filtered and concentrated. The crude material was purified by flash column chromatography on silica gel with a gradient 1-5% methanol in DCM to afford 0.48 g of desired compound as a white solid (Yield 80%). $^1$H NMR (500 MHz; CDCl$_3$): δ 0.62 (s, 3H), 0.90-2.25 (m, 30H), 3.31 (s, 2H), 3.43-3.46 (s, 2H), 3.52-3.56 (m, 4H), 3.59-3.60 (m, 6H), 4.94 (s, 1H), 6.05 (s, 1H); m/z (ESI+) 628.6 (M+H). m/z (ESI+) 607.5 (M+H).

N-(2-(2-(2-(2-Bromoacetamido)ethoxy)ethoxy)ethyl)tetradecanamide (A-3-a)

TFA (2 ml, 26 mmol) was added to a solution of A-2-a (0.46 g, 1 mmol) in 10 ml of DCM, and the mixture was stirred at RT for 3 h. The reaction mixture was concentrated, and the crude material was lyophilized to obtain a colorless oil that was dissolved in 10 ml of DCM. Bromoacetic anhydride (0.31 g, 1.2 mmol) was added, followed by DIEA (0.52 ml, 2.5 mmol), and the mixture was stirred at RT for 3 h. The reaction mixture was extracted with DCM and EtOAc, washed with 1% HCl, saturated NaHCO$_3$ and brine, dried over Na$_2$SO$_4$, filtered and concentrated. The crude material was purified by flash column chromatography on silica gel with a gradient 20-50% EtOAc in petroleum ether with 5% methanol to obtain 0.37 g of desired compound as a white solid (combined yield over two steps, 78%). $^1$H NMR (500 MHz; CDCl$_3$): δ 0.88 (t, J=6.5 Hz, 3H), 1.25-1.32 (m, 20H), 1.62 (t, J=7.5 Hz, 2H), 2.18 (t, J=8.0 Hz, 2H), 3.47 (dd, J=5.0, 10.0 Hz, 2H), 3.50 (dd, J=5.0, 10.0 Hz, 2H), 3.56-3.58 (m, 2H), 3.59-3.62 (m, 2H), 3.63 (d, J=5.5 Hz, 5H), 3.88 (s, 2H), 5.92-5.93 (m, 1H), 6.94 (s, 1H); 7.04-7.17 (m, 1H); 13C NMR (100 MHz; CDCl3): δ 14.55, 23.12, 26.20, 29.76, 29.79, 29.95, 30.06, 30.08, 30.09, 30.11, 32.35, 37.23, 69.84, 70.46, 70.83 (2), 166.06, 173.84; m/z (ESI+) 480.6 (M+H).

(4Z,7Z,10Z,13Z,16Z,19Z)—N-(2-(2-(2-(2-bromoacetamido)ethoxy)ethoxy)ethyl) docosa-4,7,10,13,16,19-hexaenamide (A-3-b)

The title compound was prepared using analogous conditions as the procedure for A-3-a. Yield 67%, brown oil. $^1$H NMR (500 MHz; CDCl$_3$): δ 0.96 (t, J=5.0 Hz, 3H), 2.07 (q, J=7.6 Hz, 2H), 2.23 (J=7.2 Hz, 2H), 2.40 (dd, J=7.2, 13.8 Hz, 2H), 2.79-2.84 (m, 1OH), 3.44-3.51 (m, 4H), 3.55-3.62 (m, 4H), 3.63 (s, 4H), 3.88 (s, 2H), 5.78-5.42 (m, 12H), 5.94 (s, 1H), 6.92 (s, 1H); m/z (ESI+) 559.8 (M+H).

(R)—N-(2-(2-(2-(2-bromoacetamido)ethoxy)ethoxy)ethyl)-4-((3R,5R,8R,9S,10S,13R,14S,17R)-3-hydroxy-10,13-dimethylhexadecahydro-1H-cyclopenta[a]phenanthren-17-yl)pentanamide (A-3-c)

The title compound was prepared using analogous conditions as the procedure for A-3-a, replacing A-2-a with A-2-c. Yield 87%, white solid. $^1$H NMR (500 MHz; CDCl$_3$):

δ 0.83 (t, J=4.0 Hz, 3H), 0.85-0.94 (m, 6H), 1.00-1.91 (m, 28H), 3.41-3.64 (m, 12H), 3.85-3.88 (m, 2H), 4.86-4.94 (m, 1H), 6.05 (t, J=7.2 Hz, 1H), 7.04 (s, 1H); m/z (ESI+) 628.6 (M+H).

Example 2. Synthesis of Exemplary Lipid Derivatives (Schemes B-1 and B-2)

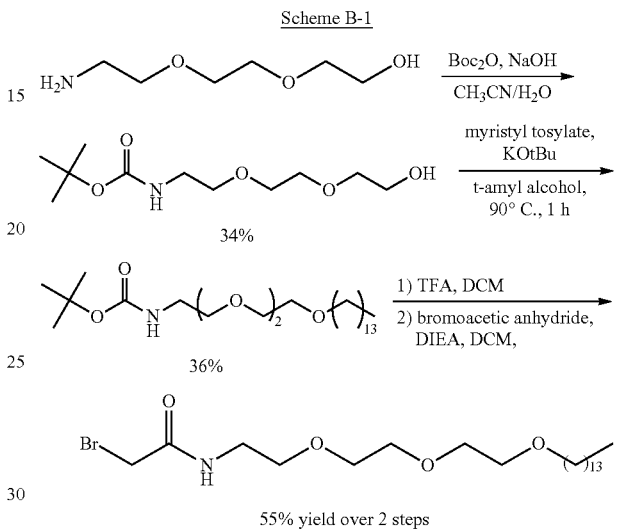

Scheme B-1

A solution of 2-(2-(2-aminoethoxy)ethoxy)ethanol (100 mg, 0.671 mmol, 89 μL) in 4.8 mL of acetonitrile/water (6:1) was treated with di-tert-butyl dicarbonate (151 mg, 0.691 mmol), followed by 0.5 mL of 1 N NaOH (aq). After stirring at RT for 45 min, the organic solvent was removed in vacuo, the residue was dissolved in saturated NH$_4$Cl (aq), and the desired carbamate was extracted with EtOAc. Removal of EtOAc provided 57 mg (34% yield) of tert-butyl 2-(2-(2-hydroxyethoxy)ethoxy)ethylcarbamate as a colorless oil.

A solution of tert-butyl 2-(2-(2-hydroxyethoxy)ethoxy)ethylcarbamate (68.5 mg, 0.275 mmol) and myristyl tosylate (101 mg, 0.275 mmol) in 1.4 mL of t-amyl alcohol was treated with potassium tert-butoxide (61.6 mg, 0.550 mmol) and potassium iodide (4.6 mg, 0.028 mmol). After heating to 90° C. for 2 h, the reaction was allowed to cool to rt, quenched with saturated NH$_4$Cl (aq), then extracted with EtOAc and dried over Na$_2$SO$_4$. Concentration and subsequent purification via flash column chromatography on silica gel afforded 44 mg (36% yield) of tert-butyl 2-(2-(2-(tetradecyloxy)ethoxy)ethoxy)ethylcarbamate as a colorless oil.

A solution of tert-butyl 2-(2-(2-(tetradecyloxy)ethoxy)ethoxy)ethylcarbamate (26 mg, 0.058 mmol) in 1.2 mL of DCM was treated with 0.29 mL of trifluoroacetic acid. After stirring at rt for 50 min, the mixture was concentrated and re-dissolved in 2 mL DCM. A 1-mL aliquot of this solution was taken into a separate vial, which was cooled to 0° C. and subsequently charged with bromoacetic anhydride (10.3 mg, 0.040 mmol) and DIEA (11 μL, 0.063 mmol). After stirring at rt for 12 h, the reaction mixture was purified via flash column chromatography to provide 7.5 mg (55% yield over 2 steps) of 2-bromo-N-(2-(2-(2-(tetradecyloxy)ethoxy)-ethyl)acetamide as an off-white solid.

Scheme B-2
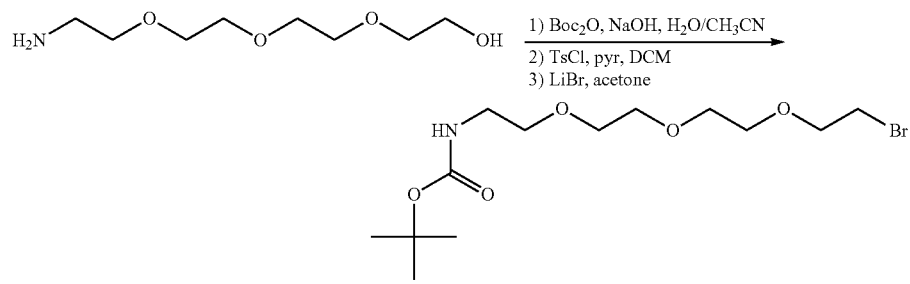
B-2-a
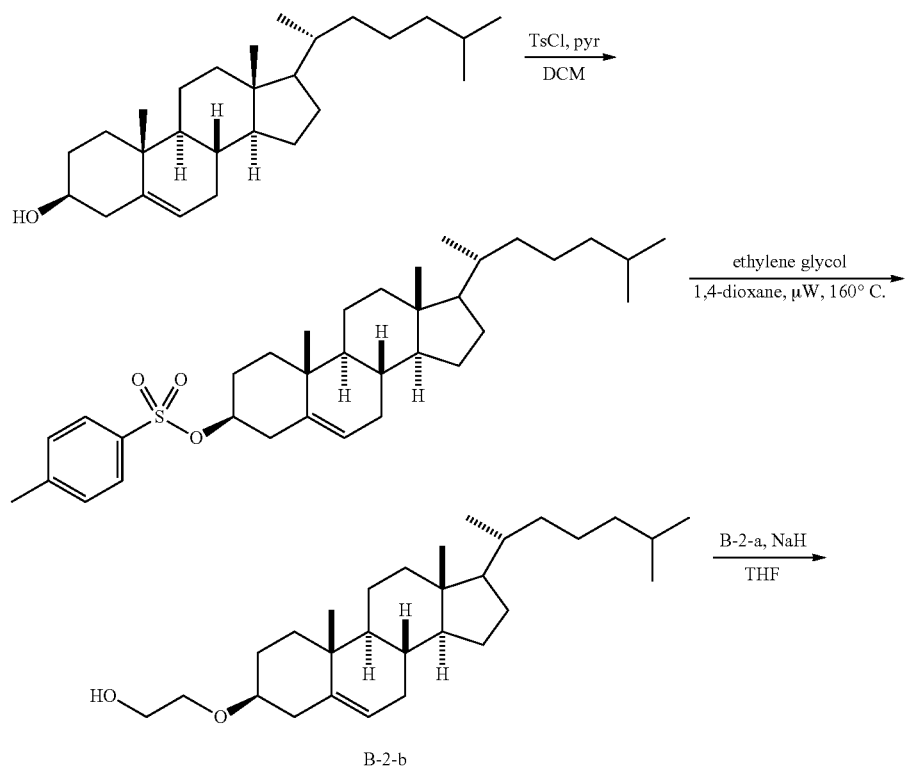
B-2-b
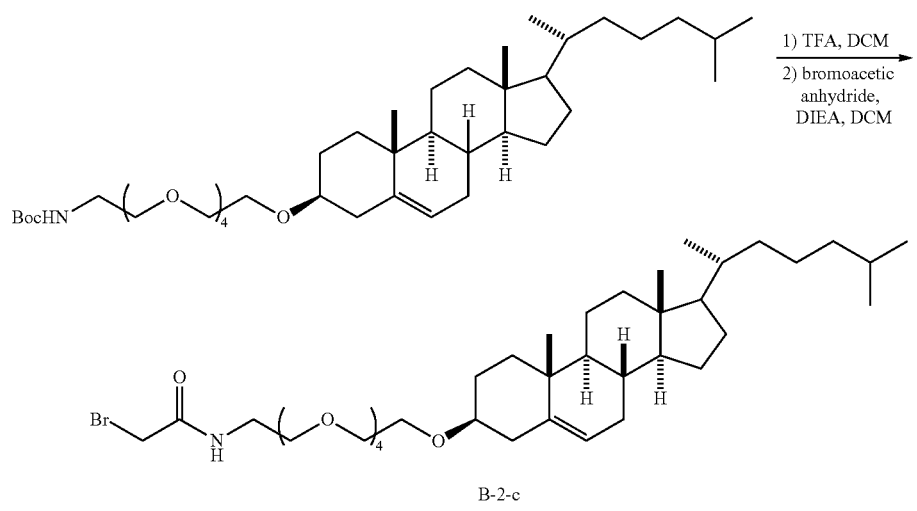
B-2-c tert-Butyl 2-(2-(2-(2-bromoethoxy)ethoxy)ethoxy) ethylcarbamate (B-2-a)

A solution of 2-(2-(2-(2-aminoethoxy)ethoxy)ethoxy) ethanol (400 mg, 2.07 mmol, 0.33 mL) in 15 mL of acetonitrile/water (6:1) was treated with di-tert-butyl dicarbonate (603 mg, 2.77 mmol), followed by 2.8 mL of 1 N NaOH (aq). After stirring at RT for 45 min, the organic solvent was removed in vacuo, the residue was dissolved in saturated NH$_4$Cl (aq), and the desired carbamate was extracted with EtOAc. Removal of EtOAc provided the crude carbamate as a colorless oil.

This oil was dissolved in DCM and treated with p-toluenesulfonyl chloride (1.18 g, 6.21 mmol) and pyridine (0.84 mL, 10.4 mmol). After stirring at 40° C. for 12 h, the mixture was diluted with DCM and washed with 1N HCl (2×10 mL), H$_2$O (10 mL), and brine (10 mL), then dried over Na$_2$SO$_4$ and concentrated. Purification via flash column chromatography on silica gel gave 330 mg (36% yield over 2 steps) of the tosylate as a colorless oil.

A solution of the tosylate (203 mg, 0.453 mmol) in 3.1 mL of anhydrous acetone was treated with LiBr (385 mg, 4.53 mmol). After stirring at 60° C. for 8 h, the solvent was removed and the resulting residue was dissolved in EtOAc. The organic mixture was washed with water, dried over MgSO$_4$, filtered, and concentrated. Purification via flash column chromatography on silica gel gave 126 mg (78% yield) of the title compound as a colorless oil.

2-((3S,8S,9S,10R,13R,14S,17R)-10,13-Dimethyl-17-(6-methylheptan-2-yl)-2,3,4,7,8,9,10,11,12,13,14,15,16,17-tetradecahydro-1H-cyclopenta[a]phenanthren-3-yloxy)ethanol (B-2-b)

A solution of cholesterol (1.50 g, 3.89 mmol) in 4 mL of DCM was treated with p-toluenesulfonyl chloride (1.49 g, 7.78 mmol), pyridine (4 mL), and DMAP (94.9 mg, 0.780 mmol). After stirring at RT for 12 h, the mixture was diluted with DCM and washed with 1N HCl (2×5 mL), H$_2$O (5 mL), and brine (5 mL), then dried over Na$_2$SO$_4$ and concentrated in vacuo. Recrystallization from chloroform and methanol gave 1.66 g (79% yield) of the tosylate intermediate as a white solid.

A microwave vial charged with the tosylate intermediate (500 mg, 0.926 mmol) in 7.7 mL of 1,4-dioxane was treated with 2.6 mL of ethylene glycol. After heating to 160° C. by microwave irradiation for 10 min, the solvent was removed, and the residue was dissolved in chloroform and washed with saturated NaHCO$_3$ (5 mL), H$_2$O (5 mL), and brine (5 mL), then dried over Na$_2$SO$_4$ and concentrated in vacuo. Purification of the crude material by flash column chromatography using silica gel provided 270 mg (68% yield) of the title compound as a white solid.

2-Bromo-N-(14-((3S,8S,9S,10R,13R,14S,17R)-10,13-dimethyl-17-(6-methylheptan-2-yl)-2,3,4,7,8,9,10,11,12,13,14,15,16,17-tetradecahydro-1H-cyclopenta[a]phenanthren-3-yloxy)-3,6,9,12-tetraoxatetradecyl)acetamide (B-2-c)

A solution of B-2-b (219 mg, 0.509 mmol) in 2.5 mL of THF was treated with sodium hydride (60% dispersion in mineral oil, 20.4 mg, 0.509 mmol) and stirred for 30 min. The mixture was cooled to 0° C. and treated with B-2-a (139 mg, 0.392 mmol) in 2.5 mL of THF. After heating to 40° C. for 6 h, the reaction was quenched with saturated NH$_4$Cl (aq) and extracted with EtOAc. Purification of the crude material by flash column chromatography using silica gel provided 101 mg (36% yield) of the ether intermediate as a colorless oil.

A solution of the ether intermediate (74 mg, 0.105 mmol) in 2.1 mL of DCM was treated with 0.53 mL of TFA. After stirring at RT for 40 min, the mixture was concentrated in vacuo and dissolved in 10 mL DCM. A 4-mL aliquot of this solution was taken into a separate vial, concentrated to a 1-mL volume, cooled to 0° C., and charged with bromoacetic anhydride (13.6 mg, 0.053 mmol) and DIEA (15 µL, 0.088 mmol). After stirring at RT for 12 h, the reaction mixture was directly purified by flash column chromatography using silica gel to give 12.6 mg (41% over 2 steps) of the title compound as an colorless oil.

Example 3. Synthesis of Oxyntomodulin-Lipid Conjugate with Staple (Scheme C)

Scheme C (Sequences shown below are disclosed as SEQ ID NO: 54).

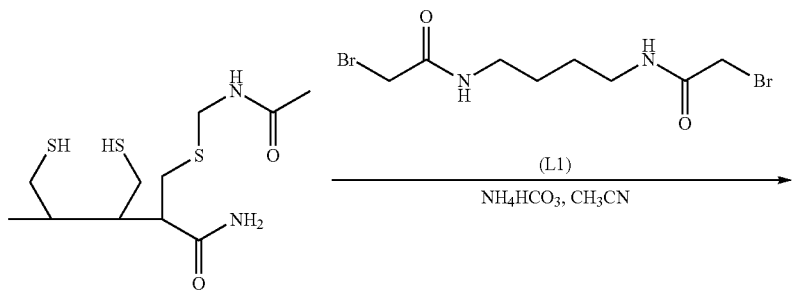

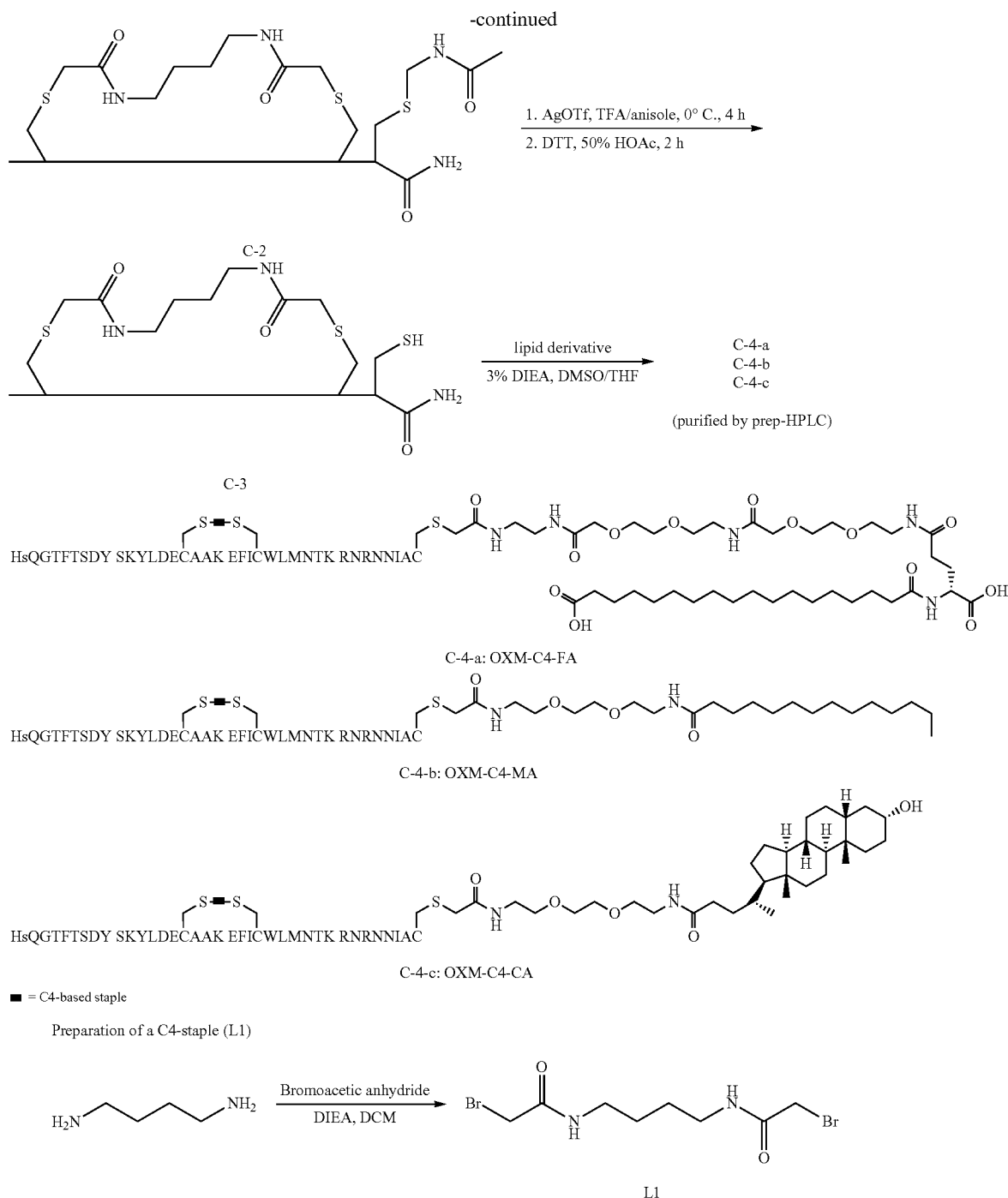

A solution of 1,4-butanediamine (0.18 g, 2 mmol) in DCM (10 mL) was treated with bromoacetic anhydride (1.1 g, 4 mmol), DIEA (0.7 mL, 4 mmol) at −20° C. The reaction mixture was then stirred for 2 h, and the solvent was removed. Purification by flash column chromatography on silica gel provided 0.53 g of L1 as a white solid (Yield 81%).

Peptide Cross-Linking with C4-Staple to Obtain Intermediate C-2.

The cross-linking reaction was carried out by incubating the purified dicysteine-containing peptide C-1 with a mixed solvent solution 1.5 equiv of 1,4-dibromoacetamide butane (L1) (1.5 equiv in 1:4 $CH_3CN$/30 mM $NH_4HCO_3$ buffer, pH 8.5) to obtain a final peptide concentration of 1 mM. The mixture was stirred at RT for 2 h. Under ice cooling, acetic acid was then added dropwise to pH 5. Crude cross-linked peptide was then purified by preparative HPLC. The main peak was collected and lyophilized to afford C-2 as a powder with greater than 95% purity and in greater than 70% product yield. The molecular weight of peptide was analyzed by ESI-MS: calcd MW 4738.59; found 1185.6 [M/4+1]$^+$, 948.7 [M/5+1]$^+$, 789.8 [M/6+1]$^+$.

Deprotection of Thiol to Obtain Intermediate C-3.

The cross-linked peptide C-2 was treated with AgOTf (50 equiv) in anisole/TFA (1:50) to obtain a final peptide concentration of 1 mM. The mixture was stirred at 0° C. for 2 h. Ether (50-fold) was added and the resulting powder was collected by centrifugation. The powder was suspended in 50% AcOH to obtain a final peptide concentration of 0.2 mM. DTT (100 equiv) was added. The mixture was stirred for 2 h in the absence of light. After centrifugation, the supernatant was purified by preparative HPLC. The fraction corresponding to the main peak was collected and lyophilized to afford C-3 as a powder with greater than 95% purity in about 35% product yield. The molecular weight of peptide was analyzed by ESI-MS: calcd MW 4667.5; found 1167.7 $[M/4+1]^+$, 934.6 $[M/5+1]^+$.

Conjugation with Lipid Derivative to Obtain Peptide Lipid Conjugate (C-4-a, C-4-b, C-4-c).

The Cys peptide intermediate C-3 was dissolved in DMSO and reacted with the appropriate lipid derivative (with haloacetamide group) dissolved in THF to obtain a final peptide concentration of 1 mM. The mixture was stirred at RT for 1 h. The reaction was quenched by the addition of TFA to a final pH of 4, and directly purified by preparative HPLC. The fraction corresponding to the main peak was collected and lyophilized to give the desired compound as a powder with greater than 95% purity in about 65% product yield. The molecular weight of peptide was analyzed by ESI-MS.

Example 4. Synthesis of Oxyntomodulin-Lipid Conjugate with Lipid-Ornithine Staple Precursor (Scheme D)

Myristic acid (0.46 g, 2 mmol) was dissolved in 5 mL of DMF. HATU (0.8 g, 2.1 mmol) and DIEPA (0.4 mL, 2.2 mmol) was added followed by the addition of tert-butyl (2-(2-(2-aminoethoxy)ethoxy)ethyl)carbamate (0.5 g, 2 mmol). The reaction mixture was then stirred for 6 h, and the solvent was removed. The product was extracted with EtOAc (3×15 mL). The organic layer was successively washed with sat. NaHCO$_3$, cooled HCl (1 M) and brine, dried over Na$_2$SO$_4$, filtered, and concentrated. Purification by flash column chromatography on silica gel provided 0.81 g of desired compound as a white solid in 90% product yield. ESI-MS: calcd MW 458.4; found 459.6 $[M+1]^+$.

di-tert-butyl (5,16-dioxo-9,12-dioxa-6,15-diazanona-cosane-1,4-diyl)dicarbamate (D-2)

A solution of D-1 (0.46 g, 1 mmol) in DCM (10 mL) was treated with TFA (2 mL) for 2 h. The mixture was concentrated and followed by the addition of Boc-Orn(Boc)-OH (0.33 g, 1 mmol), HATU (0.41 g, 1.1 mmol), DIEPA (0.4 mL, 2.2 mmol) in 5 mL of DMF. The reaction mixture was then stirred for 6 h, and the solvent was removed. The product was extracted with EtOAc (3×15 mL). The organic layer was successively washed with sat. NaHCO$_3$, cooled HCl (1 M) and brine, dried over Na$_2$SO$_4$, filtered, and concentrated. Purification by flash column chromatography on silica gel provided 0.58 g of desired compound as a white

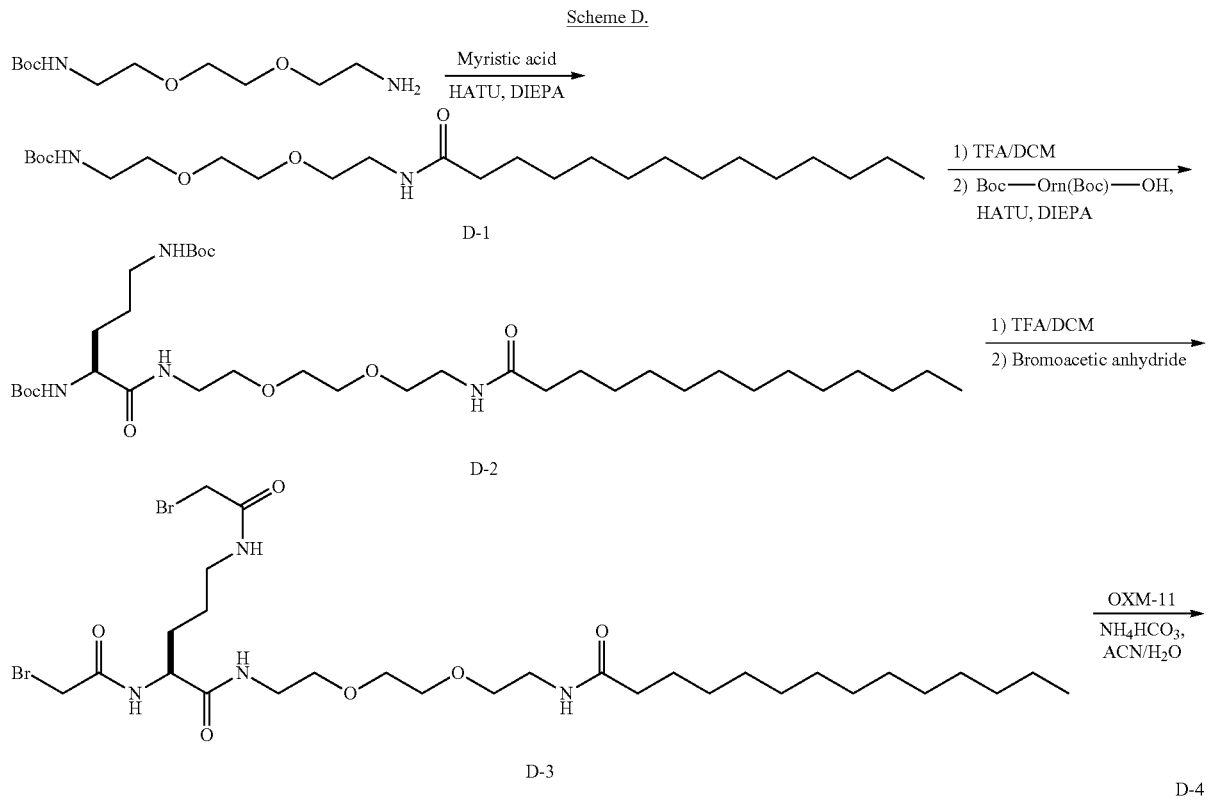

tert-butyl (2-(2-(2-tetradecanamidoethoxy)ethoxy)ethyl) carbamate (D-1).

solid in 87% product yield. ESI-MS: calcd MW 672.9; found 673.6 $[M+1]^+$.

(S)—N,N'-(5,16-dioxo-9,12-dioxa-6,15-diazanona-cosane-1,4-diyl)bis(2-bromoacetamide) (D-3, Staple L2)

A solution of D-2 (0.33 g, 0.5 mmol) in DCM (10 mL) was treated with TFA (2 mL) for 2 h. The mixture was concentrated and followed by the addition of bromoacetic anhydride (0.52 g, 1 mmol), DIEPA (0.4 mL, 2.2 mmol) in 10 mL of DCM. The reaction mixture was then stirred for 6 h, and the solvent was removed. The product was extracted with EtOAc (3×15 mL). The organic layer was successively washed with sat. NaHCO$_3$, cooled HCl (1 M) and brine, dried over Na$_2$SO$_4$, filtered, and concentrated. Purification by flash column chromatography on silica gel provided 0.59 g of desired compound as a white solid in 83% product yield. ESI-MS: calcd MW 714.6; found 715.4 [M+1]$^+$.

Peptide lipid conjugate D-4 was prepared in an analogous manner as C-2, substituting 1,4-dibromoacetamide butane with D-3. Purification by preparative HPLC lyophilized to give the desired compound as a white powder with greater than 95% purity in about 55% product yield. The molecular weight of peptide was analyzed by ESI-MS: calcd MW 4908.8; found 1228.0 [M/4+1]$^+$, 982.6 [M/5+1]$^+$, 819.0 [M/6+1]$^+$.

Example 5. Preparation of Staple L3

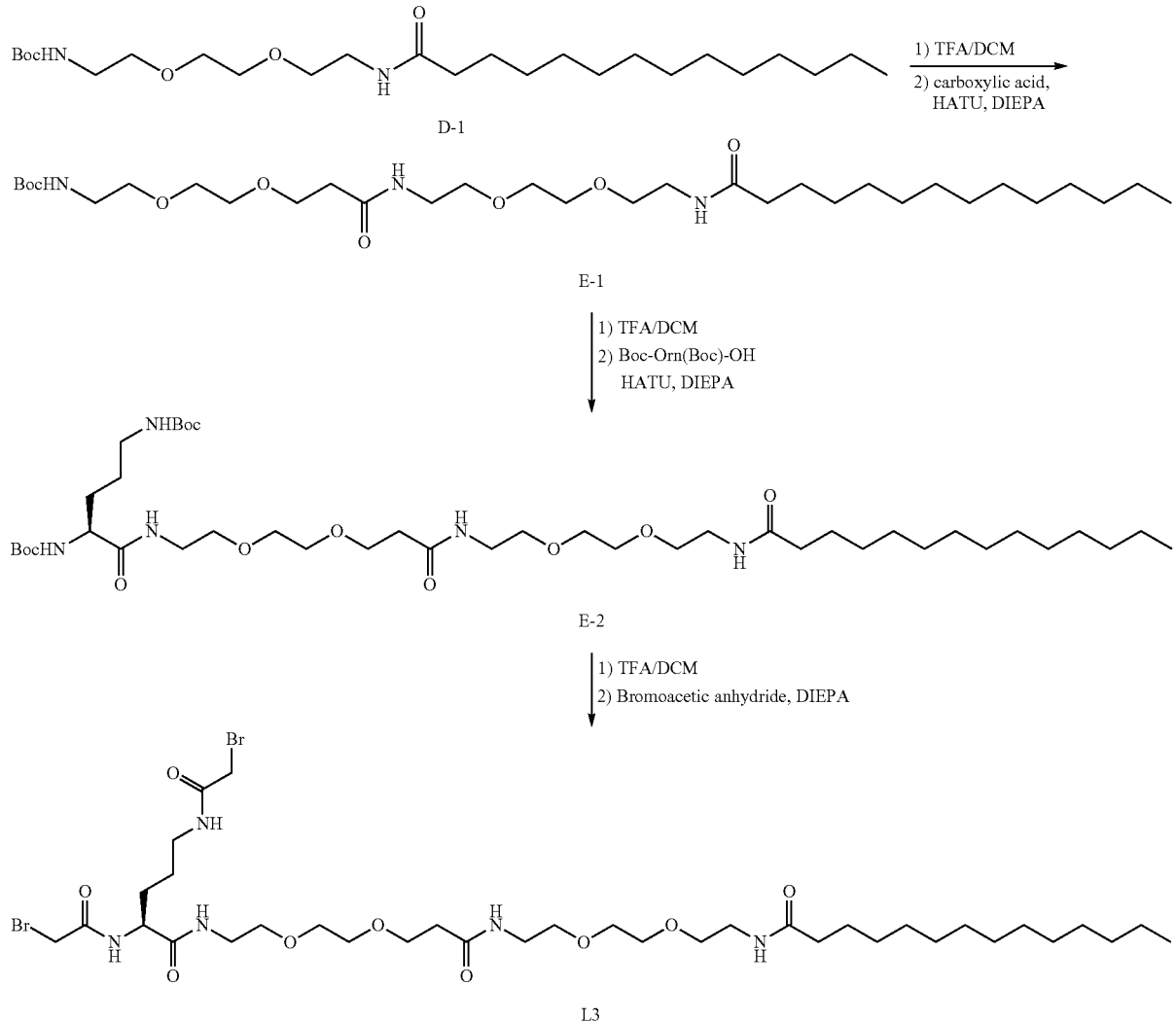

Scheme E.

tert-butyl (9,20-dioxo-3,6,13,16-tetraoxa-10,19-di-azatritriacontyl)carbamate (E-1)

A solution of tert-butyl (2-(2-(2-tetradecanamidoethoxy)ethoxy)ethyl)carbamate (D-1) (0.23 g, 0.5 mmol) in DCM (5 mL) was treated with TFA (1 mL) for 2 h. The mixture was concentrated and followed by the addition of 2,2-dimethyl-4-oxo-3,8,11-trioxa-5-azatetradecan-14-oic acid (0.214 g, 0.5 mmol), HATU (0.21 g, 0.55 mmol), DIEPA (0.2 mL, 1.1 mmol) in 2 m of DMF. The reaction mixture was then stirred for 6 h, and the solvent was removed. The product was extracted with EtOAc (3×10 mL). The organic layer was successively washed with sat. NaHCO$_3$, cooled HCl (1 M) and brine, dried over Na$_2$SO$_4$, filtered, and concentrated.

Purification by flash column chromatography on silica gel provided 0.25 g of desired compound as a white solid in 81% product yield.

(S)-di-tert-butyl (5,15,26-trioxo-9,12,19,22-tetraoxa-6,16,25-triazanonatriacontane-1,4-diyl)dicarbamate (E-2)

A solution of tert-butyl (9,20-dioxo-3,6,13,16-tetraoxa-10,19-diazatritriacontyl)carbamate (E-1) (0.15 g, 0.25 mmol) in DCM (5 mL) was treated with TFA (1 mL) for 2 h. The mixture was concentrated and followed by the addition of Boc-Orn(Boc)-OH (85 mg, 0.25 mmol), HATU (105 mg, 0.275 mmol), DIEPA (0.1 mL, 0.5 mmol) in 2 mL of DMF. The reaction mixture was then stirred for 6 h, and the solvent was removed. The product was extracted with EtOAc (3×10 mL). The organic layer was successively washed with sat. $NaHCO_3$, cooled HCl (1 M) and brine, dried over $Na_2SO_4$, filtered, and concentrated. Purification by flash column chromatography on silica gel provided 0.16 g of desired compound as a white solid in 77% product yield.

(S)—N,N'-(5,15,26-trioxo-9,12,19,22-tetraoxa-6,16,25-triazanonatriacontane-1,4-diyl)bis(2-bromoacetamide) (L3)

A solution of (S)-di-tert-butyl (5,15,26-trioxo-9,12,19,22-tetraoxa-6,16,25-triazanonatriacontane-1,4-diyl)dicarbamate (E-2) (125 mg, 0.15 mmol) in DCM (5 mL) was treated with TFA (2 mL) for 2 h. The mixture was concentrated and followed by the addition of bromoacetic anhydride (80 mg, 0.3 mmol), DIEPA (0.1 mL, 0.6 mmol) in 5 mL of DCM at 0° C. The reaction mixture was then stirred for 6 h, and the solvent was removed. The product was dissolved in 10 mL of $ACN/H_2O/TFA$ (1:1:0.1) and purified by preparative HPLC (C18 column). Lyophilization provided the desired compound as a powder in 55% yield over two steps.

Example 6. Preparation of Staple L4

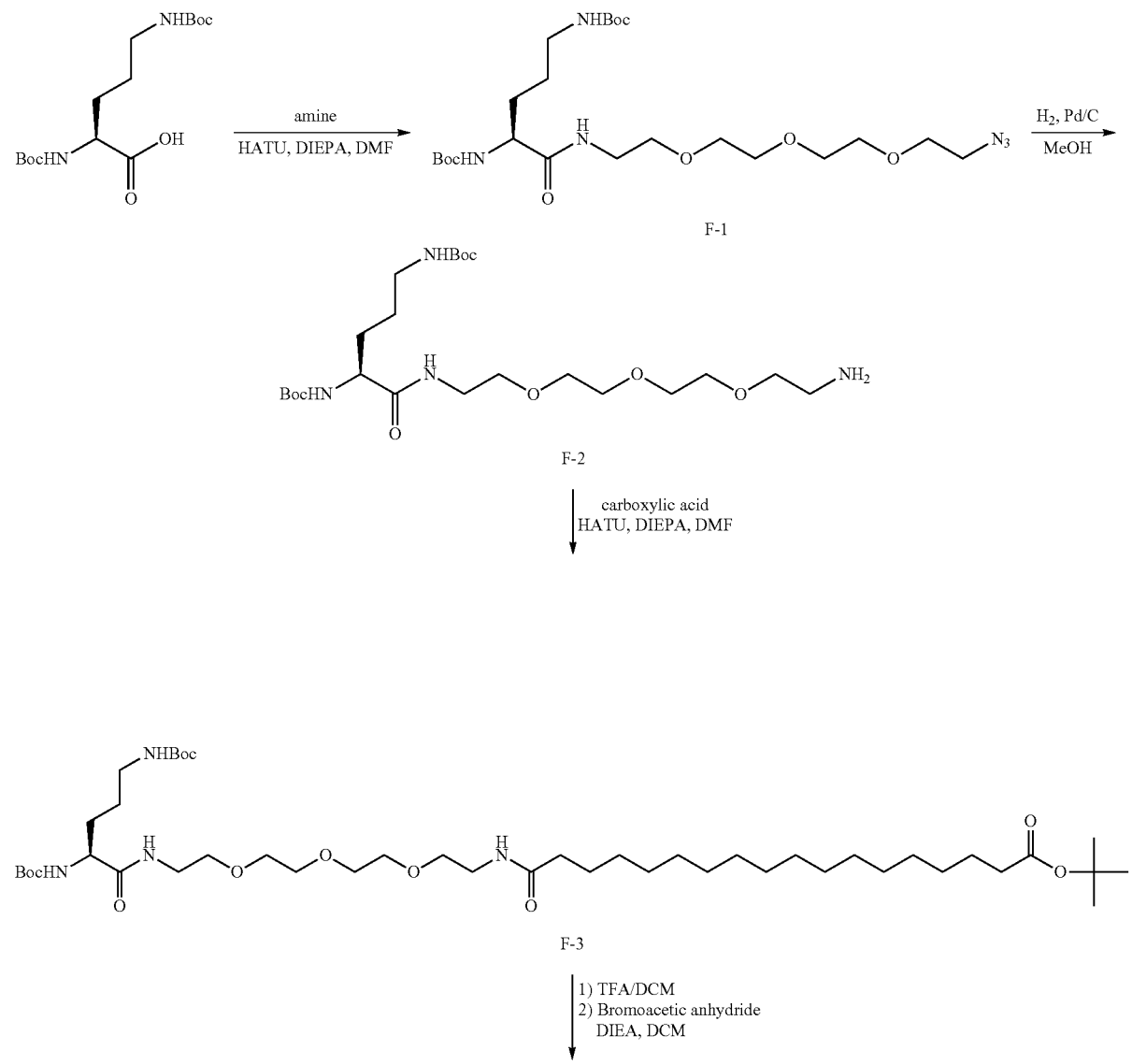

Scheme F.

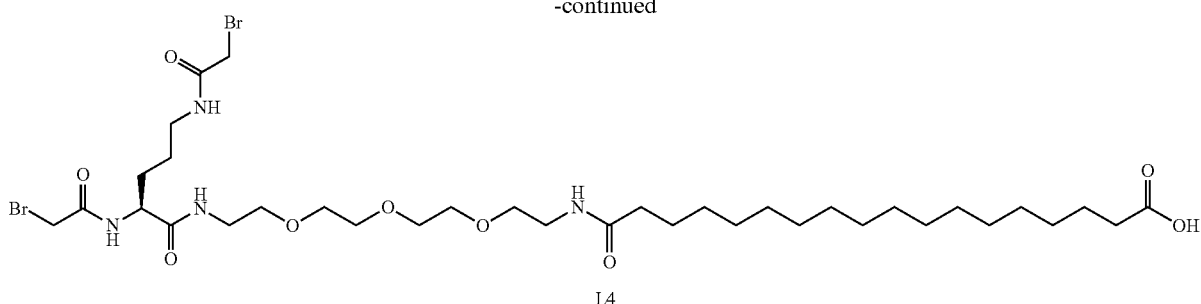

L4

(S)-di-tert-butyl (1-azido-13-oxo-3,6, 9-trioxa-12-azaheptadecane-14,17-diyl)dicarbamate (F-1)

Boc-Orn(Boc)-OH (1.32 g, 4 mmol) was dissolved in 10 mL of DMF. HATU (1.7 g, 4.4 mmol) and DIEPA (0.75 mL, 4.4 mmol) were added followed by the addition of 2-(2-(2-(2-azidoethoxy)ethoxy)ethoxy)ethanamine (0.88 g, 4 mmol). The reaction mixture was then stirred for 16 h, and the solvent was removed. The product was purification by flash column chromatography on silica gel provided 1.5 g of desired compound as a white solid in 75% product yield.

(S)-di-tert-butyl (1-amino-13-oxo-3,6,9-trioxa-12-azaheptadecane-14,17-diyl)dicarbamate (F-2)

A solution of (S)-di-tert-butyl (1-azido-13-oxo-3,6,9-trioxa-12-azaheptadecane-14,17-diyl)dicarbamate (F-1) (1.06 g, 2 mmol) in MeOH (20 mL) was treated with Pd/C (0.11 g) and 1 atm of $H_2$ for 6 h. The mixture was filtered and concentrated. The crude material was used immediately in the next step without further purification.

(S)-tert-butyl 9-((tert-butoxycarbonyl)amino)-2,2-dimethyl-4,10,24-trioxo-3,14,17,20-tetraoxa-5,11,23-triazahentetracontan-41-oate (F-3)

Octadecanedioic acid mono-tert-butyl ester (0.22 g, 0.6 mmol) was dissolved in 5 mL of DMF. HATU (0.23 g, 0.6 mmol) and DIEPA (0.1 mL, 0.6 mmol) was added followed by the addition of (S)-di-tert-butyl (1-amino-13-oxo-3,6,9-trioxa-12-azaheptadecane-14,17-diyl)dicarbamate (F-2) (0.31 g, 0.6 mmol) in 5 mL of DMF. The reaction mixture was then stirred for 24 h, and the solvent was removed. The product was purification by flash column chromatography on silica gel provided 0.37 g of desired compound as a white solid in 71% product yield.

(S)-1-bromo-7-(2-bromoacetamido)-2,8,22-trioxo-12,15,18-trioxa-3,9,21-triazanonatriacontan-39-oic Acid (L4)

A solution of (S)-tert-butyl 9-((tert-butoxycarbonyl)amino)-2,2-dimethyl-4,10,24-trioxo-3,14,17,20-tetraoxa-5,11,23-triazahentetracontan-41-oate (F-3) (0.26 g, 0.3 mmol) in DCM (10 mL) was treated with TFA (5 mL) for 6 h. The mixture was concentrated and followed by the addition of bromoacetic anhydride (0.16 g, 0.6 mmol), DIEPA (0.2 mL, 1.2 mmol) in 10 mL of DCM. The reaction mixture was then stirred for 2 h at 0° C., and the solvent was removed. The product was dissolved in 10 mL of ACN/$H_2$O/TFA (1:1:0.1) and purified by preparative HPLC (C18 column). Lyophilization provided the desired compound as a powder in 45% yield over two steps.

Example 7. Preparation of Staple L5

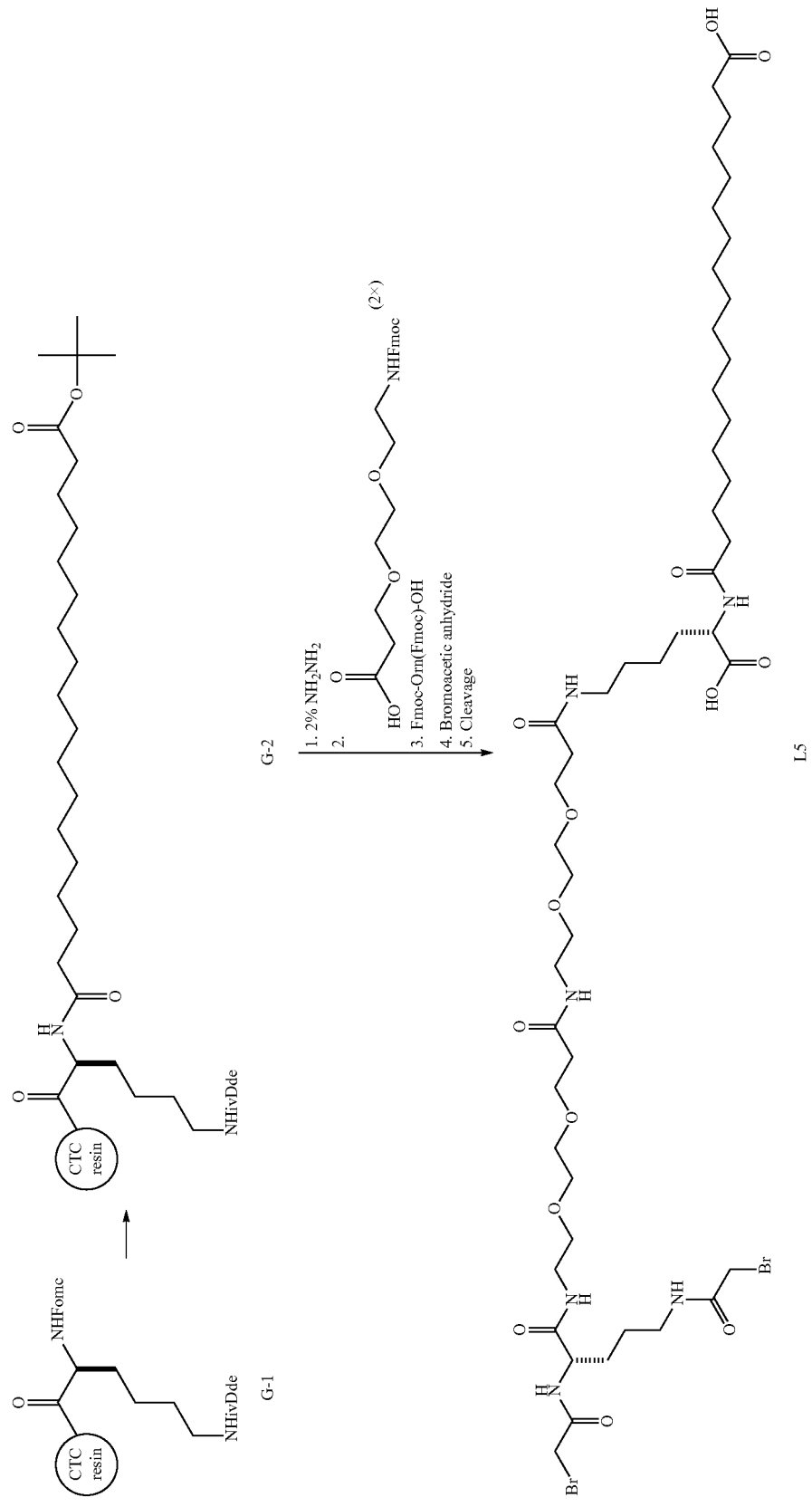

Preparation of Fmoc-Lys(ivDde)-2-chlorotrityl resin
(G-1)

2-Chlorotrityl chloride resin (Novabiochem, 100-200 mesh, 1% DVB, loaded 1.0 mmol/g) (5.0 g, 5 mmol) was swollen in DCM (80 mL) for 1 h and then drained. Fmoc-Lys(ivDde)-OH (Novabiochem, 1 equiv) was suspended in DMF (30 mL) and DCM (30 mL) and DIPEA (1.1 equiv). This suspension was added to the resin and shaken for 2 h. The resin was drained and washed with DMF (3×), DCM (3×) and treated with $CH_3OH$/DCM/DIPEA (8:1:1) for 30 min to cap the unreacted trityl chloride sites, washed with DCM (3×), and dried under vacuum, and stored in a desiccator until use.

C18-diacid-Lys(ivDde)-2-chlorotrityl Resin (G-2)

To G-1 (5 mmol) was added piperidine in DMF (20%, 100 mL). The mixture was shaken for 30 min and drained. Another 50 mL of 20% piperidine was added and the mixture was shaken for another 30 min. Positive ninhydrin test was observed. The resin was then washed as described above for G-1. The resin was then treated with octadecanedioic acid mono-tert-butyl ester (AstaTech) (3 equiv, 15 mmol), HATU (3.3 equiv), and DIPEA (3.3 equiv) in DMF (100 mL) for 2 h and repeated until a negative ninhydrin test was observed. The resin was washed with DMF and DCM as described for G-1 and used directly in the next step.

Staple L5

G-2 was treated twice with 2% hydrazine in DMF (100 mL, 15 min). Positive ninhydrin test was observed. The resin was then washed as described for G-1 and treated with Fmoc-PEG2-propionic acid (Quanta BioDesign) (3 equiv) using HATU (3.3 equiv), and DIPEA (3.3 equiv) in DMF (100 mL) for 2 h. The resin was then washed as before. Then Fmoc group was removed as described for G-2 and the above washing steps were repeated. The resin was then treated with Fmoc-Orn(Fmoc)-OH (Novabiochem, 3 equiv), HATU (3.3 equiv), and DIPEA (3.3 equiv) in DMF (100 mL) for 2 h. The resin was again washed as described above. Then Fmoc group was removed and the above washing steps were repeated. The resin was then treated with bromoacetic anhydride (4 equiv), and DIPEA (4.4 equiv) in 200 mL of DCM for 30 min. After washing with DCM (3×), the product was cleaved from the resin using 5 mL of 10% TFA in DCM containing 10% $H_2O$ and 10% triisopropylsilane for 1 h. After cleavage, TFA was removed under reduced pressure. The resulting yellow residue was washed several times with cold diethyl ether and was finally dried to a crude product as yellow powder. The crude peptide was dissolved in DMSO (5 mL) and this solution was diluted to a final volume of 100 mL with 50% $CH_3CN$-water. The solution was filtered. The filtered solution (10 mL) was loaded onto the preparative HPLC column (Phenomenex, Prep C18, 300A, 50×250 mm) equilibrated with 10% $CH_3CN$ (0.05% TFA) in water (0.05% TFA), and the column was eluted with 10% $CH_3CN$ (0.05% TFA) in water (0.05% TFA) to wash DMSO from the column. The composition of the eluent then was ramped to 35% $CH_3CN$-water (0.05% TFA) over 1 min, and a linear gradient was initiated at a rate of 1%/min of $CH_3CN$ (0.05% TFA) into water (0.05% TFA) and run for 50 min. Eluted fractions were checked for purity on an analytical scale reversed phase C18 column (Phenomenex, C18, 120A, 4.6×50 mm) and fractions containing the product in >95% purity were combined and lyophilized to afford the title compound in 31% product yield. The molecular weight of product was analyzed by ESI-MS: calcd MW 1117.0; found 1118.3 $[M+1]^+$, 1119.2 $[M+2]^+$.

Example 8. Preparation of Staple L6

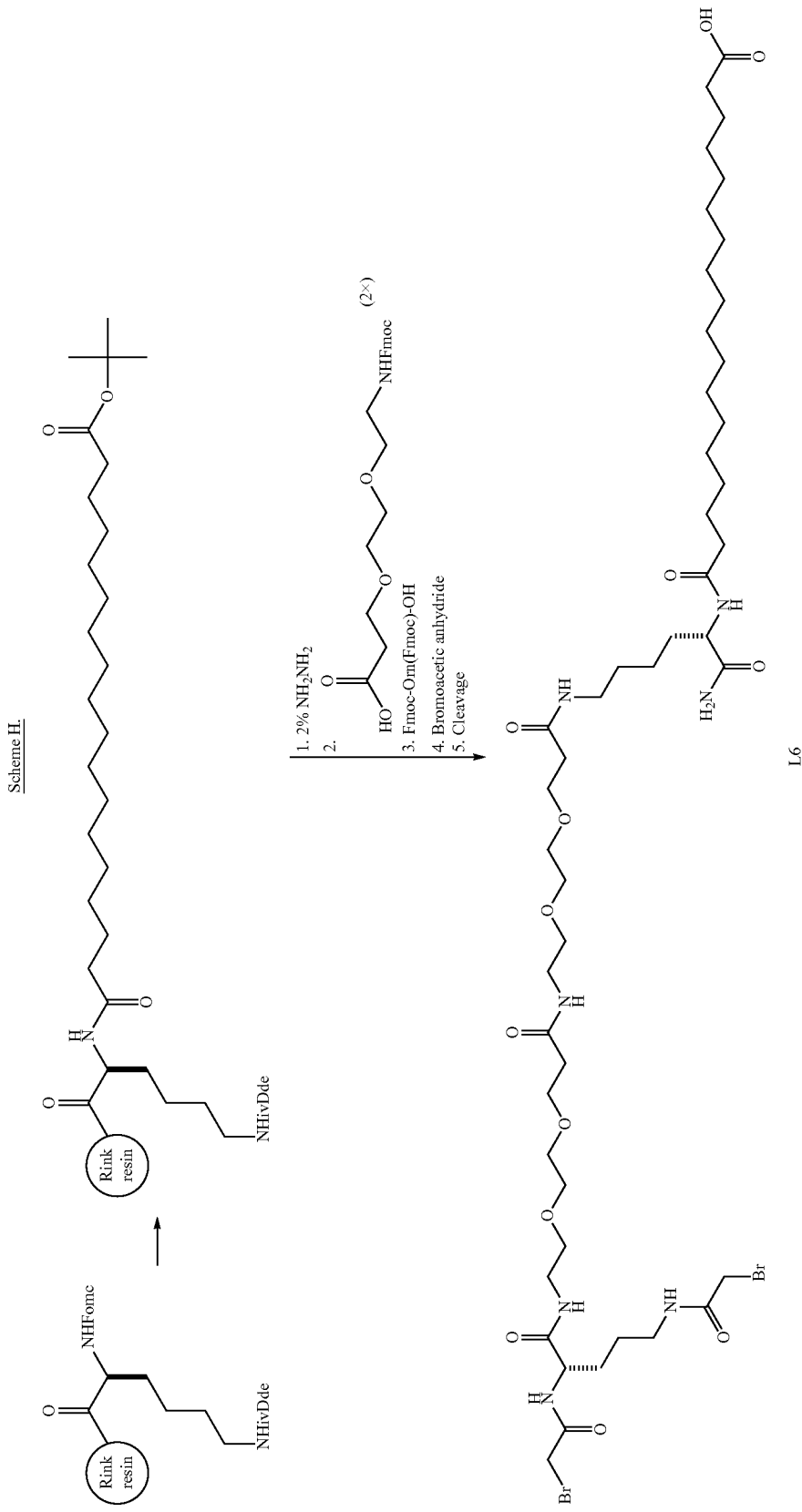

L6 was prepared in an analogous manner as L5 by substituting 2-chlorotrityl chloride resin with Rink Amide MBHA resin (Novabiochem). Purification by preparative HPLC and lyophilization gave the title compound as a white powder with greater than 95% purity in about 35% product yield. The molecular weight of peptide was analyzed by ESI-MS: calcd MW 1116.0; found 1117.2 [M+1]$^+$, 1118.7 [M+2]$^+$.

Example 9. Preparation of Staple L23

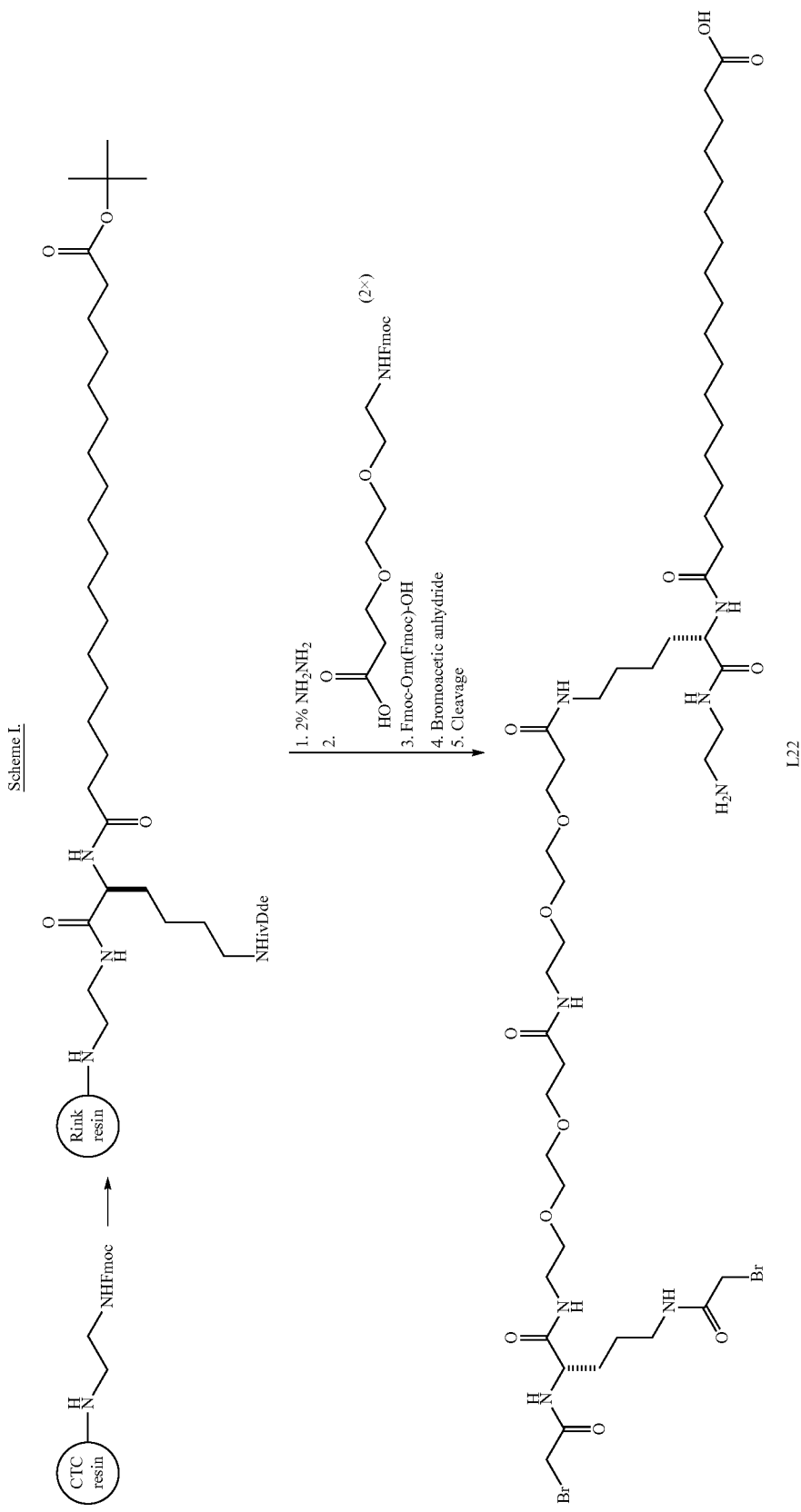

L22 was prepared in an analogous manner as L5 by starting with 2-chlorotrityl chloride resin and mono-Fmoc ethylene diamine hydrochloride (Novabiochem). Purification by preparative HPLC and lyophilization gave the title compound as a white powder with greater than 95% purity in about 15% product yield. The molecular weight of peptide was analyzed by ESI-MS: calcd MW 1159.1; found 1160.2 $[M+1]^+$.

Example 10. General Procedure of the Cross-Linking Reaction Using a Staple Via Thioether Linkage The cysteine side chain thiols were then derivatized with haloacetamides (L1 to L22) to form the bis-thioether peptidomimetic macrocycles. The cross-linking reaction was carried out by incubating the peptide with a mixed solvent solution 1.5 equiv of the linker in 1:4 $CH_3CN$/30 mM $NH_4HCO_3$ buffer, pH 8.5) to obtain a final peptide concentration of 1 mM. The mixture was stirred at rt for 2 h. Under ice cooling, acetic acid was then added dropwise to pH 5. Crude cross-linked peptide was then purified by preparative HPLC (C18 column). Lyophilization gave the desired peptide as a white solid.

Figure 7:
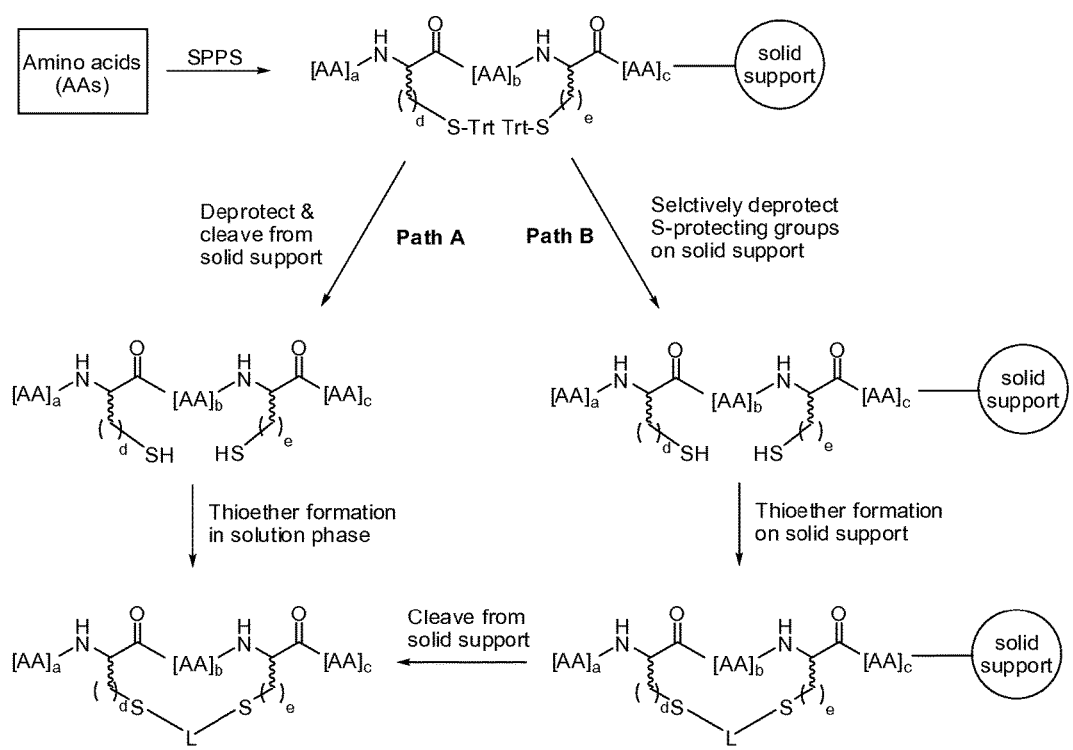
FIG. 7 depicts thioether-based macrolactonization via two different protocols.
Figure 8:
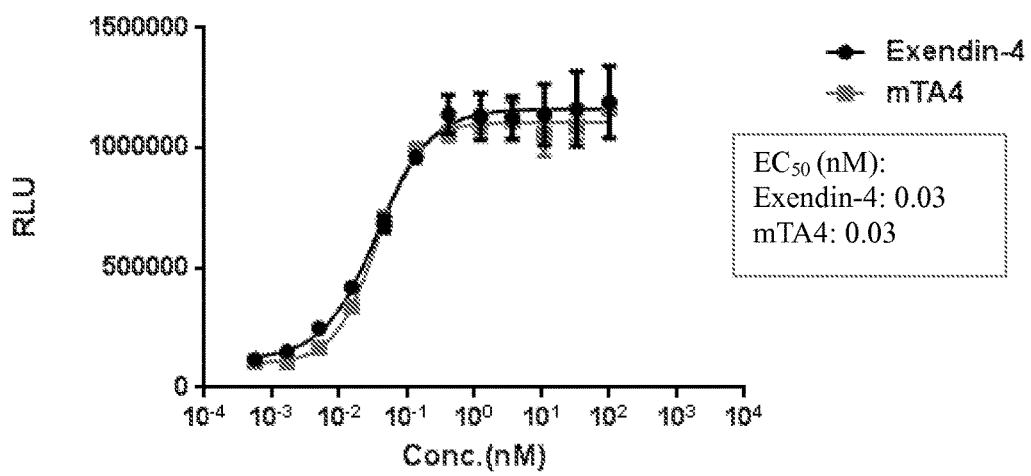
FIG. 8 shows dosage response curves for GLP-1R CRE luciferase assay.
Figure 9:
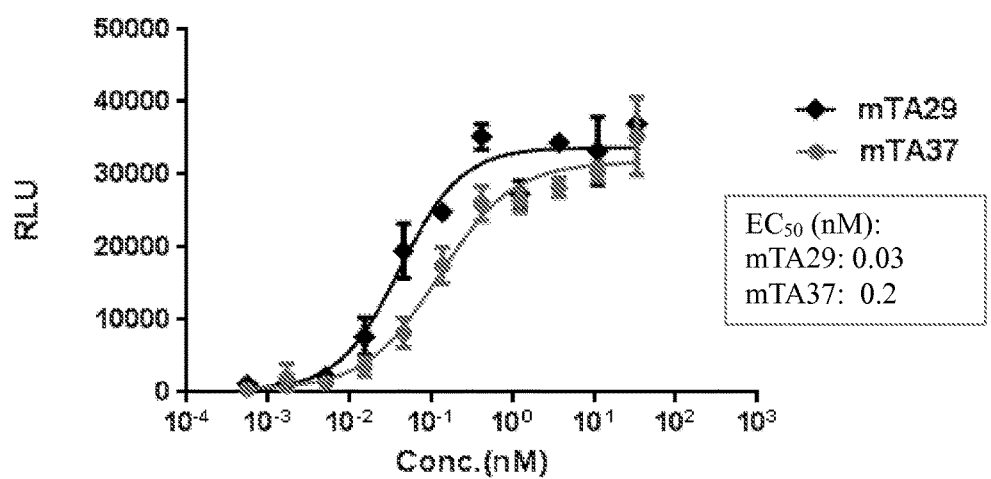
FIG. 9 shows dosage response curves for GCGR CRE luciferase assay.
Figure 10:
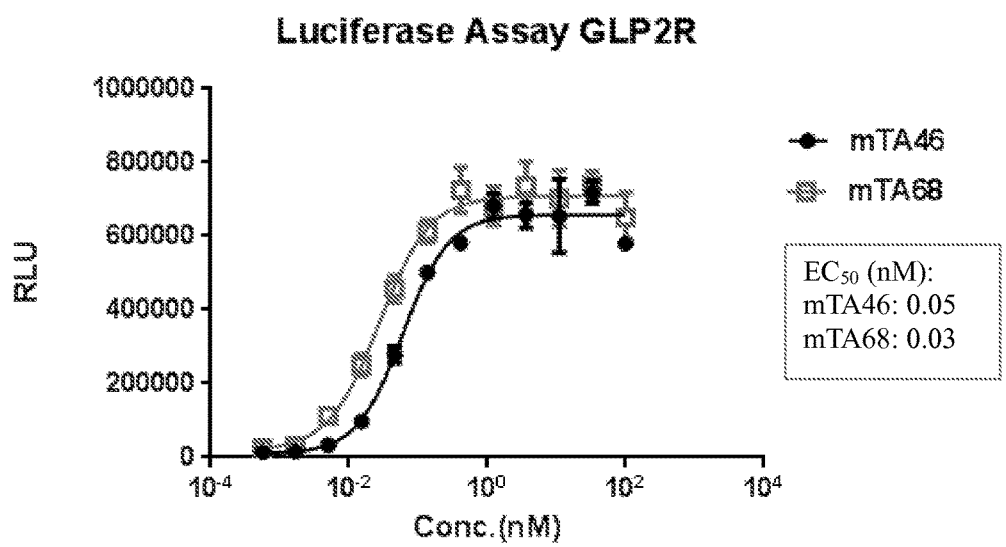
FIG. 10 shows dosage response curves for GLP-2R CRE luciferase assay.
Figure 11:
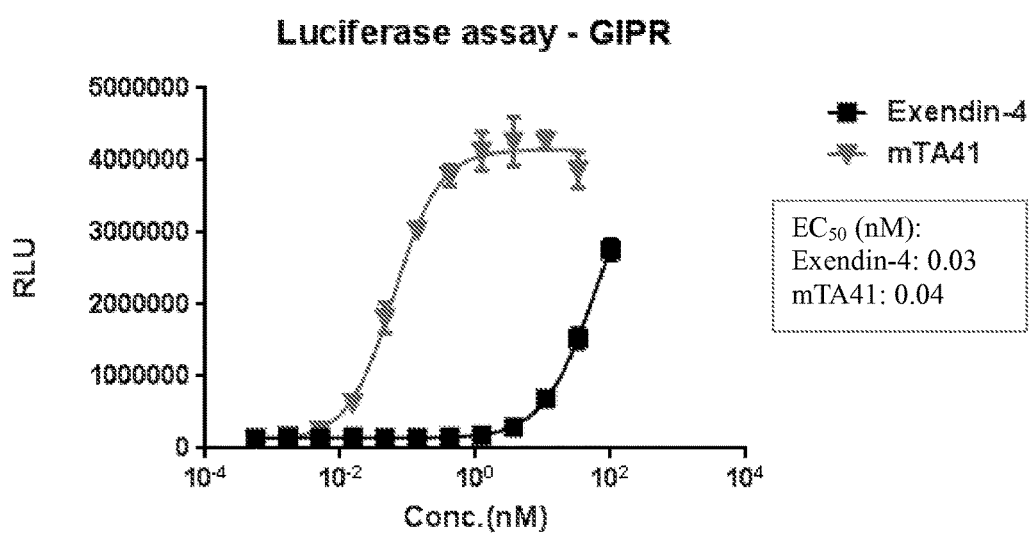
FIG. 11 shows dosage response curves for GIPR CRE luciferase assay.

FIG. 7 depicts two macrocyclization routes to obtain the desired mTAs. The staple, with or without one or more attached HEMS, is depicted as L.

Additional compounds in Tables 1, 2, and 6-9 may be prepared using analogous procedures.

TABLE 1

| entry | Structure* |
|---|---|
| 1 | PEG: n = 0 to 10   m = 1-15 |
| 2 | PEG: n = 0 to 10   m = 1-15 |
| 3 | PEG: n = 0 to 10   m = 1-15 |
| 4 | PEG: n = 0 to 10   m = 1-6 |
| 5 | PEG: n = 0 to 10 |
| 6 | PEG: n = 0 to 10 |

TABLE 1-continued
| entry | Structure* |
|---|---|
| 7 | 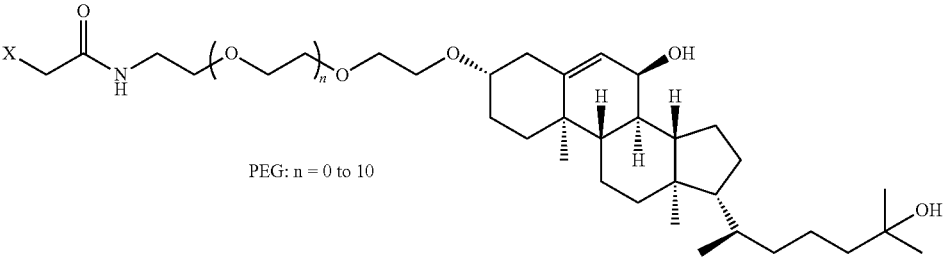<br>PEG: n = 0 to 10 |
| 8 | 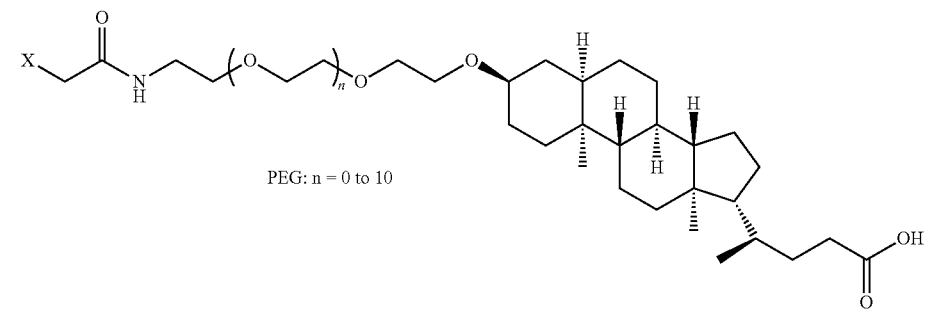<br>PEG: n = 0 to 10 |
| 9 | 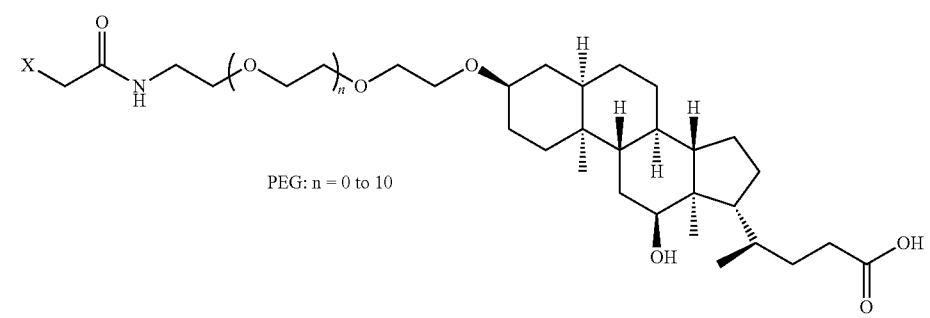<br>PEG: n = 0 to 10 |
| 10 | 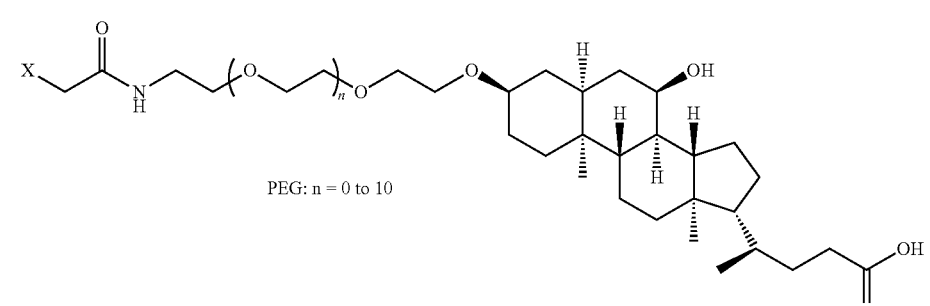<br>PEG: n = 0 to 10 |
| 11 | 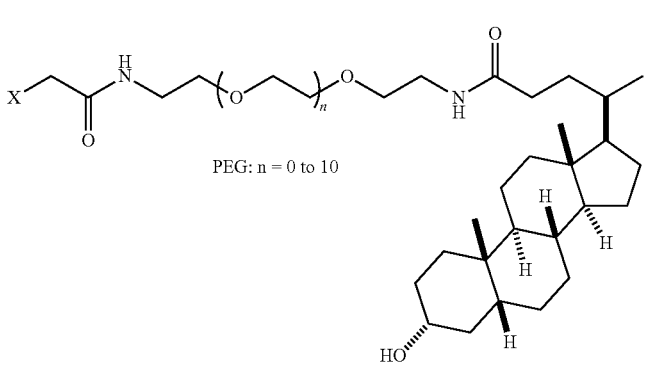<br>PEG: n = 0 to 10 |

TABLE 1-continued

| entry | Structure* |
|---|---|
| 12 | [Structure: X-CH2-C(O)-NH-CH2CH2-(O-CH2CH2)n-O-CH2CH2-NH-C(O)-CH2CH2-CH(CH3)-[steroid with 12α-OH and 3α-OH (deoxycholic acid derivative)]; PEG: n = 0 to 10] |
| 13 | [Structure: X-CH2-C(O)-NH-CH2CH2-(O-CH2CH2)n-O-CH2CH2-NH-C(O)-CH2CH2-CH(CH3)-[steroid with 7α-OH and 3α-OH (chenodeoxycholic acid derivative)]; PEG: n = 0 to 10] |
| 14 | [Structure: X-CH2-C(O)-NH-CH2CH2-(O-CH2CH2)n-O-CH2CH2-NH-C(O)-CH2-O-CH2CH2-O-CH2CH2-NH-C(O)-CH(COOH)-CH2CH2-NH-C(O)-(CH2)m-COOH; PEG: n = 1 to 10; m = 1-15] |
| 15 | [Structure: X-CH2CH2-NH-C(O)-(CH2)n-CH3; n = 1-15] |
| 16 | [Structure: X-CH2CH2-NH-C(O)-(CH2)n-CH2-C(O)-OH; n = 1-15] |
| 17 | [Structure: X-CH2CH2-NH-C(O)-CH2CH2-(CH2-CH=CH)n-CH2CH3; n = 1-6] |

TABLE 1-continued
| entry | Structure* |
|---|---|
| 18 | 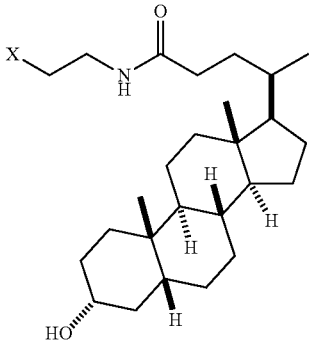 |
| 19 | 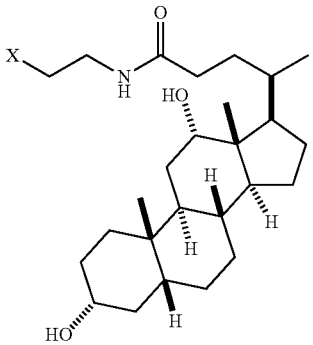 |
| 20 | 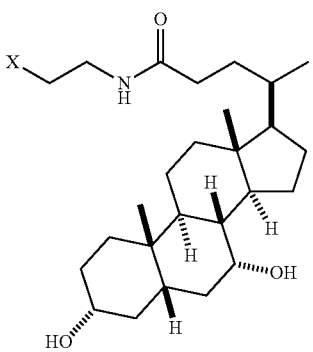 |
| 21 | 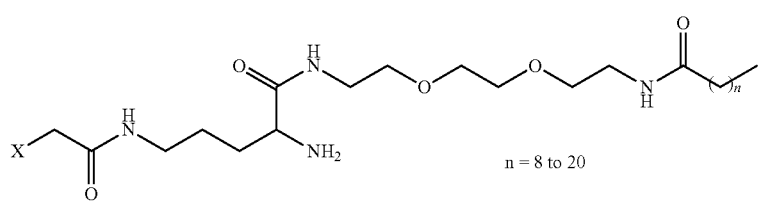<br>n = 8 to 20 |
| 22 | 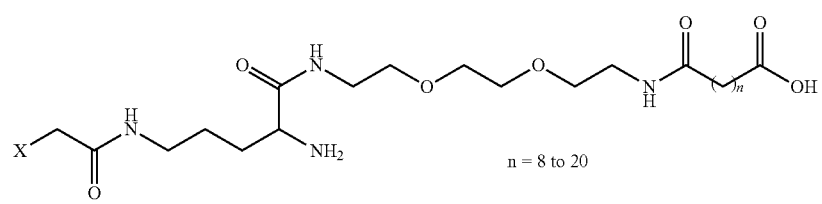<br>n = 8 to 20 |

TABLE 1-continued

| entry | Structure* |
|---|---|
| 23 | (chemical structure) n = 8 to 20 |
| 24 | (chemical structure) n = 8 to 20 |
| 25 | (chemical structure) n = 8 to 20 |
| 26 | (chemical structure) n = 8 to 20 |
| 27 | (chemical structure) n = 8 to 20 |
| 28 | (chemical structure) n = 8 to 20 |
| 29 | (chemical structure) n = 8 to 20 |
| 30 | (chemical structure) n = 8 to 20 |
| 31 | (chemical structure) n = 8 to 20 |

TABLE 1-continued

| entry | Structure* |
|---|---|
| 32 | Z–S–CH₂CH₂–NH–C(O)–CH₂–O–CH₂CH₂–O–CH₂CH₂–NH–C(O)–(CH₂)$_n$–C(O)–OH, n = 8 to 20 |
| 33 | Z–S–CH(CH₃)CH₂–NH–C(O)–CH₂–O–CH₂CH₂–O–CH₂CH₂–NH–C(O)–(CH₂)$_n$–CH₃, n = 8 to 20 |
| 34 | Z–S–C(CH₃)₂CH₂–NH–C(O)–CH₂–O–CH₂CH₂–O–CH₂CH₂–NH–C(O)–(CH₂)$_n$–CH₃, n = 8 to 20 |

*X can be Cl, I, Br, maleimide, an amino acid which is part of the peptide, or a staple; Y can be OH, an amino acid which is part of the peptide, or a staple; Z can be S which is part of an amino acid which is part of the peptide, S which is part of the staple, or S which is part of a lipid derivative (to form a disulfide).

TABLE 2

| entry | Staple | Structure |
|---|---|---|
| 35 | L1 | Br–CH₂–C(O)–NH–(CH₂)₄–NH–C(O)–CH₂–Br |
| 36 | L2 | Lysine-based staple with BrCH₂C(O)NH– on α-amine and side-chain amine, linked through PEG2 to a long alkyl chain acyl group |
| 37 | L3 | Lysine-based staple with BrCH₂C(O)NH– on α-amine and side-chain amine, linked through extended PEG linker to a long alkyl chain acyl group |
| 38 | L4 | Lysine-based staple with BrCH₂C(O)NH– on α-amine and side-chain amine, linked through PEG linker to a long-chain dicarboxylic acyl group terminating in –COOH |

TABLE 2-continued

| entry | Staple | Structure |
|---|---|---|
| 39 | L5 | 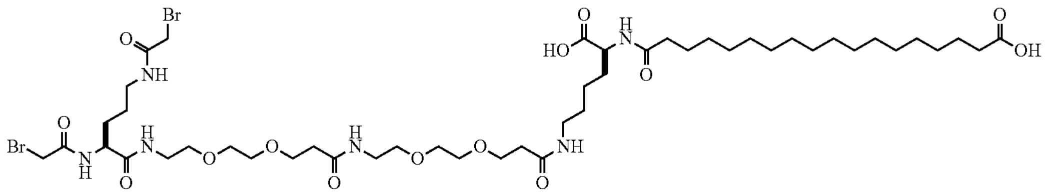 |
| 40 | L6 | 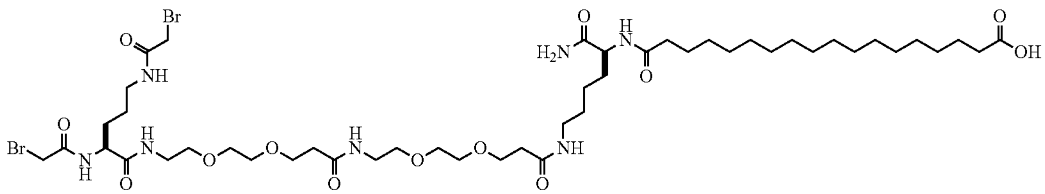 |
| 41 | L7 | 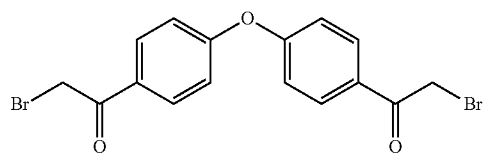 [SMILES: O=C(CBr)c1ccc(Oc2ccc(C(=O)CBr)cc2)cc1] |
| 42 | L8 | 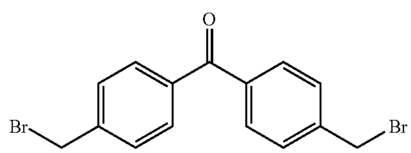 [SMILES: O=C(c1ccc(CBr)cc1)c1ccc(CBr)cc1] |
| 43 | L9 | 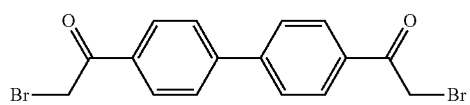 |
| 44 | L10 | 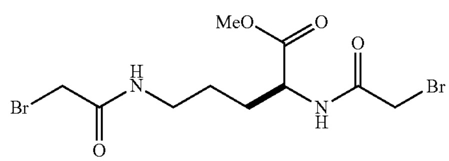 |
| 45 | L11 | 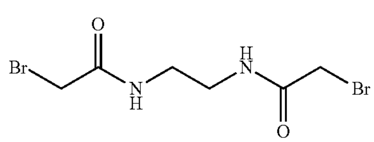 [SMILES: O=C(CBr)NCCNC(=O)CBr] |
| 46 | L12 | 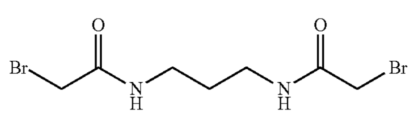 [SMILES: O=C(CBr)NCCCNC(=O)CBr] |
| 47 | L13 | 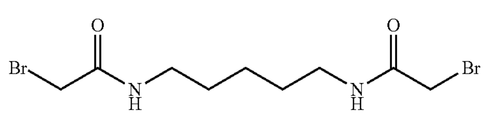 [SMILES: O=C(CBr)NCCCCCNC(=O)CBr] |
| 48 | L14 | 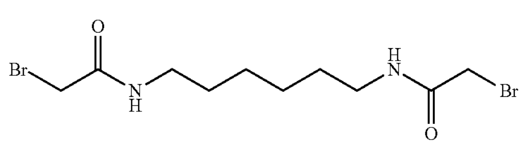 [SMILES: O=C(CBr)NCCCCCCNC(=O)CBr] |

TABLE 2-continued

| entry | Staple | Structure |
|---|---|---|
| 49 | L15 | 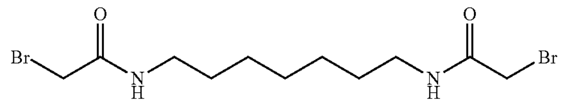 [SMILES: O=C(CBr)NCCCCCCCNC(=O)CBr] |
| 50 | L16 | 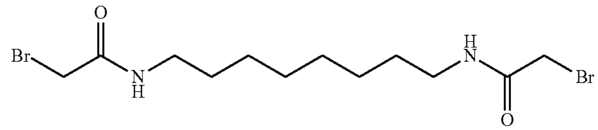 [SMILES: O=C(CBr)NCCCCCCCCNC(=O)CBr] |
| 51 | L17 | 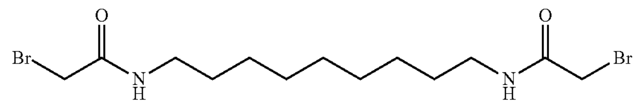 [SMILES: O=C(CBr)NCCCCCCCCCNC(=O)CBr] |
| 52 | L18 | 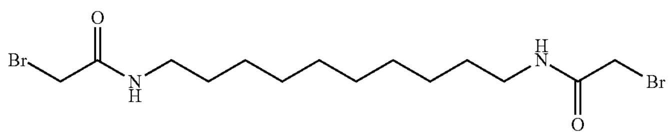 [SMILES: O=C(CBr)NCCCCCCCCCCNC(=O)CBr] |
| 53 | L19 | 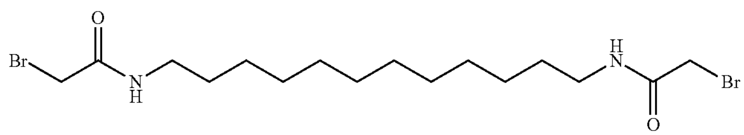 [SMILES: O=C(CBr)NCCCCCCCCCCCCNC(=O)CBr] |
| 54 | L20 | 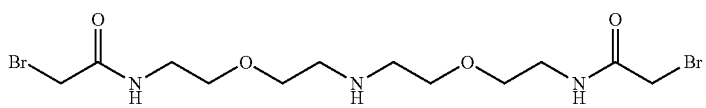 [SMILES: O=C(CBr)NCCOCCNCCOCCNC(=O)CBr] |
| 55 | L21 | 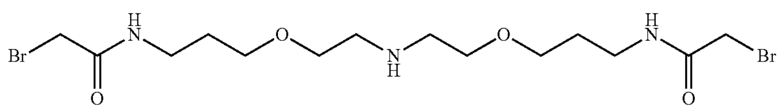 [SMILES: O=C(CBr)NCCCOCCNCCOCCCNC(=O)CBr] |
| 56 | L22 | 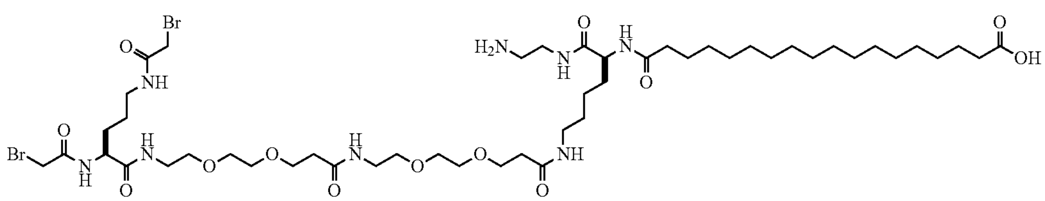 |

Example 11. Generation of CREB Responsive Luciferase Stable Cell Lines Overexpressing Glucagon, GLP-1, GIP, or GLP2 Receptor CREB responsive luciferase stable HEK 293 cell line overexpressing human glucagon receptor (GCGR), glucagon-like peptide 1 receptor (GLP-1R), Glucose-dependent insulinotropic polypeptide receptor (GIPR), or Glucagon-like peptide 2 receptor (GLP-2R) was generated as follows.

HEK293 cells were infected with lent virus encoding firefly luciferase gene under the control of CRE promoter, as described in the manual (Qiagen, Netherlands) and then were selected using 1 µg/mL puromycin (Life technologies, Carlsbad) for 1 week. The survived cells were named as CRE-HEK293, expanded and then transfected with a G418 selective mammalian expression plasmid encoding human GCGR, GLP-1R, GIPR or GLP-2R. In brief, GCGR, GLP-1R, GIPR, or GLP-2R plasmid was transfected into CRE-HEK293 cells using Lipofectamine 2000 and selected with 400 µg/mL geneticin (Life technologies, Carlsbad, Calif.). Single colony stable cell lines overexpressing both CRE-luciferase and GCGR, GLP-1R, GIPR, or GLP-2R were then established for in vitro activity assays. These four stable cell lines were named as HEK293-GCGR-CRE, HEK293-GLP-1R-CRE, HEK293-GIPR-CRE, and HEK293-GLP-2R-CRE.

Example 12. In Vitro Activity Assays (Receptor-Mediated cAMP Synthesis)

HEK293-GCGR-CRE, HEK293-GLP-1R-CRE, HEK293-GIPR-CRE, and HEK293-GLP-2R-CRE cells were seeded in a white 384-well plate at a density of 5,000 cells per well and cultured for 24 hours. Cells were treated with different peptides in a dose dependent manner. On the next day, 10 µl of Bright-Glo reagent (Promega, Madison, Wis.) were added into each well and firefly luminescence was determined using an Envision multilabel plate reader (PerkinElmer, Waltham, Mass.). $EC_{50}$ of each peptide was calculated using GraphPad Prism 6 software (GraphPad, San Diego, Calif.).

Exemplary data for select mTAs from Tables 6-9 are shown in FIGS. 8-11.

Example 13. In Vivo Pharmacokinetic (PK) Studies

Female CD-1 mice obtained from Charles River Limited were used after overnight food deprivation for in vivo PK study. Peptides were dissolved in pH adjusted Phosphate buffered saline (PBS). 100 µL of each peptide (0.3 mg/kg) was administered into each mouse through either i.v. or s.c route. Food was provided to mice immediately after bleeding at 30 minute. Blood were extracted into heparinized tubes and centrifuged at 3,000×g for 15 min. The resulting supernatant plasma were then stored at −80° C. for activity assays. The concentrations of peptides in plasma at each time point were determined by activity assay described above and in vivo half-life of each peptide was calculated by using Winnonlin Phoenix software (Pharsight Corp, St. Louis, Mo.).

Figure 12A:
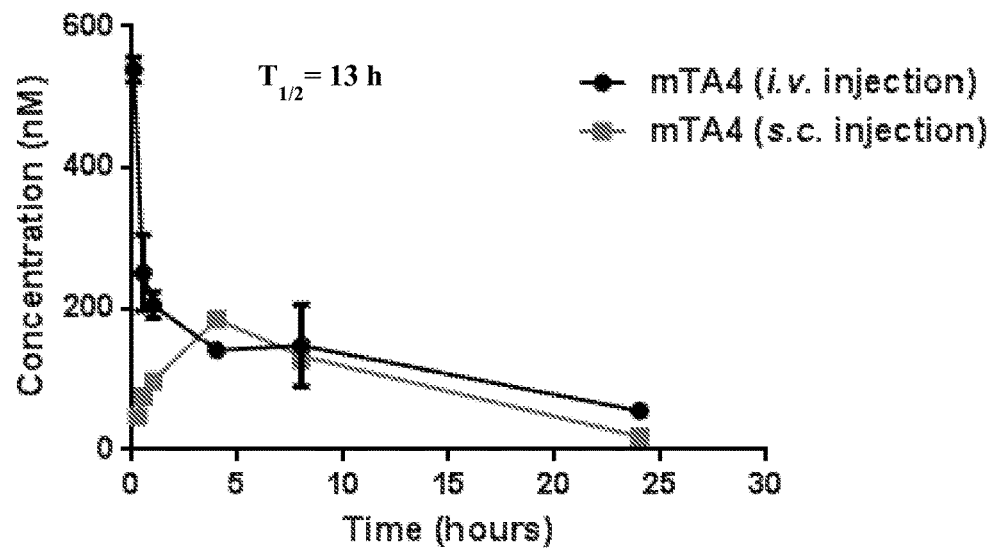
FIG. 12A shows the pharmacokinetic profiles of mTA4 in mice after i.v. or s.c. injection.
Figure 12B:
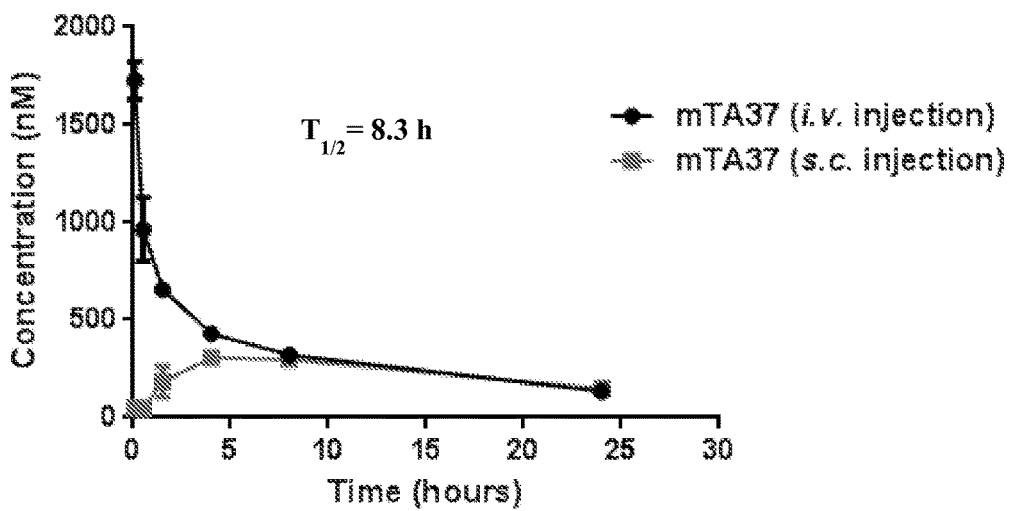
FIG. 12B shows the pharmacokinetic profile of mTA37 in mice after i.v. or s.c. injection.
Figure 12C:
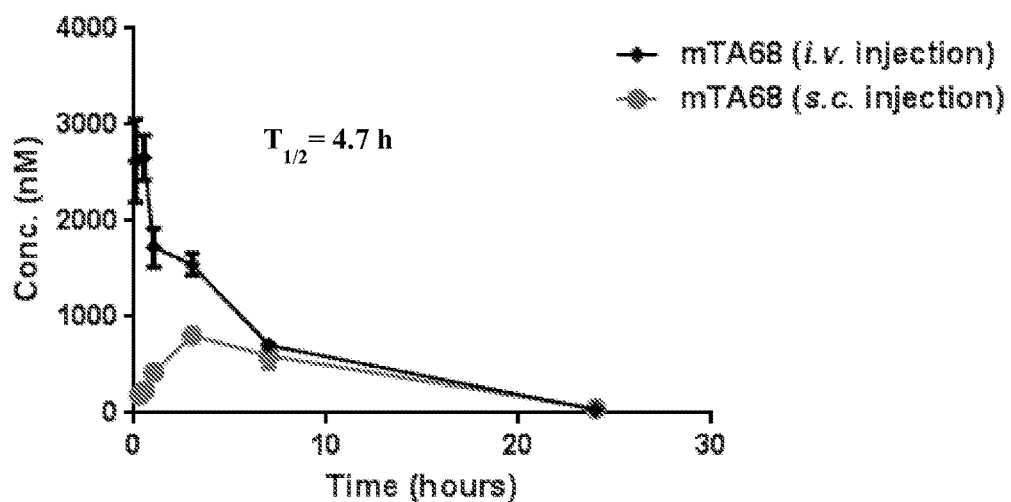
FIG. 12C shows the pharmacokinetic profile of mTA68 in mice after i.v. or s.c. injection.
Figure 13A:
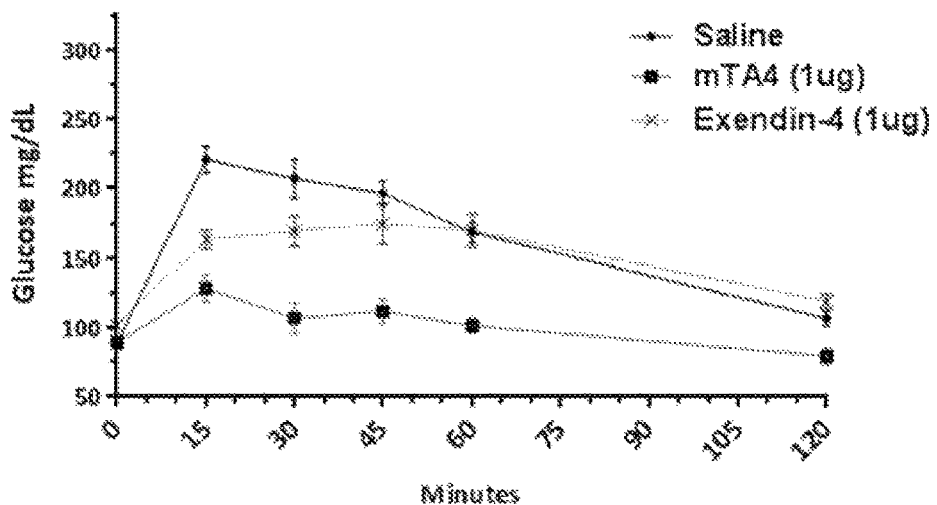
FIG. 13A shows the oral glucose tolerance test (OGTT) results for mice after mTA4 administration.
Figure 13B:
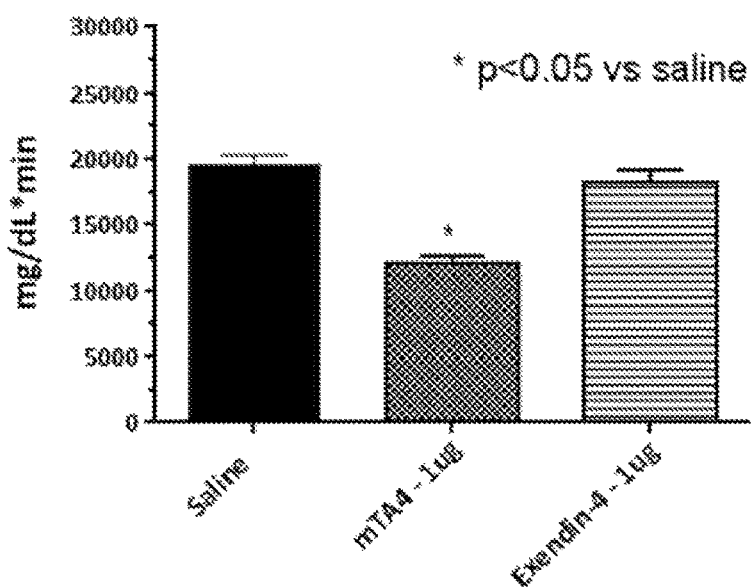
FIG. 13B shows the AUC from the oral glucose tolerance test (OGTT) results in mice after mTA4 administration.
Figure 13C:
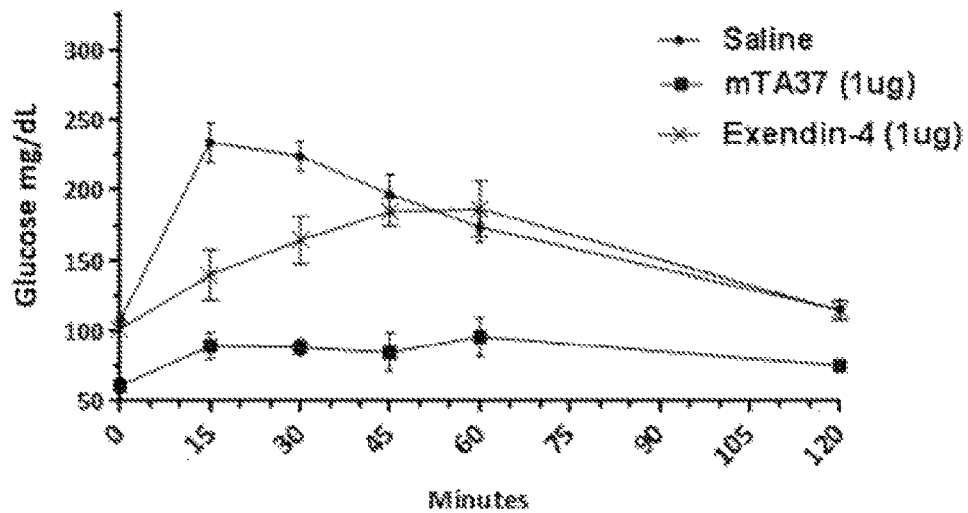
FIG. 13C shows the oral glucose tolerance test (OGTT) results for mice after mTA37 administration.
Figure 13D:
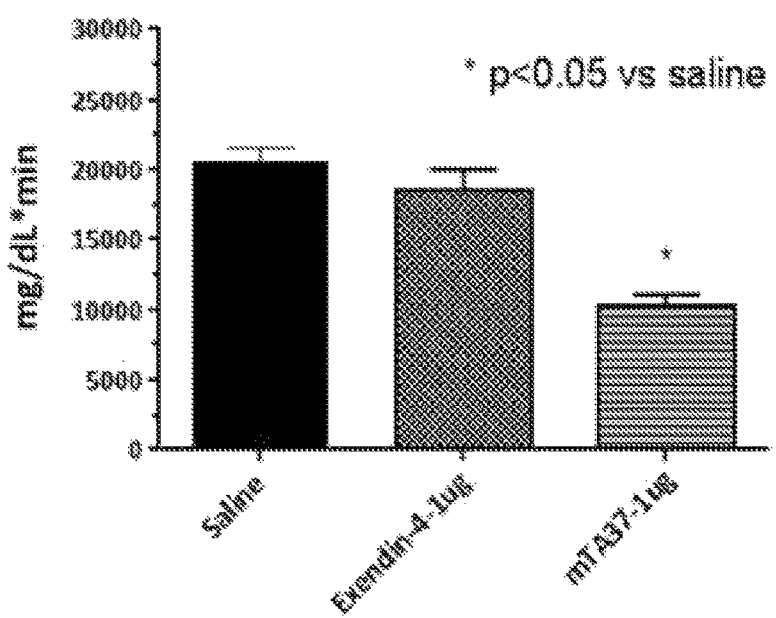
FIG. 13D shows the AUC from the oral glucose tolerance test (OGTT) results in mice after mTA37 administration.

Exemplary data are for select mTAs from Tables 6-9 are shown in FIG. 12. The curves represent the mean of five animals. Calculated half-life values are shown.

Example 14. Oral Glucose Tolerance Test (OGTT) and Intraperitoneal Glucose Tolerance Test (IPGTT)

CD1 mice were fasted for overnight and then administrated with certain amount of peptides through either i.v. or s.c. route. After 6 hours, mice were orally or intraperitoneally administrated with bolus dose of glucose solution at 2 g/kg body mass at concentration of 100 mg/mL and their tail blood glucose levels were measured before (0 min) and after glucose challenge for 2 to 3 hours.

Exemplary data for mTA4 and mTA37 (see Table 6) are shown in FIG. 13 (n=5 for both). Both mTA4 and mTA37 are functional in wild-type mice. The data indicate increased oral glucose tolerance after administration of mTA. OGTT results for mTA4 demonstrated that mTA4 had a greater effect than exendin-4 at 6 hours after a single i.v. dose of mTA.

Example 15. Body Weight, Food Intake, and Visceral Fat Mass Measurement

Diet Induced Obese (DIO) mice were purchased from Charles River and administrated by s.c. route with GLP1R agonist or GLP1R/GCGR dual agonist. Mouse body weight and food intake were monitored daily for 2 weeks, and followed before (5 days in total) and during treatment (5-weeks in total). After 5 weeks, mice were sacrificed and visceral fat mass were taken out and weighed.

Figure 14A:
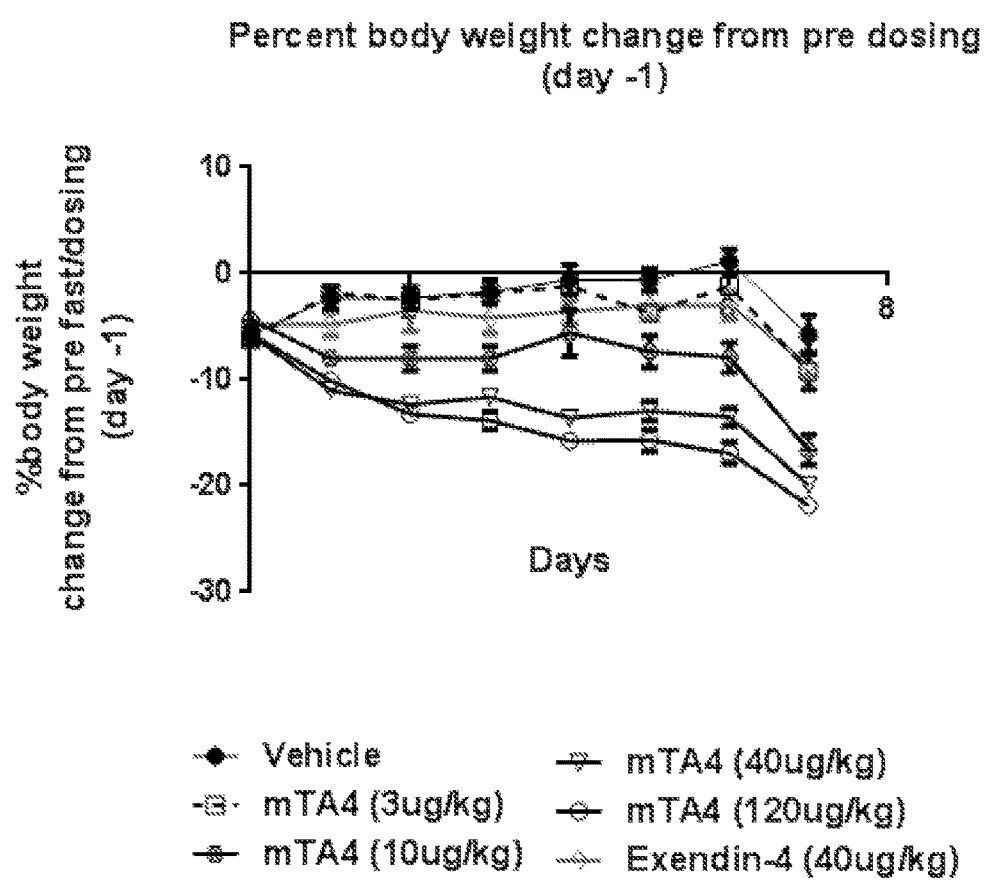
FIG. 14A shows the dose response weight loss in DIO mice after mTA4 administration.
Figure 14B:
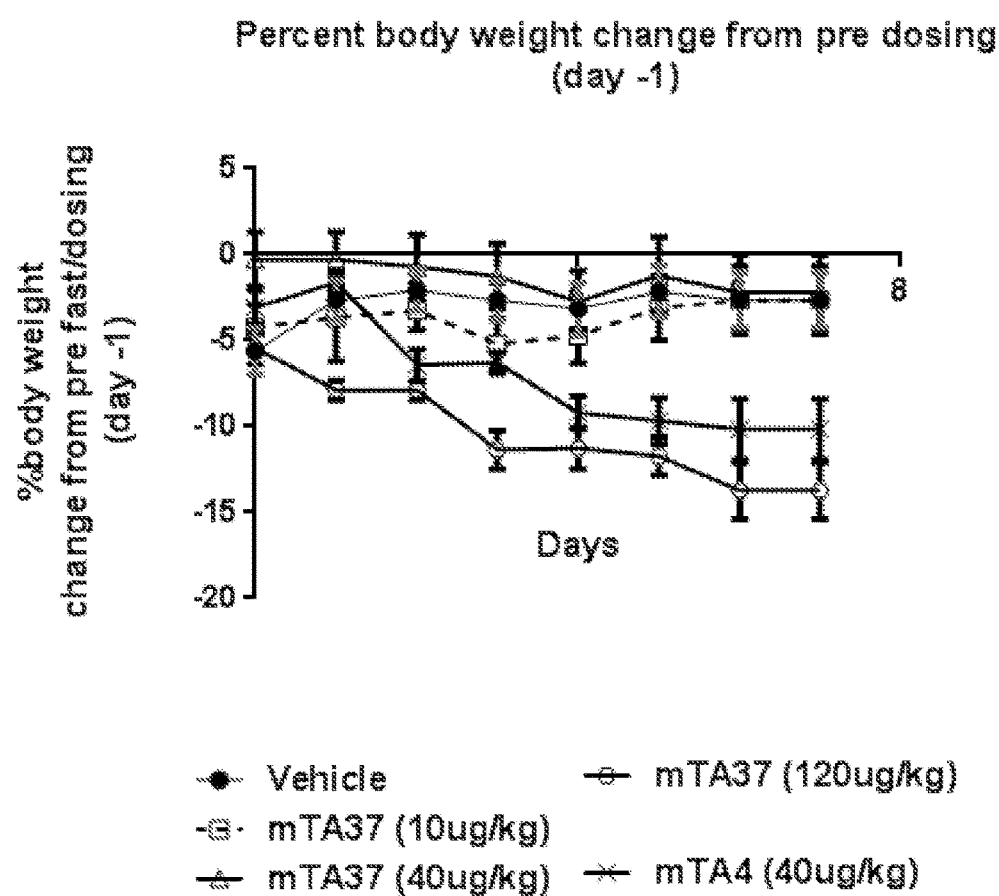
FIG. 14B shows the dose response weight loss in DIO mice after mTA37 and mTA4 administration.
Figure 15A:
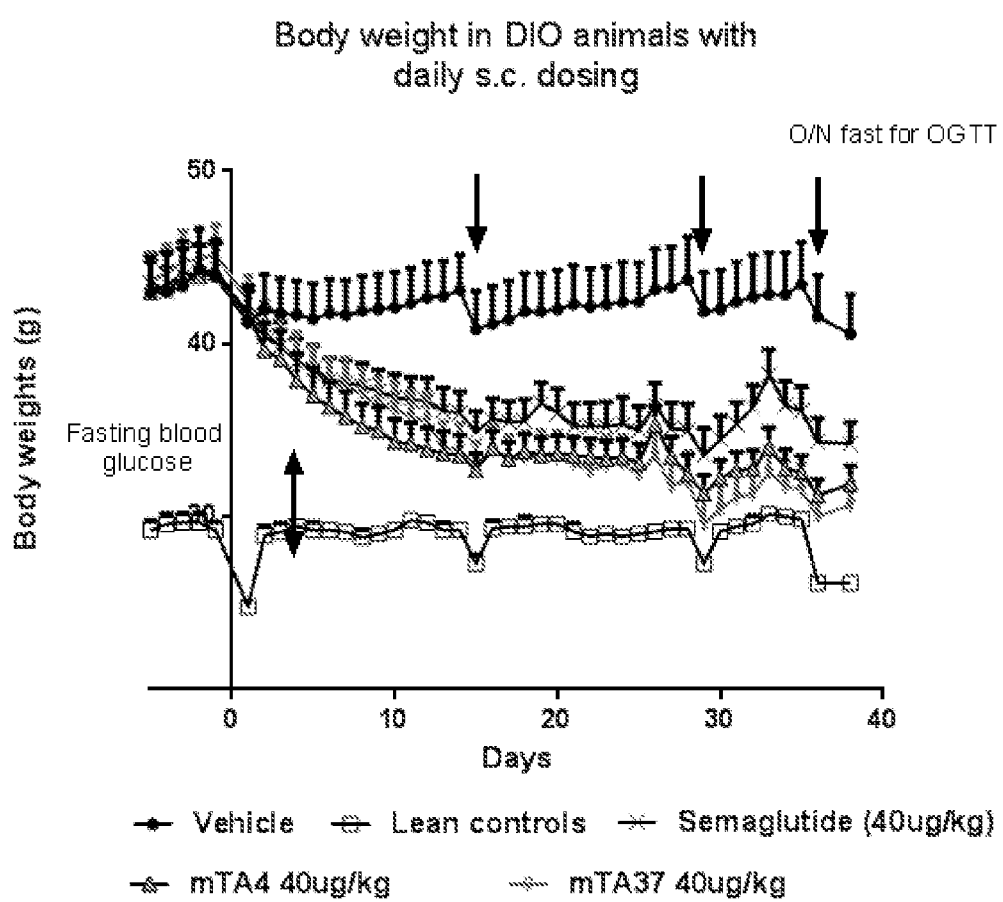
FIG. 15A shows the body weights in DIO animals with daily s.c. dosing with mTA4 and mTA37.
Figure 15B:
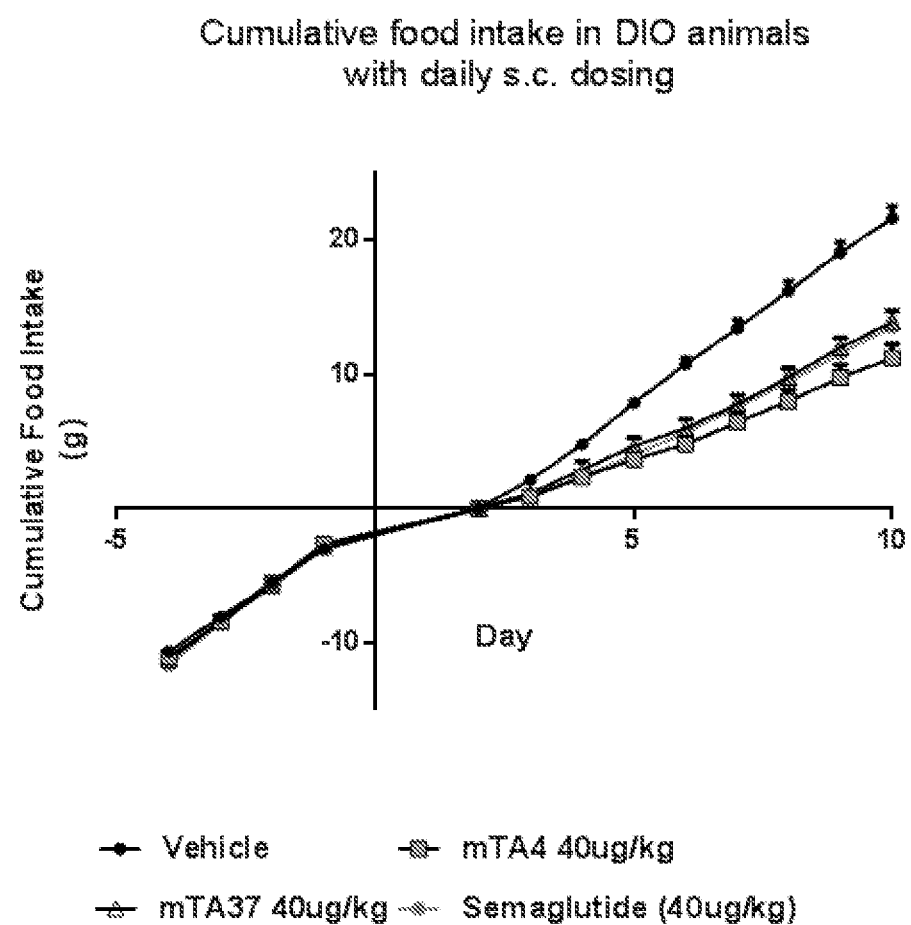
FIG. 15B shows the cumulative food intake in DIO animals with daily s.c. dosing with mTA4 and mTA37.
Figure 16A:
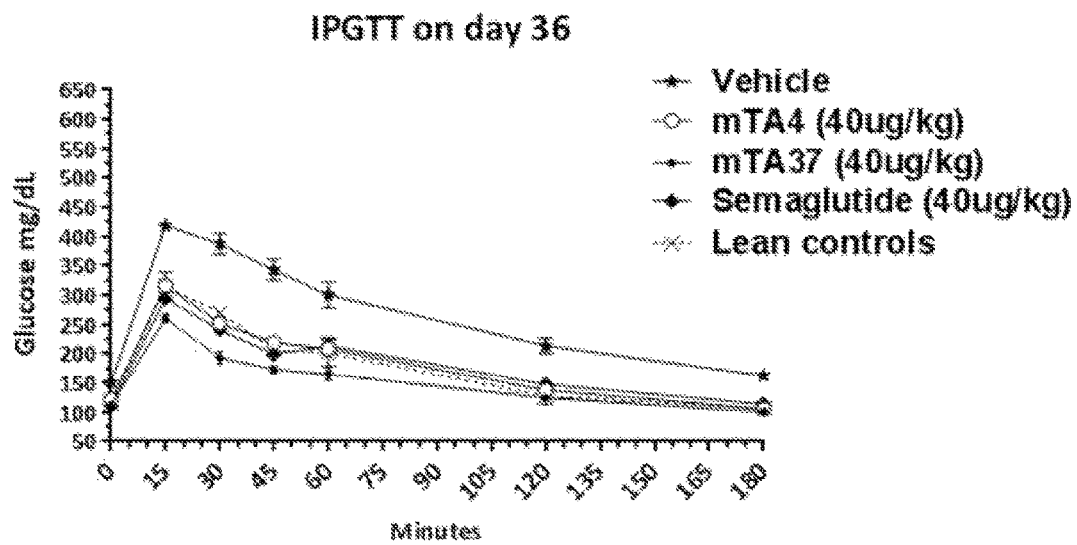
FIG. 16A shows the intraperitoneal glucose tolerance test (IPGTT) results in DIO mice after mTA4 and mTA37 administration.
Figure 16B:
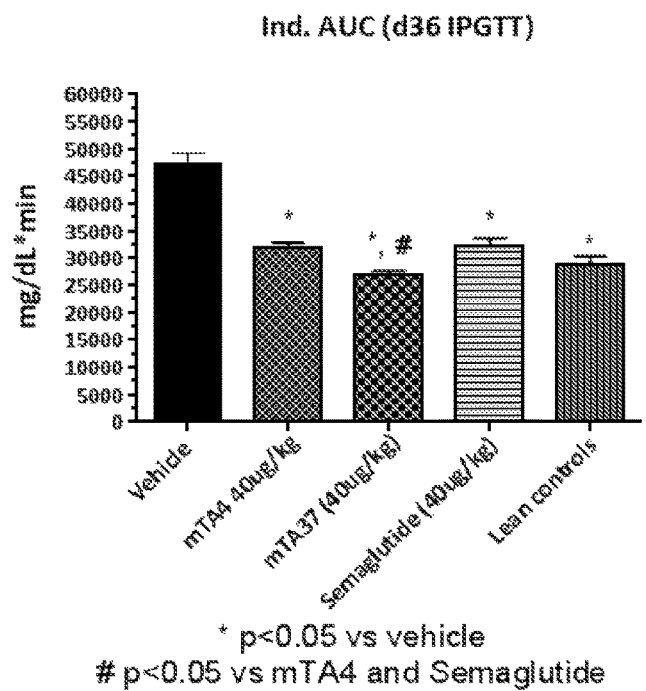
FIG. 16B shows the AUC from the intraperitoneal glucose tolerance test (IPGTT) results for mice after mTA4 and mTA37 administration.
Figure 17:
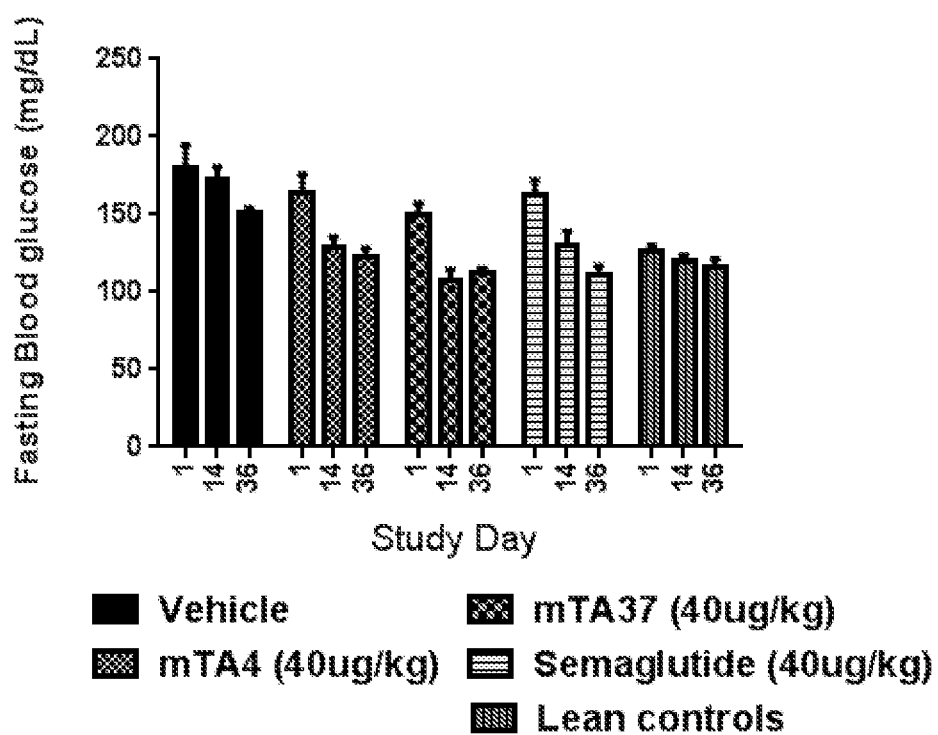
FIG. 17 shows fasting blood glucose levels after mTA administration.

Dose dependent weight loss induced by mTA4 or mTA37 (see Table 6) is shown in FIG. 14. Chronic effect on body weight loss with daily administration of mTA4 or mTA37 for 5 weeks and cumulative food intake for 2 weeks are shown in FIG. 15. Increased intra-peritoneal glucose tolerance after daily administration of mTA4 or mTA37 for 5 weeks is shown in FIG. 16. Reduced fasting blood glucose levels after daily administration of mTA4 or mTA37 for 5 weeks is shown in FIG. 17.

Example 16. Cholesterol Level Determination

Collected plasma was used for cholesterol level determination according to the manufacturer's guide (cholesterol assay kit, Abcam, Cambridge, England). Briefly, plasma was diluted using cholesterol assay buffer and then reacted with same volume of reaction mix containing cholesterol assay buffer, cholesterol probe, enzyme mix and cholesterol esterase. After incubation at 37° C. for 1 hour, the absorbance at 560 nm was measured using an Envision multilabel plate reader (PerkinElmer, Waltham, Mass.). Subsequently, the concentration of cholesterol in plasma was calculated using a standard curve.

Figure 18A:
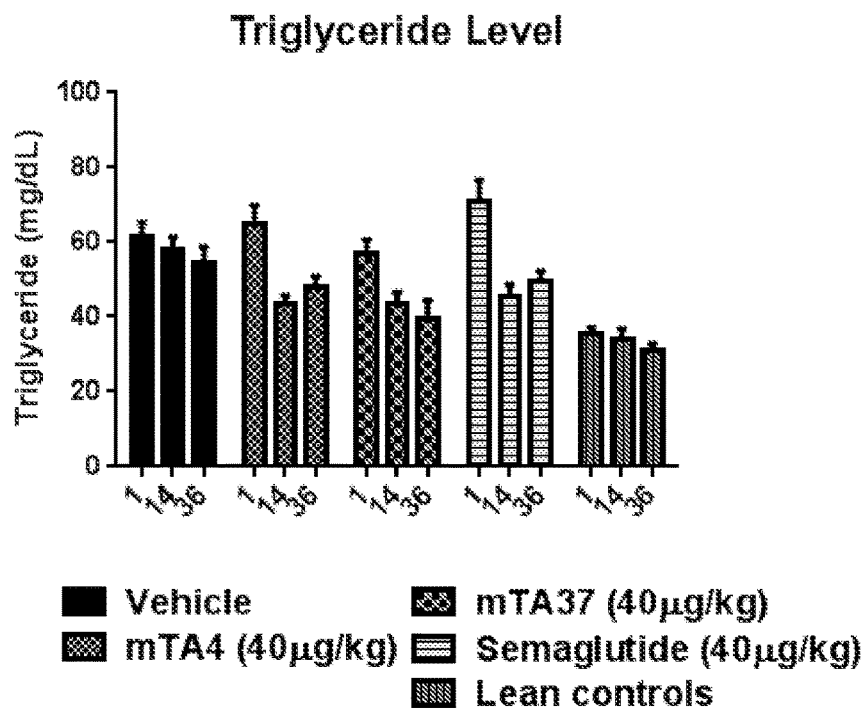
FIG. 18A shows the plasma triglyceride levels after mTA4 and mTA37 administration.
Figure 18B:
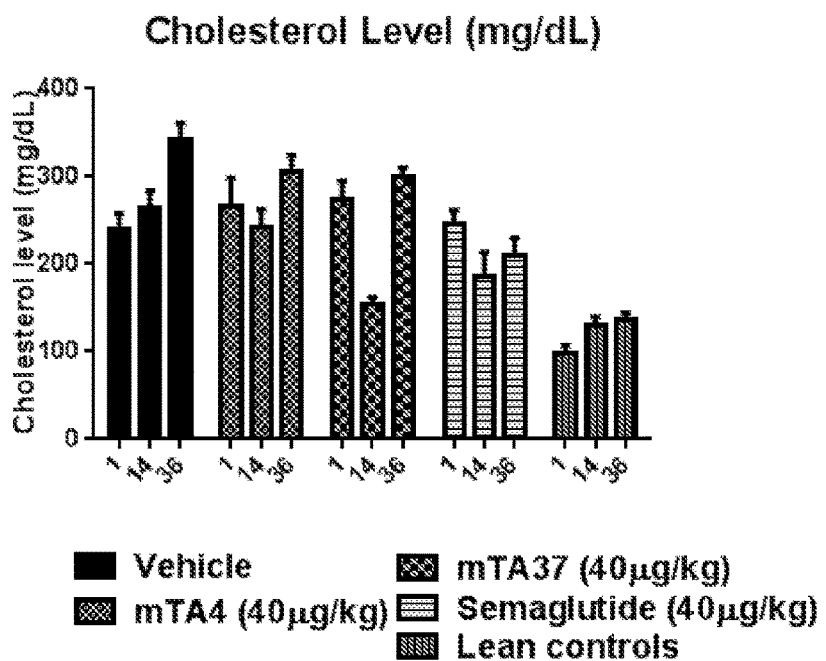
FIG. 18B shows the plasma cholesterol levels after mTA4 and mTA37 administration.

Exemplary data for select mTAs is shown in FIG. 18B. There was decreased cholesterol level in plasma after daily administration of mTA4 or mTA37 for 5 weeks.

Example 17. Triglyceride Level Measurement

Collected plasma was again used for triglyceride level determination using a triglyceride colorimetric assay kit (Cayman chemical, Ann Arbor, Mich.). 5 µL of plasma samples or standard were added into a 384 well plate and followed by adding 75 µL of diluted enzyme buffer to each well. The plate was incubated at room temperature for 15 min, and the absorbance was read at 560 nm using an Envision multilabel plate reader (PerkinElmer, Waltham, Mass.). Again, the concentration of triglyceride in plasma was calculated using a standard curve.

Exemplary data for select mTAs is shown in FIG. 18A. There was decreased triglyceride level in plasma after daily administration of mTA4 or mTA37 for 5 weeks.

Example 18. Oil Red O Staining (Lipid Droplet Staining)

Frozen tissue sections of liver were cut at 10 m and air dried to the slides. After fixation in 10% formalin for 5 min, the slides were briefly washed with running tap water for 10 min, followed by rinse with 60^ isopropanol. Subsequently, oil red O working solution (0.3% oil red O) was used for lipid staining for 15 min. Slides were again rinsed with 60% isopropanol and then nuclei were lightly stained with alum haematoxylin, followed by rinse with distilled water and mounted in glycerine jelly. After half an hour, pictures were taken under microscopy.

Figure 19:
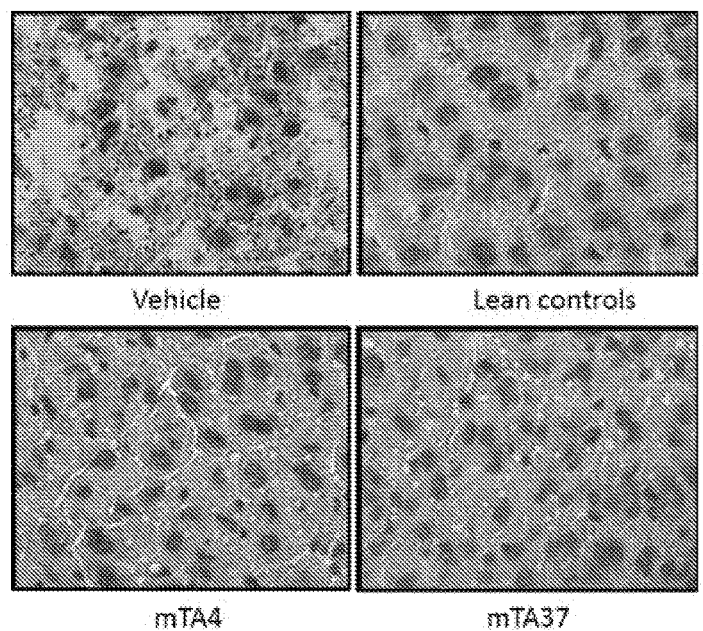
FIG. 19 shows lipid droplet staining in liver after mTA administration.

Exemplary data are shown in FIG. 19, in which reduced lipid droplet amounts were observed after daily administration of mTA4 or mTA37 for 5 weeks.

Example 19. Application of Micro-Needle Based Patch on Guinea Pigs

Microneedle patch based transdermal drug delivery was performed using guinea pigs. Guinea pigs were shaved one day before patch application. On the second day, microneedle based patches were applied onto the animal skin for 5 min and blood was extracted at different time points (5 min, 30 min, 1 h, 2 h, 3 h, 5 h, 8 h, 24 h, 32 h, 48 h, 72 h). Peptide concentration at each time point was determined using the same method (functional activity assay) as described above. Transdermal bioavailability (F) was calculated as the ratio of area under the curve (AUC) between microneedle patch application and i.v. injection groups.

Figure 20:
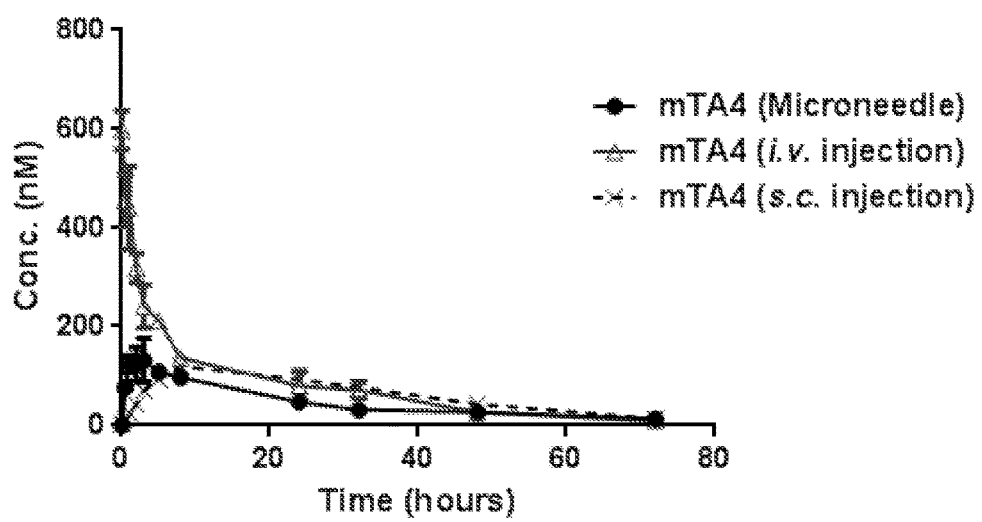
FIG. 20 shows pharmacokinetic profiles of mTA4 after i.v. or s.c. injection, and micro-needle based transdermal delivery in guinea pigs.
Figure 21A:
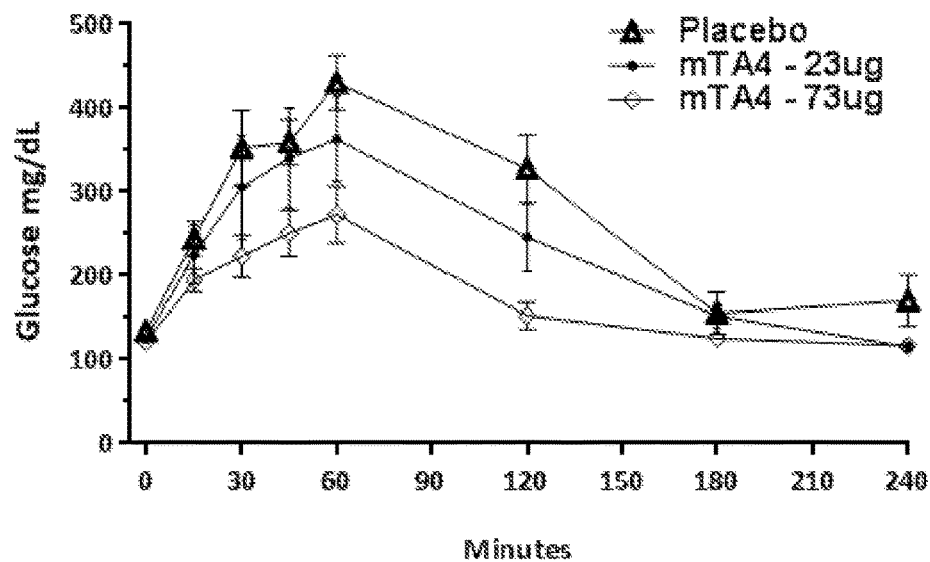
FIG. 21A shows the OGTT results after mTA4 administration through micro-needle based transdermal delivery in guinea pigs (24 h post injection).
Figure 21B:
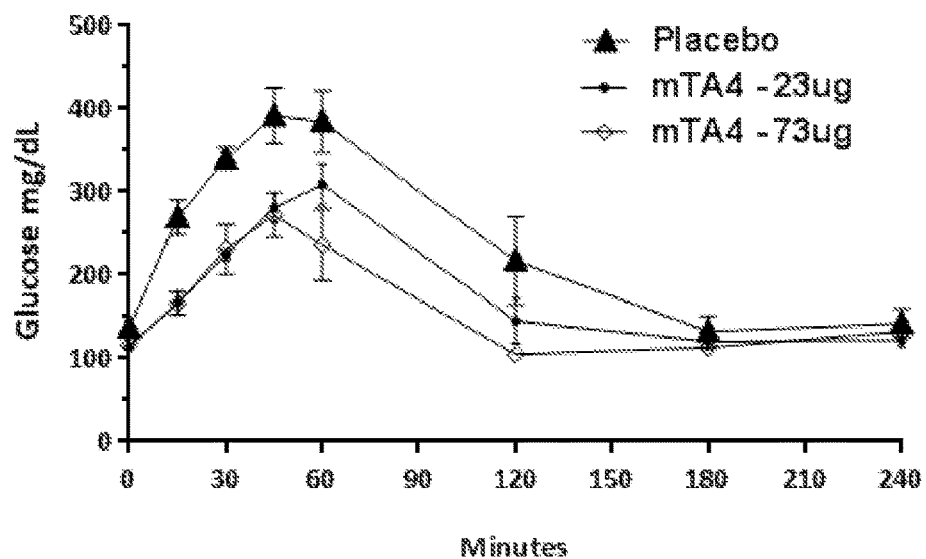
FIG. 21B shows OGTT results after mTA4 administration through micro-needle based transdermal delivery in guinea pigs (48 h post injection).
Figure 21C:
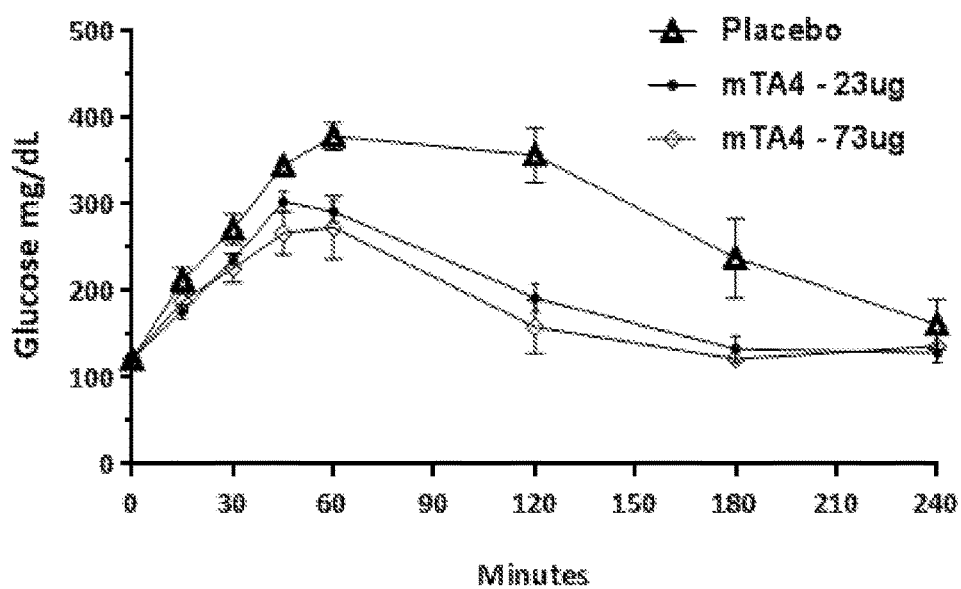
FIG. 21C shows OGTT results after mTA4 administration through micro-needle based transdermal delivery in guinea pigs (96 h post injection).
Figure 22A:
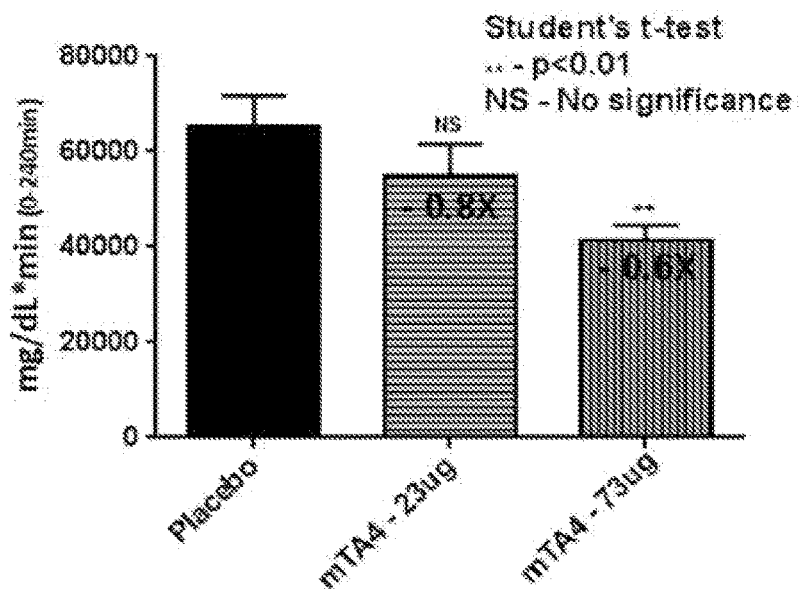
FIG. 22A shows the AUC values from OGTT results after mTA4 administration through micro-needle based transdermal delivery in guinea pigs (24 h post injection).
Figure 22B:
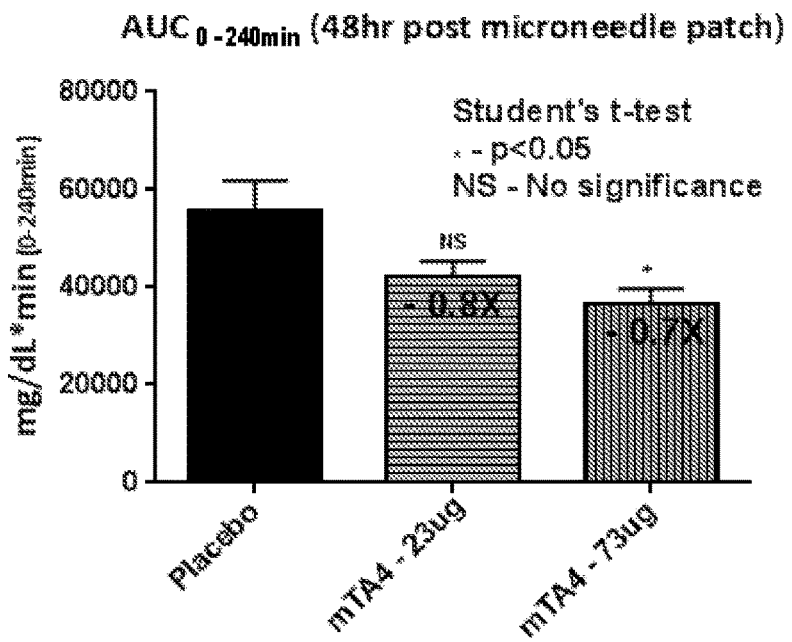
FIG. 22B shows AUC values from OGTT results after mTA4 administration through micro-needle based transdermal delivery in guinea pigs (48 h post injection).
Figure 22C:
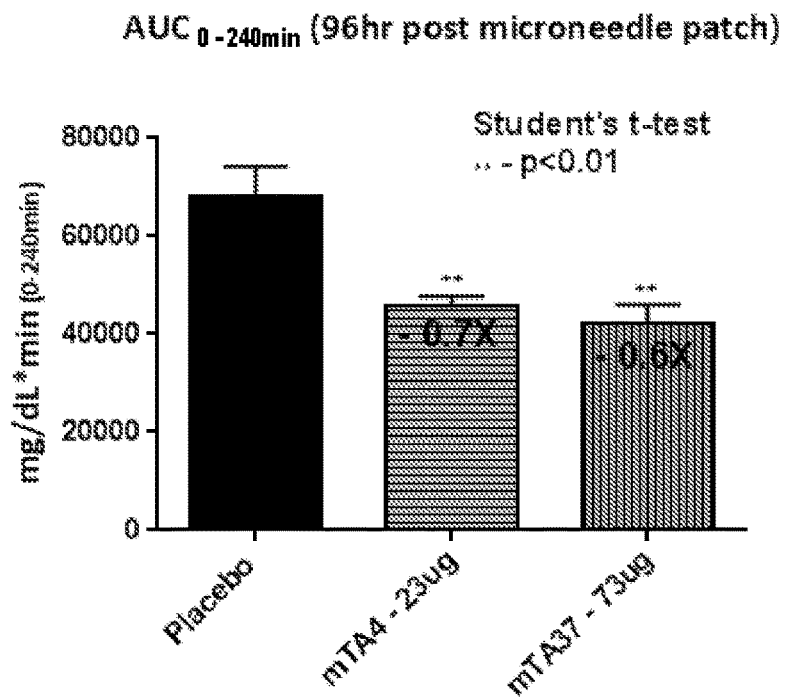
FIG. 22C shows AUC values from OGTT results after mTA4 administration through micro-needle based transdermal delivery in guinea pigs (96 h post injection).

Exemplary data are shown in FIGS. 20-22. Pharmacokinetic profiles of mTA4 after i.v. or s.c. injection or microneedle based transdermal delivery are shown in FIG. 20. Blood glucose curves and AUC values from an oral glucose tolerance test at 24 h, 48 h, and 96 h after mTA administration through micro-needle based transdermal delivery are shown in FIGS. 21 and 22.

Example 20. Murine Model of Ulcerative Colitis (DSS Model)

Colitis in mouse was induced by adding 3% DSS (dextran sulfate sodium) in the drinking water for 12 consecutive days. Besides DSS placement, mice were daily treated with GLP-2 analogs (40 μg/kg/day) [GLP-2G is the GLP2 sequence with G2S mutation and is a known drug called teduglutide]. Cyclosporine A (20 mg/kg/day) was used for the positive control group and PBS for the negative control group. During the experiment period, body weight was measured every day.

Intestinal Weight/Body Weight Measurement

Animals were sacrificed after 12 days of treatment. Small intestine was immediately excited and flushed with PBS. After PBS was gently squished out, intestinal weight was weighed using an analytical balance. Intestinal vs. body weight ratio was then calculated and analyzed.

Figure 23A:
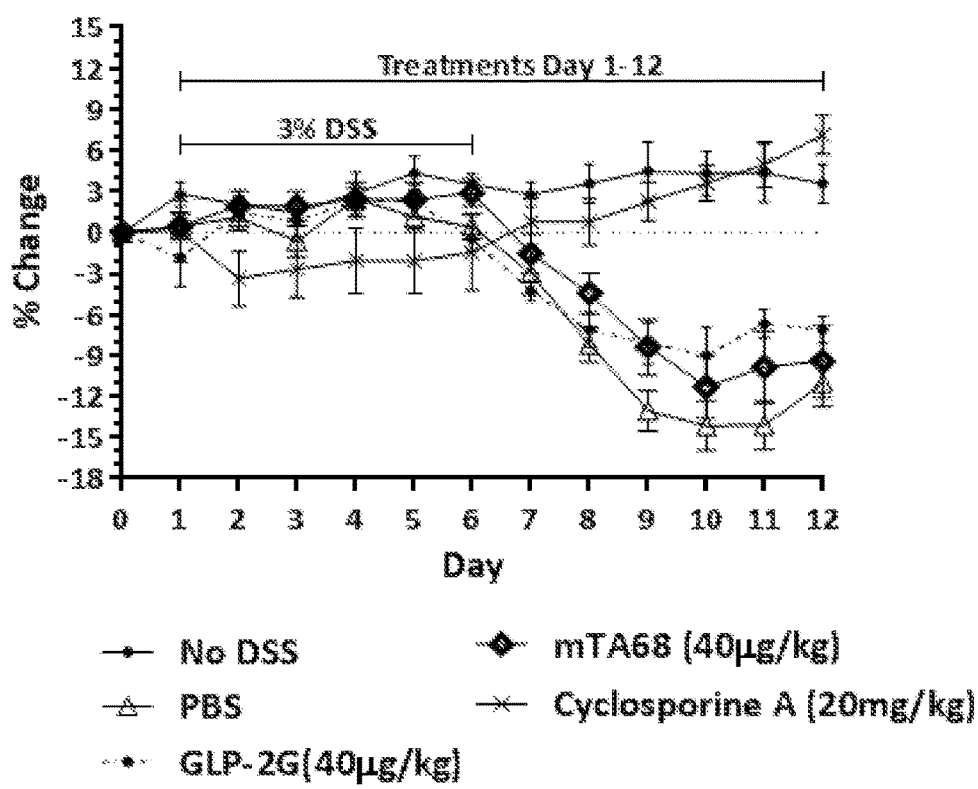
FIG. 23A shows the body weight changes in DSS-induced colitis mice after daily administration of mTA68 for 12 days.
Figure 23B:
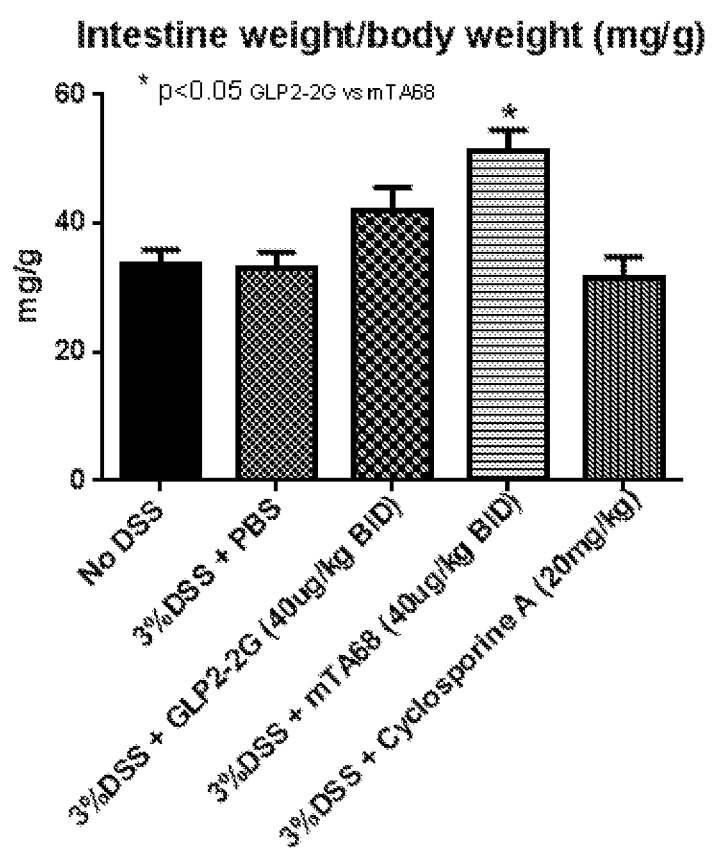
FIG. 23B shows the intestine weight vs. body weight in DSS-induced colitis mice after daily administration of mTA68 for 12 days.

Body weight and intestine weight versus body weight in DSS-induced colitis mice after daily administration of mTA68 for 12 days are shown in FIG. 23.

Example 21. Efficacy and Safety of mTA for the Treatment of Diabetes and Obesity Purpose: Different doses of mTA are compared to placebo to determine efficacy and safety for the treatment of patients with diabetes and obesity.

| Condition | Intervention | Phase |
|---|---|---|
| Diabetes and Obesity | Drug: single agonist or dual agonist mTA | Phase 1 |
| | Drug: Placebo | Phase 1 |

Study Type: Interventional
Study Design: Allocation: Randomized
Endpoint Classification: Safety/Efficacy Study
Intervention Model: Parallel Assignment
Masking: Double Blind (Subject, Caregiver, Investigator, Outcomes Assessor)
Primary Purpose: Treatment
Primary Outcome Measures: reduced blood glucose, reduced body weight and HbA1C [Time Frame: Up to 52 weeks] [Designated as safety issue: No]
Secondary Outcome Measures: improved metabolic profiles
[Time Frame: Up to day 52 weeks] [Designated as safety issue: No]

| Arms | Assigned Intervention |
|---|---|
| Placebo Comparator: Placebo subcutaneous or microneedle patch delivery | Drug: Placebo subcutaneous or microneedle patch delivery |
| Experimental: single and dual agonist mTA through subcutaneous or microneedle patch delivery | Drug: single and dual agonist mTA through subcutaneous or microneedle patch delivery |

This is an international, randomized, double-blind, placebo-controlled, Phase II/III trial of single and dual agonist mTA for the treatment of diabetes and obesity.

TABLE 3

Therapeutic Agents (TAs)-Amino acid sequences

| NAME | SEQ ID NO | SEQUENCE |
|---|---|---|
| Oxyntomodulin | 1 | HSQGTFTSDYSKYLDSRRAQDFVQWLMNTKRNRNNIA |
| Exendin-4 or Exenatide | 2 | HGEGTFTSDLSKQMEEEAVRLFIEWLKNGGPSSGAPPPS |
| hGLP-1 | 3 | HAEGTFTSDVSSYLEGQAAKEFIAWLVKGR |
| Glucagon | 4 | HSQGTFTSDYSKYLDSRRAQDFVQWLMNT |
| hGLP-2 | 5 | HADGSFSDEMNTILDNLAARDFINWLIQTKITD |
| hGIP | 6 | YAEGTFISDYSIAMDKIHQQDFVNWLLAQKGKKNDWKHNITQ |

TABLE 4

Therapeutic Agents-Amino acid sequences

| NAME | SEQ ID NO | SEQUENCE |
|---|---|---|
| Oxm-1 | 7 | HsQGTFTSDYSKYLDSRRAQDFVQWLMNTKRNRNNIAC |
| Oxm-i + 4 | 8 | HsQGTFTSDYSKYLDERAACEFICWLMNTKRNRNNIA |
| Oxm-i + 11 | 9 | HsQGTFTSDYSKCLDERAVRLFICWLMNTKRNRNNIA |
| OXM-i + 14 | 10 | HsQGTFTSDCSKYLDERAVRLFICWLMNTKRNRNNIA |
| OXM-2t + 1t | 11 | HsQGTFTSCYSKCLDECAVRLFICWLMNTKRNRNNIA |
| OXM-i + 15 | 12 | HsQGTFTSCYSKCLDERAVRLFICWLMNTKRNRNNIA |
| Ex-i + 7 | 13 | HGEGTFTSDLSKQMEECAVRLFICWLKNGGPSSGAPPPS |
| Ex-i + 7-Cys | 14 | HGEGTFTSDLSKQMEECAVRLFICWLKNGGPSSGAPPPSC |
| Ex-i + 4 | 15 | HGEGTFTSDLSKQMEEEAVCLFICWLKNGGPSSGAPPPS |
| Ex-i + 11 | 16 | HGEGTFTSDLSKCMEEEAVRLFICWLKNGGPSSGAPPPS |
| Ex-i + 14 | 17 | HGEGTFTSDCSKQMEEEAVRLFICWLKNGGPSSGAPPPS |
| Ex-i + 15 | 18 | HGEGTFTSCLSKQMEEEAVRLFICWLKNGGPSSGAPPPS |

TABLE 4-continued

Therapeutic Agents-Amino acid sequences

| NAME | SEQ ID NO | SEQUENCE |
|---|---|---|
| Ex-2t + 1t | 19 | HGEGTFTSCLSKCMEEEAVRLFICWLKNGGPSSGAPPPS |
| Dual-2a | 20 | HsQGTFTSDYSKYLDSKAAHDFVCWLLRA |
| Dual-2b | 21 | HSQGTFTSDYSKYLDSCAAHDFVCWLLRA |
| Dual-2c | 22 | HsQGTFTSDYSKCLDSKAAHDFVCWLLRA |
| Dual-2d | 23 | HsQGTFTSCYSKYLDSKAAHDFVCWLLRA |
| Dual-2e | 24 | HsQGTFTSCYSKCLDSCAAHDFVCWLLRA |
| Dual-3a | 25 | YXEGTFTSDYSIYLDKQAACEFVCWLLAGGPSSGAPPPSK |
| Dual-3b | 26 | YXEGTFTSDYSIYLDKCAAXEFVCWLLAGGPSSGAPPPSK |
| Dual-3c | 27 | YXEGTFTSDYSICLDKQAAXEFVCWLLAGGPSSGAPPPSK |
| Dual-3d | 28 | YXEGTFTSDCSIYLDKQAAXEFVCWLLAGGPSSGAPPPSK |
| Dual-3e | 29 | YXEGTFTSCYSICLDKQAAXEFVCWLLAGGPSSGAPPPSK |

Lowercase letters represent D-amino acids

TABLE 5

Therapeutic Agents: Modified Therapeutic Peptides

| NAME | SEQ ID NO | SEQUENCE$^a$ |
|---|---|---|
| Exendin-4 (A) | 30 | HGEGTFTSDLSKQMEEXAVRLFIXWLKNGGPSSGAPPPS |
| Exendin-4 (B) | 31 | HGEGTFTSDLSKXMEEEAVRLFIXWLKNGGPSSGAPPPS |
| Exendin-4 (C) | 32 | HGEGTFTSDXSKQMEEEAVRLFIXWLKNGGPSSGAPPPS |
| OXM (A) | 33 | HsQGTFTSDYSKYLDSXRAQDFVXWLMNTKRNRNNIA |
| OXM (B) | 34 | HsQGTFTSDYSKYLDEXAAKEFIXWLMNTKRNRNNIA |
| GLP-1/Glucagon (A) | 35 | HsQGTFTSDYSKYLDSXAAHDFVXWLLRA |
| GLP-1/Glucagon (B) | 36 | HsQGTFTSDYSKYLDEXAAKEFIXWLLRA |
| GLP-1/Glucagon (C) | 37 | HsQGTFTSDYSKYLDEXAAKEFIXWLLRAGPSSGAPPPS |
| GLP-1/Glucagon (D) | 38 | HsQGTFTSDYSKYLDEXAAKEFIXWLLNGGPSSGAPPPS |
| GLP-1/GIP (A) | 39 | YaEGTFTSDYSIYLDKXAAKEFVXWLLAGGPSSGAPPPSK |
| GLP-1/GIP/Glucagon (A) | 40 | YaEGTFISDYSKYLDEXAAKEFIXWLMNTKRNRNNIA |
| GLP-1/GIP/Glucagon (B) | 41 | HAibQGTFTSDKSKYLDEXAAQDFVXWLLDGGPSSGAPPPS |
| GLP-2 (A) | 42 | HGDGSFSDEMNTILDNXAARDFIXWLIQTKITD |
| GLP-2 (B) | 43 | HGDGSFSDELLTILDLXAARDFIXWLIQTKITD |
| GLP-2 (C) | 44 | HGDGSFSDEMNTILDXLAARDFIXWLIQTKITD |
| GLP-2 (D) | 45 | HGDGSFSXEMNTILXALAARDFINWLIQTKITD |
| GLP-2 (E) | 46 | HGDGSFSDEMNTILDALAARXFINWLIXTKITD |
| GLP-2 (F) | 47 | HGDGSFSDXMNTILDXLAARDFINWLIQTKITD |
| GLP-2 (G) | 48 | HGDGSFSDEMXTILDNLXARDFINWLIQTKITD |
| GLP-2 (H) | 49 | HGDGSFSDEMNTILDNXAARDFIXWLIQTKITDPSSGAPPPS |

TABLE 5-continued

Therapeutic Agents: Modified Therapeutic Peptides

| NAME | SEQ ID NO | SEQUENCE[a] |
|---|---|---|
| GLP-2 (I) | 50 | HGDGSFSDXMNTILD XLAARDFINWLIQTKITDPSSGAPPPS |
| GLP-2 (J) | 51 | HGDGSFSDEMXTILDNL XARDFINWLIQTKITDPSSGAPPPS |
| GLP-1 (A) | 52 | HGEGTFTSDVSSYLEGXAAKEFIXWLVKGR |
| GLP-1 (B) | 53 | HAibEGTFTSDVSSYLEGXAAKEFIXWLVKGR |

[a] X is cysteine.

TABLE 6

Modified Therapeutic Agents

| mTA | Structure[a] | Mass Expected | Mass Found | GLP-1R (EC$_{50}$, nM) | GCGR (EC$_{50}$, nM) | t$_{1/2}$ (h) |
|---|---|---|---|---|---|---|
| 1 | Exendin-4 (A) and L1 | 4302.9 | 1076.2 ([M + 4H]$^{4+}$), 861.4 ([M + 5H]$^{5+}$) | 0.03 | ND | ND |
| 2 | Exendin-4 (A) and L2 | 4687.5 | 1172.8 ([M + 4H]$^{4+}$), 938.4 ([M + 5H]$^{5+}$) | 0.03 | ND | ND |
| 3 | Exendin-4 (A) and L4 | 4817.6 | 1205.3 ([M + 4H]$^{4+}$), 964.4 ([M + 5H]$^{5+}$) | 0.03 | ND | ND |
| 4 | Exendin-4 (A) and L5 | 5089.9 | 1273.2 ([M + 4H]$^{4+}$), 1018.7 ([M + 5H]$^{5+}$) | 0.03 | ND | t$_{1/2}$ = 13 h (i.v.), C$_{max}$ = 4 h (s.c.) |
| 5 | Exendin-4 (B) and L14 | 4331.5 | 1444.7 ([M + 3H]$^{3+}$), 1083.8 ([M + 4H]$^{4+}$) | 0.05 | ND | ND |
| 6 | Exendin-4 (B) and L15 | 4345.5 | 1449.5 ([M + 3H]$^{3+}$), 1087.4 ([M + 4H]$^{4+}$) | 0.03 | ND | ND |
| 7 | Exendin-4 (B) and L16 | 4359.5 | 1454.1 ([M + 3H]$^{3+}$), 1090.9 ([M + 4H]$^{4+}$) | 0.03 | ND | ND |
| 8 | Exendin-4 (B) and L17 | 4373.5 | 1458.9 ([M + 3H]$^{3+}$), 1094.4 ([M + 4H]$^{4+}$) | 0.03 | ND | ND |
| 9 | Exendin-4 (C) and L16 | 4375.1 | 1458.9 ([M + 3H]$^{3+}$), 1094.4 ([M + 4H]$^{4+}$) | 0.53 | ND | ND |
| 10 | Exendin-4 (C) and L18 | 4403.2 | 1101.8 ([M + 4H]$^{4+}$), 881.6 ([M + 5H]$^{5+}$) | 2.5 | ND | ND |
| 11 | Exendin-4 (C) and L19 | 4431.2 | 1108.8 ([M + 4H]$^{4+}$), 887.2 ([M + 5H]$^{5+}$) | 0.15 | ND | ND |
| 12 | Exendin-4 (C) and L20 | 4422.1 | 1106.2 ([M + 4H]$^{4+}$), 885.2 ([M + 5H]$^{5+}$) | 0.62 | ND | ND |
| 13 | Exendin-4 (C) and L21 | 4450.2 | 1113.6 ([M + 4H]$^{4+}$), 890.8 ([M + 5H]$^{5+}$) | 0.34 | ND | ND |
| 14 | OXM (A) and L1 | 4539.2 | 1135.8 ([M + 4H]$^{4+}$), 908.8 ([M + 5H]$^{5+}$) | ND | ND | ND |

TABLE 6-continued

| | | Modified Therapeutic Agents | | | | |
|---|---|---|---|---|---|---|
| mTA | Structure[a] | Mass Expected | Mass Found | GLP-1R (EC$_{50}$, nM) | GCGR (EC$_{50}$, nM) | t$_{1/2}$ (h) |
| 15 | OXM (B) and L1 | 4524.3 | 1132.2 ([M + 4H]$^{4+}$), 906.7 ([M + 5H]$^{5+}$) | 0.03 | 0.2 | ND |
| 16 | OXM (B) and L2 | 4908.8 | 1228.0 ([M + 4H]$^{4+}$), 982.6 ([M + 5H]$^{5+}$) | 0.04 | 0.3 | t$_{1/2}$ = 2 h (i.v.), C$_{max}$ = 8 h (s.c.) |
| 17 | OXM (B) and L4 | 5038.9 | 1260.7 ([M + 4H]$^{4+}$), 1008.8 ([M + 5H]$^{5+}$) | 2.0 | 3 | ND |
| 18 | OXM (B) and L5 | 5311.23 | 1328.8 ([M + 4H]$^{4+}$), 1063.3 ([M + 5H]$^{5+}$) | 0.20 | NA | ND |
| 19 | OXM (B) and L6 | 5310.2 | 1328.6 ([M + 4H]$^{4+}$), 1063.1 ([M + 5H]$^{5+}$) | 0.20 | NA | ND |
| 20 | OXM (B) and L7 | 4596.3 | 1152.6 ([M + 4H]$^{4+}$), 922.4 ([M + 5H]$^{5+}$) | 17 | 5.4 | ND |
| 21 | OXM (B) and L8 | 4562.3 | 1141.6 ([M + 4H]$^{4+}$), 913.4 ([M + 5H]$^{5+}$) | 0.12 | 0.7 | ND |
| 22 | OXM (B) and L9 | 4590.3 | 1148.6 ([M + 4H]$^{4+}$), 919.2 ([M + 5H]$^{5+}$) | 40 | 14 | ND |
| 23 | OXM (B) and L10 | 4582.3 | 1146.6 ([M + 4H]$^{4+}$), 917.4 ([M + 5H]$^{5+}$) | ND | ND | ND |
| 24 | OXM (B) and L11 | 4496.2 | 1125.1 ([M + 4H]$^{4+}$), 890.2 ([M + 5H]$^{5+}$) | 0.20 | 3 | ND |
| 25 | OXM (B) and L12 | 4510.2 | 1128.6 ([M + 4H]$^{4+}$), 902.2 ([M + 5H]$^{5+}$) | 0.10 | 0.5 | ND |
| 26 | OXM (B) and L13 | 4538.3 | 1135.6 ([M + 4H]$^{4+}$), 908.8 ([M + 5H]$^{5+}$) | 0.05 | 0.5 | ND |
| 27 | GLP-1/Glucagon (A) and L1 | 3489.9 | 1164.0 ([M + 4H]$^{4+}$), 873.3 ([M + 5H]$^{5+}$) | 0.2 | 0.04 | ND |
| 28 | GLP-1/Glucagon (A) and L2 | 3874.5 | 1292.6 ([M + 4H]$^{3+}$), 969.8 ([M + 5H]$^{5+}$) | 0.1 | 0.1 | ND |
| 29 | GLP-1/Glucagon (B) and L1 | 3551.0 | 1184.5 ([M + 3H]$^{3+}$), 888.7 ([M + 4H]$^{4+}$) | 0.03 | 0.03 | ND |
| 30 | GLP-1/Glucagon (B) and L2 | 3935.6 | 1312.8 ([M + 3H]$^{3+}$), 984.7 ([M + 4H]$^{4+}$) | 0.03 | 0.05 | ND |
| 31 | GLP-1/Glucagon (B) and L4 | 4065.7 | 1356.8 ([M + 3H]$^{3+}$), 1017.4 ([M + 4H]$^{4+}$) | 0.03 | 0.12 | ND |
| 32 | GLP-1/Glucagon (B) and L5 | 4338.0 | 1446.6 ([M + 3H]$^{3+}$), 1085.3 ([M + 4H]$^{4+}$) | 0.3 | 1.0 | ND |

TABLE 6-continued

Modified Therapeutic Agents

| mTA | Structure[a] | Mass Expected | Mass Found | GLP-1R (EC$_{50}$, nM) | GCGR (EC$_{50}$, nM) | t$_{1/2}$ (h) |
|---|---|---|---|---|---|---|
| 33 | GLP-1/Glucagon (B) and L6 | 4337.04 | 1446.7 ([M + 3H]$^{3+}$), 1085.4 ([M + 4H]$^{4+}$) | 0.05 | 0.4 | t$_{1/2}$ = 8 h (i.v.), C$_{max}$ = 8 h (s.c.) |
| 34 | GLP-1/Glucagon (C) and L4 | 4900.8 | 1226.2 ([M + 4H]$^{4+}$), 981.4 ([M + 5H]$^{5+}$) | 0.04 | 0.4 | ND |
| 35 | GLP-1/Glucagon (C) and L5 | 5172.9 | 1294.2 ([M + 4H]$^{4+}$), 1035.6 ([M + 5H]$^{5+}$) | 0.5 | 1 | ND |
| 36 | GLP-1/Glucagon (C) and L6 | 5171.9 | 1293.7 ([M + 4H]$^{4+}$), 1035.4 ([M + 5H]$^{5+}$) | 0.3 | 0.5 | ND |
| 37 | GLP-1/Glucagon (D) and L4 | 4844.7 | 1212.2 ([M + 4H]$^{4+}$), 969.9 ([M + 5H]$^{5+}$) | 0.03 | 0.2 | t$_{1/2}$ = 8 h (i.v.), C$_{max}$ = 4~8 h (s.c.) |
| 38 | GLP-1/Glucagon (D) and L5 | 5117.0 | 1280.2 ([M + 4H]$^{4+}$), 1024.4 ([M + 5H]$^{5+}$) | 0.04 | 0.4 | ND |
| 39 | GLP-1/Glucagon (D) and L6 | 5115.2 | 1279.8 ([M + 4H]$^{4+}$), 1024.1 ([M + 5H]$^{5+}$) | 0.04 | 0.3 | ND |

[a]Structure is described by product of reaction between the peptide from Table 5 (X is cysteine) and the staple from Table 2.

TABLE 7

Modified Therapeutic Agents

| mTA | Structure[a] | Mass Expected | Mass Found | GLP-1R (EC$_{50}$, nM) | GIP-R (EC$_{50}$, nM) | t$_{1/2}$ (h) |
|---|---|---|---|---|---|---|
| 40 | GLP-1/GIP (A) and L1 | 4396.2 | 1099.8 ([M + 4H]$^{4+}$), 879.7 ([M + 5H]$^{5+}$) | 0.02 | 0.020 | ND |
| 41 | GLP-1/GIP (A) and L3 | 4939.9 | 1646.8 ([M + 3H]$^{3+}$), 1235.4 ([M + 4H]$^{4+}$) | 0.02 | 0.06 | t$_{1/2}$ = 2.7 h (i.v.), C$_{max}$ = 2 h (s.c.) |
| 42 | GLP-1/GIP (A) and L4 | 4910.8 | 1228.7 ([M + 4H]$^{4+}$), 983.2 ([M + 5H]$^{5+}$) | ND | ND | ND |
| 43 | GLP-1/GIP (A) and L5 | 5183.1 | 1727.9 ([M + 3H]$^{3+}$), 1296.3 ([M + 4H]$^{4+}$) | 0.5 | 1.1 | ND |

[a]Structure is described by product of reaction between the peptide from Table 5 (X is cysteine) and the staple from Table 2.

TABLE 8

Modified Therapeutic Agents

| mTA | Structure[a] | Mass Expected | Mass Found | GLP-1R (EC$_{50}$, nM) | GIP-R (EC$_{50}$, nM) | GCGR (EC$_{50}$, nM) |
|---|---|---|---|---|---|---|
| 44 | GLP-1/GIP/Glucagon (A) and L1 | 4547.3 | 1137.8 ([M + 4H]$^{4+}$), 910.6 ([M + 5H]$^{5+}$) | 9.7 | 0.04 | 1.6 |

TABLE 8-continued

Modified Therapeutic Agents

| mTA | Structure[a] | Mass Expected | Mass Found | GLP-1R (EC$_{50}$, nM) | GIP-R (EC$_{50}$, nM) | GCGR (EC$_{50}$, nM) |
|---|---|---|---|---|---|---|
| 45 | GLP-1/GIP/Glucagon (B) and L1 | 4271.6 | 1068.8 ([M + 4H]$^{4+}$), 855.3 ([M + 5H]$^{5+}$) | ND | ND | ND |

[a]Structure is described by product of reaction between the peptide from Table 5 (X is cysteine) and the staple from Table 2.

TABLE 9

Modified Therapeutic Agents

| mTA | Structure[a] | Mass Expected | Mass Found | GLP-2R (EG$_{50}$, nM) | t$_{1/2}$ (h) |
|---|---|---|---|---|---|
| 46 | GLP-2 (A) and L1 | 3898.5 | 1300.2 ([M + 3H]$^{3+}$), 975.3 ([M + 4H]$^{4+}$) | 0.045 | ND |
| 47 | GLP-2 (A) and L2 | 4282.9 | 1428.3 ([M + 3H]$^{3+}$), 1071.5 ([M + 4H]$^{4+}$) | 0.041 | t$_{1/2}$ = 2.3 h (i.v.), C$_{max}$ = 2 h (s.c.) |
| 48 | GLP-2 (A) and L3 | 4442.1 | 1481.9 ([M + 3H]$^{3+}$), 1111.3 ([M + 4H]$^{4+}$) | 0.045 | ND |
| 49 | GLP-2 (A) and L4 | 4413.0 | 1103.3 ([M + 4H]$^{4+}$), 882.6 ([M + 5H]$^{5+}$) | 0.241 | ND |
| 50 | GLP-2 (A) and L5 | 4685.3 | 1172.3 ([M + 4H]$^{4+}$), 938.1 ([M + 5H]$^{5+}$) | 6.4 | ND |
| 51 | GLP-2 (A) and L6 | 4684.3 | 1171.2 ([M + 4H]$^{4+}$), 936.9 ([M + 5H]$^{5+}$) | 0.7 | ND |
| 52 | GLP-2 (C) and L1 | 3897.6 | 1300.2 ([M + 3H]$^{3+}$), 975.2 ([M + 4H]$^{4+}$) | 5.6 | ND |
| 53 | GLP-2 (D) and L1 | 3852.6 | 1284.4 ([M + 3H]$^{3+}$), 963.2 ([M + 4H]$^{4+}$) | 14.3 | ND |
| 54 | GLP-2 (E) and L1 | 3839.6 | 1280.9 ([M + 3H]$^{3+}$), 960.7 ([M + 4H]$^{4+}$) | 0.13 | ND |
| 55 | GLP-2 (F) and L1 | 3882.6 | 1295.2 ([M + 3H]$^{3+}$), 971.5 ([M + 4H]$^{4+}$) | 0.064 | ND |
| 56 | GLP-2 (F) and L5 | 4669.6 | 1168.4 ([M + 3H]$^{3+}$), 934.2 ([M + 4H]$^{4+}$) | 0.77 | ND |
| 57 | GLP-2 (G) and L1 | 3940.6 | 1314.5 ([M + 3H]$^{3+}$), 986.2 ([M + 4H]$^{4+}$) | 0.046 | ND |
| 58 | GLP-2 (G) and L5 | 4727.6 | 1182.1 ([M + 4H]$^{4+}$), 946.5 ([M + 5H]$^{5+}$) | 7.98 | ND |
| 59 | GLP-2 (H) and L1 | 4676.4 | 1169.9 ([M + 4H]$^{4+}$), 936.3 ([M + 5H]$^{5+}$) | 0.064 | ND |
| 60 | GLP-2 (H) and L2 | 5060.9 | 1266.2 ([M + 4H]$^{4+}$), 1012.3 ([M + 5H]$^{5+}$) | 0.068 | ND |
| 61 | GLP-2 (H) and L3 | 5220.1 | 1306.2 ([M + 4H]$^{4+}$), 1045.1 ([M + 5H]$^{5+}$) | 0.068 | ND |
| 62 | GLP-2 (H) and L4 | 5191.1 | 1298.8 ([M + 4H]$^{4+}$), 1039.2 ([M + 5H]$^{5+}$) | ND | ND |
| 63 | GLP-2 (H) and L5 | 5463.4 | 1366.7 ([M + 4H]$^{4+}$), 1093.3 ([M + 5H]$^{5+}$) | 2.66 | ND |
| 64 | GLP-2 (H) and L6 | 5462.2 | 1366.4 ([M + 4H]$^{4+}$), 1093.3 ([M + 5H]$^{5+}$) | 0.7 | ND |
| 65 | GLP-2 (I) and L3 | 5204.2 | 1302.2 ([M + 4H]$^{4+}$), 1040.6 ([M + 5H]$^{5+}$) | 0.06 | t$_{1/2}$ = 3.1 h (i.v.), C$_{max}$ = 3 h (s.c.) |
| 66 | GLP-2 (I) and L4 | 5175.1 | 1294.8 ([M + 4H]$^{4+}$), 1035.1 ([M + 5H]$^{5+}$) | ND | ND |
| 67 | GLP-2 (I) and L5 | 5447.4 | 1362.9 ([M + 4H]$^{4+}$), 1090.6 ([M + 5H]$^{5+}$) | 3.1 | ND |
| 68 | GLP-2 (J) and L3 | 5262.2 | 1316.6 ([M + 4H]$^{4+}$), 1053.4 ([M + 5H]$^{5+}$) | 0.028 | t$_{1/2}$ = 4.7 h (i.v.), C$_{max}$ = 3 h (s.c.) |
| 69 | GLP-2 (J) and L4 | 5233.2 | 1309.3 ([M + 4H]$^{4+}$), 1047.6 ([M + 5H]$^{5+}$) | ND | ND |
| 70 | GLP-2 (J) and L5 | 5505.5 | 1377.7 ([M + 4H]$^{4+}$), 1102.2 ([M + 5H]$^{5+}$) | 8.8 | ND |

[a]Structure is described by product of reaction between the peptide from Table 5 (X is cysteine) and the staple from Table 2.

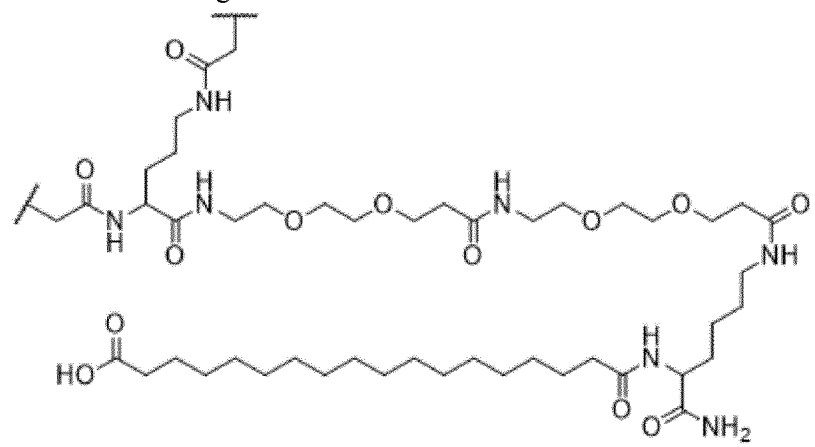

What is claimed is:

1. A modified therapeutic agent (mTA) comprising a therapeutic agent comprising the amino acid sequence selected from the group consisting of SEQ ID NOs: 30-32 and 35-53, a staple, and a half-life extending molecule, wherein the therapeutic agent is covalently attached to the staple via two amino acid residues in the therapeutic agent; the half-life extending molecule is covalently attached to the staple; and the half-life of the mTA is longer than the half-life of the therapeutic agent alone.

2. The mTA of claim 1, wherein the half-life extending molecule comprises a lipid, a polyglycol region selected from 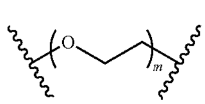 and

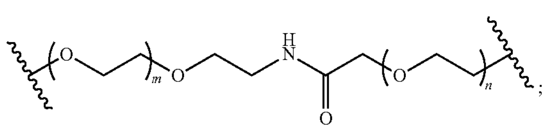

;

wherein m and n are independently 1, 2, 3, 4, 5, 6, 7, 8, 9, 10, 11, 12, 13, 14, 15, 16, 17, 18, 19, or 20; or a combination thereof.

3. The mTA of claim 2, wherein the lipid is selected from a group consisting of sterols, bile acids, vitamin E, fatty di-acids, fatty acids, fatty amides, fatty amines, fatty alcohols, and derivatives thereof.

4. The mTA of claim 1, wherein at least one of the two amino acid residues is an amino acid addition or substitution on the therapeutic agent.

5. The mTA of claim 1, wherein each of the two amino acid residues is cysteine.

6. The mTA of claim 1, wherein the staple comprises a group selected from:

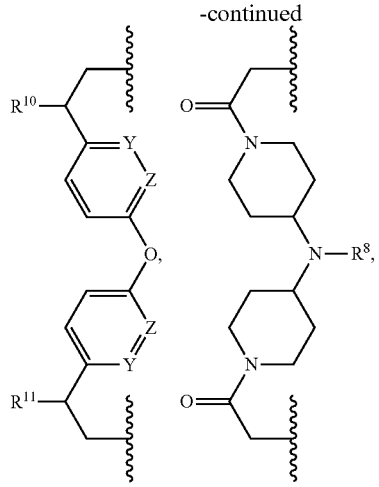
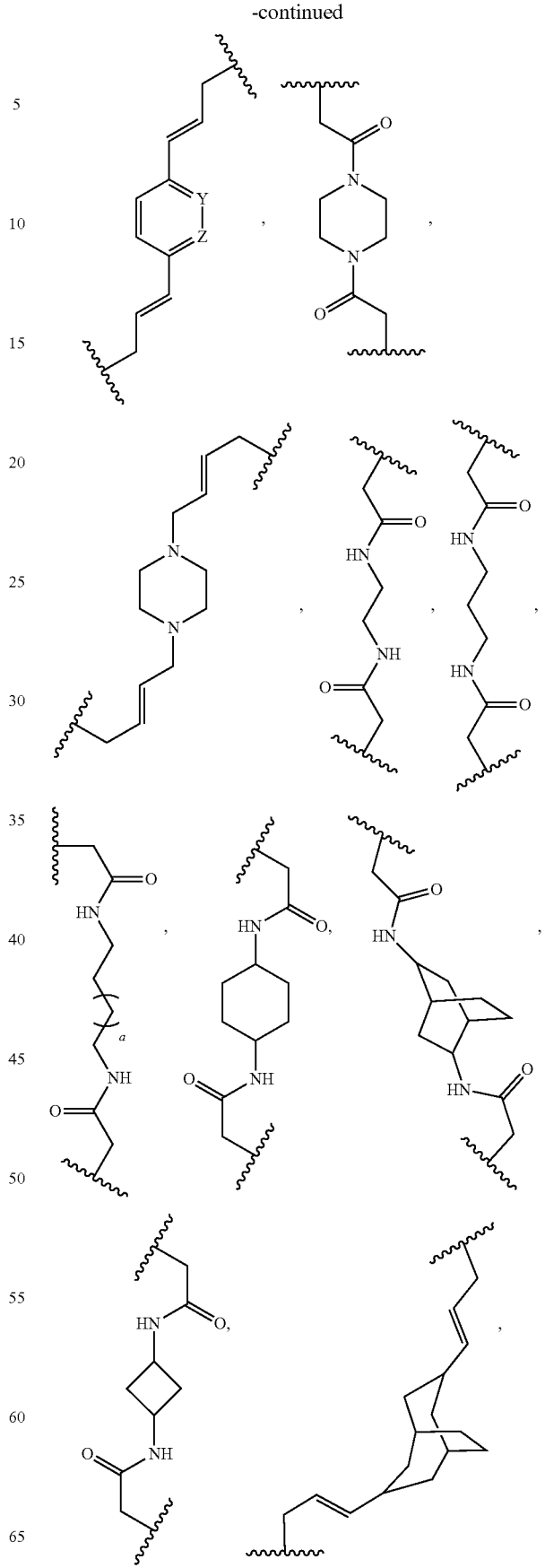

217
-continued
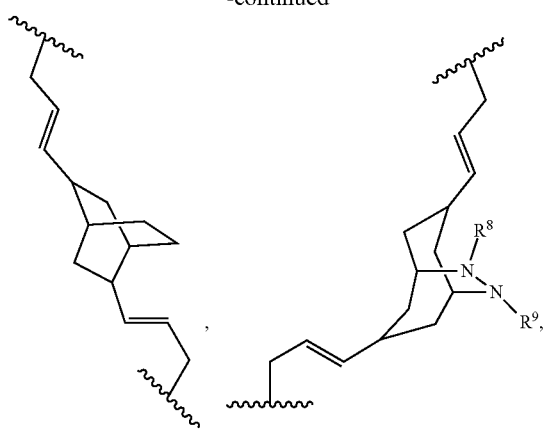
218
-continued
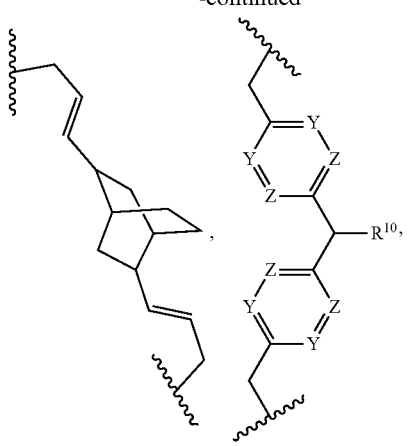
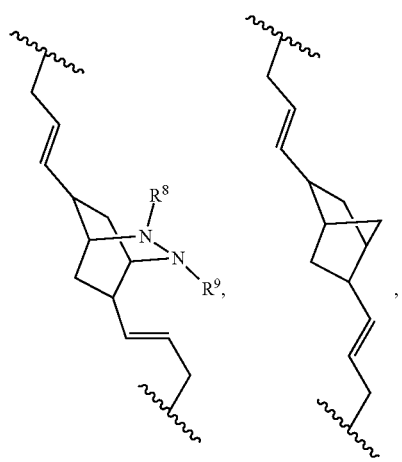
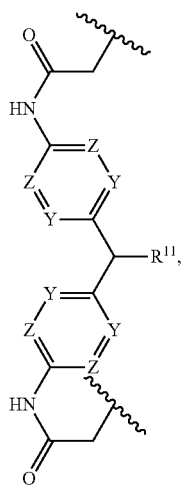 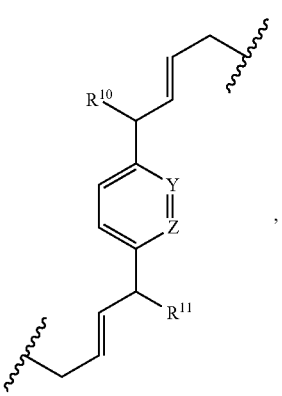
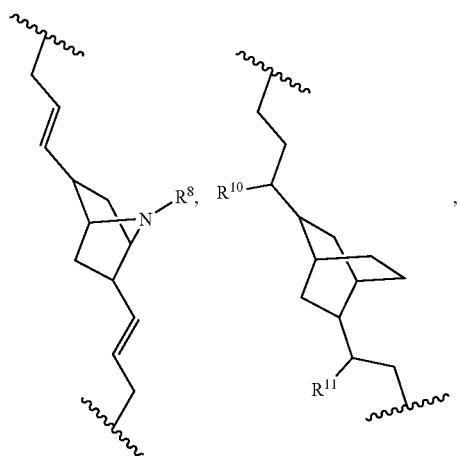
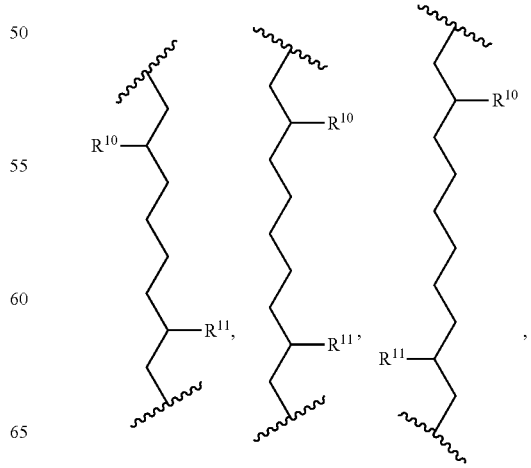

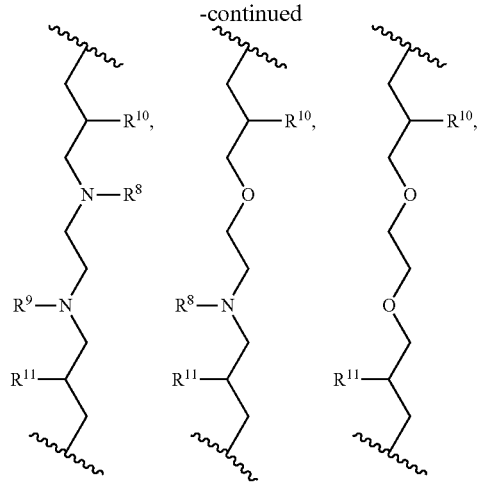
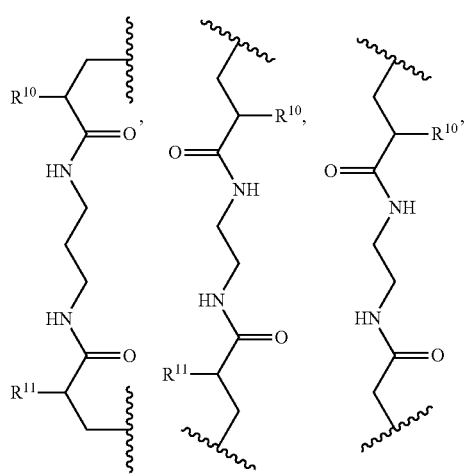
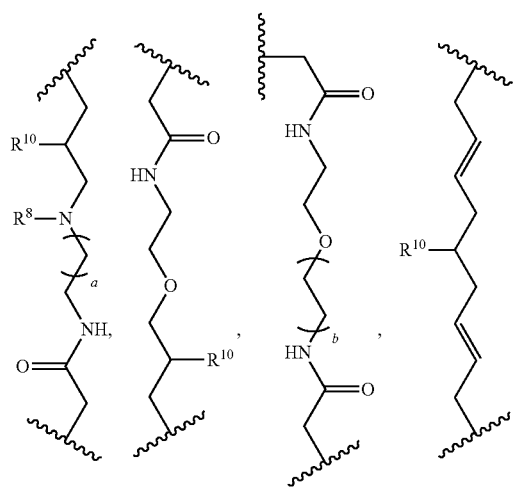
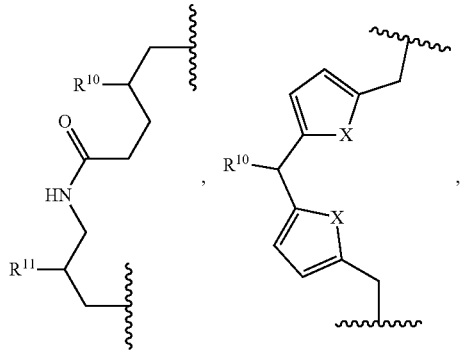
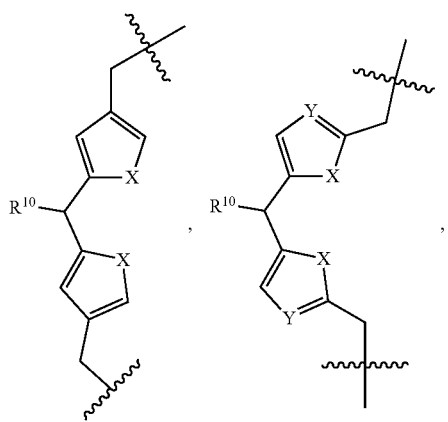
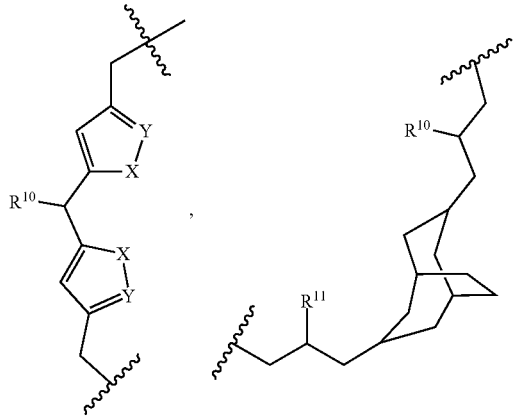
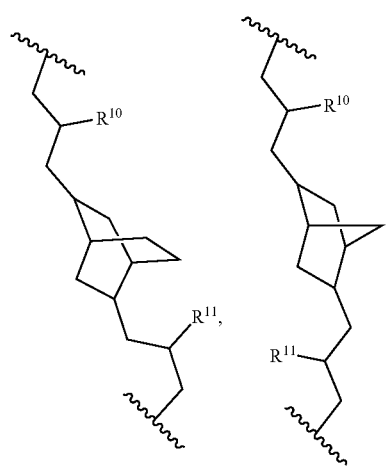

221
-continued

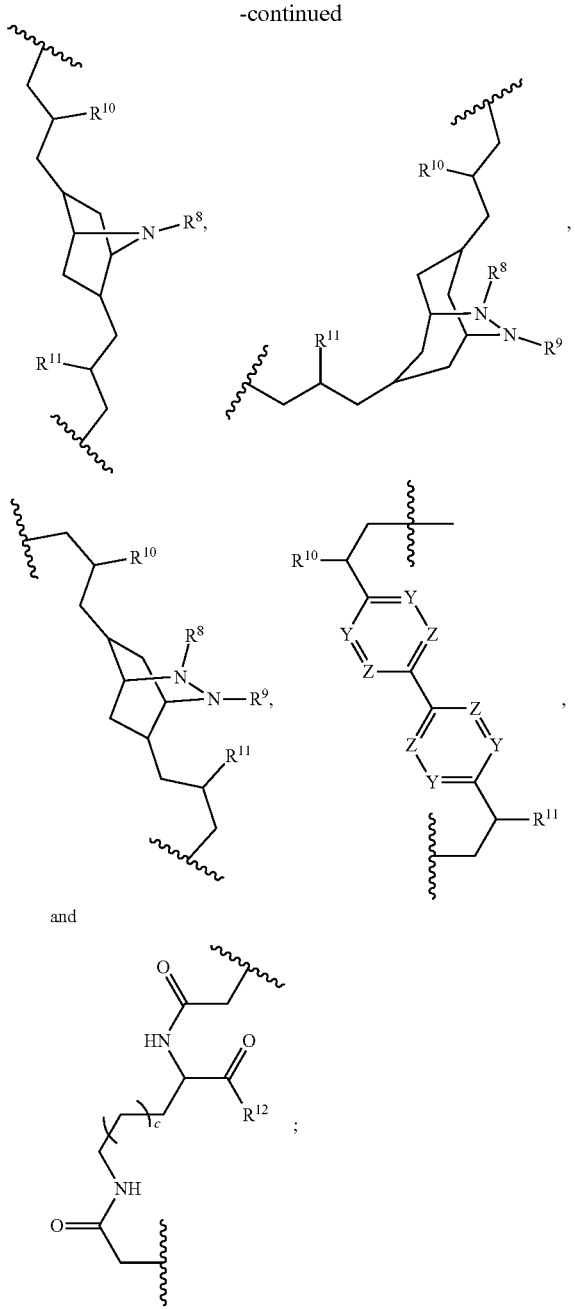

and wherein
  each X is independently selected from O, NH, and S;
  each Y is independently selected from N and CH;
  each Z is independently selected from N and CH;
  each $R^8$ and $R^9$ is independently H, —C(O)(alkyl), or comprises the half-life extending molecule;
  each $R^{10}$ and $R^{11}$ is independently oxo or comprises the half-life extending molecule;
  $R^{12}$ is independently hydroxy, alkoxy, or comprises the half-life extending molecule;
  a is 1, 2, 3, 4, 5, 6, 7, 8, 9, 10, 11, 12, 13, 14, 15, 16, or 17;
  b is 1, 2, 3, 4, 5, or 6; and
  c is 1 or 2.

222

7. The mTA of claim 6, wherein the half-life extending molecule comprises a lipid, a polyglycol region selected from

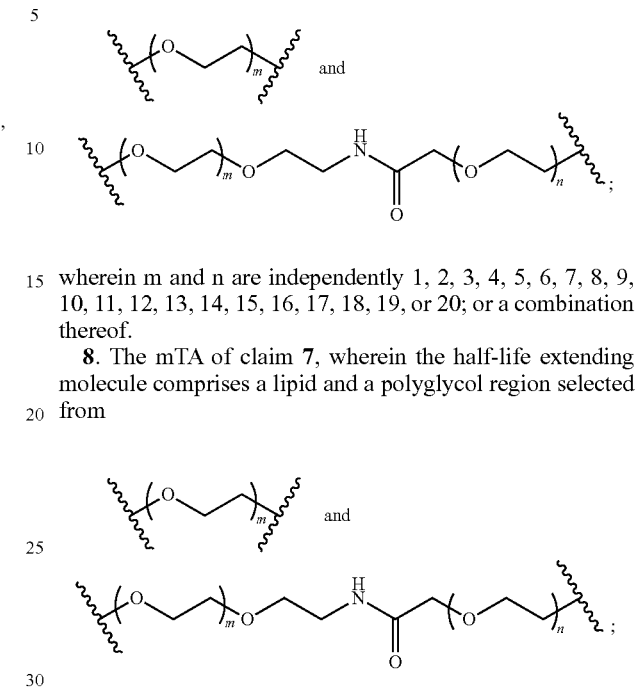

wherein m and n are independently 1, 2, 3, 4, 5, 6, 7, 8, 9, 10, 11, 12, 13, 14, 15, 16, 17, 18, 19, or 20; or a combination thereof.

8. The mTA of claim 7, wherein the half-life extending molecule comprises a lipid and a polyglycol region selected from wherein m and n are independently 1, 2, 3, 4, 5, 6, 7, 8, 9, 10, 11, 12, 13, 14, 15, 16, 17, 18, 19, or 20.

9. The mTA of claim 8, wherein the lipid is selected from a group consisting of sterols, bile acids, vitamin E, fatty di-acids, fatty acids, fatty amides, fatty amines, fatty alcohols, and derivatives thereof.

10. The mTA of claim 1, wherein the half-life of the mTA is 5-fold longer than the half-life of the therapeutic agent alone.

11. A pharmaceutical composition comprising the mTA of claim 1 and a pharmaceutically acceptable excipient.

12. The mTA of claim 6, wherein the staple comprises:

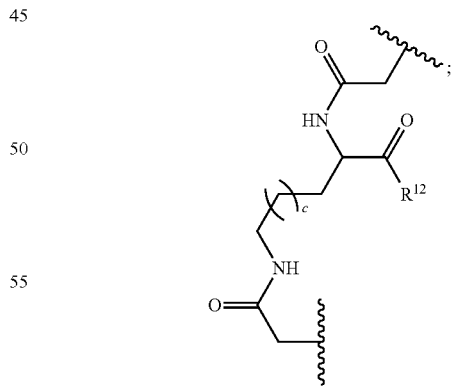

wherein
  $R^{12}$ is independently hydroxy, alkoxy, or comprises the half-life extending molecule; and
  c is 1 or 2.

13. The mTA of claim 1, wherein the staple covalently attached to the half-life extending molecule is selected from the group consisting of:

223
224
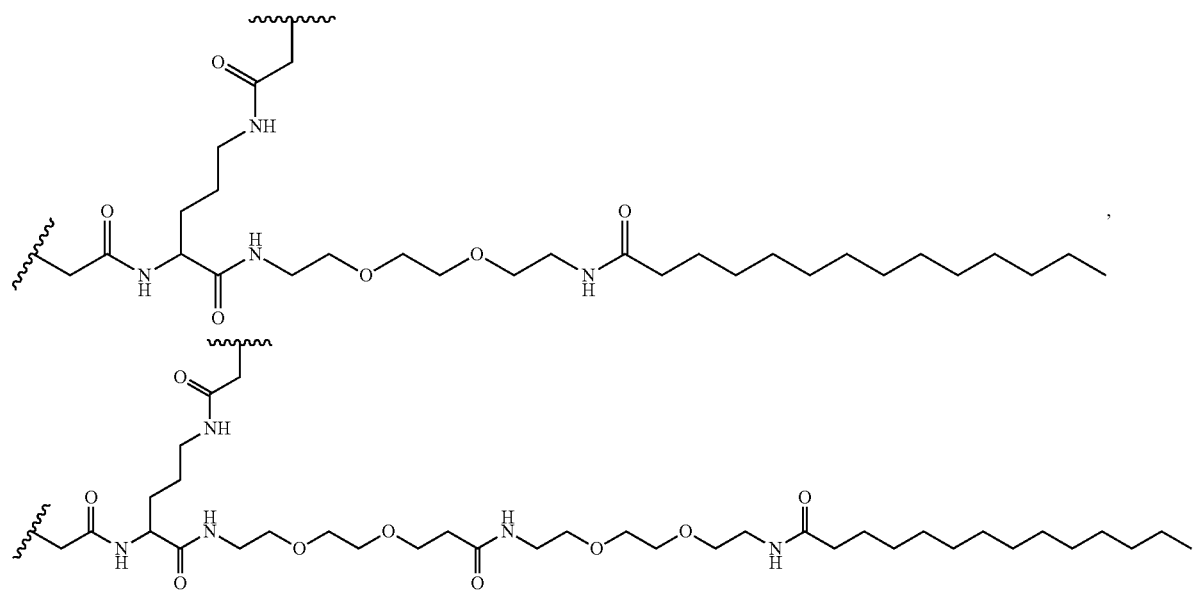
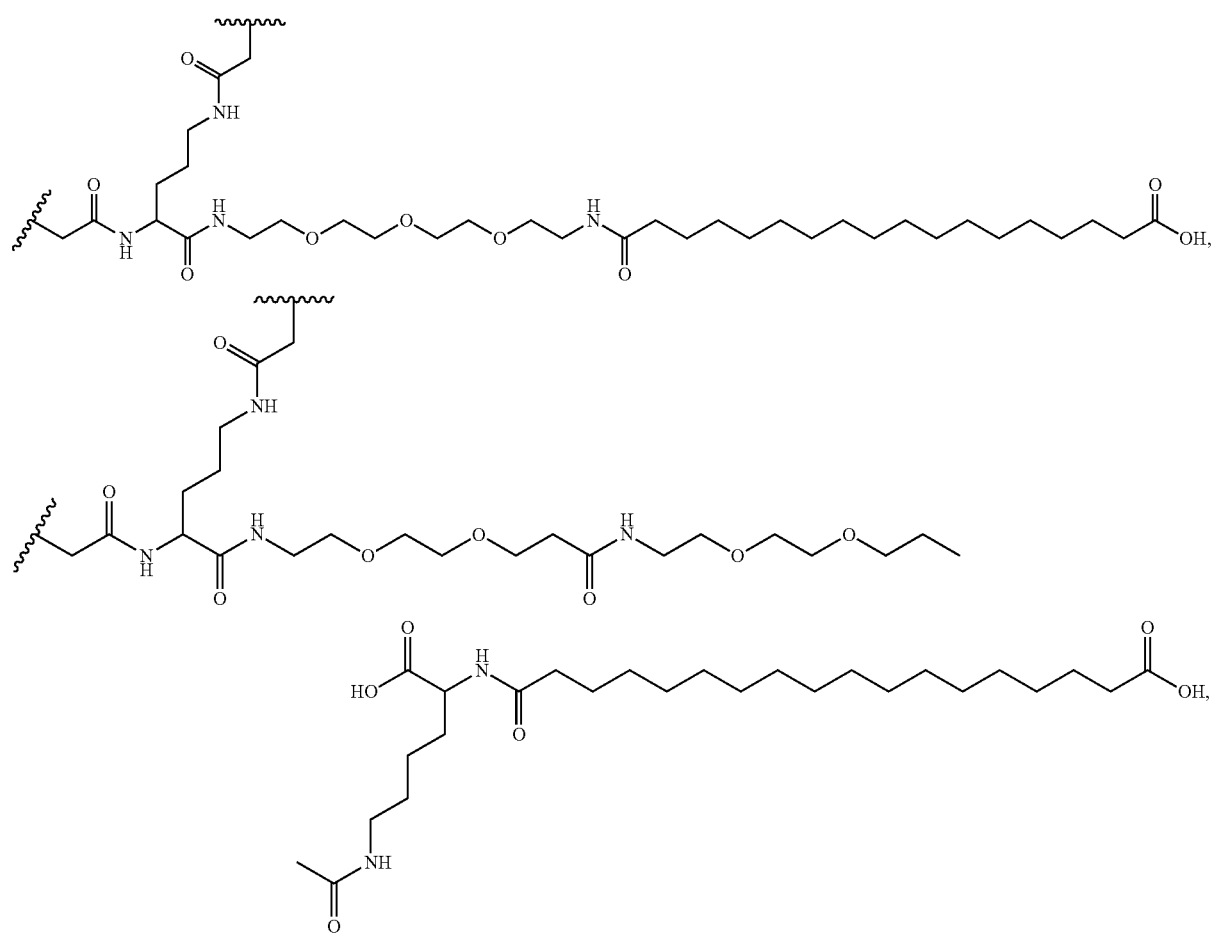
and

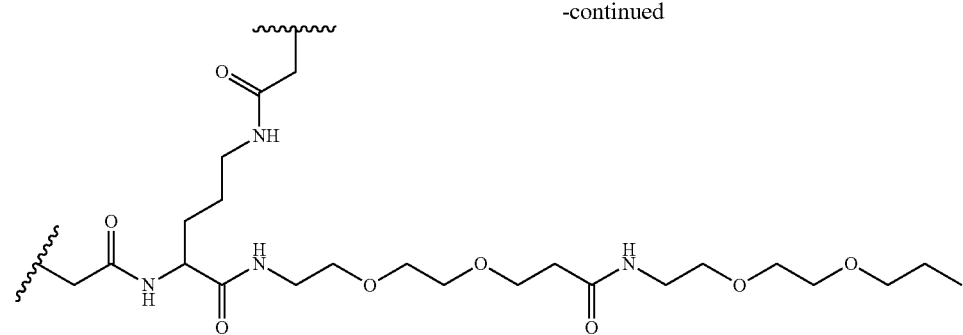
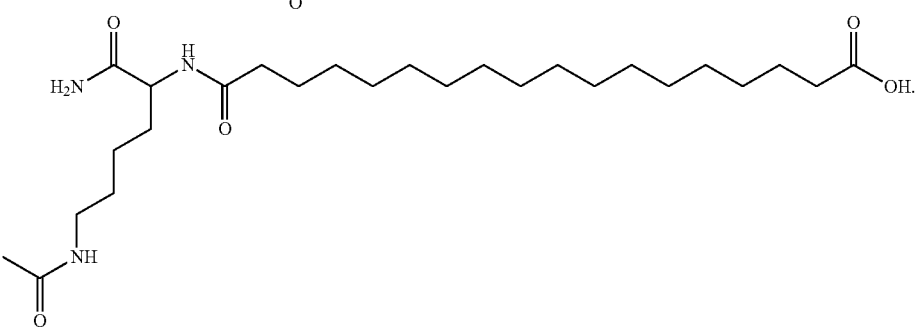
* * * * *

UNITED STATES PATENT AND TRADEMARK OFFICE
CERTIFICATE OF CORRECTION

PATENT NO. : 10,039,809 B2
APPLICATION NO. : 15/104807
DATED : August 7, 2018
INVENTOR(S) : Shen et al.

Page 1 of 2

It is certified that error appears in the above-identified patent and that said Letters Patent is hereby corrected as shown below:

In the Claims

In Claim 13, Columns 223 and 224 (last structure), replace:

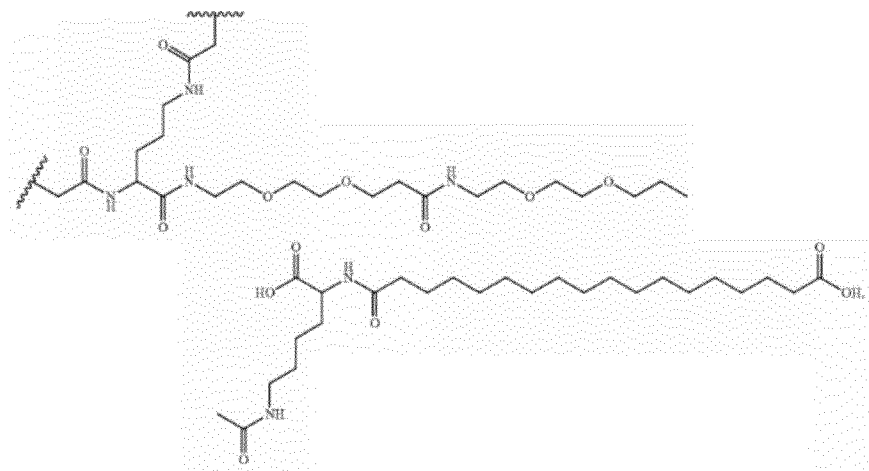

With the following structure:

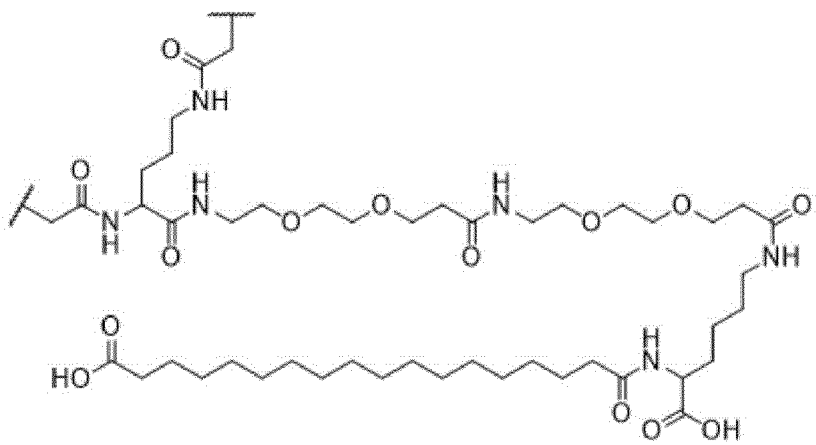

Signed and Sealed this
Eleventh Day of December, 2018

Andrei Iancu
*Director of the United States Patent and Trademark Office*

CERTIFICATE OF CORRECTION (continued)
U.S. Pat. No. 10,039,809 B2

In Claim 13, Columns 225 and 226, replace:

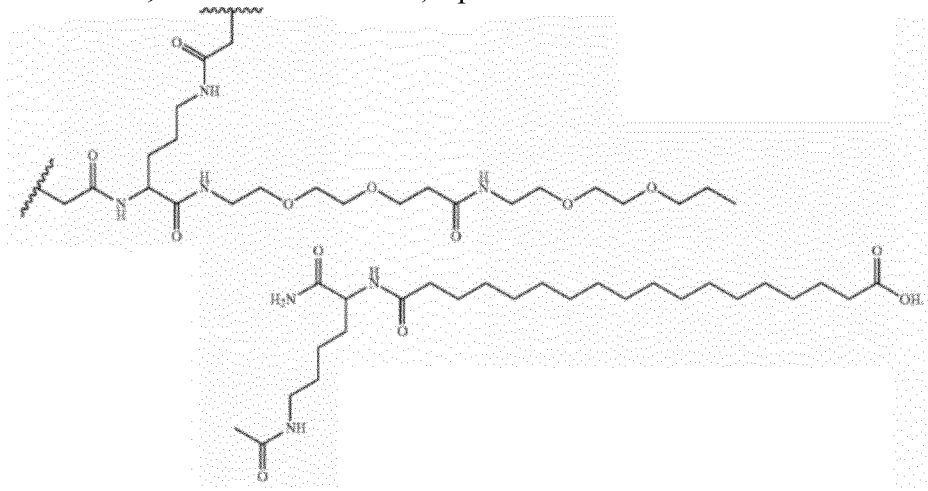

With the following structure:

SEQUENCE LISTING

<160> NUMBER OF SEQ ID NOS: 54

<210> SEQ ID NO 1
<211> LENGTH: 37
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 39
<212> TYPE: PRT
<213> ORGANISM: Homo sapiens

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 30
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 29
<212> TYPE: PRT
<213> ORGANISM: Homo sapiens

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 5
<211> LENGTH: 33
<212> TYPE: PRT
<213> ORGANISM: Homo sapiens

<400> SEQUENCE: 5

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 6
<211> LENGTH: 42
<212> TYPE: PRT
<213> ORGANISM: Homo sapiens

<400> SEQUENCE: 6

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

<400> SEQUENCE: 7

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

<400> SEQUENCE: 8

His Ser Gln Gly Thr Phe Thr Ser Asp Tyr Ser Lys Tyr Leu Asp Glu
1               5                   10                  15

Arg Ala Ala Cys Glu Phe Ile Cys Trp Leu Met Asn Thr Lys Arg Asn
            20                  25                  30

Arg Asn Asn Ile Ala
        35

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

```
<400> SEQUENCE: 9

His Ser Gln Gly Thr Phe Thr Ser Asp Tyr Ser Lys Cys Leu Asp Glu
1               5                   10                  15

Arg Ala Val Arg Leu Phe Ile Cys Trp Leu Met Asn Thr Lys Arg Asn
            20                  25                  30

Arg Asn Asn Ile Ala
        35

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

<400> SEQUENCE: 10

His Ser Gln Gly Thr Phe Thr Ser Asp Cys Ser Lys Tyr Leu Asp Glu
1               5                   10                  15

Arg Ala Val Arg Leu Phe Ile Cys Trp Leu Met Asn Thr Lys Arg Asn
            20                  25                  30

Arg Asn Asn Ile Ala
        35

<210> SEQ ID NO 11
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

<400> SEQUENCE: 11

His Ser Gln Gly Thr Phe Thr Ser Cys Tyr Ser Lys Cys Leu Asp Glu
1               5                   10                  15

Cys Ala Val Arg Leu Phe Ile Cys Trp Leu Met Asn Thr Lys Arg Asn
            20                  25                  30

Arg Asn Asn Ile Ala
        35

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

<400> SEQUENCE: 12

His Ser Gln Gly Thr Phe Thr Ser Cys Tyr Ser Lys Cys Leu Asp Glu
1               5                   10                  15

Arg Ala Val Arg Leu Phe Ile Cys Trp Leu Met Asn Thr Lys Arg Asn
            20                  25                  30
```

Arg Asn Asn Ile Ala
        35

<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

His Gly Glu Gly Thr Phe Thr Ser Asp Leu Ser Lys Gln Met Glu Glu
1               5                   10                  15

Cys Ala Val Arg Leu Phe Ile Cys Trp Leu Lys Asn Gly Gly Pro Ser
            20                  25                  30

Ser Gly Ala Pro Pro Pro Ser
        35

<210> SEQ ID NO 14
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

His Gly Glu Gly Thr Phe Thr Ser Asp Leu Ser Lys Gln Met Glu Glu
1               5                   10                  15

Cys Ala Val Arg Leu Phe Ile Cys Trp Leu Lys Asn Gly Gly Pro Ser
            20                  25                  30

Ser Gly Ala Pro Pro Pro Ser Cys
        35                  40

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

His Gly Glu Gly Thr Phe Thr Ser Asp Leu Ser Lys Gln Met Glu Glu
1               5                   10                  15

Glu Ala Val Cys Leu Phe Ile Cys Trp Leu Lys Asn Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

His Gly Glu Gly Thr Phe Thr Ser Asp Leu Ser Lys Cys Met Glu Glu
1               5                   10                  15

Glu Ala Val Arg Leu Phe Ile Cys Trp Leu Lys Asn Gly Gly Pro Ser

```
                    20                  25                  30

Ser Gly Ala Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

His Gly Glu Gly Thr Phe Thr Ser Asp Cys Ser Lys Gln Met Glu Glu
1               5                   10                  15

Glu Ala Val Arg Leu Phe Ile Cys Trp Leu Lys Asn Gly Gly Pro Ser
                20                  25                  30

Ser Gly Ala Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

His Gly Glu Gly Thr Phe Thr Ser Cys Leu Ser Lys Gln Met Glu Glu
1               5                   10                  15

Glu Ala Val Arg Leu Phe Ile Cys Trp Leu Lys Asn Gly Gly Pro Ser
                20                  25                  30

Ser Gly Ala Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

His Gly Glu Gly Thr Phe Thr Ser Cys Leu Ser Lys Cys Met Glu Glu
1               5                   10                  15

Glu Ala Val Arg Leu Phe Ile Cys Trp Leu Lys Asn Gly Gly Pro Ser
                20                  25                  30

Ser Gly Ala Pro Pro Ser
        35

<210> SEQ ID NO 20
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ser

<400> SEQUENCE: 20
```

His Ser Gln Gly Thr Phe Thr Ser Asp Tyr Ser Lys Tyr Leu Asp Ser
1               5                   10                  15

Lys Ala Ala His Asp Phe Val Cys Trp Leu Leu Arg Ala
            20                  25

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His Ser Gln Gly Thr Phe Thr Ser Asp Tyr Ser Lys Tyr Leu Asp Ser
1               5                   10                  15

Cys Ala Ala His Asp Phe Val Cys Trp Leu Leu Arg Ala
            20                  25

<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ser

<400> SEQUENCE: 22

His Ser Gln Gly Thr Phe Thr Ser Asp Tyr Ser Lys Cys Leu Asp Ser
1               5                   10                  15

Lys Ala Ala His Asp Phe Val Cys Trp Leu Leu Arg Ala
            20                  25

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ser

<400> SEQUENCE: 23

His Ser Gln Gly Thr Phe Thr Ser Cys Tyr Ser Lys Tyr Leu Asp Ser
1               5                   10                  15

Lys Ala Ala His Asp Phe Val Cys Trp Leu Leu Arg Ala
            20                  25

<210> SEQ ID NO 24
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ser

```
<400> SEQUENCE: 24

His Ser Gln Gly Thr Phe Thr Ser Cys Tyr Ser Lys Cys Leu Asp Ser
1               5                   10                  15

Cys Ala Ala His Asp Phe Val Cys Trp Leu Leu Arg Ala
            20                  25

<210> SEQ ID NO 25
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid

<400> SEQUENCE: 25

Tyr Xaa Glu Gly Thr Phe Thr Ser Asp Tyr Ser Ile Tyr Leu Asp Lys
1               5                   10                  15

Gln Ala Ala Cys Glu Phe Val Cys Trp Leu Leu Ala Gly Gly Pro Ser
            20                  25                  30

Ser Gly Ala Pro Pro Pro Ser Lys
        35                  40

<210> SEQ ID NO 26
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (20)..(20)
<223> OTHER INFORMATION: Any amino acid

<400> SEQUENCE: 26

Tyr Xaa Glu Gly Thr Phe Thr Ser Asp Tyr Ser Ile Tyr Leu Asp Lys
1               5                   10                  15

Cys Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 27
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (20)..(20)
<223> OTHER INFORMATION: Any amino acid

<400> SEQUENCE: 27
```

```
Tyr Xaa Glu Gly Thr Phe Thr Ser Asp Tyr Ser Ile Cys Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Ser Lys
        35              40
```

<210> SEQ ID NO 28
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (20)..(20)
<223> OTHER INFORMATION: Any amino acid

<400> SEQUENCE: 28

```
Tyr Xaa Glu Gly Thr Phe Thr Ser Asp Cys Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Ser Lys
        35              40
```

<210> SEQ ID NO 29
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (20)..(20)
<223> OTHER INFORMATION: Any amino acid

<400> SEQUENCE: 29

```
Tyr Xaa Glu Gly Thr Phe Thr Ser Cys Tyr Ser Ile Cys Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Ser Lys
        35              40
```

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
His Gly Glu Gly Thr Phe Thr Ser Asp Leu Ser Lys Gln Met Glu Glu
1               5                   10                  15
```

Cys Ala Val Arg Leu Phe Ile Cys Trp Leu Lys Asn Gly Gly Pro Ser
            20                  25                  30

Ser Gly Ala Pro Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

His Gly Glu Gly Thr Phe Thr Ser Asp Leu Ser Lys Cys Met Glu Glu
1               5                   10                  15

Glu Ala Val Arg Leu Phe Ile Cys Trp Leu Lys Asn Gly Gly Pro Ser
            20                  25                  30

Ser Gly Ala Pro Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

His Gly Glu Gly Thr Phe Thr Ser Asp Cys Ser Lys Gln Met Glu Glu
1               5                   10                  15

Glu Ala Val Arg Leu Phe Ile Cys Trp Leu Lys Asn Gly Gly Pro Ser
            20                  25                  30

Ser Gly Ala Pro Pro Pro Ser
        35

<210> SEQ ID NO 33
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

<400> SEQUENCE: 33

His Ser Gln Gly Thr Phe Thr Ser Asp Tyr Ser Lys Tyr Leu Asp Ser
1               5                   10                  15

Cys Arg Ala Gln Asp Phe Val Cys Trp Leu Met Asn Thr Lys Arg Asn
            20                  25                  30

Arg Asn Asn Ile Ala
        35

<210> SEQ ID NO 34
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: MOD_RES
<222> LOCATION: (2)..(2)
<223> OTHER INFORMATION: D-Ser

<400> SEQUENCE: 34

His Ser Gln Gly Thr Phe Thr Ser Asp Tyr Ser Lys Tyr Leu Asp Glu
1               5                   10                  15

Cys Ala Ala Lys Glu Phe Ile Cys Trp Leu Met Asn Thr Lys Arg Asn
            20                  25                  30

Arg Asn Asn Ile Ala
        35

<210> SEQ ID NO 35
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ser

<400> SEQUENCE: 35

His Ser Gln Gly Thr Phe Thr Ser Asp Tyr Ser Lys Tyr Leu Asp Ser
1               5                   10                  15

Cys Ala Ala His Asp Phe Val Cys Trp Leu Leu Arg Ala
            20                  25

<210> SEQ ID NO 36
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ser

<400> SEQUENCE: 36

His Ser Gln Gly Thr Phe Thr Ser Asp Tyr Ser Lys Tyr Leu Asp Glu
1               5                   10                  15

Cys Ala Ala Lys Glu Phe Ile Cys Trp Leu Leu Arg Ala
            20                  25

<210> SEQ ID NO 37
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

<400> SEQUENCE: 37

His Ser Gln Gly Thr Phe Thr Ser Asp Tyr Ser Lys Tyr Leu Asp Glu
1               5                   10                  15

Cys Ala Ala Lys Glu Phe Ile Cys Trp Leu Leu Arg Ala Gly Pro Ser
            20                  25                  30

Ser Gly Ala Pro Pro Pro Ser
```

<210> SEQ ID NO 38
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

<400> SEQUENCE: 38

His Ser Gln Gly Thr Phe Thr Ser Asp Tyr Ser Lys Tyr Leu Asp Glu
1               5                   10                  15

Cys Ala Ala Lys Glu Phe Ile Cys Trp Leu Leu Asn Gly Gly Pro Ser
            20                  25                  30

Ser Gly Ala Pro Pro Pro Ser
        35

<210> SEQ ID NO 39
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ala

<400> SEQUENCE: 39

Tyr Ala Glu Gly Thr Phe Thr Ser Asp Tyr Ser Ile Tyr Leu Asp Lys
1               5                   10                  15

Cys Ala Ala Lys Glu Phe Val Cys Trp Leu Leu Ala Gly Gly Pro Ser
            20                  25                  30

Ser Gly Ala Pro Pro Pro Ser Lys
        35                  40

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ala

<400> SEQUENCE: 40

Tyr Ala Glu Gly Thr Phe Ile Ser Asp Tyr Ser Lys Tyr Leu Asp Glu
1               5                   10                  15

Cys Ala Ala Lys Glu Phe Ile Cys Trp Leu Met Asn Thr Lys Arg Asn
            20                  25                  30

Arg Asn Asn Ile Ala
        35

<210> SEQ ID NO 41
<211> LENGTH: 39
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 41

His Xaa Gln Gly Thr Phe Thr Ser Asp Lys Ser Lys Tyr Leu Asp Glu
1               5                   10                  15

Cys Ala Ala Gln Asp Phe Val Cys Trp Leu Leu Asp Gly Gly Pro Ser
            20                  25                  30

Ser Gly Ala Pro Pro Pro Ser
        35

<210> SEQ ID NO 42
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

His Gly Asp Gly Ser Phe Ser Asp Glu Met Asn Thr Ile Leu Asp Asn
1               5                   10                  15

Cys Ala Ala Arg Asp Phe Ile Cys Trp Leu Ile Gln Thr Lys Ile Thr
            20                  25                  30

Asp

<210> SEQ ID NO 43
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

His Gly Asp Gly Ser Phe Ser Asp Glu Leu Leu Thr Ile Leu Asp Leu
1               5                   10                  15

Cys Ala Ala Arg Asp Phe Ile Cys Trp Leu Ile Gln Thr Lys Ile Thr
            20                  25                  30

Asp

<210> SEQ ID NO 44
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

His Gly Asp Gly Ser Phe Ser Asp Glu Met Asn Thr Ile Leu Asp Cys
1               5                   10                  15

Leu Ala Ala Arg Asp Phe Ile Cys Trp Leu Ile Gln Thr Lys Ile Thr
            20                  25                  30

Asp

<210> SEQ ID NO 45
<211> LENGTH: 33
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

His Gly Asp Gly Ser Phe Ser Cys Glu Met Asn Thr Ile Leu Cys Ala
1               5                   10                  15

Leu Ala Ala Arg Asp Phe Ile Asn Trp Leu Ile Gln Thr Lys Ile Thr
            20                  25                  30

Asp

<210> SEQ ID NO 46
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

His Gly Asp Gly Ser Phe Ser Asp Glu Met Asn Thr Ile Leu Asp Ala
1               5                   10                  15

Leu Ala Ala Arg Cys Phe Ile Asn Trp Leu Ile Cys Thr Lys Ile Thr
            20                  25                  30

Asp

<210> SEQ ID NO 47
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

His Gly Asp Gly Ser Phe Ser Asp Cys Met Asn Thr Ile Leu Asp Cys
1               5                   10                  15

Leu Ala Ala Arg Asp Phe Ile Asn Trp Leu Ile Gln Thr Lys Ile Thr
            20                  25                  30

Asp

<210> SEQ ID NO 48
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

His Gly Asp Gly Ser Phe Ser Asp Glu Met Cys Thr Ile Leu Asp Asn
1               5                   10                  15

Leu Cys Ala Arg Asp Phe Ile Asn Trp Leu Ile Gln Thr Lys Ile Thr
            20                  25                  30

Asp

<210> SEQ ID NO 49
<211> LENGTH: 42
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 49

His Gly Asp Gly Ser Phe Ser Asp Glu Met Asn Thr Ile Leu Asp Asn
1               5                   10                  15

Cys Ala Ala Arg Asp Phe Ile Cys Trp Leu Ile Gln Thr Lys Ile Thr
            20                  25                  30

Asp Pro Ser Ser Gly Ala Pro Pro Ser
        35                  40

<210> SEQ ID NO 50
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

His Gly Asp Gly Ser Phe Ser Asp Cys Met Asn Thr Ile Leu Asp Cys
1               5                   10                  15

Leu Ala Ala Arg Asp Phe Ile Asn Trp Leu Ile Gln Thr Lys Ile Thr
            20                  25                  30

Asp Pro Ser Ser Gly Ala Pro Pro Ser
        35                  40

<210> SEQ ID NO 51
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

His Gly Asp Gly Ser Phe Ser Asp Glu Met Cys Thr Ile Leu Asp Asn
1               5                   10                  15

Leu Cys Ala Arg Asp Phe Ile Asn Trp Leu Ile Gln Thr Lys Ile Thr
            20                  25                  30

Asp Pro Ser Ser Gly Ala Pro Pro Ser
        35                  40

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

His Gly Glu Gly Thr Phe Thr Ser Asp Val Ser Ser Tyr Leu Glu Gly
1               5                   10                  15

Cys Ala Ala Lys Glu Phe Ile Cys Trp Leu Val Lys Gly Arg
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide -continued

```
<220> FEATURE:
<221> NAME/KEY: MOD_RES
<222> LOCATION: (2)..(2)
<223> OTHER INFORMATION: Aib

<400> SEQUENCE: 53

His Xaa Glu Gly Thr Phe Thr Ser Asp Val Ser Ser Tyr Leu Glu Gly
1               5                   10                  15

Cys Ala Ala Lys Glu Phe Ile Cys Trp Leu Val Lys Gly Arg
            20                  25                  30

<210> SEQ ID NO 54
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser

<400> SEQUENCE: 54

His Ser Gln Gly Thr Phe Thr Ser Asp Tyr Ser Lys Tyr Leu Asp Glu
1               5                   10                  15

Cys Ala Ala Lys Glu Phe Ile Cys Trp Leu Met Asn Thr Lys Arg Asn
            20                  25                  30

Arg Asn Asn Ile Ala Cys
        35
```